US008389792B2

(12) United States Patent
Glimcher et al.

(10) Patent No.: US 8,389,792 B2
(45) Date of Patent: Mar. 5, 2013

(54) COMPOSITIONS AND METHODS FOR THE TREATMENT AND PREVENTION OF ULCERATIVE COLITIS AND COLON CANCER AND SCREENING METHODS TO IDENTIFY SAME

(75) Inventors: Laurie H. Glimcher, West Newton, MA (US); Wendy Sarah Garrett, Brookline, MA (US)

(73) Assignee: Cornell University, Ithaca, NY (US)

( * ) Notice: Subject to any disclaimer, the term of this patent is extended or adjusted under 35 U.S.C. 154(b) by 280 days.

(21) Appl. No.: 12/730,985

(22) Filed: Mar. 24, 2010

(65) Prior Publication Data

US 2010/0242124 A1   Sep. 23, 2010

Related U.S. Application Data

(63) Continuation-in-part of application No. PCT/US2008/077455, filed on Sep. 24, 2008, and a continuation-in-part of application No. PCT/US2008/077452, filed on Sep. 24, 2008.

(60) Provisional (Continued)

(51) Int. Cl.
*G01N 33/00* (2006.01)
*A61K 49/00* (2006.01)
(52) U.S. Cl. .............................. 800/3; 424/9.1
(58) Field of Classification Search ........ 800/3; 424/9.1
See application file for complete search history.

(56) References Cited

U.S. PATENT DOCUMENTS

| 2003/0104528 A1 | 6/2003 | Glimcher et al. |
| 2003/0186377 A1 | 10/2003 | Glimcher et al. |
| 2006/0223116 A1 | 10/2006 | Glimcher et al. |
| 2007/0012866 A1 | 1/2007 | Carlson et al. |

FOREIGN PATENT DOCUMENTS

| WO | 03/048379 A1 | 6/2003 |
| WO | 2006/079119 A2 | 7/2006 |
| WO | 2006/130620 A2 | 12/2006 |

OTHER PUBLICATIONS

Veiga et al., Proc Natl Acad Sci U S A. Oct. 19, 2010;107(42):18132-7. Epub Oct 4, 2010 *Bifidobacterium animalis* subsp. *lactis* fermented milk product reduces inflammation by altering a niche for colitogenic microbes.*
Seksik et al., Microbiote intestinal et MICI 2010 Gastroenterologie Clinique Et Biologique p. 48-55. Abstract.*
Wang et al., J Clin Invest. Feb. 2006;116(2):414-21. Epub Jan. 12, 2006.Transcription factor T-bet regulates inflammatory arthritis through its function in dendritic cells.*
Ermann et al., Proc Natl Acad Sci U S A. Apr. 26, 2011;108(17):7137-41. Epub Apr. 11, 2011.Severity of innate immune-mediated colitis is controlled by the cytokine deficiency-induced colitis susceptibility-1 (Cdcs1) locus.*
Lugo-Villarino et al Proc Natl Acad Sci U S A. Sep. 13, 2005;102(37):13248-53. Epub Aug. 31, 2005. The adjuvant activity of CpG DNA requires T-bet expression in dendritic cells.*
Gerlai R. Gene-targeting studies of mammalian behavior: is it the mutation or the background genotype? Trends Neurosci. May 1996;19(5):177-81.*
Holschneider DP, Shih JC. Genotype to phenotype: challengesl and opportunities. Int J Dev Neurosci. Oct. 2000;18(6):615-8.*
Leonard W J, Shores EW, Love PE. Role of the common cytokine receptor gamma chain in cytokine signaling and lymphoid development. Immunol Rev. Dec. 1995;148:97-114.*
Griffiths I, et al., Current concepts of PLP and its role in the nervous system. Microsc Res Tech. Jun. 1, 1998 ;41 (5):344-58.*
Schalkwyk et al., "Interpretation of knockout experiments: the congenic footprint," Genes Brain Behav, 6:299-303, Feb. 23, 2007.*
Crabbe et al Genetics of mouse behavior: Interactions with laboratory environment Science 284: 1670-1672, 1999.*
Wang et al., Transcription factor T-bet regulates inflammatory arthritis through its function in dendritic cells J Clin Invest. 2006;116(2):414-421.*
Fujiwara et al., T-bet inhibits both TH2 cell-mediated eosinophil recruitment and TH17 cell-mediated neutrophil recruitment into the airways J Allergy Clin Immunol vol. 119, No. 3 Mar. 2007, pp. 662-670.*
Garrett et al., Communicable Ulcerative Colitis Induced by T-bet Deficiency in the Innate Immune System vol. 131, Issue 1, Oct. 5, 2007, pp. 33-45.*
Backhed, Fredrik et al., "Host-Bacterial Mutualism in the Human Intestine," Science, vol. 307:1915-1920 (2005).
Baroja, M. Lorea et al., "Anti-inflammatory effects of probiotic yogurt in inflammatory bowel disease patients," Clinical and Experimental Immunology, vol. 149:470-479 (2007).
Boirivant, Monica et al., "Oxazolone Colitis: A Murine Model of T Helper Cell Type 2 Colitis Treatable with Antibodies to Interleukin 4," The Journal of Experimental Medicine, vol. 188(10):1929-1939 (1998).
Boone, David L. et al., "Connecting the dots from Toll-like receptors to innate immune cells and inflammatory bowel disease," The Journal of Clinical Investigation, vol. 111(9):1284-1286 (2003).
Dieleman, L.A. et al., "Chronic experimental colitis induced by dextran sulphate sodium (DSS) is characterized by Th1 and Th2 cytokines," Clin. Exp. Immunol., vol. 114:385-391 (1998).
Egger, Bernhard et al., "Characterisation of Acute Murine Dextran Sodium Sulphate Colitis: Cytokine Profile and Dose Dependency," Digestion, vol. 62:240-248 (2000).
Elson, Charles O. et al., "Experimental models of inflammatory bowel disease reveal innate, adaptive, and regulatory mechanisms of host dialogue with the microbiota," Immunological Reviews, vol. 206:260-276 (2005).

(Continued)

*Primary Examiner* — Maria Leavitt
(74) *Attorney, Agent, or Firm* — Nelson Mullins Riley & Scarborough LLP; Debra J. Milasincic, Esq.

(57) ABSTRACT

The instant invention is based, at least in part, on the discovery that T-bet maintains host commensal relationships in the gastrointestinal tract. Accordingly, this invention provides methods of treating and/or preventing ulcerative colitis, and/or colon cancer, and/or preventing colonization of a subject's gastrointestinal tract with commensal bacteria that promote ulcerative colitis as well as methods of identifying agents that treat and prevent the same.

9 Claims, 31 Drawing Sheets

Related U.S. Application Data application No. 61/066,319, filed on Feb. 20, 2008, provisional application No. 60/995,036, filed on Sep. 24, 2007, provisional application No. 61/128,376, filed on May 21, 2008.

(56) References Cited

OTHER PUBLICATIONS

Garrett, Wendy S. et al., "Communicable Ulcerative Colitis Induced by T-bet Deficiency in the Innate Immune System," Cell, vol. 131:33-45 (2007).
Gerth, Andrea J. et al., "An Innate Cell-Mediated, Murine Ulcerative Colitis-like Syndrome in the Absence of Nuclear Factor of Activated T Cells," Gastroenterology, vol. 126:1115-1121 (2004).
Glimcher, Laurie H., "Trawling for treasure: tales of T-bet," Nature Immunology, vol. 8(5):448-450 (2007).
Hoffmann, Jorg C. et al., "Animal Models of Inflammatory Bowel Disease: An Overview," Pathobiology, vol. 70:121-130 (2002).
Horton, R.M. et al., "PCR screening of transgenic RAG-2 'knockout' immunodificient mice," Biotechniques, vol. 19 (5):690-691 (1995).
Jurjus, Abdo R. et al., "Appraisal of state-of-the art Animal models of inflammatory bowel disease," Journal of Pharmacological and Toxicological Methods, vol. 50:81-92 (2004).
Kanai, Takanori et al., "Clinical application of human CD4+CD25+ regulatory T cells for the treatment of inflammatory bowel diseases," Expert Opin. Biol. Ther., vol. 5(4):451-462 (2005).
Komatsu, Masanobu et al., "Antigen-primed CD8+ T cells can mediate resistance, preventing allogeneic marrow engraftment in the simultaneous absence of perforin-, CD95L-, TNFR1-, and TRAIL-dependent killing," Blood, vol. 101 (10):3991-3999 (2003).
Leach, Michael W. et al., "Inflammatory Bowel Disease in C.B-17 scid Mice Reconstituted with the CD45RBhigh Subset of CD4+ T Cells," American Journal of Pathology, vol. 148(5):1503-1515 (1996).
Ley, Ruth E. et al., "Ecological and Evolutionary Forces Shaping Microbial Diversity in the Human Intestine," Cell, vol. 124:837-848 (2006).
Lugo-Villarino, Geanncarlo et al., "T-bet is required for optimal production of IFN-gamma and antigen-specific T cell activation by dendritic cells," PNAS, vol. 100(13):7749-7754 (2003).
Ma, Averil et al., "T Cells, but Not B cells, Are Required for Bowel Inflammation in Interleukin 2-deficient Mice," J. Exp. Med., vol. 182:1567-1572 (1995).
Maloy, Kevin J. et al., "CD4+CD25+ TR Cells Suppress Innate Immune Pathology Through Cytokine-dependent Mechanisms," J. Exp. Med., vol. 197(1):111-119 (2003).
Maloy, Kevin J. et al., "Cure of innate intestinal immune pathology by CD4+CD25+ regulatory T cells," Immunology Letters, vol. 97:189-192 (2005).
Mottet, Christian et al., "Cutting Edge: Cure of Colitis by CD4+CD25+ Regulatory T Cells," The Journal of Immunology, vol. 170:3939-3943 (2003).
Murthy, Sreekant, "Animal models of inflammatory bowel disease," In Vivo Models of Inflammation, Christpher S. Stevenson (Ed.) Birkhauser Verlag Basel/Switzerland, vol. II, pp. 137-174 (2006).
Neurath, Markus F. et al., "The role of Th1/Th2 polarization in mucosal immunity," Nature Medicine, vol. 8:567-573 (2002).
Neurath, M.F. et al., "The Transcription Factor T-bet Regulators Mucosal T Cell Activation in Expreimental Colitis and Crohn's Disease," J. Exp. Med., vol. 195(9):1129-1143 (2002).
Nieuwenhuis, Edward E.S. et al., "The Role of the Epithelial Barrier in Inflammatory Bowel Disease," Immune Method in Inflammatory Bowel Disease, Richard S. Blumberg (Ed.), Eurekah.com and Springer Science+Business Media, Chapter 7, pp. 108-116 (2006).
Osawa, Emi et al., "Predominant T helper type 2-inflammatory responses promote murine colon cancers," Int. J. Cancer, vol. 118:2232-2236 (2006).
Peng, Stanford L., "The T-box Transcription Factor T-bet in Immunity and Autoimmunity," Cellular & Molecular Immunology, vol. 3(2):87-95 (2006).
Powrie, Fiona et al., "Phenotypically distinct subsets of CD4+ T cells induce or protect from chronic intestinal inflammation in C. B-17 scid mice," International Immunology, vol. 5(11):1461-1471 (1993).
Rakoff-Nahoum, S. et al., "Role of the Innate Immune System and Host-Commensal Mutualism," CTMI, vol. 308:1-18 (2006).
Sartor, R. Balfour, "Probiotic therapy of intestinal inflammation and infections," Curr. Opin. Gastroenterol., vol. 21:44-50 (2004).
Sartor, R. Balfour, "Targeting enteric bacteria in treatment of inflammatory bowel diseases: why, how, and when," Current Opinion in Gastroenterology, vol. 19:358-365 (2003).
Schultz, Michael et al., "Rationale for Probiotic and Antibiotic Treatment Strategies in Inflammatory Bowel Diseases," Digestive Diseases, vol. 21:105-128 (2003).
Sullivan, Brandon M. et al., "Antigen-driven effector CD8 T cell function regulated by T-bet," PNAS, vol. 100 (26):15818-15823 (2003).
Sundberg, John P. et al., "Spontaneous Heritable Colitis in a New Substrain of C3H/HeJ Mice," Gastroenterology, vol. 107:1726-1735 (1994).
Szabo, Susanne J. et al., "A Novel Transcription Factor, T-bet, Directs Th1 Lineage Commitment," Cell, vol. 100:655-669 (2000).
Szabo, Susanne J. et al., "Distinct Effects of T-bet in TH1 Lineage Commitment and IFN-gamma Production in CD4 and CD8 T Cells," Science, vol. 295(5553):338-342 (2002).
Weber, C.R. et al., "Inflammatory bowel disease: is it really just another break in the wall?" Gut, vol. 56(1):6-8 (2007).
Weigmann, B. et al., "T-bet and mucosal Th1 responses in the gastrointestinal tract," Gut, vol. 51:301-303 (2002).
International Search Report for Application No. PCT/US2008/077452, 7 pages, dated Mar. 26, 2009.
International Search Report for Application No. PCT/US2008/077455, 6 pages, dated Apr. 22, 2009.
International Preliminary Report on Patentability and Written Opinion for Application No. PCT/US2008/077452, 11 pages, dated Mar. 24, 2010.
International Preliminary Report on Patentability and Written Opinion for Application No. PCT/US2008/077455, 8 pages, dated Mar. 24, 2010.

\* cited by examiner

In vitro sensitivities

Strptococcus bovis:         Vancomycin sensitive
Clostridium ciostridioforme: Vancomycin sensitive
Fusobacter mortiferum:      Gentamicin resistant
B. thetaiotaomicron:        Gentamicin resistant
Prevotella tannerae:        Gentamicin resistant
Klebsiella pneumoniae       Gentamicin sensitive
Proteus mirabilis           Gentamicin sensitive All species identified in the culture-dependent time course screen of Rag2⁻/⁻ and TRUC

| Bacterial species | Rag2⁻/⁻ Mother | TRUC Mother | #Rag2⁻/⁻ offspring 2 wk | 4 wk | 6 wk | # TRUC offspring* 8 wk | 10 wk |
|---|---|---|---|---|---|---|---|
| Acinetobacter baumannii | + | - | 0 | 0 | 0 | 0 | 0 |
| Actinomyces sp. | + | - | 0 | 0 | 0 | 0 | 0 |
| Bacteroides distasonis | - | + | 3 | 0 | 0 | 3 | 0 |
| Bacteroides fragilis | - | - | 0 | 1 | 2 | 0 | 0 |
| Bacteroides ovalus | - | - | 1 | 0 | 0 | 0 | 0 |
| Bacteroides putredinis | - | - | 0 | 0 | 0 | 0 | 0 |
| Bacteroides thetaiotaomicron | - | - | 2 | 1 | 1 | 0 | 0 |
| Bacteroides urealyticus | - | - | 0 | 0 | 0 | 0 | 1 |
| Bacteroides vulgatus | + | + | 3 | 2 | 3 | 3 | 0 |
| Campylobacter gracilis | - | - | 0 | 1 | 2 | 2 | 0 |
| Clostridium clostridioforme | - | + | 3 | 0 | 0 | 0 | 0 |
| Clostridium hastiforme | + | - | 0 | 0 | 0 | 0 | 0 |
| Comamonas testosteroni | - | - | 1 | 0 | 0 | 0 | 1 |
| Corynebacterium pseudodiptherium | - | - | 0 | 0 | 0 | 0 | 0 |
| Enterococcus casseflavus | - | - | 0 | 0 | 3 | 3 | 3 |
| Enterococcus faecalis | - | - | 0 | 2 | 0 | 2 | 3 |
| Enterococcus gallinarum | - | - | 1 | 2 | 0 | 0 | 0 |
| Escherichia coli | + | - | 0 | 3 | 3 | 3 | 3 |
| Eubacterium biforme | - | - | 1 | 0 | 0 | 0 | 0 |
| Eubacterium lentum | - | - | 0 | 0 | 0 | 1 | 0 |
| Eubacterium sp. | - | - | 0 | 0 | 0 | 0 | 0 |
| Fusobacterium mortiferum | - | - | 0 | 0 | 2 | 0 | 0 |
| Gemella morbillorum | - | - | 0 | 3 | 0 | 0 | 3 |
| Klebsiella pneumoniae | - | + | 0 | 0 | 3 | 3 | 1 |
| Lactobacillus alimentarius | - | - | 0 | 0 | 1 | 2 | 0 |
| Lactobacillus animalis | + | + | 3 | 2 | 3 | 2 | 3 |
| Lactobacillus casei | - | - | 0 | 3 | 0 | 3 | 0 |
| Lactobacillus curvatus | + | + | 3 | 1 | 3 | 0 | 3 |
| Lactobacillus delbrueckii-lactis | - | - | 0 | 0 | 0 | 0 | 0 |

Fig. 18

All species identified in the culture-dependent time course screen of *Rag2⁻/⁻* and TRUC

| | Rag2⁻/⁻ Mother | TRUC Mother | #Rag2⁻/⁻ offspring 2 wk | # TRUC offspring* 2 wk | #Rag2⁻/⁻ 4 wk | # TRUC 4 wk | #Rag2⁻/⁻ 6 wk | # TRUC 6 wk | #Rag2⁻/⁻ 8 wk | # TRUC 8 wk | #Rag2⁻/⁻ 10 wk | # TRUC 10 wk |
|---|---|---|---|---|---|---|---|---|---|---|---|---|
| Bacterial species | | | | | | | | | | | | |
| Lactobacillus farciminis | - | - | 1 | 0 | 0 | 0 | 0 | 0 | 0 | 0 | 0 | 0 |
| Lactobacillus leichmannii | - | + | 0 | 0 | 0 | 0 | 0 | 0 | 0 | 0 | 0 | 0 |
| Lactobacillus sp. | + | + | 2 | 2 | 0 | 0 | 0 | 0 | 0 | 0 | 0 | 1 |
| Prevotella loescheii | - | - | 0 | 0 | 0 | 0 | 0 | 1 | 0 | 1 | 0 | 0 |
| Prevotella oralis gp. | + | + | 0 | 2 | 0 | 0 | 3 | 1 | 3 | 1 | 1 | 0 |
| Prevotella sp. | - | + | 0 | 0 | 0 | 0 | 0 | 0 | 0 | 0 | 0 | 0 |
| Prevotella tannarae | - | + | 0 | 1 | 0 | 3 | 0 | 3 | 0 | 3 | 0 | 3 |
| Prevotella veroralis | + | - | 1 | 0 | 0 | 0 | 0 | 0 | 0 | 0 | 0 | 0 |
| Propionibacterium-D06 | - | - | 0 | 3 | 0 | 3 | 0 | 2 | 0 | 2 | 0 | 3 |
| Preteus mirabilis | - | + | 0 | 0 | 0 | 1 | 0 | 0 | 0 | 0 | 0 | 0 |
| Pseudomonas fluorescens | - | - | 0 | 0 | 0 | 0 | 0 | 0 | 0 | 0 | 0 | 0 |
| Pseudomonas putida | + | - | 0 | 0 | 0 | 0 | 0 | 0 | 0 | 0 | 0 | 0 |
| Ruminococcus sp. | - | - | 0 | 0 | 3 | 2 | 0 | 0 | 0 | 0 | 0 | 0 |
| Staphylococcus arlettae | - | + | 0 | 0 | 0 | 0 | 0 | 0 | 0 | 0 | 0 | 0 |
| Staphylococcus capitis-capitis | - | - | 0 | 0 | 0 | 1 | 0 | 1 | 0 | 1 | 0 | 0 |
| Staphylococcus chromogenes | - | - | 0 | 3 | 0 | 0 | 0 | 0 | 0 | 0 | 0 | 0 |
| Staphylococcus cohnii-urealyticus | - | + | 2 | 0 | 1 | 1 | 1 | 0 | 1 | 0 | 0 | 0 |
| Staphylococcus hyicus | - | - | 0 | 0 | 0 | 1 | 0 | 0 | 0 | 1 | 0 | 0 |
| Staphylococcus kloosii | - | - | 0 | 0 | 0 | 0 | 0 | 2 | 0 | 2 | 0 | 3 |
| Staphylococcus lentus | - | - | 0 | 0 | 1 | 0 | 2 | 2 | 2 | 2 | 1 | 0 |
| Staphylococcus lutrae | - | + | 0 | 0 | 0 | 0 | 0 | 0 | 0 | 0 | 0 | 0 |
| Staphylococcus saprophyticus | - | - | 1 | 0 | 2 | 0 | 0 | 0 | 0 | 0 | 0 | 2 |
| Staphylococcus sciuri | + | - | 0 | 0 | 1 | 0 | 0 | 1 | 0 | 0 | 0 | 0 |
| Staphylococcus xylosus | + | + | 2 | 0 | 1 | 1 | 2 | 0 | 2 | 0 | 3 | 3 |
| Streptococcus anginosus gp. | - | + | 0 | 0 | 3 | 3 | 0 | 1 | 0 | 1 | 0 | 0 |
| Streptococcus bovis | + | - | 0 | 0 | 0 | 0 | 0 | 2 | 0 | 2 | 0 | 0 |
| Streptococcus intermedius | - | - | 0 | 0 | 0 | 0 | 0 | 0 | 0 | 0 | 0 | 0 |
| Streptococcus oralis | - | - | 0 | 0 | 0 | 0 | 3 | 0 | 3 | 0 | 1 | 3 |

Fig. 18 *(cont'd)*

COMPOSITIONS AND METHODS FOR THE TREATMENT AND PREVENTION OF ULCERATIVE COLITIS AND COLON CANCER AND SCREENING METHODS TO IDENTIFY SAME

RELATED APPLICATIONS

This application claims is a continuation-in-part of PCT/US2008/077452 and of PCT/US2008/077455, both filed on 24 Sep. 2008, which claim the benefit of U.S. Provisional Application No. 60/995,036, filed Sep. 24, 2007, U.S. Provisional Application No. 61/066,319, and U.S. Provisional Application No. 61/128,376, filed May 21, 2008.

This application is related to U.S. patent application Ser. No. 11/920,868, filed Nov. 20, 2007 (pending), U.S. patent application Ser. No. 11/593,811, filed Nov. 7, 2006 (pending), and U.S. patent application Ser. No. 11/335,927, filed Jan. 20, 2006 (pending).

This application is also related to U.S. application Ser. No. 10/309,747, filed Dec. 3, 2002 (pending), which is a continuation-in-part application of U.S. application Ser. No. 10/008,264, filed on Dec. 3, 2001, now U.S. Pat. No. 7,393,944 B2, issued Jul. 1, 2008, which is a continuation-in-part application of PCT/US00/15345, filed on Jun. 1, 2000, published pursuant to PCT Article 21, in English, which claims priority to U.S. Provisional Application Ser. No. 60/137,085, filed Jun. 2, 1999.

This application is also related to U.S. application Ser. No. 12/070,856, filed Feb. 21, 2008, which is a divisional application of U.S. application Ser. No. 11/291,426, filed Nov. 30, 2005, now U.S. Pat. No. 7,365,169 B2, issued Apr. 29, 2008, which is a divisional of U.S. application Ser. No. 10/008,264, filed on Dec. 3, 2001, now U.S. Pat. No. 7,393,944 B2, issued Jul. 1, 2008 (supra).

This application is also related to U.S. Provisional Application No. 60/734,324, filed Nov. 7, 2005 (expired), U.S. Provisional Application No. 60/686,222, filed May 31, 2005 (expired), and U.S. Provisional Application No. 60/645,698, filed Jan. 20, 2005 (expired).

The entire contents of all of these applications are incorporated herein by this reference.

GOVERNMENT FUNDING

Work described herein was supported, at least in part, under grant CA1 12663 awarded by the National Institutes of Health. The U.S. government therefore has certain rights in this invention.

BACKGROUND OF THE INVENTION

The intestinal lumen is massively colonized by bacteria and for most metazoans this relationship is mutually beneficial (Ley, R. E., et al. (2006). Cell 124, 837-848). Prokaryotes productively partner with their eukaryotic hosts to aid in the digestion and extraction of energy and nutrients from food, and non-pathogenic bacteria suppress pathogenic species (Backhed, F., et al. (2005). Science 307, 1915-1920; Rakoff-Nahoum, S., and Medzhitov, R. (2006). Curr Top Microbiol Immunol 308, 1-18). An epithelial cell barrier is essential for this symbiosis as it creates a boundary necessary for coexistence by preventing mucosal inflammation in response to bacterial or other luminal stimuli (Nieuwenhuis, E. E., and Blumberg, R. S. (2006). Adv Exp Med Biol 579, 108-116; Weber, C. R., and Turner, J. R. (2007). Gut 56, 6-8). However, in some individuals this balance is upset, resulting in persistent intestinal inflammation, that manifests as the two distinct clinical entities of inflammatory bowel disease, Crohn's disease and ulcerative colitis (UC) (Boone, D. L., and Ma, A. (2003). J Clin Invest 111, 1284-1286; Rakoff-Nahoum, S., and Medzhitov, R. (2006). Curr Top Microbiol Immunol 308, 1-18; Rakoff-Nahoum, S., and Medzhitov, R. (2006). Curr Top Microbiol Immunol 308, 1-18). Determining the factors that regulate these complex host-commensal relationships and promote the development of colitis is of great clinical import and scientific interest.

SUMMARY OF THE INVENTION

The instant invention is based, at least in part, on the discovery that T-bet deficiency in the innate immune system results in aggressive, spontaneous, and communicable ulcerative colitis in the absence of adaptive immunity and also results in increased susceptibility to colitis in immunologically intact hosts which can progress to the development of dysplatic and neoplastic lesions and, ultimately, adenocarcinoma of the colon. In addition, the appended examples demonstrate that T-bet controls the response of the mucosal immune system to commensal bacteria by regulating TNF-α production in cells of the innate immune system, e.g., dendritic cells, such as bone marrow dendritic cells or colonic dendritic cells, which are critical for maintenance of the colonic epithelial barrier. Cells of the innate immune system also include, e.g., NK cells, macrophages, monocytes, etc. With the loss of T-bet, the commensal bacterial population becomes colitogenic. The colitis that occurs in this situation is communicable to genetically intact hosts. It has also been discovered that treatment of T-bet deficient animals with antibiotics abolishes both ulcerative colitis and colorectal carcinoma, and that feeding T-bet deficient animals probiotics abolishes ulcerative colitis. Accordingly, the present invention provides methods and compositions for treating and/or preventing ulcerative colitis and/or colon cancer and/or for preventing colonization of a subject's gastrointestinal tract with the commensal bacteria that promote ulcerative colitis. Still further, as shown in the appended examples, the presence of *Klebsiella pneumonia* and *Proteus mirabilis* correlate with colitis in T-bet$^{-/-}$×Rag2$^{-/-}$ animals. In addition, T-bet$^{-/-}$× Rag2$^{-/-}$ derived strains can elisit colitis in Rag 2$^{-/-}$ and in wild-type adults. In one embodiment, these organisms can be used as predictors of disease. In another embodiment, animals harboring these organisms (e.g., wild-type or T-bet$^{-/-}$× Rag2$^{-/-}$ animals) can be used as a model of ulcerative colitis or inflammatory bowel disease to screen for compounds capable of reducing the severity of disease.

In one aspect, the present invention provides methods of preventing ulcerative colitis in a subject comprising selectively increasing T-bet activity in cells of the innate immune system.

Another aspect of the invention features methods for treating ulcerative colitis in a subject comprising, selectively increasing T-bet activity in cells of the innate immune system of the subject to thereby treat ulcerative colitis.

In another aspect, the invention features methods for preventing colorectal cancer in a subject comprising, selectively increasing T-bet activity in cells of the innate immune system of the subject to thereby prevent colorectal cancer.

Yet another aspect of the invention features methods for treating colorectal cancer in a subject comprising, selectively increasing T-bet activity in cells of the innate immune system of the subject to thereby treat colorectal cancer.

One aspect of the invention features methods for preventing colonization of a subject's gastrointestinal tract with commensal bacteria that promote ulcerative colitis comprising, selectively increasing T-bet activity in cells of the innate immune system of the subject to thereby prevent colonization of the subject's gastrointestinal tract with commensal bacteria that promote ulcerative colitis.

In one embodiment of the methods of the invention, TNF-α production is decreased in the cells.

In one embodiment, the cells of the innate immune system are dendritic cells. In one embodiment, the dendritic cells are colonic dendritic cells. In another embodiment, the dendritic cells are bone marrow dendritic cells. In another embodiment, the cells of the innate immune system are macrophages. In yet another embodiment, the cells of the innate immune system are monocytes. In another embodiment, the cells of the innate immune system are Natural Killer cells.

In one embodiment, T-bet activity is selectively increased using a polycation:DNA complex conjugated to an antibody that targets a cell of the innate immune system. In one embodiment, the polycation:DNA complex is a PEI:DNA complex and the antibody is an anti-dendritic cell antibody, e.g., an anti-CD11c antibody. In another embodiment, the polycation:DNA complex is a PEI:DNA complex and the antibody is an anti-macrophage antibody, e.g., an anti-CD11a antibody. In another embodiment, the polycation:DNA complex is a PEI:DNA complex and the antibody is an anti-macrophage antibody, e.g., an anti-CD16 antibody. In another embodiment, the polycation:DNA complex is a PEI:DNA complex and the antibody is an anti-Natural Killer cell antibody, e.g., an anti-CD56 antibody. In another embodiment, the polycation:DNA complex is a PEI:DNA complex and the antibody is an anti-monocyte antibody, e.g., an anti-CD14 antibody.

In one embodiment, the methods of the invention further comprise administering an antibiotic to the subject. In another embodiment, the methods of the invention further comprise administering a probiotic to the subject. In another embodiment, the methods of the invention further comprise administering a prebiotic to the subject.

In one embodiment, the methods of the invention further comprise administering regulatory T cells in the subject. In one embodiment the regulatory T cells are obtained by isolating cells peripheral blood from the subject, treating the cells to obtain a population of treated cells comprising T regulatory cells.

In one embodiment, the methods of the invention further comprise increasing the number of regulatory T cells in the subject.

Another aspect of the invention features methods for evaluating the ability of a test compound to treat ulcerative colitis in a subject comprising, administering the test compound to a postnatal mouse whose genome is disrupted by recombination at each T-bet gene locus and at each RAG2 locus, said mouse having a phenotype, relative to a wild-type phenotype, of spontaneous ulcerative colitis, determining the ability of the test compound to reduce the phenotype of spontaneous ulcerative colitis, to thereby evaluate the ability of the test compound to treat ulcerative colitis in a subject.

One aspect of the invention features methods for evaluating the ability of a test compound to treat ulcerative colitis in a subject comprising, administering the test compound to a postnatal mouse, wherein said mouse is genetically intact at each T-bet locus and each Rag2 locus and has been cohoused with a mouse whose genome is disrupted by recombination at each T-bet gene locus and at each RAG2 locus, and wherein said cohoused mouse has a phenotype of transmitted ulcerative colitis; determining the ability of the test compound to reduce the phenotype of transmitted ulcerative colitis; to thereby evaluate the ability of the test compound to treat ulcerative colitis in a subject.

Yet another aspect of the invention features methods for evaluating the ability of a test compound to treat colorectal cancer in a subject comprising, administering the test compound to a postnatal mouse whose genome is disrupted by recombination at each T-bet gene locus and at each RAG2 locus, said mouse having a phenotype, relative to a wild-type phenotype, of spontaneous ulcerative colitis, determining the ability of the test compound to reduce the phenotype of spontaneous ulcerative colitis, to thereby evaluate the ability of the test compound to treat colorectal cancer in a subject.

Another aspect of the invention features methods for evaluating the ability of a test compound to treat colorectal cancer in a subject comprising, administering the test compound to a postnatal mouse, wherein said mouse is genetically intact at each T-bet locus and each Rag2 locus and has been cohoused with a mouse whose genome is disrupted by recombination at each T-bet gene locus and at each RAG2 locus, and wherein said cohoused mouse has a phenotype of transmitted ulcerative colitis; determining the ability of the test compound to reduce the phenotype of transmitted ulcerative colitis; to thereby evaluate the ability of the test compound to treat colorectal cancer in a subject.

Another aspect of the invention features methods for evaluating the ability of a test compound to inhibit colonization of a subject's gastrointestinal tract with commensal bacteria that promote ulcerative colitis in a subject comprising, administering the test compound to a postnatal mouse whose genome is disrupted by recombination at each T-bet gene locus and at each RAG2 locus, said mouse having a phenotype, relative to a wild-type phenotype, of spontaneous ulcerative colitis, determining the ability of the test compound to reduce the phenotype of spontaneous ulcerative colitis, to thereby evaluate the ability of the test compound to inhibit colonization of the subject's gastrointestinal tract with commensal bacteria that promote ulcerative colitis in a subject.

One aspect of the invention features methods for evaluating the ability of a test compound to inhibit colonization of a subject's gastrointestinal tract with commensal bacteria that promote colitis in a subject comprising,
administering the test compound to a postnatal mouse, wherein said mouse is genetically intact at each T-bet locus and each Rag2 locus and has been cohoused with a mouse whose genome is disrupted by recombination at each T-bet gene locus and at each RAG2 locus, and wherein said cohoused mouse has a phenotype of transmitted ulcerative colitis; determining the ability of the test compound to reduce the phenotype of transmitted ulcerative colitis; to thereby evaluate the ability of the test compound to inhibit colonization of a subject's gastrointestinal tract with commensal bacteria that promote colitis in a subject.

In one embodiment, the ability of the compound to reduce TNF-α production by cells of the innate immune system, e.g., dendritic cells, e.g., colonic dendritic cells, and/or monoctes, and/or Natural Killer cells, and/or macrophages, is measured. In another embodiment, the effect of the compound on the permeability of the intestine is measured. In yet another embodiment, the effect of the compound on apoptosis of colonic epithelium is determined.

Other aspects of the invention provide methods for of treating and/or preventing ulcerative colitis and/or colon cancer, and preventing the colonization of a subject's gastrointestinal tract with commensal bacteria that cause ulcerative colitis in a subject that would benefit from increased T-bet activity (e.g., a subject producing a T-bet protein having reduced activity or a subject producing a lower than normal or desirable level of T-bet protein). Such methods comprise administering to the subject a sufficient amount of an antibiotic and/or probiotic. In one embodiment, these methods also comprise identifying a subject as one that would benefit from increased T-bet activity prior to administering an agent to increase T-bet activity, an antibiotic, a probiotic, or combinations thereof.

In another aspect the invention provides methods of determining the predisposition of a subject to develop ulcerative colitis or colon cancer by determining the activity of T-bet in a biological sample derived from the subject and comparing the activity of T-bet in the sample to the activity of T-bet in an appropriate control sample, wherein a decrease in the activity of T-bet in the sample relative to the activity of T-bet in the control sample indicates that the subject is at risk of developing ulcerative colitis or colon cancer. In one embodiment, the activity of T-bet is determined by determining the level of T-bet mRNA.

In yet other aspects of the invention, methods are provided for determining the predisposition of a human subject to develop ulcerative colitis and/or colon cancer, said method comprising detecting at least one single nucleotide polymorphism (SNP) in the human T-bet gene.

BRIEF DESCRIPTION OF THE DRAWINGS

FIG. 18 illustrates species identified in the culture dependent time course screen of Rag2−/− and TRUC mice.

DETAILED DESCRIPTION OF THE INVENTION

Figure 1A:
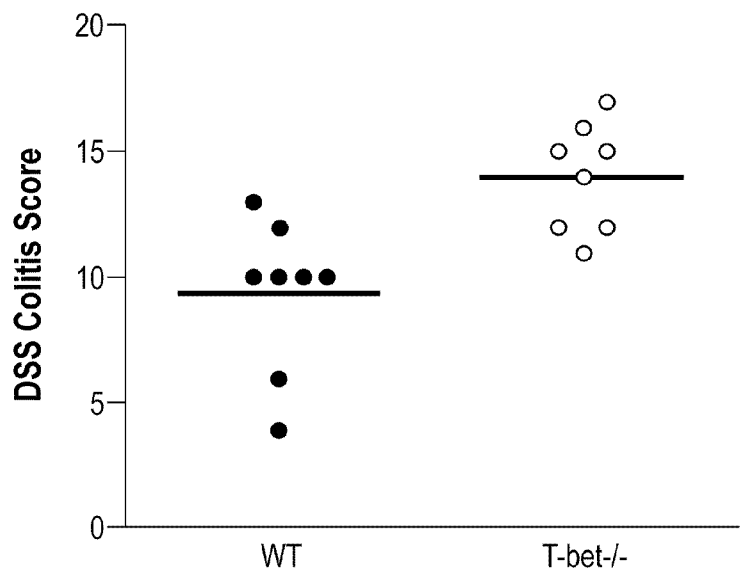
FIG. 1 shows that T-bet expression protects against colitis and T-bet−/−×RAG2−/− (TRUC) mice develop spontaneous colitis. (A) WT and T-bet−/− mice, age eight weeks, were treated with 4% DSS for eight days. Loss of T-bet resulted in more severe DSS-induced colitis. One representative experiment of three is shown, with eight per group, p=0.0031. (B) Photomicrographs of representative DSS treated WT (upper panel) and T-bet−/−(lower panel) colons are shown. (C) TRUC mice develop a spontaneous, highly penetrant colitis while genotype controls do not. The colitis score for each mouse is denoted by a dot and the mean colitis score for each group is shown as a horizontal bar. The seven mice in each group were 12 weeks of age. (D) The severity of TRUC colitis increases with time. The mean colitis score±standard deviation is shown for each group. The colons from 10, sex-matched mice were scored at each age with the exception of the one week old age group where eight mice were scored.

The articles "a" and "an" are used herein to refer to one or to more than one (i.e. to at least one) of the grammatical object of the article. By way of example, "an element" means one element or more than one element.

T-bet (Tbx21) is a member of the T-box transcription factor family that regulates the expression of a number of proteins produced by cells of the immune system. Although initially described as the transcription factor that directs the development of a major subset of lymphocytes called T helper 1 cells, recent work has firmly established T-bet as a regulator of the Type 1 proinflammatory immune response in cells of both the adaptive and innate immune systems (Glimcher, L. (2007). Nat Immunol 8, 448-450). In addition to its critical role in dictating T cell lineage commitment in developing CD4+ T cells and controlling their migration to inflammatory sites (Szabo, S. J., et al. (2000). Cell 100, 655-669; Szabo, S. J., et al. (2002). Science 295, 338-342), T-bet is required for the development and effector function of CD8 cells, and the development, trafficking, and survival of NK and canonical NK T cells (Sullivan, B. M., et al. (2003). Proc Natl Acad Sci USA 700, 15818-15823). T-bet expression in dendritic cells (DCs) is required for optimal expression of Type 1 and Type II interferons, and in the pathogenesis of inflammatory arthritis (Lugo-Villarino, et al. (2005). Proc Natl Acad Sci USA 702, 13248-13253; Lugo-Villarino, G., et al. (2003). Proc Natl Acad Sci USA100, 7749-7754; Wang, J., et al. (2006). J Clin Invest 116, 414-421). DCs also require T-bet to protect against death from infection with the intracellular bacterium, *Listeria monocytogenes* (Lugo-Villarino, et al. (2005). Proc Natl Acad Sci USA 702, 13248-13253). Although T-bet has been implicated as a key effector protein in a number of autoimmune, allergic, and neoplastic diseases (Neurath, M. F., et al. (2002a). Nat Med 5, 567-573; Peng, S. L. (2006). Cell Mol Immunol 3, 87-95; Weigmann, B., and Neurath, M. F. (2002). Gut 57, 301-303), its role in balancing immunity and autoimmunity is complex.

The instant invention is based, at least in part, on the discovery that T-bet is involved in maintaining host commensal relationships in the gastrointestinal tract. This invention pertains to methods of treating and/or preventing ulcerative colitis, inflammatory bowel disease, and/or colon cancer, and/or preventing colonization of a subject's gastrointestinal tract with commensal bacteria that promote ulcerative colitis as well as methods of identifying agents that treat ulcerative colitis, and/or colon cancer, and/or prevent colonization of a subject's gastrointestinal tract with commensal bacteria that promote ulcerative colitis. As discussed in more detail below, it has now been demonstrated that T-bet deficiency in the innate immune system results in aggressive, spontaneous, and communicable ulcerative colitis in the absence of adaptive immunity and also results in increased susceptibility to colitis in immunologically intact hosts. Furthermore, this ulcerative colitis may progress to adenocarcinoma of the colon. In addition, the appended examples demonstrate that T-bet controls the response of the mucosal immune system to commensal bacteria by regulating TNF-α production in cells of the innate immune system, e.g., colonic dendritic cells, which are critical for maintenance of the colonic epithelial barrier. The commensal bacterial population becomes colitogenic with the loss of T-bet and this colitis is communicable to genetically intact hosts. It has also been discovered that treatment of T-bet deficient animals with antibiotics abolishes both ulcerative colitis and colorectal carcinoma, and that feeding T-bet deficient animals probiotics abolishes ulcerative colitis.

So that the invention may be more readily understood, certain terms are first defined.

I. Definitions

As used herein, ulcerative colitis" ("UC") is chronic inflammation and ulceration of the colon and the anus. Microscopically, ulcerative colitis is restricted to the mucosa (epithelial lining of the gut). Diagnosis of UC in a subject is routine to the skilled artisan and includes, for example, presence of abdominal pain, rectal bleeding, and diarrhea. Stool and blood specimens may be collected for analysis to exclude infection. Blood tests may show anemia and an elevated white blood cell count or sedimentation rate. Confirmation of ulcerative colitis requires, for example, X-ray, barium enema, sigmoidoscopy or colonoscopy, and biopsy to determine the severity of the colitis. In one embodiment of the invention, a subject with UC is a subject that would benefit from increased T-bet activity.

As used herein, "colon cancer" or "colorectal cancer" refers to a tumor that arises from the inner lining of the large intestine, or colon. The term "colon cancer" also refers to carcinomas, lymphomas, carcinoid tumors, melanomas, and sarcomas of the colon. The risk for colorectal cancer is increased 6-fold in patients with colorectal cancer compared with the general population, and it is a significant cause of mortality in UC (Ekbom A, et al. N Engl J. Med. 1990; 323:1228-1233). Diagnosis of UC in a subject is routine to the skilled artisan and includes, for example, fecal occult blood test (FOBT), barium enema, virtual colonoscopy, sigmoidoscopy, colonoscopy and biopsy. In one embodiment of the invention, a subject with colorectal cancer is a subject that would benefit from increased T-bet activity.

The term "carcinoma" refers to any of various types of malignant neoplasias derived from epithelial cells, e.g., glandular cells ("adenoma" or "adenocarcinoma") or squamous cells ("squamous cell carcinoma"). Carcinomas often infiltrate into adjacent tissue and spread ("metastasize") to distant organs, e.g., bone, liver, lung or brain.

As used herein, the term "T-bet" includes T-bet nucleic acid molecules, or biologically active fragments thereof, that share structural features with the nucleic acid molecules shown in SEQ ID NOs: 1 and 3 and T-bet proteins that share the distinguishing structural and functional features of the T-bet proteins, or biologically active fragments thereof, shown in SEQ ID Nos: 2 and 4. The T-bet proteins are members of the T-box family of proteins and share some amino acid sequence homology to Brachyury, Tbx1-6, T-brain-1 (Tbr-1). T-box proteins comprise a T-box domain which binds to DNA at a T-box binding site. The amino acid and nucleotide sequence of T-bet are known in the art and can be found in, for example, GenBank accession numbers, gi:7019548 (human), gi:9507178 (mouse), and gi:157824179 (rat).

As used herein, the term "T-bet gene" refers to the coding sequence of T-bet found in genomic DNA, as well as the intronic sequences and 5' and 3' untranslated/regulatory regions of the T-bet gene. For example, in one embodiment, a T-bet gene includes, for example, about 5 kb, about 4 kb, about 3 kb, about 2 kb, about 1 kb of genomic DNA upstream of the T-bet ATG initiation codon or downstream of the T-bet termination codon. The genomic sequence containing T-bet coding sequences, intronic sequences, and promoter regions is also known in the art and can be found in, for example, GenBank accession number gi:51511734 and gi:37544107.

As used herein "selectively increasing T-bet acivity" refers to directly enhancing or increasing the activity of T-bet in a specific cell type using a "stimulatory agent". In one embodiment, T-bet activity is selectively increased in cells of the innate immune system, e.g., dendritic cells, natural killer cells, monocytes, macrophages, of a subject, while it is not increased in cells of the adaptive immune system, e.g., T cells, B cells, and this selective increase is sufficient to treat and/or prevent ulcerative colitis, and/or colon cancer, and/or inhibit colonization of a subject's gastrointestinal tract with commensal bacteria that promote ulcerative colitis.

As used herein, the term "a stimulatory agent" ("an agent that selectively increases T-bet activity") includes agents that enhance T-bet expression, processing, post-translational modification, and/or activity. The term includes agents, for example a compound or compounds which increase transcription of a T-bet gene, processing of a T-bet mRNA, translation of T-bet mRNA, post-translational modification of a T-bet protein (e.g., glycosylation, ubiquitinization or phosphorylation) or activity of a T-bet protein. Examples of agents that directly increase T-bet activity include e.g., nucleic acid molecules that encode T-bet, or biologically active portions thereof, T-bet polypeptides, or biologically active portions thereof, expression vectors encoding T-bet that allow for increased expression of T-bet activity in a cell, chemical compounds, or small molecules, that act to specifically enhance the activity of T-bet.

As used herein, a "transgenic animal" refers to a non-human animal, preferably a mammal, more preferably a mouse, in which one or more of the cells of the animal includes a "transgene". The term "transgene" refers to exogenous DNA which is integrated into the genome of a cell from which a transgenic animal develops and which remains in the genome of the mature animal, for example directing the expression of an encoded gene product in one or more cell types or tissues of the transgenic animal.

As used herein, a "homologous recombinant animal" refers to a type of transgenic non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

As used herein a "postnatal mouse whose genome is disrupted by recombination at each T-bet gene locus and at each RAG2 gene locus" is a post-birth transgenic mouse in which both copies of T-bet and both copies of RAG2 have been rendered non-functional, i.e., is deficient in T-bet and RAG2, i.e., a mouse that does not produce active T-bet and RAG2 protein, i.e., a mouse that is homozygously deficient in both T-bet and RAG2. The generation of such mice is described below. In one embodiment, such a postnatal mouse has been weaned, e.g., is approximately 21 days old. In another embodiment, a postnatal mouse whose genome is disrupted by recombination at each T-bet gene locus and at each RAG2 gene locus has not been weaned.

"A subject that would benefit from increased T-bet activity" is a subject producing a T-bet protein having reduced activity or a subject producing a lower than normal or desirable level of T-bet protein. Such a subject may be one in which the amount of T-bet, e.g., the mRNA and/or protein level of T-bet, and/or biological activity of T-bet, is less than the amount and/or activity of T-bet as compared to a normal or control subject, and who is at risk of (predisposed to) or who has developed ulcerative colitis, colorectal cancer, and/or colonization of commensal bacteria that cause ulcerative colitis. In one embodiment, such a subject is identified by determining, e.g., genotyping, a sample from the subject for a polymorphism in the T-bet gene, using methods described herein and known in the art. In another embodiment, such a subject is identified by determining, e.g., phenotyping, a sample from the subject to determine the level, e.g., mRNA, protein, biological activity, of T-bet, as described herein and known in the art.

The term "polymorphism" refers to the coexistence of more than one form of a gene, or portion thereof, or a segment of DNA. A portion of a gene or segment of DNA of which there are at least two different forms, i.e., two different nucleotide sequences, is referred to as a "polymorphic region." A polymorphic locus can be a single nucleotide, the identity of which differs in the other alleles. A polymorphic locus can also be more than one nucleotide long. The allelic form occurring most frequently in a selected population is often referred to as the reference and/or wildtype form. Other allelic forms are typically designated or alternative or variant alleles. Diploid organisms may be homozygous or heterozygous for allelic forms. A diallelic or biallelic polymorphism has two forms. A trialleleic polymorphism has three forms.

In one embodiment, a polymorphism is a single nucleotide polymorphism. The term "single nucleotide polymorphism" (SNP) refers to a polymorphic site occupied by a single nucleotide, which is the site of variation between allelic sequences. A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine)

at the polymorphic site, the altered allele can contain a "C" (cytidine), "G" (guanine), or "A" (adenine) at the polymorphic site.

SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence, i.e., an intron or promoter region. This may result in defective protein expression, e.g., as a result of alternative spicing, defective expression (temporal or spatial expression), or it may have no effect.

DNA polymorphisms can occur, e.g., when one nucleotide sequence comprises at least one of 1) a deletion of one or more nucleotides from a polymorphic sequence; 2) an addition of one or more nucleotides to a polymorphic sequence; 3) a substitution of one or more nucleotides of a polymorphic sequence, or 4) a chromosomal rearrangement of a polymorphic sequence as compared with another sequence. As described herein, there are a large number of assay techniques known in the art which can be used for detecting alterations in a polymorphic sequence The term "linkage" describes the tendency of genes, alleles, loci or genetic markers to be inherited together as a result of their location on the same chromosome. It can be measured by percent recombination between the two genes, alleles, loci, or genetic markers. The term "linkage disequilibrium," also referred to herein as "LD," refers to a greater than random association between specific alleles at two marker loci within a particular population. In general, linkage disequilibrium decreases with an increase in physical distance. If linkage disequilibrium exists between two markers, or SNPs, then the genotypic information at one marker, or SNP, can be used to make probabilistic predictions about the genotype of the second marker.

As used herein "colonization of a subject's gastrointestinal tract with commensal bacteria that cause ulcerative colitis" is the increased growth and/or proliferation of commensal bacteria (anaerobic bacteria) that normally populate the gastrointestinal tract to a level that leads to the development of at least one symptom associated with ulcerative colitis (discussed below). In one embodiment, the colonization of a subject's gastrointestinal tract with commensal bacteria that cause ulcerative colitis occurs in the colon. In another embodiment, the colonization of a subject's gastrointestinal tract with commensal bacteria that cause ulcerative colitis occurs in the rectum.

As used herein, the term "detect" with respect to polymorphic elements includes various methods of analyzing for a polymorphism at a particular site in the genome. The term "detect" includes both "direct detection," such as sequencing, and "indirect detection," using methods such as amplification and/or hybridization.

An used herein, an "isolated nucleic acid molecule" refers to a nucleic acid molecule that is free of gene sequences which naturally flank the nucleic acid in the genomic DNA of the organism from which the nucleic acid is derived (i.e., genetic sequences that are located adjacent to the gene for the isolated nucleic molecule in the genomic DNA of the organism from which the nucleic acid is derived). For example, in various embodiments, an isolated T-bet nucleic acid molecule typically contains less than about 10 kb of nucleotide sequences which naturally flank the nucleic acid molecule in genomic DNA of the cell from which the nucleic acid is derived, and more preferably contains less than about 5, kb, 4 kb, 3 kb, 2 kb, 1 kb, 0.5 kb or 0.1 kb of naturally flanking nucleotide sequences. An "isolated" T-bet nucleic acid molecule may, however, be linked to other nucleotide sequences that do not normally flank the T-bet sequences in genomic DNA (e.g., the T-bet nucleotide sequences may be linked to vector sequences and/or other non-T-bet sequences). In certain preferred embodiments, an "isolated" nucleic acid molecule, such as a cDNA molecule, also may be free of other cellular material. However, it is not necessary for the T-bet nucleic acid molecule to be free of other cellular material to be considered "isolated" (e.g., a T-bet DNA molecule separated from other mammalian DNA and inserted into a bacterial cell would still be considered to be "isolated").

As used herein, an "isolated protein" or "isolated polypeptide" refers to a protein or polypeptide that is substantially free of other proteins, polypeptides, cellular material and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the protein is derived, or substantially free from chemical precursors or other chemicals when chemically synthesized. The language "substantially free of cellular material" includes preparations of T-bet protein in which the protein is separated from cellular components of the cells from which it is isolated or recombinantly produced.

As used herein, the term "cell" includes prokaryotic and eukaryotic cells. In one embodiment, a cell of the invention is a bacterial cell. In another embodiment, a cell of the invention is a fungal cell, such as a yeast cell. In another embodiment, a cell of the invention is a vertebrate cell, e.g., an avian or mammalian cell. In a preferred embodiment, a cell of the invention is a murine or human cell.

As used herein, the term "immune cell" includes cells that are of hematopoietic origin and that play a role in the immune response. Immune cells include cells of the innate immune system and cells of the adaptive immune system. Immune cells include, for example, lymphocytes, such as B cells and T cells; natural killer cells; and myeloid cells, such as monocytes, macrophages, eosinophils, mast cells, basophils, and granulocytes.

In one embodiment, an immune cell is a cell of the innate immune system. The "innate immune system" is the nonspecific immune system that controls the body's response to an agent until the more specific adaptive immune system can produce specific antibodies and/or T cells (Modlin et al., N. Engl. J. Med 1999, 340:1834-1835; Das, Grit Care 2000; 4:290-296). The innate immune system generally involves phagocytic cells (e.g., neutrophils, monocytes, and macrophages); cells that release inflammatory mediators (e.g., basophils, mast cells, and eosinophils); natural killer cells (NK cells); and dendritic cells (DCs). In contrast, the "adaptive", or "acquired, immune system", is very specific in its responses. It is called an adaptive system because is occurs during the lifetime of an individual as an adaptation to infection with a pathogen. Adaptive immunity can be artificially acquired in response to a vaccine (antigens) or by administering antibodies, or can be naturally acquired by infection.

"Monocytes' and "macrophages" are cells of the innate immune system. Both monocytes and macrophages are responsible for phagocytosis (ingestion) of foreign substances in the body and the processing of antigens for presentation to B and T cells, invoking humoral or cell-mediated immune responses. A monocyte is an immature macrophage that has moved from the general circulation into the tissues of an organism.

Monocytes are CD14+. In one embodiment, monocytes are CD14+ CD16+. In another embodiment, monocytes are CD14+ CD16−. Monocytes may be obtained in large numbers by, for example, ex vivo expansion from CD14(+) peripheral blood mononuclear cells (PBMC). Monocytes may also be obtained by adherence methods or negative selection. For the adherence method PBMC are cultured by seeding PMBC onto plastic cell culture dishes. Nonadherent cells are removed and adherent cells are washed. Negative selection (depletion of non-monocytes such as T cells, NK cells, B cells, dendritic cells, and basophils) uses a combination of monoclonal Abs against CD3, CD7, CD19, CD45RA, and CD56 and an anti-immunoglobulin E to deplete B and T lymphocytes and NK cells.

Macrophages are CD16+. Macrophages are also CD11a+ and may be obtained in large numbers by, for example, ex vivo expansion of CD11a+ cells from cell suspensions of spleen, lymph node, peritoneal cavity, liver, muscle tissue, or blood.

In another embodiment, monocytes and macrophages may also express one or more of: ADAM8, C5R1, CD14, CD163, CD33, CD40, CD63, CD68, CD74, CD86, CHIT1, CHST10, CSF1R, DPP4, FABP4, FCGR1A, HLA-DRA, ICAM2, IL1R2, ITGA1, ITGA2, S100A8, TNFRSF8, TNFSF7.

Natural killer (NK) cells are cells of the innate immune system that have diverse biological functions including recognition and destruction of certain microbial infections and neoplasms (Moretta, A., Bottino, C., Mingari, M. C., Biassoni, R. and Moretta, L., Nat. Immunol., 3, 6, 2002). Resting NK cells circulate in the blood, but following activation by cytokines, they are capable of extravasation and infiltration into most tissues that contain pathogen-infected or malignant cells (Colucci, F., Di Santo, J. P. and Leibson, P. J., Nat. Immunol., 3, 807, 2002; Kelly J. M., Darcy P. K., Markby J. L., Godfrey D. I., Takeda K., Yagita H., Smyth M. J., Nat. Immunol., 3, 83, 2002; Shi F. D., Wang H. B., Li H., Hong S., Taniguchi M., Link H., Van Kaer L., Ljunggren H. G, Nat. Immunol., 1, 245, 2000; Korsgren M., Persson C. G., Sundler F., Bjerke T., Hansson T., Chambers B. J., Hong S., Van Kaer L., Ljunggren H. G, Korsgren O., J. Exp. Med., 189, 553, 1999). In general, the phenotype of NK cells is characterized by the expression of the CD56 and CD16 and the lack of CD3.

In one embodiment, NK cells are $CD56^+CD16^+$. $CD56^+CD16^+$ cells are the major NK cell subset in blood. These cells also express killer cell immunoglobulin-like receptors (KIRs) and CD94-associated lectin-like NKG2 receptors. Accordingly, they exhibit strong antibody-dependent cell-mediated cytotoxicity (ADCC) and natural cell-mediated cytotoxicity. They have a low cytokine production capacity.

In one embodiment, NK cells are $CD56^+CD16^-$. $CD56^+CD16^-$ cells are a minor subset of NK cells in blood. These cells lack expression of killer cell immunoglobulin-like receptors (KIRs) and do not have antibody-dependent cell-mediated cytotoxicity (ADCC) activity or strong natural cell-mediated cytotoxicity. Unlike $CD56^+CD16^+$ NK cells, which only secrete low levels of cytokines, $CD56^+CD16^-$ cells have a high cytokine production capacity, e.g., IFN-γ.

In another embodiment, NK cells may also express one or more of: CD2, CD244, CD3Z, CD7, CD96, CHST10, FCGR3B, IL12RB1, KLRB1, KLRC1, KLRD1, LAG3, NCAM1.

NK cells may be isolated from PMBC by depletion of non-NK such as T cells, B cells, stem cells, dendritic cells, monocytes, granulocytes, and erythroid cells or by positive selection, e.g., CD56 selection.

A "dendritic cell" is a cell of the innate immune system that is an antigen-presenting cell which is particularly active in stimulating T cells. Dendritic cells can be obtained in large numbers by, for example, ex vivo expansion from CD34(+) bone marrow-derived precursor cells or monocytes (Caux et al, 1996, 1997; Sallusto and Lanzavecchia, 1994; Freudenthal and Steinman, 1990; Thomas et al, 1993; Fong and Engleman, 2000; Syme and Gluck, 2001). Dendritic cells are $CD11c^+$, major histocompatibility complex (MHC) class $II^+$. Dendritic cells may express one or more of CD11a, CD50, CD54, CD58, CD102, CD4, CD8, B220, and CD86 and do not express cell surface markers for T-cells (e.g., CD3, CD16, CD19, and CD28), monocytes (e.g., CD14) B-cells (e.g., CD19, CD20, and immunoglobulins), natural killer cells (e.g., CD16, CD56, and CD57), and granulocytes (CD66b).

In one embodiment, a dendritic cell is a "bone marrow dendritic cell". Bone marrow dendritic cells can be obtained by, for example, culturing bone marrow cells in the presence of GM-CSF and removing cells positive for MHC class II, CD8, CD4, and B220 by monoclonal antibody magnetic-activated cell sorting (MACS) bead depletion.

In another embodiment, a dendritic cell is a "colonic dendritic cell". Colonic dendritic cells can be obtained by, for example, isolating colon cells and removing cells positive for MHC class II molecules and CD11c from a colonic cell suspension enriched for mononuclear cells by Percoll gradient filtration.

In another embodiment, dendritic cells also express $CD11b^+$, $DEC-205^+$, $CD8-alpha^+$, and/or DC-SIGN. In yet another embodiment, dendritic cells can be identified following incubation with the monoclonal antibody 33D1 (Nussenzweig M C et al Proceedings of the National Academy of Sciences (USA) 79: 161-165 (1982)).

The terms "antigen presenting cell" and "APC", as used interchangeably herein, include professional antigen presenting cells (e.g., B lymphocytes, monocytes, dendritic cells, and Langerhans cells) as well as other antigen presenting cells (e.g., keratinocytes, endothelial cells, astrocytes, fibroblasts, and oligodendrocytes).

As used herein, the term "T cell" (i.e., T lymphocyte) is intended to include all cells within the T cell lineage, including thymocytes, immature T cells, mature T cells and the like, from a mammal (e.g., human). T cells include mature T cells that express either CD4 or CD8, but not both, and a T cell receptor. The various T cell populations described herein can be defined based on their cytokine profiles and their function.

As used herein "progenitor T cells" ("Thp") are naïve, pluripotent cells that express CD4.

As used herein, the term "naïve T cells" includes T cells that have not been exposed to cognate antigen and so are not activated or memory cells. Naïve T cells are not cycling and human naïve T cells are CD45RA+. If naïve T cells recognize antigen and receive additional signals depending upon but not limited to the amount of antigen, route of administration and timing of administration, they may proliferate and differentiate into various subsets of T cells, e.g., effector T cells.

As used herein, the term "effector T cell" includes T cells which function to eliminate antigen (e.g., by producing cytokines which modulate the activation of other cells or by cytotoxic activity). The term "effector T cell" includes T helper cells (e.g., Th1 and Th2 cells) and cytotoxic T cells. Th1 cells mediate delayed type hypersensitivity responses and macrophage activation while Th2 cells provide help to B cells and are critical in the allergic response (Mosmann and Coffman, 1989, *Annu. Rev. Immunol.* 7, 145-173; Paul and Seder, 1994, *Cell* 76, 241-251; Arthur and Mason, 1986, *J. Exp. Med.* 163, 774-786; Paliard et al., 1988, *J. Immunol.* 141, 849-855; Finkelman et al., 1988, *J. Immunol.* 141, 2335-2341). As used herein, the term "T helper type 1 response" (Th1 response) refers to a response that is characterized by the production of one or more cytokines selected from IFN-γ, IL-2, TNF, and lymphotoxin (LT) and other cytokines produced preferentially or exclusively by Th1 cells rather than by Th2 cells.

As used herein, the term "regulatory T cell" includes T cells which produce low levels of IL-2, IL-4, IL-5, and IL-12. Regulatory T cells produce TNFα, TGFβ, IFN-γ, and IL-10, albeit at lower levels than effector T cells. Although TGFβ is the predominant cytokine produced by regulatory T cells, the cytokine is produced at lower levels than in Th1 or Th2 cells, e.g., an order of magnitude less than in Th1 or Th2 cells. Regulatory T cells can be found in the CD4+CD25+ population of cells (see, e.g., Waldmann and Cobbold. 2001. *Immunity*. 14:399). Regulatory T cells actively suppress the proliferation and cytokine production of Th1, Th2, or naïve T cells which have been stimulated in culture with an activating signal (e.g., antigen and antigen presenting cells or with a signal that mimics antigen in the context of MHC, e.g., anti-CD3 antibody plus anti-CD28 antibody).

As used herein, the term "contacting" (i.e., contacting a cell e.g. a cell, with a compound) includes incubating the compound and the cell together in vitro (e.g., adding the compound to cells in culture) as well as administering the compound to a subject such that the compound and cells of the subject are contacted in vivo. The term "contacting" does not include exposure of cells to an agent that selectively increases T-bet activity that may occur naturally in a subject (i.e., exposure that may occur as a result of a natural physiological process).

As used herein, the term "target molecule" or "binding partner" is a molecule with which T-bet binds or interacts in nature, and which interaction results in a biological response. The target molecule can be a protein or a nucleic acid molecule. Exemplary target molecules of the invention include proteins in the same signaling pathway as the T-bet protein, e.g., proteins which may function upstream (including both stimulators and inhibitors of activity) or downstream of the T-bet protein in a pathway involving for example, maintaining host commensal relationships in the gastrointestinal tract. In one embodiment, an agent that modulates T-bet activity modulates an activity of T-bet directly (selectively modulates T-bet), such as an association with a T-bet-target molecule or complex of T-bet with a binding partner, e.g., TNF-α, e.g., a TNF-α promoter region.

The term "interact" as used herein is meant to include detectable interactions between molecules, such as can be detected using, for example, a yeast two hybrid assay, chromatin immunoprecipitation, or coimmunoprecipitation. The term interact is also meant to include "binding" interactions between molecules. Interactions may be protein-protein or protein-nucleic acid in nature.

The term "agent" or "compound" or "test compound" includes reagents or test agents which are employed in the methods or assays or present in the compositions of the invention. The term "agent" or "compound" or "test compound" includes compounds that have not previously been identified as, or recognized to be, agents that treat ulcerative colitis and/or colon cancer, and/or prevent colonization of a subject's gastrointestinal tract with commensal bacteria that cause ulcerative colitis. In one embodiment, more than one compound, e.g., a plurality of compounds, can be tested at the same time in a screening assay for their ability to treat and/or prevent ulcerative colitis and/or colon cancer, and/or prevent colonization of a subject's gastrointestinal tract with commensal bacteria that cause ulcerative colitis. The term "library of test compounds" refers to a panel comprising a multiplicity of test compounds.

In one embodiment, the agent or test compound is a compound that directly interacts with T-bet or directly interacts with a molecule with which T-bet interacts (e.g., a compound that stimulates the interaction between T-bet and a T-bet target molecule, e.g., DNA or another protein). Such compounds can be identified using screening assays that select for such compounds, as described in detail below.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. 1998. Science 282: 63), and natural product extract libraries. In another embodiment, the compounds are small, organic non-peptidic compounds. In a further embodiment, a small molecule is not biosynthetic.

In one embodiment, animal models of IBD or colitis described herein can be used to develop metabolic profiles associated with the disease. As used herein the term "metabolic profile" refers to the inventory of "small molecule metabolites" that can be measured within a biological sample and that are necessary and/or sufficient to provide information relating to diagnostics and/or prognostics to a user. The inventory includes the quantity and/or type of small molecule metabolites present. Metabolic profiles determined from biological samples can be compared to those from control samples and can be used to develop profiles that can be used to diagnose whether a subject has a disorder or is likely to develop a disorder or whether a subject is responding to treatment for a disorder.

The term "small molecule metabolites" includes organic and inorganic molecules which are present in a biological sample. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecule metabolites of the cell are generally found free in solution in the cytoplasm or in other organelles, such as the mitochondria, where they form a pool of intermediates which can be metabolized further or used to generate large molecules, called macromolecules. The term "small molecule metabolites" includes signaling molecules and intermediates in the chemical reactions that transform energy derived from food into usable forms. Examples of small molecules include sugars, fatty acids, amino acids, nucleotides, intermediates formed during cellular processes, and other small molecules found within the cell. In one embodiment, the small molecules of the invention are isolated.

Metabolic profiles can be generated by several methods, such as, by using HPLC (Kristal, et al. Anal. Biochem. 263: 18-25 (1998)), thin layer chromatography (TLC), or electrochemical separation techniques (see, WO 99/27361, WO 92/13273, U.S. Pat. Nos. 5,290,420, 5,284,567, 5,104,639, 4,863,873, and RE32,920). Other techniques for determining the presence of metabolic small molecules or determining the identity of metabolic small molecules of a biological sample are also included, such as refractive index spectroscopy (RI), Ultra-Violet spectroscopy (UV), fluorescent analysis, radio-chemical analysis, Near-InfraRed spectroscopy (Near-IR), Nuclear Magnetic Resonance spectroscopy (NMR), Light Scattering analysis (LS) and other methods known in the art. The term "subject" is intended to include living organisms. Preferred subjects are mammals. Particularly preferred subjects are humans. Other examples of subjects include monkeys, dogs, cats, mice, rats cows, horses, goats, sheep as well as other farm and companion animals. Selectively increasing T-bet activity to treat and/or prevent ulcerative colitis and/or colon cancer and/or prevent colonization of a subject's gastrointestinal tract with commensal bacteria that cause ulcerative colitis in humans as well as veterinary applications is encompassed by the present invention.

II. Methods of Screening for Agents that Increase T-bet Activity

A. Exemplary Screening Assays

The screening methods of the invention may be performed as cell based assays or as cell-free assays that utilize isolated T-bet nucleic acid molecules and/or polypeptides.

In one embodiment, the invention further provides methods for identifying compounds that increase the activity of a T-bet polypeptide in a cell, e.g., in a cell of the innate immune system, e.g., a dendritic cell, a monocyte, a macrophage, an NK cell. For example, the invention provides a method for identifying a compound that increases the activity of a T-bet polypeptide, comprising providing an indicator composition that comprises a T-bet polypeptide;

contacting the indicator composition with a test compound; and determining the effect of the test compound on the activity of the T-bet polypeptide in the indicator composition to thereby identify a compound that increases the activity of a T-bet polypeptide in a cell. Other assays appropriate for identifying agents that increase T-bet activity in a cell are described, e.g., in U.S. Patent Application Publication Nos. 20030104528, 20030186377, 20060223116, 2007012866, and PCT Publication No. WO 2006/130620, incorporated herein by reference.

In another embodiment, cells deficient in T-bet and RAG2 (also referred to herein as T-bet/RAG2 deficient cells or TRUC cells) or animals comprising such cells can be used in the subject assays. As described herein, inhibition of T-bet activity (e.g., by disruption of the T-bet gene) in the absence of adaptive immunity, i.e., the absence of T and B lymphocytes, e.g., by disruption of RAG2, results in the development of spontaneous and transmissible ulcerative colitis which may progress to adenocarcinoma of the colon and results in the colonization of the colonic epithelium by commensal bacteria that promote ulcerative colitis. Thus, cells deficient in T-bet and RAG2 can be used to identify agents that prevent the colonization of a subject's gastrointestinal tract with commensal bacteria that cause ulcerative colitis and/or that treat and/or prevent ulcerative colitis and/or colon cancer due to loss of T-bet by means other than modulating T-bet itself (i.e., compounds that "rescue" the T-bet deficient phenotype).

Compounds identified in the subject assays may be further tested for their ability to increase T-bet activity in a cell, e.g., a cell of the innate immune system. In one embodiment, compounds identified in the subject assays can be selectively targeted to cells of the innate immune system (described below).

The compounds identified using such methods can be used to treat and/or prevent ulcerative colitis and/or colorectal cancer, in a subject and/or to prevent colonization of a subject's gastrointestinal tract with commensal bacteria that cause ulcerative colitis.

It will be understood that comparison to an appropriate control can be made to verify the effect of the compound on T-bet activity when using a readout that may be influenced by factors other than T-bet. For example, in one embodiment, comparison to results obtained using a control cell (e.g., a cell other than a cell of the innate immune system) or cell-free system comprising all of the same components as in the test system, but lacking T-bet, can be made. In another embodiment, e.g., when using cells lacking T-bet to identify compounds that rescue the phenotype, an appropriate control may comprise all of the components of a test system except for the test compound. An appropriate control may also be, for example, wild-type cells (e.g., T-bet+/−RAG2−/−. T-bet+/+ Rag2−/−, T-bet+/+RAG2+/+), untreated cells or cells treated with a control agent).

In one embodiment, T-bet/RAG2 deficient cells for use in the methods of the invention are obtained by disruption of the T-bet gene in one mouse and the disruption of RAG2 in a second mouse. T-bet deficient mice are subsequently crossed with RAG2 deficient mice and their progeny intercrossed and ultimately mice deficient in both T-bet and RAG2 are produced.

In another embodiment, a "conditional knock-out" system, in which the T-bet gene is rendered non-functional in a conditional manner, can be used to create T-bet/RAG2 deficient cells for use in screening assays. For example, a tetracycline-regulated system for conditional disruption of a gene as described in WO 94/29442 and U.S. Pat. No. 5,650,298 can be used to create cells, or T-bet deficient animals. Such animals can be intercrossed with RAG2 deficient animals to create animals with a conditional T-bet gene and RAG2 deficiency. Cells from such animals can be isolated, and rendered T-bet deficient and RAG2 deficient in a controlled manner through modulation of the tetracycline concentration in contact with the cells, i.e., conditionally disrupt the T-bet gene.

In one embodiment, of a screening method of the invention, cells deficient in T-bet and RAG2 (e.g., isolated cells (such as a cell of the innate immune system) or cells present in vivo in an animal subject) are contacted with a test compound. In one embodiment, an indicator of T-bet activity is measured in the deficient cells in the presence and absence of the test compound.

B. Exemplary Readouts

In one embodiment, TNF-alpha production in, e.g., cells of the innate immune system, e.g., dendritic cells, e.g., colonic and/or bone marrow dendritic cells, is determined to identify a compound in a screening assay described herein. Decreased TNF-alpha production by cells contacted with a test compound is indicative of a test compound that is effective at treating and/or preventing ulcerative colitis, and/or colorectal cancer, and/or inhibiting the colonization of a subject's gastrointestinal tract with commensal bacteria that cause ulcerative colitis. TNF-alpha production can be measured using methods known in the art, such as, for example, by measuring the production of TNF-alpha mRNA, by, for example, quantitative RT-PCR, and/or measuring TNF-alpha protein production using, for example Western blot analysis or ELISA. In one embodiment, cells of the innate immune system can be isolated using methods known in the art. In one embodiment, an agent that decreases TNF-alpha production binds the TNF-alpha promoter. The binding of an agent to the TNF-alpha promoter can be determined by, for example chromatin immunoprecipitation.

In one embodiment, the effect of a test compound on the development of ulcerative colitis in a non-human model of ulcerative colitis is measured. The presence of ulcerative colitis is indicated by, for example, continuous inflammation and edema of the rectum and left colon, analrectal prolapse, colonic thickening, ulceration and crypt loss, mixed inflammatory cell infiltrate in the lamina propria containing both mononuclear and polymorphonuclear cells and neutrophil infiltration of the crypt and surface epithelium, epithelial injury as evidenced by, for example, surface denudations/erosions and frank ulcerations associated with crypt distortion, crypt loss, and epithelial mucodepletion, regenerative changes of colonic epithelium with crypt elongation, nuclear hyperchromasia, and increased mitotic activity, increased colonic permeability, and increased cell death greater that the intrinsic normal rate of epithelial turnover. In another embodiment, the presence or absence of certain bacterial organisms, e.g., *Klebsiella pneumoniae* and *Proteus mirabilis* as set forth in the working examples, can be indicative of colitis. Accordingly, the ability of a compound to prevent and/or ameliorate one or more of the theses symptoms (e.g., a delay in onset, reduction of severity of symptome and/or disease) is indicative of a test compound that is effective at treating and/or preventing ulcerative colitis, and/or colorectal cancer, and/or inhibiting the colonization of a subject's gastrointestinal tract with commensal bacteria that cause ulcerative colitis.

In another embodiment, the effect of a test compound in a non-human model of colorectal cancer, e.g., an animal model of transmissible or spontaneous UC, e.g., a TRUC mouse, an APC deficient mouse, etc., is measured. The presence of colorectal cancer is indicated by, for example, intramucosal and submucosal dysplastic and neoplastic lesions and/or tumors, nuclear enlargement, increased mitotic rate, expansion of crypts showing loss of the normal columnar architecture, increases in TP53, β-catenin, COX-2, Ki-67 expression and/or activity. Accordingly, the ability of a compound to prevent and/or ameliorate one or more of the theses symptoms and/or phenotypes (e.g., a delay in onset, reduction of severity of disease) or decrease expression and/or activity of a marker of colon cancer is indicative of a test compound that is effective at treating and/or preventing ulcerative colitis, and/or colorectal cancer, and/or inhibiting the colonization of a subject's gastrointestinal tract with commensal bacteria that cause ulcerative colitis.

In another embodiment, the effect of a test compound on colonization of commensal bacteria in the gastrointestinal tract of an animal model (e.g., an animal model of transmissible or spontaneous UC, e.g., a mouse comprising T-bet/RAG2 deficient cells (e.g., T-bet+/−RAG2−/−. T-bet+/+Rag2−/−, T-bet+/+RAG2+/+) as compared to an appropriate control such as, for example, wild-type cells, untreated cells or cells treated with a control agent) can be used to identify a test compound as an agent that prevents colonization of the gastrointestinal tract of a host with commensal bacteria that promote ulcerative colitis, and/or that treats and/or prevents ulcerative colitis, and/or colorectal cancer or that restores a desired balance to intestinal flora. Commensal bacteria that promote ulcerative colits include, for example, anaerobic commensals, e.g., *Bacteroides* species, *Clostridium* species, e.g., C13-5 *Clostridium*, p4154 *Clostridium*, L10-9 *Clostridium*, *Clostridium fusiformis*, *Heliobacter* species, e.g., *Helicobacter hepaticus, bilis, muridarum, pylori*, *Enterococcus* species, *Prevotella* species, *Lactobacillus* anaerobic cocci, e.g., S25-9, *Monilia* species, *Bifidobacterium* species, *Eubacteria* species, *Fusobacteria* species, *Propionibacteria* species, *Ruminococcus* species, *E. Coli, Gemmiger* species, *Desulfomonas* species, *Klebsiella pneumonia* and *Proteus mirabilis*. The presence, e.g., the amount, of such organisms in the colon of a non-human animal can be measured by, for example, 16S rRNA PCR analysis and/or sequence analysis, and/or use of appropriate culturing techniques of fecal samples, e.g., universal and differential media, known to one of skill in the art. The ability of a compound to decrease the presence of such commensal organisms or prevent such organisms from colonizing a host is indicative of a test compound that is effective at treating and/or preventing ulcerative colitis, and/or colorectal cancer and/or prevents colonization of the gastrointestinal tract of a host with commensal bacteria that promote ulcerative colitis.

In another embodiment, the effect of a test compound in a non-human animal model of intestinal permeability is measured. For example, using a catheter, fluorescein-dextran is delivered to the rectum of a mouse that has been contacted with a test compound and blood samples are obtained via the tail vein to measure mean fluorescence intensity in the serum. A decrease in intestinal permeability is indicative of a compound that is effective at treating and/or preventing ulcerative colitis, and/or colorectal cancer, and/or inhibiting the colonization of a subject's gastrointestinal tract with commensal bacteria that cause ulcerative colitis.

In another embodiment, a compound is identified as an agent that treats and/or prevents ulcerative colitis and/or colorectal cancer and/or prevents colonization of a subject's gastrointestinal tract with commensal bacteria that cause ulcerative colitis by measuring mucosal epithelial apoptisis by, for example TUNEL staining of colonic epithelial cells. A decrease in mucosal epithelial apoptisis is indicative of a compound that is effective at treating and/or preventing ulcerative colitis, and/or colorectal cancer, and/or inhibiting the colonization of a subject's gastrointestinal tract with commensal bacteria that cause ulcerative colitis.

In yet another embodiment, a compound is identified as an agent that treats and/or prevents ulcerative colitis and/or colorectal cancer and/or prevents colonization of a subject's gastrointestinal tract with commensal bacteria that cause ulcerative colitis by measuring dysplastic changes in colon cells using, for example, flow cytometry based aneuploidy analysis (see, e.g., Olah E, et al. Ann N Y Acad. Sci. 1997; 824:8-27; Nikolaeva T G, et al. Vestn Ross Akad Med. Nauk. January 2002:45-54; Magennis D P. Br J Biomed Sci. 1997; 54:140-148). A reduction in dysplastic changes in colon cells is indicative of a compound that is effective at treating and/or preventing ulcerative colitis, and/or colorectal cancer, and/or inhibiting the colonization of a subject's gastrointestinal tract with commensal bacteria that cause ulcerative colitis.

In yet another embodiment, a compound is identified as an agent that treats and/or prevents ulcerative colitis and/or colorectal cancer and/or prevents colonization of a subject's gastrointestinal tract with commensal bacteria that cause ulcerative colitis by measuring cycloxegenase-(COX-)$_2$ expression using, for example, immunohistochemistry of colon sections and/or biopsies. A decrease in the expression of COX-2 is indicative of an agent that treats and/or prevents ulcerative colitis and/or colorectal cancer and/or prevents colonization of a subject's gastrointestinal tract with commensal bacteria that cause ulcerative colitis.

In yet another embodiment, a compound is identified as an agent that treats and/or prevents ulcerative colitis and/or colorectal cancer and/or prevents colonization of a subject's gastrointestinal tract with commensal bacteria that cause ulcerative colitis by measuring β-catenin expression. The expression of β-catenin can be determined by, for example immunohistochemical analysis of colon sections and/or biopsies. A decrease in the expression of β-catenin is indicative of an agent that treats and/or prevents ulcerative colitis and/or colorectal cancer and/or prevents colonization of a subject's gastrointestinal tract with commensal bacteria that cause ulcerative colitis.

In yet another embodiment, a compound is identified as an agent that treats and/or prevents ulcerative colitis and/or colorectal cancer and/or prevents colonization of a subject's gastrointestinal tract with commensal bacteria that cause ulcerative colitis by determining the presence of TP53 mutations. A decrease in the presence of TP53 mutations is indicative of an agent that treats and/or prevents ulcerative colitis and/or colorectal cancer and/or prevents colonization of a subject's gastrointestinal tract with commensal bacteria that cause ulcerative colitis.

As used herein, "TP53" refers to the tumor suppressor protein p53 involved in the regulation of cell proliferation, which is well known in the art. The nucleotide and amino acid sequence of human TP53 are known and can be found in, for example, GenBank accession gi:8400737 and gi:8400738. TP53 is a tumor suppressor protein that is activated by a variety of cellular stresses through several pathways and transactivates its downstream genes, including regulators of cell cycle, apoptosis and DNA repair. Mutation of the TP53 gene therefore results in a failure to activate these genes and causes carcinogenesis and/or tumor progression. The presence or absence of TP53 mutations in colon sections and/or biopsies may be determined using, for example immunohistochemical analysis. For example, an antibody that binds to this protein, such as, for example, the DO-7 antibody which recognizes an epitope between amino acids 21-25 or TP53 (Vojtesek, et al. (1992) J Immunol Meth 151:237) or Pab240 which recognizes a conformation dependent epitope of TP53 (Legros, et al. (1994) Oncogene 9:3689; Vojtesek, et al. (1995) Oncogene10:389) may be used. The presence or absence of TP53 mutations in colon sections and/or biopsies may also be determined using an antibody such as CM1 (Novocastra Laboratories, Ltd).

In other embodiments, the presence or absence of TP53 mutations are detected at the nucleic acid level. Nucleic acid-based techniques for assessing expression are well known in the art and include, for example, determining the level of TP53 mRNA in a sample. Many expression detection methods use isolated RNA. Any RNA isolation technique that does not select against the isolation of mRNA can be utilized for the purification of RNA from cells that express TP53 (see, e.g., Ausubel et al., ed., (1987-1999) Current Protocols in Molecular Biology (John Wiley & Sons, New York). In one embodiment, the presence or absence of TP53 mutations involves nucleic acid amplification, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. In particular aspects of the invention, the presence or absence of TP53 mutations assessed by quantitative fluorogenic RT-PCR (i.e., the TaqMan™ System).

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array.

In another embodiment, a compound is identified as an agent that treats and/or prevents ulcerative colitis and/or colorectal cancer and/or prevents colonization of a subject's gastrointestinal tract with commensal bacteria that cause ulcerative colitis by determining morphological changes of the gastrointestinal tract using, e.g., the colon and/or rectum, for example, histological changes as a read-out. Standard methods can be used, e.g., sectioning, staining and microscopic analysis of colon biopsies and/or whole colons. An agent that results in, for example, decreased crypt loss, decreased edema, decreased mucosal damage, decrease or lack of anorectal prolapse, decreased crypt distortion, decreased epithelial mucodepletion, is an agent that treats and/or prevents ulcerative colitis and/or colorectal cancer and/or prevents colonization of a subject's gastrointestinal tract with commensal bacteria that cause ulcerative colitis.

In another embodiment, a compound, e.g., a probiotic, is identified as an agent that treats and/or prevents ulcerative colitis and/or colorectal cancer and/or prevents colonization of a subject's gastrointestinal tract with commensal bacteria that cause ulcerative colitis by, for example, administering, e.g., orally and/or rectally, the probiotic to an animal model of ulcerative colitis and/or colorectal cancer, e.g., an animal model of transmissible or spontaneous UC, e.g., a TRUC mouse, and determining whether the probiotic has colonized the intestinal tract of the animal model. Quantitative and qualitative methods to determine whether the probiotic has colonized the intestinal tract are known to one of skill in the art, and include, for example, culturing of cecal and fecal samples, morphological and histological analyses, as well as 16S rRNA PCR analysis and/or sequence analysis. The use of such methods may include the use of one or more appropriate controls, such as a T-bet$^{-/-}$ mice, wild-type mice, RAG2$^{-/-}$ mice, and T-bet$^{-/-}$, RAG2$^{-/-}$ mice, etc.

In one embodiment, the methods of the invention identify a compound as a T-bet dependent compound, i.e., a compound that has a beneficial effect in the absence of T-bet, i.e., is effective for the treatment and/or prevention of, for example ulcerative colitis, that is driven by the absence of T-bet and/or a decreased activity of T-bet. In another embodiment, a compound is identified as a T-bet independent compound, i.e., a compound that has a beneficial effect in the presence of T-bet, i.e., is effective for the treatment and/or prevention of, for example ulcerative colitis, that is not driven by the absence of T-bet and/or a decrease in T-bet activity.

In one embodiment, the test compound is administered directly to a non-human animal model of transmissible or spontaneous UC, e.g., T-bet/Rag2 deficient animal, preferably a mouse (e.g., a mouse in which the T-bet gene and the RAG2 gene are disrupted), to identify a test compound that treats and/or prevents ulcerative colitis and/or colorectal cancer and/or prevents colonization of a subject's gastrointestinal tract with commensal bacteria that cause ulcerative colitis in cells deficient in T-bet and RAG2. In another embodiment, cells for use in the methods of the invention are isolated from the animal model of transmissible or spontaneous UC, e.g., T-bet/RAG2 deficient mouse, and contacted with the test compound ex vivo to identify a test compound that treats and/or prevents ulcerative colitis and/or colorectal cancer and/or prevents colonization of the gastrointestinal tract with commensal bacteria that cause ulcerative colitis in the cells.

Cells for use in the methods of the invention may be obtained from an animal in which UC has been transmitted to as described herein or cells may be obtained from non-human animals created to be deficient in T-bet and RAG2. Preferred non-human animals include monkeys, dogs, cats, mice, rats, cows, horses, goats and sheep. In preferred embodiments, the T-bet/RAG2 deficient animal is a mouse. Mice deficient in T-bet and RAG2 can be made as described in, e.g., Lugo-Villarino et al. (2005) Proc Natl Acad Sci USA. 102(37): 13248-13253. Non-human animals deficient in a particular gene product typically are created by homologous recombination. For example, a vector is prepared which contains at least a portion of the T-bet gene into which a deletion, addition or substitution has been introduced to thereby alter, e.g., functionally disrupt, the endogenous T-bet gene. In one embodiment, a T-bet gene is a mouse T-bet gene. For example, a mouse T-bet gene can be isolated from a mouse genomic DNA library using the mouse T-bet cDNA as a probe. The mouse T-bet gene then can be used to construct a homologous recombination vector suitable for altering an endogenous T-bet gene in the mouse genome. In a preferred embodiment, the vector is designed such that, upon homologous recombination, the endogenous T-bet gene is functionally disrupted (i.e., no longer encodes a functional polypeptide; also referred to as a "knock out" vector). Alternatively, the vector can be designed such that, upon homologous recombination, the endogenous T-bet gene is mutated or otherwise altered but still encodes functional polypeptide (e.g., the upstream regulatory region can be altered to thereby alter the expression of the endogenous T-bet polypeptide). In the homologous recombination vector, the altered portion of the T-bet gene is flanked at its 5' and 3' ends by additional nucleic acid of the T-bet gene to allow for homologous recombination to occur between the exogenous T-bet gene carried by the vector and an endogenous T-bet gene in an embryonic stem cell. The additional flanking T-bet nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) Cell 51:503 for a description of homologous recombination vectors). The vector is introduced into an embryonic stem cell line (e.g., by electroporation) and cells in which the introduced T-bet gene has homologously recombined with the endogenous T-bet gene are selected (see e.g., Li, E. et al. (1992) Cell 69:915). The selected cells are then injected into a blastocyst of an animal (e.g., a mouse) to form aggregation chimeras (see e.g., Bradley, A. in Teratocarcinomas and Embryonic Stem Cells: A Practical Approach, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) Current Opinion in Biotechnology 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

Similarly, a mouse deficient in RAG2 can be generated as described in, for example, Chen, J., et al. (1993) Proc Natl Acad Sci USA. 15; 90(10):4528-32 or purchased from a commercial vendor, e.g., Taconic Farms, and crossed with a mouse deficient in T-bet and their progeny subsequently intercrossed to create double mutants, i.e., mice deficient in both T-bet and RAG2. In one embodiment, such mice comprise a genome in which each T-bet gene locus has been disrupted by recombination and in which each RAG2 gene locus has been disrupted by recombination, i.e., T-bet-/-RAG2-/- mice.

In one embodiment of the screening assay, compounds are tested for their ability to treat and/or prevent ulcerative colitis and/or colorectal cancer and/or prevent colonization of a subject's gastrointestinal tract with commensal bacteria that cause ulcerative colitis in cells by administering the test compound to a non-human T-bet-/- Rag2-/- (TRUC) mouse in vivo. The test compound can be administered to such mice as a pharmaceutical composition. Such compositions typically comprise the test compound and a pharmaceutically acceptable carrier. As used herein the term "pharmaceutically acceptable carrier" is intended to include any and all solvents, dispersion media, coatings, antibacterial and antifungal compounds, isotonic and absorption delaying compounds, and the like, compatible with pharmaceutical administration. The use of such media and compounds for pharmaceutically active substances is well known in the art. Supplementary active compounds can also be incorporated into the compositions.

The compounds of the instant invention may be administered once or more than once. The compounds of the invention may also be administered prior to and/or after ulcerative colitis and/or colorectal cancer and/or colonization of the colon by commensal bacteria that promote ulcerative colitis has developed. Furthermore, the ability of such compounds to treat and/or prevent ulcerative colitis and/or colorectal cancer and/or colonization of the colon by commensal bacteria that promote ulcerative colitis may be monitored throughout the course of treatment.

In another aspect, the invention pertains to a combination of two or more of the assays described herein or known in the art.

In addition, an agent that has been identified as a stimulator, e.g., a direct stimulator, of T-bet expression and/or activity using the cell based or cell free assays described in U.S. Patent Application Publication Nos. 20030104528, 20030186377, 20060223116, 2007012866, and PCT Publication No. WO 2006/130620, may be further assayed, e.g., as described herein. For example, an agent identified as an agent that directly increases Th2 lineage commitment and/or directly increases cytokine production, and/or the ability of T-bet to bind to an IL-2 or IFN-gamma promoter, and/or to regulate the expression of a Th1-associated cytokine gene, e.g., by repressing the IL-2 gene, and/or transactivating the IFN-gamma gene, may be further assayed for its ability to treat and/or prevent ulcerative colitis and/or colorectal cancer and/or prevent colonization of a subject's gastrointestinal tract with commensal bacteria that cause ulcerative colitis using the methods described herein.

Moreover, an agent described herein can be used in an animal model to determine the efficacy, toxicity, or side effects of treatment with such a compound. Alternatively, an agent identified as described herein can be used in an animal model to determine the mechanism of action of such a modulator.

III. Test Agents

A variety of test compounds can be evaluated using the screening assays described herein. Exemplary compounds which can be screened for activity include, but are not limited to, peptides, nucleic acids, carbohydrates, small organic molecules, and natural product extract libraries. In one embodiment, an agent or compound that directly increases T-bet activity in a cell is an agent that has not been previously identified as one that increases T-bet activity. In another embodiment, an agent or compound that directly increases T-bet activity in a cell is a known agent, e.g., a T-bet nucleic acid molecule, or biologically active fragment thereof or T-bet polypeptides, or biologically active fragments thereof.

Candidate/test compounds include, for example, 1) peptides such as soluble peptides, including Ig-tailed fusion peptides and members of random peptide libraries (see, e.g., Lam, K. S. et al. (1991) Nature 354:82-84; Houghten, R. et al. (1991) Nature 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) Cell 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); 4) small organic and inorganic molecules (e.g., molecules obtained from combinatorial and natural product libraries); 5) enzymes (e.g., endoribonucleases, hydrolases, nucleases, proteases, synthatases, isomerases, polymerases, kinases, phosphatases, oxido-reductases and ATPases), and 6) mutant forms or T-bet molecules, e.g., dominant negative mutant forms of the molecules.

Other agents that can be used to selectively increase the activity of T-bet include chemical compounds that directly enhance T-bet activity or compounds that enhance the interaction between T-bet and target DNA or another polypeptide. Such compounds can be identified using screening assays that select for such compounds, as described in detail above.

In certain embodiments, the compounds to be tested can be derived from libraries (i.e., are members of a library of compounds). While the use of libraries of peptides is well established in the art, new techniques have been developed which have allowed the production of mixtures of other compounds, such as benzodiazepines (Bunin et al. (1992). J. Am. Chem. Soc. 114:10987; DeWitt et al. (1993). Proc. Natl. Acad. Sci. USA 90:6909) peptoids (Zuckermann. (1994). J. Med. Chem. 37:2678) oligocarbamates (Cho et al. (1993). Science. 261: 1303-), and hydantoins (DeWitt et al. supra). An approach for the synthesis of molecular libraries of small organic molecules with a diversity of $10^4$-$10^5$ as been described (Carell et al. (1994). Angew. Chem. Int. Ed. Engl. 33:2059; Carell et al. (1994) Angew. Chem. Int. Ed. Engl. 33:2061-2064).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Compound Des. 12:145). Other exemplary methods for the synthesis of molecular libraries can be found in the art, for example in: Erb et al. (1994). Proc. Natl. Acad. Sci. USA 91:11422; Horwell et al. (1996) Immunopharmacology 33:68-; and in Gallop et al. (1994); J. Med. Chem. 37:1233-.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc Natl Acad Sci USA 89:1865-1869) or on phage (Scott and Smith (1990) Science 249:386-390); (Devlin (1990) Science 249:404-406); (Cwirla et al. (1990) Proc. Natl. Acad. Sci. 87:6378-6382); (Felici (1991) J. Mol. Biol. 222:301-310); In still another embodiment, the combinatorial polypeptides are produced from a cDNA library.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Compound Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

In one embodiment, an agent that selectively stimulates T-bet activity is a small molecule which interacts with the T-bet protein to thereby increase the activity of T-bet. Small molecule enhancers of T-bet can be identified using database searching programs capable of scanning a database of small molecules of known three-dimensional structure for candidates which fit into the target protein site known in the art. Suitable software programs include, for example, CATALYST (Molecular Simulations Inc., San Diego, Calif.), UNITY (Tripos Inc., St Louis, Mo.), FLEXX (Rarey et al., *J. Mol. Biol.* 261: 470-489 (1996)), CHEM-3 DBS (Oxford Molecular Group, Oxford, UK), DOCK (Kuntz et al., *J. Mol. Biol.* 161: 269-288 (1982)), and MACCS-3D (MDL Information Systems Inc., San Leandro, Calif.).

The molecules found in the search may not necessarily be leads themselves, however, such candidates might act as the framework for further design, providing molecular skeletons to which appropriate atomic replacements can be made. The scaffold, functional groups, linkers and/or monomers may be changed to maximize the electrostatic, hydrogen bonding, and hydrophobic interactions with the target protein. Goodford (Goodford *J Med Chem* 28:849-857 (1985)) has produced a computer program, GRID, which seeks to determine regions of high affinity for different chemical groups (termed probes) on the molecular surface of the binding site. GRID hence provides a tool for suggesting modifications to known ligands that might enhance binding. A range of factors, including electrostatic interactions, hydrogen bonding, hydrophobic interactions, desolvation effects, conformational strain or mobility, chelation and cooperative interaction and motions of ligand and enzyme, all influence the binding effect and should be taken into account in attempts to design small molecule enhancers.

Small molecule enhancers of T-bet can also be identified using computer-assisted molecular design methods comprising searching for fragments which fit into a binding region subsite and link to a predefined scaffold can be used. The scaffold itself may be identified in such a manner. Programs suitable for the searching of such functional groups and monomers include LUDI (Boehm, *J Comp. Aid. Mol. Des.* 6:61-78 (1992)), CAVEAT (Bartlett et al. in "Molecular Recognition in Chemical and Biological Problems", special publication of *The Royal Chem. Soc.*, 78:182-196 (1989)) and MCSS (Miranker et al. *Proteins* 11: 29-34 (1991)).

Yet another computer-assisted molecular design method for identifying small molecule enhancers of the T-bet protein comprises the de novo synthesis of potential enhancers by algorithmic connection of small molecular fragments that will exhibit the desired structural and electrostatic complementarity with the active binding site of the T-bet protein. The methodology employs a large template set of small molecules with are iteratively pieced together in a model of the T-bet binding site. Programs suitable for this task include GROW (Moon et al. *Proteins* 11:314-328 (1991)) and SPROUT (Gillet et al. *J Comp. Aid. Mol. Des.* 7:127 (1993)).

The suitability of small molecule candidates can be determined using an empirical scoring function, which can rank the binding affinities for a set of enhancers. For an example of such a method see Muegge et al. and references therein (Muegge et al., *J Med. Chem.* 42:791-804 (1999)). Other modeling techniques can be used in accordance with this invention, for example, those described by Cohen et al. (*J. Med. Chem.* 33: 883-894 (1994)); Navia et al. (*Current Opinions in Structural Biology* 2: 202-210 (1992)); Baldwin et al. (*J. Med. Chem.* 32: 2510-2513 (1989)); Appelt et al. (*J. Med. Chem.* 34: 1925-1934 (1991)); and Ealick et al. (*Proc. Nat. Acad. Sci. USA* 88: 11540-11544 (1991)).

Other agents that can be assessed using the screening methods described herein to identify compounds useful in the treatment and/or prevention methods of the invention include numerous probiotics, i.e., beneficial nonpathologic bacteria that are functionally defined by their ability to reduce inflammation when introduced into the inflamed intestine, to a subject. See, e.g., Sleator and Hill (2007) *Letts Applied Microbiol* 1-5, the contents of which is incorporated herein by reference. Non-limiting examples of suitable probiotics include *Bifidobacteria* sp. (e.g., *Bifidobacterium animalis lactis, Bifidobacterium longum, Bifidobacterium bifidum, Bifidobacterium breve*), *Lactobacillus* sp. (e.g., *Lactobacillus delbrueckii bulgaricus, Lactobaccillus acidophilus, Lactobacillus rhamnosus* GG, *Lactobacillus reuterii, Lactobacillus casei, Lactobacillus paracasei, Lactobacillus gasseri, Lactobacillus johnsonii*), and *Bacteriodes* sp. (e.g., *Bacteroides thetaiotaomicron, Bacteroides fragilis*). (See, e.g., *Bergey's Manual of Microbiology*; Felis and Dellaglio (*Curr Issues Intestinal Microbiol.* 8:44-61).

A. Known Agents That Increase T-Bet Activity

In one embodiment, an agent that is known to increase T-bet activity may be selectively targeted to cells of the innate immune system, e.g., dendritic cells, and/or monocytes, and/or macrophages, and/or NK cells, as described below.

1. T-bet Nucleic Acid Molecules

In one embodiment, isolated nucleic acid molecules that encode T-bet or a biologically active portion thereof, such as a nucleic acid molecule comprising a nucleotide sequence encoding the DNA binding domain (the nucleotide sequence encoding amino acid residues 138-327 of SEQ ID NO:2 or the nucleotide sequence encoding amino acid residues 138-326 of SEQ ID NO:4) may be used to increase T-bet activity in a cell. In one embodiment, the nucleic acid molecule of the invention comprises the nucleotide sequence shown in SEQ ID NO:1 or SEQ ID NO:3. In another embodiment, a nucleic acid molecule of the invention comprises at least about 700 contiguous nucleotides of SEQ ID NO:1 or at least about 500 contiguous nucleotides of SEQ ID NO:3 and includes the DNA binding domain. In another embodiment, a nucleic acid molecule of the invention comprises at least about 800, at least about 1000, at east about 1200, at least about 1400 or at least about 1600 contiguous nucleotides of SEQ ID NO:1 and includes the DNA binding domain. In another embodiment, a nucleic acid molecule of the invention comprises at least about 600, at least about 800, at least about 1000, at least about 1200, or at least about 1400 contiguous nucleotides of SEQ ID NO:3 and includes the DNA binding domain.

In other embodiments, the nucleic acid molecule has at least 70% identity, more preferably 80% identity, and even more preferably 90% identity with a nucleic acid molecule comprising: at least about 700, at least about 800, at least about 1000, at least about 1200, at least about 1400 or at least about 1600 contiguous nucleotides of SEQ ID NO:1 and includes the DNA binding domain. In other embodiments, the nucleic acid molecule has at least 70% identity, more preferably 80% identity, and even more preferably 90% nucleotide identity with a nucleic acid molecule comprising: at least about 600, at least about 800, at least about 1000, at least about 1200, or at least about 1400 contiguous nucleotides of SEQ ID NO:3 and includes the DNA binding domain.

Nucleic acid molecules that differ from SEQ ID NO: 1 or 3 due to degeneracy of the genetic code, and thus encode the same T-bet protein as that encoded by SEQ ID NO: 1 and 3, are encompassed by the invention. Accordingly, in another embodiment, an isolated nucleic acid molecule of the invention has a nucleotide sequence encoding a protein having an amino acid sequence shown in SEQ ID NO: 2 or SEQ ID NO:4.

In addition, nucleic acid molecules encoding T-bet proteins can be isolated from other sources using standard molecular biology techniques and the sequence information provided herein. For example, a T-bet DNA can be isolated from a human genomic DNA library using all or portion of SEQ ID NO:1 or 3 as a hybridization probe and standard hybridization techniques (e.g., as described in Sambrook, J., et al. *Molecular Cloning: A Laboratory Manual.* 2nd, ed., Cold Spring Harbor Laboratory, Cold Spring Harbor, N.Y., 1989). Moreover, a nucleic acid molecule encompassing all or a portion of a T-bet gene can be isolated by the polymerase chain reaction using oligonucleotide primers designed based upon the sequence of SEQ ID NO: 1 or 3. For example, mRNA can be isolated from cells (e.g., by the guanidinium-thiocyanate extraction procedure of Chirgwin et al. (1979) *Biochemistry* 18: 5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO: 1 or 3. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a T-bet nucleotide sequence can be prepared by standard synthetic techniques, e.g., using an automated DNA synthesizer.

In addition to the T-bet nucleotide sequence shown in SEQ ID NO: 1 and 3, it will be appreciated by those skilled in the art that DNA sequence polymorphisms that lead to minor changes in the nucleotide or amino acid sequences of T-bet may exist within a population. Such genetic polymorphism in the T-bet gene may exist among individuals within a population due to natural allelic variation. Such natural allelic variations can typically result in 1-2% variance in the nucleotide sequence of a gene. Any and all such nucleotide variations and resulting amino acid polymorphisms in T-bet that are the result of natural allelic variation and that do not alter the functional activity of T-bet are intended to be within the scope of the invention.

Nucleic acid molecules corresponding to natural allelic variants of the T-bet DNAs of the invention can be isolated based on their homology to the T-bet nucleic acid molecules disclosed herein using the human DNA, or a portion thereof, as a hybridization probe according to standard hybridization techniques under high stringency hybridization conditions. Exemplary high stringency conditions include hybridization in a hybridization buffer that contains 6× sodium chloride/sodium citrate (SSC) at a temperature of about 45° C. for several hours to overnight, followed by one or more washes in a washing buffer containing 0.2×SSC, 0.1% SDS at a temperature of about 50-65° C. Accordingly, in another embodiment, an isolated nucleic acid molecule of the invention hybridizes under high stringency conditions to a second nucleic acid molecule comprising the nucleotide sequence of SEQ ID NO: 1 or 3. Preferably, an isolated nucleic acid molecule of the invention that hybridizes under high stringency conditions to the sequence of SEQ ID NO: of SEQ ID NO:1 or 3. In one embodiment, such a nucleic acid molecule is at least about 700, 800, 900, 1000, 1200, 1300, 1400, 1500, or 1600 nucleotides in length and includes the DNA binding domain. In another embodiment, such a nucleic acid molecule and comprises at least about 700, 800, 900, 1000, 1200, 1300, 1400, 1500, or 1600 contiguous nucleotides of SEQ ID NO: 1 or at least about 500, 600, 700, 800, 900, 1000, 1100, 1200, 1300, 1400, or 1500 contiguous nucleotides of SEQ ID NO: 3 and includes the DNA binding domain. Preferably, an isolated nucleic acid molecule corresponds to a naturally-occurring allelic variant of a T-bet nucleic acid molecule.

In addition to naturally-occurring allelic variants of the T-bet sequence that may exist in the population, the skilled artisan will further appreciate that minor changes may be introduced by mutation into the nucleotide sequence of SEQ ID NO: 1 or 3, thereby leading to changes in the amino acid sequence of the encoded protein, without altering the functional activity of the T-bet protein. For example, nucleotide substitutions leading to amino acid substitutions at "non-essential" amino acid residues may be made in the sequence of SEQ ID NO: 1 or 3. A "non-essential" amino acid residue is a residue that can be altered from the wild-type sequence of T-bet (e.g., the sequence of SEQ ID NO: 1 or 3) without altering the functional activity of T-bet, such as its ability to interact with DNA or its ability to enhance transcription from an IFN-γ promoter, whereas an "essential" amino acid residue is required for functional activity.

Accordingly, another aspect of the invention pertains to nucleic acid molecules encoding T-bet proteins that contain changes in amino acid residues that are not essential for T-bet activity. Such T-bet proteins differ in amino acid sequence from SEQ ID NO: 2 or 4 yet retain T-bet activity. An isolated nucleic acid molecule encoding a non-natural variant of a T-bet protein can be created by introducing one or more nucleotide substitutions, additions or deletions into the nucleotide sequence of SEQ ID NO: 1 or 3 such that one or more amino acid substitutions, additions or deletions are introduced into the encoded protein. Mutations can be introduced into SEQ ID NO: 1 or 3 by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in T-bet is preferably replaced with another amino acid residue from the same side chain family.

Alternatively, in another embodiment, mutations can be introduced randomly along all or part of the T-bet coding sequence, such as by saturation mutagenesis, and the resultant mutants can be screened for their ability to bind to DNA and/or activate transcription, to identify mutants that retain functional activity. Following mutagenesis, the encoded T-bet mutant protein can be expressed recombinantly in a host cell and the functional activity of the mutant protein can be determined using assays available in the art for assessing T-bet activity (e.g., by measuring the ability of the protein to bind to a T-box binding element present in DNA or by measuring the ability of the protein to modulate IL2 production).

Yet another aspect of the invention pertains to isolated nucleic acid molecules encoding T-bet fusion proteins. Such nucleic acid molecules, comprising at least a first nucleotide sequence encoding a T-bet protein, polypeptide or peptide operatively linked to a second nucleotide sequence encoding a non-T-bet protein, polypeptide or peptide, can be prepared by standard recombinant DNA techniques.

In one embodiment, a nucleic acid molecule encoding T-bet or a biologically active portion thereof is present in an expression vector for expression in a host cell. Such expression vectors can be used to make recombinant T-bet or to increase T-bet activity in a cell, e.g., a cell of the innate immune system. The expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., T-bet proteins, mutant forms of T-bet proteins, T-bet fusion proteins and the like).

The recombinant expression vectors of the invention can be designed for expression of T-bet protein in prokaryotic or eukaryotic cells. For example, T-bet can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector may be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors can serve one or more purposes: 1) to increase expression of recombinant protein; 2) to increase the solubility of the recombinant protein; 3) to aid in the purification of the recombinant protein by acting as a ligand in affinity purification; 4) to provide an epitope tag to aid in detection and/or purification of the protein; and/or 5) to provide a marker to aid in detection of the protein (e.g., a color marker using β-galactosidase fusions). Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc.; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Recombinant proteins also can be expressed in eukaryotic cells as fusion proteins for the same purposes discussed above.

Examples of suitable inducible non-fusion *E. coli* expression vectors include pTrc (Amann et al., (1988) *Gene* 69:301-315) and pET 11 d (Studier et al., *Gene Expression Technology Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11 d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nuc. Acids Res.* 20:2111-2118). Such alteration of nucleic acid sequences of the invention can be carried out by standard DNA synthesis techniques.

In another embodiment, the T-bet expression vector is a yeast expression vector. Examples of vectors for expression in yeast *S. cerivisae* include pYepSec1 (Baldari. et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.).

Alternatively, T-bet can be expressed in insect cells using baculovirus expression vectors. Baculovirus vectors available for expression of proteins in cultured insect cells (e.g., Sf 9 cells) include the pAc series (Smith et al., (1983) *Mol. Cell. Biol.* 3:2156-2165) and the pVL series (Lucklow, V. A., and Summers, M. D., (1989) *Virology* 170:31-39).

In yet another embodiment, a nucleic acid of the invention is expressed in mammalian cells using a mammalian expression vector. Examples of mammalian expression vectors include pMex-NeoI, pCDM8 (Seed, B., (1987) *Nature* 329:840) and pMT2PC (Kaufman et al. (1987), *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), the albumin promoter (liver-specific; Pinkert et al. (1987) *Genes Dev.* 1:268-277), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

In one embodiment, a dendritic cell specific promoter is operably linked to a T-bet nucleic acid molecule. For example, the promoter of the, e.g., DC-CK1, DC-STAMP, CD11c, or DC-SIGN, genes are preferentially expressed by dendritic cells and can be used to direct expression of T-bet in a dendritic cell (see, e.g., Adema, et al. (2005) *Current Opinion in Immunology* 17, 170-174).

In one embodiment, a macrophage specific promoter is operably linked to a T-bet nucleic acid molecule. For example, the promoter of the, e.g., acetyl-LDL receptor, gene is preferentially expressed by macrophages, and can be used to direct expression of T-bet in a macrophage (see, e.g., Horvai, A., Palinski, W., Wu, H., Moulton, K. S., Kalla, K. & Glass, C. A. (1995) *Proc. Natl. Acad. Sci. USA* 92, 5391-5395).

In one embodiment, a monocyte specific promoter is operably linked to a T-bet nucleic acid molecule. For example, the promoter of the, e.g., CD14, gene is preferentially expressed by monocytes, and can be used to direct expression of T-bet in a monocyte (see, e.g., Zhnag, et al. (1994) *J Biol Chem* 269, 11425-11434).

In one embodiment, a NK cell specific promoter is operably linked to a T-bet nucleic acid molecule. For example, the promoter of the, e.g., FcgRIIIa gene, killer immunoglobulin-like receptor (KIR), genes are preferentially expressed by NK cells, and can be used to direct expression of T-bet in NK cells (see, e.g., Heushon, Frank, et al. J. immunol 2002, vol. 168, no6, pp. 2857-2864).

Moreover, inducible regulatory systems for use in mammalian cells are known in the art, for example systems in which gene expression is regulated by heavy metal ions (see e.g., Mayo et al. (1982) *Cell* 29:99-108; Brinster et al. (1982) *Nature* 296:39-42; Searle et al. (1985) *Mol. Cell. Biol.* 5:1480-1489), heat shock (see e.g., Nouer et al. (1991) in *Heat Shock Response*, e.d. Nouer, L., CRC, Boca Raton, Fla., pp 167-220), hormones (see e.g., Lee et al. (1981) *Nature* 294:228-232; Hynes et al. (1981) *Proc. Natl. Acad. Sci. USA* 78:2038-2042; Klock et al. (1987) *Nature* 329:734-736; Israel & Kaufman (1989) *Nucl. Acids Res.* 17:2589-2604; and PCT Publication No. WO 93/23431), FK506-related molecules (see e.g., PCT Publication No. WO 94/18317) or tetracyclines (Gossen, M. and Bujard, H. (1992) *Proc. Natl. Acad. Sci. USA* 89:5547-5551; Gossen, M. et al. (1995) *Science* 268:1766-1769; PCT Publication No. WO 94/29442; and PCT Publication No. WO 96/01313). Accordingly, in another embodiment, the invention provides a recombinant expression vector in which T-bet DNA is operatively linked to an inducible eukaryotic promoter, thereby allowing for inducible expression of T-bet protein in eukaryotic cells.

Another aspect of the invention pertains to recombinant host cells into which a vector, preferably a recombinant expression vector, of the invention has been introduced. A host cell may be any prokaryotic or eukaryotic cell. For example, T-bet protein may be expressed in bacterial cells such as *E. coli*, insect cells, yeast or mammalian cells (such as Chinese hamster ovary cells (CHO) or COS cells). Other suitable host cells are known to those skilled in the art. Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual*, 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to compounds, such as G418, hygromycin and methotrexate. Nucleic acid encoding a selectable marker may be introduced into a host cell on the same vector as that encoding T-bet or may be introduced on a separate vector. Cells stably transfected with the introduced nucleic acid can be identified by compound selection (e.g., cells that have incorporated the selectable marker gene will survive, while the other cells die).

A host cell of the invention, such as a prokaryotic or eukaryotic host cell in culture, can be used to produce (i.e., express) T-bet protein. Accordingly, the invention further provides methods for producing T-bet protein using the host cells of the invention. In one embodiment, the method comprises culturing the host cell of invention (into which a recombinant expression vector encoding T-bet has been introduced) in a suitable medium until T-bet is produced. In another embodiment, the method further comprises isolating T-bet from the medium or the host cell. In its native form the T-bet protein is an intracellular protein and, accordingly, recombinant T-bet protein can be expressed intracellularly in a recombinant host cell and then isolated from the host cell, e.g., by lysing the host cell and recovering the recombinant T-bet protein from the lysate. Alternatively, recombinant T-bet protein can be prepared as a extracellular protein by operatively linking a heterologous signal sequence to the amino-terminus of the protein such that the protein is secreted from the host cells. In this case, recombinant T-bet protein can be recovered from the culture medium in which the cells are cultured.

Certain host cells of the invention can also be used to produce nonhuman transgenic animals. For example, in one embodiment, a host cell of the invention is a fertilized oocyte or an embryonic stem cell into which T-bet-coding sequences have been introduced. Such host cells can then be used to create non-human transgenic animals in which exogenous T-bet sequences have been introduced into their genome or homologous recombinant animals in which endogenous T-bet sequences have been altered. Such animals are useful for studying the function and/or activity of T-bet and for identifying and/or evaluating modulators of T-bet activity. Accordingly, another aspect of the invention pertains to non-human transgenic animals which contain cells carrying a transgene encoding a T-bet protein or a portion of a T-bet protein. In a subembodiment, of the transgenic animals of the invention, the transgene alters an endogenous gene encoding an endogenous T-bet protein (e.g., homologous recombinant animals in which the endogenous T-bet gene has been functionally disrupted or "knocked out", or the nucleotide sequence of the endogenous T-bet gene has been mutated or the transcriptional regulatory region of the endogenous T-bet gene has been altered).

A transgenic animal of the invention can be created by introducing T-bet-encoding nucleic acid into the male pronuclei of a fertilized oocyte, e.g., by microinjection, and allowing the oocyte to develop in a pseudopregnant female foster animal. The T-bet nucleotide sequence of SEQ ID NO: 1 or 3 can be introduced as a transgene into the genome of a non-human animal. Intronic sequences and polyadenylation signals can also be included in the transgene to increase the efficiency of expression of the transgene. A tissue-specific regulatory sequence(s) can be operably linked to the T-bet transgene to direct expression of T-bet protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the T-bet transgene in its genome and/or expression of T-bet mRNA in tissues or cells of the animals. A transgenic founder animal can then be used to breed additional animals carrying the transgene. Moreover, transgenic animals carrying a transgene encoding T-bet can further be bred to other transgenic animals carrying other transgenes.

To create a homologous recombinant animal, a vector is prepared which contains at least a portion of a T-bet gene into which a deletion, addition or substitution has been introduced to thereby alter, e.g., functionally disrupt, the endogenous T-bet gene. In one embodiment, a homologous recombination vector is designed such that, upon homologous recombination, the endogenous T-bet gene is functionally disrupted (i.e., no longer encodes a functional protein; also referred to as a "knock out" vector). Alternatively, the vector can be designed such that, upon homologous recombination, the endogenous T-bet gene replaced by the T-bet gene. In the homologous recombination vector, the altered portion of the T-bet gene is flanked at its 5' and 3' ends by additional nucleic acid of the T-bet gene to allow for homologous recombination to occur between the exogenous T-bet gene carried by the vector and an endogenous T-bet gene in an embryonic stem cell. The additional flanking T-bet nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced T-bet gene has homologously recombined with the endogenous T-bet gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In addition to the foregoing, the skilled artisan will appreciate that other approaches known in the art for homologous recombination can be applied to the instant invention. Enzyme-assisted site-specific integration systems are known in the art and can be applied to integrate a DNA molecule at a predetermined location in a second target DNA molecule. Examples of such enzyme-assisted integration systems include the Cre recombinase-lox target system (e.g., as described in Baubonis, W. and Sauer, B. (1993) *Nucl. Acids Res.* 21:2025-2029; and Fukushige, S, and Sauer, B. (1992) *Proc. Natl. Acad. Sci. USA* 89:7905-7909) and the FLP recombinase-FRT target system (e.g., as described in Dang, D. T. and Perrimon, N. (1992) *Dev. Genet.* 13:367-375; and Fiering, S. et al. (1993) *Proc. Natl. Acad. Sci. USA* 90:8469-8473). Tetracycline-regulated inducible homologous recombination systems, such as described in PCT Publication No. WO 94/29442 and PCT Publication No. WO 96/01313, also can be used.

Alternatively, null mutations can be generated by targeted mutagenesis in ES cells (Ranger, A. M., et al. 1998. *Nature* 392, 186; Hodge, M. R., et al. 1996. *Immunity* 4:1., 144; Grusby, M. J., et al. 1991. *Science* 253, 1417; Reimold, A. M., et al. 1996. *Nature* 379: 262; Kaplan, M. H., 1996. *Immunity:* 313; Kaplan, M. H., et al. 1996. *Nature* 382, 174; Smiley, S. T., et al. 1997. *Science* 275, 977). For example using techniques which are known in the art, a genomic T-bet clone can be isolated from a genomic library, the intron-exon organization delineated, and a targeting construct in the cre-lox vector (see discussion below) created which should delete the first exon and 450 by of upstream promoter sequence. This construct can be electroporated into an ES cell line, and double compound resistant (e.g., neomycin, gancyclovir) clones identified by Southern blot analysis. Clones bearing homologous recombinant events in the T-bet locus can then be identified and injected into blastocysts obtained from day 3.5 BALB/c pregnant mice. Chimeric mice can then be produced and mated to wildtype BALB/c mice to generate germline transmission of the disrupted T-bet gene.

In another embodiment, implantation into RAG2-deficient blastocysts (Chen, J., et al. 1993. *Proc. Natl. Acad. Sci. USA* 90, 4528) or the cre-lox inducible deletion approach can be used to develop mice that are lacking T-bet only in the immune system. For example, the targeting construct can be made in the cre-lox vector. The blastocyst complementation system has been used to study NFATc, an embryonic lethal phenotype (Ranger, A. M., et al. 1998. *Immunity* 8:125). This approach requires disrupting the T-bet gene on both chromosomes in ES cells, which can be accomplished, e.g., by using a mutant neomycin gene and raising the concentration of G418 in the ES cultures, as described (Chen, J., 1993. *Proc. Natl. Acad. Sci. USA* 90; 4528) or by flanking the neo gene with cre-lox sites. To disrupt the second allele, the neomycin gene can be deleted by transfecting the ES clone with the cre recombinase, and then the ES clone can be retransfected with the same targeting construct to select clones with T-bet deletions on both alleles. A third transfection with cre-recombinase yields the desired doubly-deficient ES cells. Such doubly targeted ES cells are then implanted into RAG2 blastocysts and the lymphoid organs of the chimeric mice thus generated will be entirely colonized by the transferred ES cells. This allows assessment of the effect of the absence of T-bet on cells of the lymphoid system without affecting other organ systems where the absence of T-bet might cause lethality.

The conditional ablation approach employing the cre-lox system can also be used. Briefly, a targeting construct is generated in which lox recombination sequences are placed in intronic regions flanking the exons to be deleted. This construct is then transfected into ES cells and mutant mice are generated as above. The resulting mutant mice are then mated to mice transgenic for the cre recombinase driven by an inducible promoter. When cre is expressed, it induces recombination between the introduced lox sites in the T-bet gene, thus effectively disrupting gene function. The key feature of this approach is that gene disruption can be induced in the adult animal at will by activating the cre recombinase.

A tissue-specific promoter can be used to avoid abnormalities in organs outside the immune system. The cre-expressing transgene may be driven by an inducible promoter. Several inducible systems are now being used in cre-lox recombination strategies, the most common being the tetracycline and ecdysone systems. A tissue-specific inducible promoter can be used if there is embryonic lethality in the T-bet null mouse.

An alternative approach is to generate a transgenic mouse harboring a regulated T-bet gene (for example using the tetracycline off promoter; e.g., St-Onge, et al. 1996. *Nuc. Acid Res.* 24, 3875-3877) and then breed this transgenic to the T-bet deficient mouse. This approach permits creation of mice with normal T-bet function; tetracycline can be administered to adult animals to induce disruption of T-bet function in peripheral T cells, and then the effect of T-bet deficiency can be examined over time. Repeated cycles of provision and then removal of compound (tetracycline) permits turning the T-bet gene on and off at will.

2. T-bet Proteins

In one embodiment, an isolated T-bet proteins or a biologically active portion thereof is used to increase T-bet activity in a cell. In one embodiment, the T-bet protein comprises the amino acid sequence encoded by SEQ ID NO:1 or 3. In another embodiment, the protein comprises the amino acid sequence of SEQ ID NO: 2 or 4. In other embodiments, the protein has at least 60% amino acid identity, more preferably 70% amino acid identity, more preferably 80%, and even more preferably, 90% or 95% amino acid identity with the amino acid sequence shown in SEQ ID NO: 2 or 4 and retains a T-bet biological activity, such as binding to DNA, e.g., a T-box site in DNA.

In other embodiments, the invention provides isolated portions of the T-bet protein or chimeric proteins comprising at least a biological active portion of T-bet and another non-T-bet polypeptide. For example, the invention further encompasses a polypeptide comprising or consisting of an amino-terminal portion of T-bet that includes a T-box domain. In various embodiments, a polypeptide comprising or consisting of this amino terminal portion encompasses at least amino acids 138-327 of human T-bet or at least amino acids 137-326 of mouse T-bet. Another isolated polypeptide comprising or consisting of portion of T-bet provided by the invention is a portion encompassing a tyrosine phosphorylation site. This portion comprises or consists of at least about 20, at least about 50, at least about 100, or at least about 200 amino acids of T-bet and includes at least amino acids Tyr 76, Tyr 119, and/or Tyr 531 of human T-bet or amino acids Tyr 525 of murine T-bet. Yet another isolated polypeptide of the invention comprises or consists of a portion of T-bet encompassing a nuclear localization sequence shown in amino acids 498-501 of human T-bet or 493-496 of murine T-bet. Another isolated polypeptide of the invention comprises or consists of a portion of T-bet encompassing a serine phosphorylation site. This portion comprises or consists of at least about 20, at least about 50, at least about 100, or at least about 200 amino acids of T-bet and includes at least amino acid Ser 508 of human T-bet or amino acid Ser 507 of murine T-bet.

T-bet proteins of the invention are preferably produced by recombinant DNA techniques. For example, a nucleic acid molecule encoding the protein is cloned into an expression vector (as described above), the expression vector is introduced into a host cell (as described above) and the T-bet protein is expressed in the host cell. The T-bet protein can then be isolated from the cells by an appropriate purification scheme using standard protein purification techniques. Alternative to recombinant expression, a T-bet polypeptide can be synthesized chemically using standard peptide synthesis techniques. Moreover, native T-bet protein can be isolated from cells (e.g., from T cells), for example by immunoprecipitation using an anti-T-bet antibody.

The present invention also pertains to variants of the T-bet proteins which function as T-bet agonists (mimetics). Variants of the T-bet proteins can be generated by mutagenesis, e.g., discrete point mutation or truncation of a T-bet protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the T-bet protein. In one embodiment, the invention pertains to derivatives of T-bet which may be formed by modifying at least one amino acid residue of T-bet by oxidation, reduction, or other derivatization processes known in the art.

In one embodiment, variants of a T-bet protein which function as T-bet agonists (mimetics) can be identified by screening combinatorial libraries of mutants, e.g., truncation mutants, of a T-bet protein for T-bet protein agonist activity.

In one embodiment, a variegated library of T-bet variants is generated by combinatorial mutagenesis at the nucleic acid level and is encoded by a variegated gene library. A variegated library of T-bet variants can be produced by, for example, enzymatically ligating a mixture of synthetic oligonucleotides into gene sequences such that a degenerate set of potential T-bet sequences is expressible as individual polypeptides, or alternatively, as a set of larger fusion proteins (e.g., for phage display) containing the set of T-bet sequences therein. There are a variety of methods which can be used to produce libraries of potential T-bet variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential T-bet sequences. Methods for synthesizing degenerate oligonucleotides are known in the art (see, e.g., Narang, S. A., 1983, *Tetrahedron* 39:3; Itakura et al., 1984, *Annu. Rev. Biochem.* 53:323; Itakura et al., 1984, *Science* 198:1056; Ike et al., 1983, *Nucleic Acid Res.* 11:477).

In addition, libraries of fragments of a T-bet protein coding sequence can be used to generate a variegated population of T-bet fragments for screening and subsequent selection of variants of a T-bet protein. In one embodiment, a library of coding sequence fragments can be generated by treating a double stranded PCR fragment of a T-bet coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the T-bet protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of T-bet proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify T-bet variants (Arkin and Yourvan, 1992, *Proc. Natl. Acad. Sci. USA* 89:7811-7815; Delgrave et al., 1993, *Protein Engineering* 6(3):327-331).

The invention also provides T-bet fusion proteins. As used herein, a T-bet "fusion protein" comprises a T-bet polypeptide operatively linked to a polypeptide other than T-bet. A "T-bet polypeptide" refers to a polypeptide having an amino acid sequence corresponding to T-bet protein, or a peptide fragment thereof which is unique to T-bet protein whereas a "polypeptide other than T-bet" refers to a polypeptide having an amino acid sequence corresponding to another protein. Within the fusion protein, the term "operatively linked" is intended to indicate that the T-bet polypeptide and the other polypeptide are fused in-frame to each other. The other polypeptide may be fused to the N-terminus or C-terminus of the T-bet polypeptide. For example, in one embodiment, the fusion protein is a GST-T-bet fusion protein in which the T-bet sequences are fused to the C-terminus of the GST sequences. In another embodiment, the fusion protein is a T-bet-HA fusion protein in which the T-bet nucleotide sequence is inserted in a vector such as pCEP4-HA vector (Herrscher, R. F. et al. (1995) *Genes Dev.* 9:3067-3082) such that the T-bet sequences are fused in frame to an influenza hemagglutinin epitope tag. Such fusion proteins can facilitate the purification of recombinant T-bet.

In certain embodiments of the invention a fusion protein comprises a protein transduction domain (PTD) operatively linked to a T-bet polypeptide. Examples of suitable protein transduction domains are discussed below (Section IV.C.2).

Preferably, a T-bet fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide or an HA epitope tag). A T-bet-encoding nucleic acid can be cloned into such an expression vector such that the fusion moiety is linked in-frame to the T-bet protein.

IV. Methods of Identifying Subjects that would Benefit from Increased T-bet Activity A subject that would benefit from increased T-bet activity is a subject producing a T-bet protein having reduced activity or a subject producing a lower than normal or desirable level of T-bet protein. Such a subject may be one in which the amount of T-bet, e.g., the mRNA and/or protein level and/or activity of T-bet, is less than the level of T-bet as compared to a normal or control subject, and who is not at risk of or has not developed ulcerative colitis, colorectal cancer, and/or colonization of a subject's gastrointestinal tract with commensal bacteria that cause ulcerative colitis. In one embodiment, such a subject is identified by, e.g., genotyping, a sample from the subject for a polymorphism in the T-bet gene, e.g., a missense and/or nonsense SNP(s). In another embodiment, such a subject is identified by, e.g., phenotyping, a sample from a subject to determine the level of T-bet mRNA. In another embodiment, such a subject is identified by, e.g., phenotyping, a sample from a subject to determine the level of T-bet protein. In yet another embodiment, such a subject is identified by, e.g., phenotyping, a sample from a subject to determine the level of T-bet activity.

As used herein, the term "amount", with respect to T-bet present in a cell or sample refers to either (a) an absolute amount as measured in molecules, moles or weight per unit volume or cell or (b) a relative amount as designated, for example, by a numerical rating from 0 to 5.

The level or amount of T-bet in a cell or a sample derived from a subject is "altered" ("increased or decreased" or "higher or lower" than the normal level or amount of T-bet, if the amount of T-bet is greater or less, respectively, than the control amount by an amount that is greater than the standard error of the assay employed to assess the amount. The level or amount of T-bet in a cell or a sample derived from a subject can be considered "higher" or "lower" than the control amount if the difference in the control amount and the sample amount is at least about two, and preferably at least about three, four, or five times, higher or lower, respectively, than the standard error of control and sample measurements of T-bet.

The term "control level" or "control amount" of T-bet, refers to the level of T-bet in a cell or a sample derived from a subject not afflicted with or not at risk of developing ulcerative colitis, colorectal cancer, and/or colonization of a subject's gastrointestinal tract with commensal bacteria that cause ulcerative colitis. The "control level" may, for example, be determined by calculating the average level of T-bet present in cells or tissues that are known to express T-bet.

In general, it is preferable that the difference between the level of T-bet in a sample from a subject with ulcerative colitis, colorectal cancer, and/or colonization of a subject's gastrointestinal tract with commensal bacteria that cause ulcerative colitis and the level of T-bet in control sample, is as great as possible. Although this difference can be as small as the limit of detection of the method for determining the level it is preferred that the difference be at least greater than the standard error of the assessment method, and preferably a difference of at least 2-, 3-, 4-, 5-, 6-, 7-, 8-, 9-, 10-, 15-, 20-, 25-, 100-, 500-, 1000-fold or greater than the standard error of the assessment method.

An alteration in the level of T-bet in control (e.g., non-ulcerative colitis, non-colorectal cancer) tissue can be assessed in a variety of ways. In one embodiment, the amount is assessed by assessing the level of T-bet in cells which appear to be, e.g., non-cancerous, non-colitogenic, and by comparing the foregoing normal level of T-bet with the amount of T-bet in the cells which are suspected of being, e.g., cancerous, colitogenic.

For example, when colonoscopy, laparoscopy or other medical procedure, reveals the presence of a tumor on one portion of an organ, the normal level of T-bet may be assessed using the non-affected portion of the organ, and this normal level may be compared with the level of T-bet in an affected portion (e.g., the tumor) of the organ.

Alternatively, and particularly as further information becomes available as a result of routine performance of the methods described herein, population-average values for "normal" level of T-bet may be used. In other embodiments, the "normal" level of T-bet may be determined by assessing the level of T-bet in a subject sample obtained from a non-ulcerative colitis, non-cancerous, non-commensal bacteria that cause ulcerative colitis colonized afflicted subject, from a subject sample obtained from a subject before the suspected onset of, e.g., cancer, in the subject, from archived subject samples, and the like.

A "higher level of expression and/or activity" of T-bet refers to an expression level and/or activity in a test sample that is greater than the standard error of the assay employed to assess expression and/or activity, and is preferably at least twice, and more preferably three, four, five or ten or more times the expression level and/or activity of T-bet in a control sample (e.g., a sample from a healthy subject not afflicted with or not at risk of developing ulcerative colitis, colorectal cancer, and/or colonization of a subject's gastrointestinal tract with commensal bacteria that cause ulcerative colitis) and preferably, the average expression level and/or activity of T-bet in several control samples.

A "lower level of expression and/or activity" of T-bet refers to an expression level and/or activity in a test sample that is greater than the standard error of the assay employed to assess expression and/or activity, but is preferably at least twice, and more preferably three, four, five or ten or more times less than the expression level of T-bet in a control sample (e.g., a sample that has been calibrated directly or indirectly against a panel of gastrointestinal or breast cancers with follow-up information which serve as a validation standard for prognostic ability of the She proteins) and preferably, the average expression level and/or activity of T-bet in several control samples.

As used herein, "known standard" or "control" refers to one or more of a level of T-bet. A known standard preferably reflects such levels characteristic of ulcerative colitis, colorectal cancer, and/or colonization of a subject's gastrointestinal tract with commensal bacteria that cause ulcerative colitis. Reagents for generating a known standard include, without limitation, cells, e.g., dendritic cells, from a subject who does not have or is not at risk of developing ulcerative colitis, colorectal cancer, and/or colonization of a subject's gastrointestinal tract with commensal bacteria that cause ulcerative colitis. Known standards may also include tissue culture cell lines (including, but not limited to, cell lines that have been manipulated to express T-bet or manipulated to lose T-bet expression and/or T-bet and Rag2).

The methods of the present invention can be practiced in conjunction with any other method used by the skilled practitioner to prognose and/or diagnose ulcerative colitis, colorectal cancer, and/or colonization of a subject's gastrointestinal tract with commensal bacteria that cause ulcerative colitis. For example, the methods of the invention may be performed in conjunction with a biochemical, morphological or cytological analysis of the sample obtained from the subject.

A. Detecting and Determining the Level of T-bet

Material suitable for use in assays to identify a subject that would benefit from increased T-bet activity can be derived from a variety of sources. For example, nucleic acid molecules (e.g., mRNA or DNA, genomic DNA) or polypeptides can be isolated from a cell from a living or deceased individual using standard methods. Cells can be obtained from biological samples, e.g., from tissue samples or from bodily fluid samples that contain cells, such as blood, urine, semen, or saliva. The term "biological sample" is intended to include tissues, cells and biological fluids containing cells which are isolated from a subject, as well as tissues, cells and fluids present within a subject. Samples useful in the methods of the invention include any tissue, cell, biopsy, or bodily fluid sample that expresses T-bet. In one embodiment, a sample may be a tissue, a cell, whole blood, serum, plasma, buccal scrape, saliva, cerebrospinal fluid, urine, stool, or bronchoalveolar lavage. In certain embodiments, the tissue sample is a large intestine tissue sample.

Body samples may be obtained from a subject by a variety of techniques known in the art including, for example, by the use of a biopsy or by scraping or swabbing an area or by using a needle to aspirate bodily fluids. Methods for collecting various body samples are well known in the art. In particular embodiments, the body sample comprises gastrointestinal tissue samples.

Tissue samples suitable for detecting and determining the level of T-bet may be fresh, frozen, or fixed according to methods known to one of skill in the art. Suitable tissue samples are preferably sectioned and placed on a microscope slide for further analyses. Alternatively, solid samples, i.e., tissue samples, may be solubilized and/or homogenized and subsequently analyzed as soluble extracts.

Once the sample is obtained any method known in the art to be suitable for detecting and determining the level of T-bet may be used (either at the nucleic acid or at the protein level). Such methods are well known in the art and include but are not limited to western blots, northern blots, southern blots, immunohistochemistry, ELISA, e.g., amplified ELISA, immunoprecipitation, immunofluorescence, flow cytometry, immunocytochemistry, mass spectrometrometric analyses, e.g., MALDI-TOF and SELDI-TOF, nucleic acid hybridization techniques, nucleic acid reverse transcription methods, and nucleic acid amplification methods.

In one embodiment, an antibody-based method is used for detecting and determining the level of T-bet may be used (either at the nucleic acid or at the protein level). Such methods are the level of T-bet proteins. Techniques for detecting antibody binding are well known in the art. Antibody binding to T-bet may be detected through the use of chemical reagents that generate a detectable signal that corresponds to the level of antibody binding and, accordingly, to the level of T-bet protein expression. In one of the immunohistochemistry or immunocytochemistry methods of the invention, antibody binding is detected through the use of a secondary antibody that is conjugated to a labeled polymer. Examples of labeled polymers include but are not limited to polymer-enzyme conjugates. The enzymes in these complexes are typically used to catalyze the deposition of a chromogen at the antigen-antibody binding site, thereby resulting in cell staining that corresponds to expression level of the biomarker of interest. Enzymes of particular interest include, but are not limited to, horseradish peroxidase (HRP) and alkaline phosphatase (AP).

In one embodiment of the invention, proteomic methods, e.g., mass spectrometry, are used for detecting and determining the level of T-bet may be used (either at the nucleic acid or at the protein level). Such methods are the level of T-bet proteins. For example, matrix-associated laser desorption/ionization time-of-flight mass spectrometry (MALDI-TOF MS) or surface-enhanced laser desorption/ionization time-of-flight mass spectrometry (SELDI-TOF MS) which involves the application of a biological sample, such as serum, to a protein-binding chip (Wright, G. L., Jr., et al. (2002) Expert Rev Mol Diagn 2:549; Li, J., et al. (2002) Clin Chem 48:1296; Laronga, C, et al. (2003) Dis Markers 19:229; Petricoin, E. F., et al (2002) 359:572; Adam, B. L., et al. (2002) Cancer Res 62:3609; Tolson, J., et al. (2004) Lab Invest 84:845; Xiao, Z., et al. (2001) Cancer Res 6 1:6029) can be used to detect and quantitate the T-bet proteins. Mass spectrometric methods are described in, for example, U.S. Pat. Nos. 5,622,824, 5,605,798 and 5,547,835, the entire contents of each of which are incorporated herein by reference.

In other embodiments, the level of T-bet is determined by determining the level of expression of T-bet at the nucleic acid level. Nucleic acid-based techniques for assessing expression are well known in the art and include, for example, determining the level of T-bet mRNA in a body sample. Many expression detection methods use isolated RNA. Any RNA isolation technique that does not select against the isolation of mRNA can be utilized for the purification of RNA from cells that express T-bet (see, e.g., Ausubel et al., ed., (1987-1999) Current Protocols in Molecular Biology (John Wiley & Sons, New York). Additionally, large numbers of tissue samples can readily be processed using techniques well known to those of skill in the art, such as, for example, the single-step RNA isolation process of Chomczynski (1989, U.S. Pat. No. 4,843,155).

The term "probe" refers to any molecule that is capable of selectively binding to T-bet, for example, a T-bet nucleotide transcript or T-bet protein. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to the T-bet mRNA. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to T-bet genomic DNA.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in detecting the level of T-bet mRNA.

An alternative method for determining the level of T-bet mRNA in a sample involves the process of nucleic acid amplification, e.g., by RT-PCR (the experimental embodiment set forth in Mullis, 1987, U.S. Pat. No. 4,683,202), ligase chain reaction (Barany (1991) Proc. Natl. Acad. ScL USA 88:189-193), self sustained sequence replication (Guatelli et al. (1990) Proc. Natl. Acad. ScL USA 87: 1874-1 878), transcriptional amplification system (Kwoh et al. (1989) Proc. Natl. Acad. ScL USA 86:1 173-1 177), Q-Beta Replicase (Lizardi et al. (1988) Bio/Technology 6:1 197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, T-bet expression is assessed by quantitative fluorogenic RT-PCR (i.e., the TaqMan™ System). Such methods typically utilize pairs of oligonucleotide primers that are specific for T-bet. Methods for designing oligonucleotide primers specific for a known sequence are well known in the art.

The expression levels of T-bet mRNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection T-bet expression may also comprise using nucleic acid probes in solution.

In one embodiment of the invention, microarrays are used to detect T-bet expression. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, U.S. Pat. Nos. 6,040,138, 5,800,992 and 6,020,135, 6,033,860, and 6,344,316, which are incorporated herein by reference.

In one embodiment, the level of T-bet is determined by measuring an activity of T-bet as described supra.

In one embodiment, the level of T-bet is determined by determining a polymorphism in a T-bet nucleic acid molecule. There are a large number of assay techniques known in the art which can be used for detecting alterations in a polymorphic sequence.

Suitable T-bet polymorphism can be known or identified as described herein using methods routine to one of skill in the art. For example, given that the human T-bet coding sequence and flanking sequences are publicly available, as are polymorphisms (SNPs) in the T-bet gene, primers can readily be designed to amplify polymorphic sequences and/or detect T-bet polymorphisms by one of ordinary skill in the art. For example, a T-bet sequence comprising a polymorphism (e.g., SNP) can be identified in the NCBI Variation Database (dbSNP) or by homology searching of another database containing human genomic sequences (e.g., using Blast or another program), and the location of the SNP sequence and/or flanking sequences can be determined and the appropriate primers identified and/or designed by one of skill in the art. Non-limiting examples of known polymorphisms in the coding and non-coding regions of T-bet available through dbSNP include Accession Nos. rs17250932, rs12943851, rs34168885, rs59070891, rs11650451, rs3922359, rs17244544, rs2240017, rs2074190, rs41444548, rs41519545, rs34660770, rs10595771, rs59709252, rs55690005, rs10588766, rs57781320, rs62074058, rs10514934, rs8081095, rs9889416, rs11079787, rs16946264, rs41321047, rs34473357, rs8082611, rs62074059, rs34449847, rs8078974, rs11653146, rs59341832, rs56366102, rs56941567, rs59802366, rs9675050, rs11652969, rs9675078, rs4794071, rs4794072, rs12945996, rs12451552, rs2158079, rs8065304, rs58721292, rs56282776, rs56308324, rs34123804, rs58067360, rs11657388, rs11079788, rs12451801, rs41407050, rs58156929, rs16946878, rs17250953, rs11650354, rs12721471, rs12721469, rs12721470, rs12721468, rs17244573, rs11657479, rs17244587, rs7502875, rs41447544, rs17250967. Also see, ee, e.g., Chung et al. (2003) Human Mutation 22(3):257.

In another embodiment, a T-bet polymorphism(s) is identified and a statistically significant association with the development or the likelihood of developing ulcerative colitis, colorectal cancer or colonization of a subject's gastrointestinal tract with commensal bacteria that cause ulcerative colitis is determined using the methods described herein. It should be noted that it is possible for methods in the art to detect chromosomal variation without specifying an exact SNP site. For example, a tag SNP may be a representative SNP in a region discovered to have high linkage disequilibrium. As such, the methods of the present invention may make use of the named SNPs or other SNPs which reside nearby in the genome or are within the identified regions of linkage disequilibrium.

In one embodiment, analysis of polymorphisms is amenable to highly sensitive PCR approaches using specific primers flanking the sequence of interest. Oligonucleotide primers corresponding to T-bet sequences can be prepared by standard synthetic techniques, e.g., using an automated DNA synthesizer. In one embodiment, detection of the polymorphism involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) PNAS 91:360-364). In one embodiment, genomic DNA of a cell is exposed to two PCR primers and amplification for a number of cycles sufficient to produce the required amount of amplified DNA.

This method can include the steps of collecting a sample of cells from a patient, isolating nucleic acid (e.g., genomic, DNA) from the cells of the sample, contacting the nucleic acid sample with one or more primers which specifically amplify a subject SNP under conditions such that hybridization and amplification of the sequence occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting polymorphisms described herein.

In one preferred embodiment, detection of single nucleotide polymorphisms ("SNP") and point mutations in nucleic acid molecule is based on primer extension of PCR products by DNA polymerase. (See, e.g., U.S. Pat. No. 6,972,174, the contents of which are incorporated by reference).

In one preferred embodiment, a polymorphism is detected by primer extension of PCR products, as described above, followed by chip-based laser deionization time-of-flight (MALDI-TOF) analysis, as described in, for example U.S. Pat. No. 6,602,662, the contents of which are incorporated by reference.

Alternative amplification methods include: self sustained sequence replication (Guatelli, J. C. et al., 1990, Proc. Natl. Acad. Sci. USA 87:1874-1878), transcriptional amplification system (Kwoh, D. Y. et al., 1989, Proc. Natl. Acad. Sci. USA 86:1173-1177), Q-Beta Replicase (Lizardi, P. M. et all, 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment, after extraction of genomic DNA, amplification is performed using standard PCR methods, followed by molecular size analysis of the amplified product (Tautz, 1993; Vogel, 1997). In one embodiment, DNA amplification products are labeled by the incorporation of radiolabelled nucleotides or phosphate end groups followed by fractionation on sequencing gels alongside standard dideoxy DNA sequencing ladders. By autoradiography, the size of the repeated sequence can be visualized and detected heterogeneity in alleles recorded. In another embodiment, the incorporation of fluorescently labeled nucleotides in PCR reactions is followed by automated sequencing. (Yanagawa, T., et al., (1995). J Clin Endocrinol Metab 80: 41-5 Huang, D., et al., (1998). J Neuroimmunol 88: 192-8.

In other embodiments, polymorphisms can be identified by hybridizing a sample and control nucleic acids to high density arrays containing hundreds or thousands of oligonucleotides probes (Cronin, M. T. et al. (1996) Human Mutation 7: 244-255; Kozal, M. J. et al. (1996) Nature Medicine 2: 753-759).

In one embodiment, any of a variety of sequencing reactions known in the art can be used to directly sequence T-bet, or a region surrounding T-bet and detect allelic variants, e.g., mutations, by comparing the sequence of the sample sequence with the corresponding reference (control) sequence. Exemplary sequencing reactions include those based on techniques developed by Maxam and Gilbert (Proc. Natl. Acad Sci USA (1977) 74:560) or Sanger (Sanger et al. (1977) Proc. Nat. Acad. Sci. 74:5463). It is also contemplated that any of a variety of automated sequencing procedures may be utilized when performing the subject assays (Biotechniques (1995) 19:448), including sequencing by mass spectrometry (see, for example, U.S. Pat. No. 5,547,835 and international patent application Publication Number WO 94/16101, entitled DNA Sequencing by Mass Spectrometry by H. Köster; U.S. Pat. No. 5,547,835 and international patent application Publication Number WO 94/21822 entitled "DNA Sequencing by Mass Spectrometry Via Exonuclease Degradation" by H. Köster), and U.S. Pat. No. 5,605,798 and International Patent Application No. PCT/US96/03651 entitled DNA Diagnostics Based on Mass Spectrometry by H. Köster; Cohen et al. (1996) Adv Chromatogr 36:127-162; and Griffin et al. (1993) Appl Biochem Biotechnol 38:147-159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732 entitled "Method of DNA sequencing employing a mixed DNA polymer chain probe" and U.S. Pat. No. 5,571,676 entitled "Method for mismatch directed in vitro DNA sequencing".

In some cases, the presence of a specific polymorphism of T-bet in DNA from a subject can be shown by restriction enzyme analysis. For example, a specific nucleotide polymorphism can result in a nucleotide sequence comprising a restriction site which is absent from the nucleotide sequence of another allelic variant.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (Myers, et al. (1985) Science 230:1242; Cotton et al. (1988) Proc. Natl Acad Sci USA 85:4397; Saleeba et al (1992) Methods Enzymol. 217:286-295.

In another embodiment, an allelic variant can be identified by denaturing high-performance liquid chromatography (DHPLC) (Oefner and Underhill, (1995) Am. J. Human Gen. 57:Suppl. A266; O'Donovan et al. (1998) Genomics 52:44-49).

In other embodiments, alterations in electrophoretic mobility is used to identify the type of T-bet polymorphism. For example, single strand conformation polymorphism (SSCP) may be used to detect differences in electrophoretic mobility between mutant and wild type nucleic acids (Orita et al. (1989) Proc Natl. Acad. Sci. USA 86:2766; see also Cotton (1993) Mutat Res 285:125-144; and Hayashi (1992) Genet Anal Tech Appl 9:73-79). In another preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment, the identity of an allelic variant of a polymorphic region is obtained by analyzing the movement of a nucleic acid comprising the polymorphic region in polyacrylamide gels containing a gradient of denaturant is assayed using denaturing gradient gel electrophoresis (DGGE) (Myers et al. (1985) Nature 313:495; Rosenbaum and Reissner (1987) Biophys Chem 265:1275).

Examples of techniques for detecting differences of at least one nucleotide between two nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) Nature 324:163); Saiki et al (1989) Proc. Natl. Acad. Sci. USA 86:6230; and Wallace et al. (1979) Nucl. Acids Res. 6:3543). Such allele specific oligonucleotide hybridization techniques may be used for the simultaneous detection of several nucleotide changes in different polymorphic regions of T-bet. For example, oligonucleotides having nucleotide sequences of specific allelic variants are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238; Newton et al. (1989) Nucl. Acids Res. 17:2503). This technique is also termed "PROBE" for Probe Oligo Base Extension. In addition it may be desirable to introduce a novel restriction site in the region of the mutation to create cleavage-based detection (Gasparini et al. (1992) Mol. Cell. Probes 6:1).

In another embodiment, identification of the allelic variant is carried out using an oligonucleotide ligation assay (OLA), as described, e.g., in U.S. Pat. No. 4,998,617 and in Landegren, U. et al., (1988) Science 241:1077 1080. (Nickerson, D. A. et al., (1990) Proc. Natl. Acad. Sci. (U.S.A.) 87:8923 8927. U.S. Pat. No. 5,593,826 Tobe et al. ((1996) Nucleic Acids Res 24: 3728), In another embodiment, the single base polymorphism can be detected by using a specialized exonuclease resistant nucleotide, as disclosed, e.g., in Mundy, C. R. (U.S. Pat. No. 4,656,127).

In another embodiment of the invention, a solution based method is used for determining the identity of the nucleotide of a polymorphic site (Cohen, D. et al. (French Patent 2,650, 840; PCT Application No. WO91/02087).

An alternative method, known as Genetic Bit Analysis or GBA™ is described by Goelet, P. et al. (PCT Application No. 92/15712).

Several primer guided nucleotide incorporation procedures for assaying polymorphic sites in DNA have been described (Komher, J. S. et al., Nucl. Acids. Res. 17:7779 7784 (1989); Sokolov, B. P., Nucl. Acids Res. 18:3671 (1990); Syvanen, A. C., et al., Genomics 8:684 692 (1990); Kuppuswamy, M. N. et al., Proc. Natl. Acad. Sci. (U.S.A.) 88:1143 1147 (1991); Prezant, T. R. et al., Hum. Mutat. 1:159 164 (1992); Ugozzoli, L. et al., GATA 9:107 112 (1992); Nyren, P. et al., Anal. Biochem. 208:171 175 (1993)). (Syvanen, A. C., et al., Amer. J. Hum. Genet. 52:46 59 (1993)).

The methods described herein may be performed, for example, by utilizing pre-packaged diagnostic kits comprising at least one probe/primer nucleic acid or antibody reagent described herein, which may be conveniently used, e.g., in clinical settings to diagnose patients exhibiting symptoms or family history of a disease or illness involving a polymorphic elements. In addition, a readily available commercial service can be used to analyze samples for the polymorphic elements of the invention.

V. Methods of Treatment and/or Prevention

A. Methods to Selectively Increase T-bet Activity in Cells

As described in the appended examples, T-bet deficiency in the innate immune system results in aggressive, spontaneous, and communicable ulcerative colitis in the absence of adaptive immunity and increased susceptibility to colitis in immunologically intact hosts. Furthermore, the ulcerative colitis that develops in the absence of T-bet may progress to colon cancer. In addition, the appended examples demonstrate that T-bet controls the response of the mucosal immune system to commensal bacteria by regulating TNF-α production in colonic dendritic cells which are critical for maintenance of the colonic epithelial barrier. The loss of T-bet influences the commensal bacterial population to become colitogenic, and this colitis is communicable to genetically intact hosts.

In one embodiment, the present invention provides methods of treating and/or preventing ulcerative colitis and/or colon cancer in a subject comprising selectively increasing T-bet activity in cells, e.g., cells of the innate immune system, e.g., dendritic cells, e.g., colonic dendritic cells and/or bone marrow dendritic cells, and/or monocytes, and/or macrophages, and/or NK cells. The present invention also provides methods of preventing colonization of a host with commensal bacteria that promote ulcerative colitis in a subject comprising selectively increasing T-bet activity in cells, e.g., cells of the innate immune system, e.g., dendritic cells, e.g., colonic dendritic cells and/or bone marrow dendritic cells, and/or monocytes, and/or macrophages, and/or NK cells.

The agent may act by selectively increasing the activity of T-bet polypeptide in the cell, (e.g., by contacting a cell with an agent that, e.g., increases the amount of T-bet nucleic acid in a cell, the amount of T-bet protein in a cell, enhances the binding of T-bet to a molecule with which it interacts, changes the binding specificity of T-bet or post-translationally modification of T-bet, enhances the transcription of the T-bet gene, enhances the translation of the T-bet mRNA).

According to the methods of the invention, T-bet activity is selectively increased in a cell by contacting the cell with, for example, a stimulatory agent. Non-limiting examples of such stimulatory agents include active T-bet polypeptide and nucleic acid molecules encoding T-bet that are introduced into the cell to increase T-bet activity in the cell. A preferred stimulatory agent is a nucleic acid molecule encoding a T-bet polypeptide, wherein the nucleic acid molecule is introduced into the cell in a form suitable for expression of the active T-bet polypeptide in the cell. To express a T-bet polypeptide in a cell, typically a T-bet-encoding DNA is first introduced into a vector, e.g., a recombinant expression vector, using standard molecular biology techniques, as described herein. A T-bet-encoding DNA can be obtained, for example, by amplification using the polymerase chain reaction (PCR), using primers based on the T-bet nucleotide sequence. Following isolation or amplification of T-bet-encoding DNA, the DNA fragment is introduced into an expression vector and transfected into target cells by standard methods, as described herein.

In one embodiment, stimulatory compounds of the invention include agents that selectively increase T-bet activity to thereby decrease, for example, TNF-alpha production.

Other stimulatory agents that can be used to stimulate the activity of a T-bet polypeptide are chemical compounds that stimulate T-bet activity in cells, such as compounds that directly stimulate T-bet polypeptide activity and compounds that promote the interaction between T-bet and target DNA or other polypeptides. Such compounds can be identified using screening assays that select for such compounds, as described in detail above.

1. In vitro Methods

In one embodiment, the methods of the invention are performed in vitro (e.g., by culturing the cell with the agent or by introducing the agent into cells in culture). In another embodiment, the methods of the invention are performed ex vivo, e.g., using cells isolated from a subject that would benefit from the selective increase of T-bet activity, e.g., a subject with ulcerative colitis and/or colon cancer and/or at risk of developing ulcerative colitis and/or colon cancer, and/or that would benefit from preventing colonization of a subject's gastrointestinal tract with commensal bacteria that promote ulcerative colitis (e.g., T-bet activity can be selectively increased in a cell in vitro and then the treated cells can be administered to a subject).

a. Isolation of Cells of the Innate Immune System

For practicing the methods of the invention in vitro, cells can be obtained from a subject by standard methods and incubated (i.e., cultured) in vitro with a stimulatory agent of the invention to selectively increase T-bet activity in the cells. For example, peripheral blood mononuclear cells (PBMCs) can be obtained from a subject and isolated by density gradient centrifugation, e.g., with Ficoll/Hypaque. Specific cell populations can be depleted or enriched using standard methods. For example, cells can be enriched for example, by positive selection using antibodies to specific cell surface markers, for example by incubating cells with a specific primary monoclonal antibody (mAb), followed by isolation of cells that bind the mAb using magnetic beads coated with a secondary antibody that binds the primary mAb. Specific cell populations can also be isolated by fluorescence activated cell sorting according to standard methods. If desired, cells treated in vitro with a stimulatory agent of the invention can be readministered to the subject. For administration to a subject, it may be preferable to first remove residual agents in the culture from the cells before administering them to the subject. This can be done for example by a Ficoll/Hypaque gradient centrifugation of the cells. For further discussion of ex vivo genetic modification of cells followed by readministration to a subject, see also U.S. Pat. No. 5,399,346 by W. F. Anderson et al.

In one embodiment of the invention a cell of the innate immune system, e.g., dendritic cell, e.g., colonic dendritic cell and/or bone marrow dendritic cell, monocyte, macrophage, NK cell, is contacted with an agent that selectively increases T-bet activity. Dendritic cells, monocytes, NK cells, and macrophages, can be isolated from a subject and enriched for by methods routine to one of skill in the art using a variety of methodologies incorporating, for example, multiple-step density-gradient based isolation, monoclonal antibody panning, depletion of lineage positive cells, adhesion methods, and serum-supplemented cultures. See, generally, Macatonia, S. E., et al., Immunology 74: 399-406, 1991; Markowicz, S., and Engleman, E. G., J. Clin. Invest. 85:955-961, 1990; Young, J. W., and Steinman, R. M., Cell. Immunol. 111:167-182, 1987). For example, to isolate dendritic cells, peripheral blood is isolated from a subject and mononuclear cells are isolated by, for example, centrifugation over Ficoll-Hypaque. Lymphocytes may be removed by, for example centrifugation over metrizamide, and monocytes and natural killer cells may be removed by, for example, incubation on IgG coated plates. Dendritic cells may be further enriched for by, for example, isolation of lineage positive cells, e.g., CD11c$^+$, MHC class II$^+$ cells (Freudenthal, P. S., R. M. Steinman. 1990. Proc. Natl. Acad. Sci. USA 87:7689; Zhou, L. J., T. F. Tedder. 1995. J. Immunol. 154:3821).

Similar methods may be used to isolate and enrich dendritic cells from bone marrow aspirated from, for example the iliac crest (see, e.g., Hoehn G T, et al. Oncogene 12:903, 1996) or from fetal cord blood (see, e.g., Markowicz, et al. (2006) Acta Biochimica Polonica 53:203).

Colonic dendritic cells may be isolated and enriched for by disaggregation of an intestinal (colonic and/or rectal) mucosa biopsy and subsequent purification and positive enrichment as described above (see, e.g., P Pavli, et al. Immunology. 1993 78(1): 132-141; Bell, et al. Journal of Immunology, 2001, 166: 4958-4967).

Monocytes/macrophages may be isolated from tissue or blood using standard methods by, for example by gradient centrifugation followed by positive selection with specific monoclonal antibodies coupled to paramagnetic beads (Maria Gonzalez-Barderas, et al. (2004) PROTEOMICS Volume 4, Issue 2, Pages 432-437), negative selection, and/or by adhesion to plastic (Ho (1993) *J Infect Dis* 165:344).

NK cells may be solated from PBMC by, for example, immunomagnetic bead depletion and FACS sorting for CD56+ cells (Matos et al. (1993) *J Exp Med* 178:1079).

2. In vivo Methods

In another embodiment, the modulatory methods of the invention are performed in vivo, e.g., in a subject that would benefit from the selective increase of T-bet activity as described herein. Generally, such methods involve administering an agent that selectively increases T-bet activity to a subject. For example, an agent that selectively increases T-bet activity can be incorporated into pharmaceutical compositions suitable for administration. Such compositions typically comprise the agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. A pharmaceutical composition of the invention is formulated to be compatible with its intended route of administration.

The term "administering" includes any method of delivery of a pharmaceutical composition or agent into a subject's system or to a particular region in or on a subject. The phrases "systemic administration," "administered systemically", "peripheral administration", and "administered peripherally" as used herein mean the administration of a compound, drug or other material other than directly into the central nervous system, such that it enters the subject's system and, thus, is subject to metabolism and other like processes, for example, subcutaneous administration. "Parenteral administration" and "administered parenterally" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

In most embodiments, the agent will be delivered in an amount sufficient to deliver to a subject a therapeutically effective amount of the agent as part of a prophylactic or therapeutic treatment. The desired concentration of the agent will depend on absorption, inactivation, and excretion rates of the agent as well as the delivery rate of the agent. It is to be noted that dosage values may also vary with the severity of the condition to be alleviated. It is to be further understood that for any particular subject, specific dosage regimens should be adjusted over time according to the individual need and the professional judgment of the person administering or supervising the administration of the agent. Typically, dosing will be determined using techniques known to one skilled in the art. The selected dosage level will depend upon a variety of factors including the activity of the particular agent, the route of administration, the time of administration, the rate of excretion or metabolism of the agent, the duration of the treatment, other drugs, compounds and/or materials used in combination with the agent, the age, sex, weight, condition, general health and prior medical history of the patient being treated, and like factors well known in the medical arts.

Dosage may be based on the amount of the composition per kg body weight of the patient. Other amounts will be known to those of skill in the art and readily determined. Alternatively, the dosage of the subject invention may be determined by reference to the plasma concentrations of the composition. For example, the maximum plasma concentration (Cmax) and the area under the plasma concentration-time curve from time 0 to infinity (AUC (0-4)) may be used. Dosages for the present invention include those that produce the above values for Cmax and AUC (0-4) and other dosages resulting in larger or smaller values for those parameters.

A physician or veterinarian having ordinary skill in the art can readily determine and prescribe the effective amount of the agent required. For example, the physician or veterinarian could start doses of the agent at levels lower than that required in order to achieve the desired therapeutic effect and gradually increase the dosage until the desired effect is achieved.

In general, a suitable dose of an agent will be that amount which is the lowest dose effective to produce a therapeutic effect. Such an effective dose will generally depend upon the factors described above.

3. Stimulatory Agents a. Nucleic Acid Agents

For stimulatory agents that comprise nucleic acids (including recombinant expression vectors encoding T-bet polypeptide, the agents can be introduced into cells using methods known in the art for introducing nucleic acid (e.g., DNA) into cells in vivo or in vitro. Examples of such methods include, but are not limited to, viral and non-viral methods. Exemplary, non-limiting non-viral methods include, for example, microinjection, combining the nucleic acid fragment with lipid vesicles, such as anionic or cationic lipid vesicles, particle bombardment, electroporation, DNA condensing reagents (e.g., calcium phosphate, polylysine or polyethyleneimine). Exemplary viral methods generally involve incorporating the nucleic acid fragment into a viral vector and contacting the viral vector with the cell. A viral vector can include any of a variety of viral vectors known in the art including, for example, retroviral vectors, adenoviral vectors or an adeno-associated viral vectors (see below).

In one embodiment of the invention, a T-bet nucleic acid molecule is introduced into a cell using a non-viral delivery method, such as, a non-viral nucleic acid delivery composition described below. See, generally, U.S. Pat. No. 7,060,498.

In certain embodiments, the nucleic acid delivery compositions of the present invention may comprise one or more lipids. A lipid is a substance that is characteristically insoluble in water and extractable with an organic solvent. Lipids include, for example, the substances comprising the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

Lipids can be obtained from natural sources, commercial sources or chemically synthesized, as would be known to one of ordinary skill in the art. For example, phospholipids can be from natural sources, such as egg or soybean phosphatidylcholine, brain phosphatidic acid, brain or plant phosphatidylinositol, heart cardiolipin and plant or bacterial phosphatidylethanolamine. In another example, lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). In certain embodiments, stock solutions of lipids in chloroform or chloroform/methanol can be stored at about −20° C. Preferably, chloroform is used as the only solvent since it is more readily evaporated than methanol.

In one embodiment of the invention, a nucleic acid delivery composition may be associated with a lipid. A nucleic acid delivery composition associated with a lipid may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure. A lipid associated composition of the present invention is not limited to any particular structure. For example, the lipids may also simply be interspersed in a solution, possibly forming aggregates which are not uniform in either size or shape. In another example, the lipids may be present in a bilayer structure, as micelles, or with a "collapsed" structure. In another non-limiting example, a lipofectamine(Gibco BRL)-nucleic acid delivery composition or Superfect (Qiagen)-nucleic acid delivery composition complex is also contemplated.

A nucleic acid delivery composition may be comprised in an emulsion. A lipid emulsion is a substantially permanent heterogeneous liquid mixture of two or more liquids that do not normally dissolve in each other, by mechanical agitation or by small amounts of additional substances known as emulsifiers. Methods for preparing lipid emulsions and adding additional components are well known in the art (e.g., Modern Pharmaceutics, 1990, incorporated herein by reference).

A nucleic acid delivery composition may be comprised in a micelle. A micelle is a cluster or aggregate of lipid compounds, generally in the form of a lipid monolayer, and may be prepared using any micelle producing protocol known to those of skill in the art (e.g., Canfield et al., 1990; El-Gorab et al, 1973; Colloidal Surfactant, 1963; and Catalysis in Micellar and Macromolecular Systems, 1975, each incorporated herein by reference). For example, one or more lipids are typically made into a suspension in an organic solvent, the solvent is evaporated, the lipid is resuspended in an aqueous medium, sonicated and then centrifuged.

In a further embodiment, a nucleic acid delivery composition of the present invention may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen). Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In one embodiment, a non-viral nucleic acid delivery composition of the invention comprises a recombinant expression vector comprising a T-bet nucleic acid molecule and a (poly) cationic lipid-(liposome-) that form a lipid: (liposome:) DNA complex (lipoplex). Exemplary, non-limiting examples of (poly)cationic lipids that can be complexed with a T-bet nucleic acid molecule include, DOTMA/DOPE (N-1, -(2,3-dioleoyloxy) propyl-N,N,N-trimethyl ammonium chloride/ dioleoyl phosphatidylethanolamine) (Feigner et al., 1987), DC-Chol/DOPE (3-,8-N-(N',N' dimethylaminoethane)-carbamoyl cholesterol/(dioleoyl phosphatidylethanolamine) (Gao and Huang, 1991), and N-[-1-(2,3-dioleoyloxy)propyl] N,N,N-triethylammonium chloride (DOTMA) and a 1:1 molar ratio of 1,2-dimyristyloxy-propyl-3-dimethylhydroxyethylammonium bromide (DMRIE) and dioleoyl phosphatidylethanolamine (DOPE) (see e.g., Logan, J. J. et al. (1995) *Gene Therapy* 2:38-49; San, H. et al. (1993) *Human Gene Therapy* 4:781-788). Also see, e.g., U.S. Pat. Nos. 5,283,185, and 5,753,262.

In a preferred embodiment, a non-viral nucleic acid delivery composition of the invention comprises a recombinant expression vector comprising a T-bet nucleic acid molecule and a polycationic polymer that form a polycationic:DNA complex (a polyplex). Exemplary, non-limiting examples of polycationic polymers that can be complexed with the T-bet nucleic acid molecule include, chitosan, polyalkylamine (PAM), a polypeptide, chitosan, a polysaccharide, or copolymers thereof, poly-L-lysine, poly-L-ornithine, polyalkylenimine (PAI), and polyethylenimine (PEI). (see, e.g., US20060147376; WO06052649A2, D. W. Pack, Bioconjugate Chemistry Vol. 14 page 934 (2003), D. W. Pack Pharmaceutical Research Vol. 2 1 page 365 (2004); Langer et al., JACS Vol. 123 pages 8155-8156, (2001); JACS Vol. 122. pages 10761-10768, (2000)), U.S. Pat. Nos. 6,071,533, 6,846,809, incorporated herein by reference).

In certain embodiments, the polycation is a polyamine, such as, for example, spermidine, spermine, polyammonium molecules such as, for example, polybrene (hexadimethrine bromide), basic polyamino acids (e.g., polylysine), basic proteins or a combination thereof. Other polycations include, but are not limited to, those described in U.S. Pat. Nos. 5,656,611, 5,354,844, 5,462,866, 5,462,866 and 5,494,682, each incorporated herein by reference.

In other embodiments, the polycation is a protamine, histone, heterologous polypeptide, non-peptide cations such as polyethyleneimines, or a combination thereof (U.S. Pat. No. 5,792,645, incorporated herein by reference).

In other embodiments, a polycation may comprise, for example, a cationized albumin, DEAE-dextran, a histone, polybrene, polyornithine, protamine, spermine, a cascade amidoamine "dentritic" polymer, gramicidin S cyclic peptide, spermidine, polylysine, such as, for example, the (bromide salt, mol. wt. 25,600; Sigma Chemical Corporation St. Louis, Mo.), a short, synthetic cationic peptide, or combinations thereof. (U.S. Pat. No. 5,908,777; Haensler and Szoka, 1993, each incorporated herein by reference).

In another embodiment, the polycation comprises a dendrimer polycation. Dendrimer polycations and methods of preparing them are described in Tomalia et al., 1990; PCT/ US83/02052; U.S. Pat. Nos. 6,113,946, 4,507,466, 4,558, 120, 4,568,737, 4,587,329, 4,631,337, 4,694,064, 4,713,975, 4,737,550, 4,871,779 and 4,857,599, each incorporated herein by reference. Dendrimer polycations generally comprise oligomeric and/or polymeric compounds attached to a core molecule. As used herein "attached" may include, but is not limited to, such attachment means as a covalent bond.

In another embodiment, the polycation comprises a cationic proteinaceous sequence. Such cationic proteinaceous sequences will preferably comprise one or more cationic amino acid residues or one or more cationic moeities attached to the cationic proteinaceous sequence. Preferred cationic proteinaceous sequences include, but are not limited to poly (1-arginine acid), poly(d-arginine acid), poly(dl-arginine acid), poly(1-histidine acid), poly(d-histidine acid), poly(dl-histidine acid), poly(-lysine), poly(d-lysine), poly(dl-lysine), copolymers of the above listed polyamino acids with polyethylene glycol, polycaprolactone, polyglycolic acid and polylactic acid, as well as poly(2-hydroxyethyl 1-glutamine), chitosan, carboxymethyl dextran, hyaluronic acid, human serum albumin, and/or alginic acid.

Other polymers that are suitable for combining with a recombinant expression vector comprising a T-bet nucleic acid molecule to form a non-viral nucleic acid delivery composition include, for example, NIH Approved Implantable materials, including, polyacids such as polyacrylates (e.g., sodium), polymethacrylates and olefin Maleic anhydride copolymers; polyesters, such as polyglycolic acid, poly lactic acid, poly caprolactane and copolymers of these polyesters; polyorthoesters, such as polydioxyalkyltetrahydrofuran and poly 3,9-bismethylene-2,4,8,10 tetra aspiro 5,5 undecane-co-1,6hexanediol; hydrogels, such as, hydroxyethylmethacrylate, polyethyleneglycol, monomethyacrylate and gelatin crosslinked with formaldehyde; polysaccharides such as cellulose and dextran; polypeptides, such as, polyglutamic acid, glutamic acid leucine copolymers, polyaminotriazole/alkyleneaminotriazole copolymers and albumin beads (i.e, albumin crosslinked with glutaraldehyde); amino acid polymers, such as poly D- or L-lysine HCL, poly D- or L-ornithine HCL and poly D- or L-arginine; and combinations thereof. Other polymers described included water soluble polymers such as polysaccharides (–): starch, gums, carrageenans, dextran, xanthan, sulfated algal polysaccharide (–), alginate (–), hyaluronic acid films (–), heparin (–), chondroitin sulfates (–), polygalacturonic acid (–), alginic acid (–), sodium carboxymethylcellulose (–), sodium carboxymethylcellulose-diethylaminoethyldextran copolymer (–), agar, hyaluronate (–), sulfated hyaluronic acid (–), sulfated deacetylated hyaluronic acid (–), heparin (–), polyguluronate (normal or acetylated) (–), polymannuronate (–), chondroitin sulphate (–), ascopyllan (–), pectin (made of 1,4 polyglacteronic acid) (–), dextran sulfate (–), fucoidan (–), oxdized cellulose (–), polypeptides and proteins such as hydrophobic (e.g., polyphenylalanine), polar (e.g., serine), acidic (–) (e.g., asparatic acid, chondroitin-6-sulfate, heparin, human serum albumin, basic (+) (e.g., lysine, 1-argine, collagen); polynucleic acids (RNA, DNA) (nonionic), pullan (nonionic), cellulose (nonionic), algal pectin, modified celuloses such as hydroxypropylcellulose (nonionic, forms a thin film), hydroxypropylcellulose (nonionic), carboxymethylcellulose (nonionic); forms a gel/film, diethylaminohydroxypropylcellulose (+), diethylaminoethylcellulose (+) and chitosan (+).

In one embodiment, a non-viral nucleic acid delivery composition of the invention comprises a recombinant expression vector comprising a T-bet nucleic acid molecule, or biologically active fragment thereof, and PEI.

In one embodiment, a non-viral delivery composition of the invention comprises a recombinant expression vector comprising a T-bet nucleic acid molecule, a polyethylenimine (PEI), a lipid, and, optionally a biocompatible hydrophilic polymer (see, e.g., WO05060934A1, U.S. Pat. No. 7,060, 498).

In another embodiment, a non-viral delivery composition of the invention comprises a recombinant expression vector comprising a T-bet nucleic acid molecule, PEI and cholesterol forming a water soluble lipopolymer (WSLP). See, Mol. Ther., 2001, 4, 130.

In certain embodiments, a non-viral nucleic acid delivery composition comprising a polycationic molecule may be joined to a nucleic acid molecule via a biologically-releasable bond, such as a selectively-cleavable linker or amino acid sequence. For example, peptide linkers that include a cleavage site for an enzyme preferentially located or active within a particular in vivo environment are contemplated. Exemplary forms of such peptide linkers are those that are cleaved by urokinase, plasmin, thrombin, Factor IXa, Factor Xa, or a metallaproteinase, such as collagenase, gelatinase, or stromelysin.

In one embodiment, polyethylene glycol (PEG) is a linker/coupling agent. Polyethylene glycol may coat the polycation/nucleic acid combination, as well as serve as a point of attachment for additional agents such as, for example, targeting ligands. In certain embodiments, for example, the PEG may be attached to the other nucleic acid delivery components by charge (e.g., ionic interactions) and/or covalent bonds. For example, heterobifunctional PEG comprising one or more coupling groups (e.g., a coupling group at each end the PEG molecule) may be covalently bonded to, for example, a polycation and a targeting agent.

In one embodiment, a non-viral delivery composition of the invention comprises a recombinant expression vector comprising a T-bet nucleic acid molecule, PEI and, PEG-PEI-Cholesterol (PPC). See, e.g., US 20060127482A1.

In other embodiments, bispecific antibodies may be used as a linker/coupling agent. For example, a bispecific antibody may bind one or more components of the nucleic acid delivery composition, and foster binding to another agent.

Additionally, while numerous types of disulfide-bond containing linkers are known which can successfully be employed to conjugate moeities, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the moeity prior to binding at the site of action.

In one embodiment, nucleic acid delivery compositions described herein may comprise at least one targeting agent to an organelle, cell, tissue, organ or organism. In one embodiment, a nucleic acid delivery composition further comprises a targeting agent which directs the composition to a cell of the innate immune system, e.g., a dendritic cell, e.g., colonic dendritic cell and/or bone marrow dendritic cell, and/or a monocyte, and/or a macrophage, and/or an NK cell. Any targeting agent described herein or known to one of ordinary skill in the art may be used in the compositions and methods of the present invention, either alone in combination with other targeting agents. In specific embodiments, the targeting agent may be attached to, for example, a polycation, nucleic acid, and/or other composition component.

In one embodiment, a targeting agent is a monoclonal antibody. A nucleic acid delivery composition can be coupled, e.g., covalently coupled, to a targeting moiety, such as a monoclonal antibody using a coupling agent as described herein or known in the art. Various coupling agents include for example, disuccinimidyl suberate (DSS) and ethylene glycol-succinimidylsuccinate (EGS) (see, e.g., Klibanov et al Pharmaceutical Res. Vol. 22. pages 373-380, (2005)), N-succinimidyl-3-(2-pyridyldithio)proprionate (SPDP), N-succinimidyl-4-(maleimidomethyl)-cyclohexancarboxylate (SMCC), and 3-(2-(2-(vinylsulfonyl)ethylthio)ethyl)quinazoline-2,4(1H,3H)-dione (IBFB 110001) (see, e.g., Strehblow C, et al. J Control Release. 2005 Feb. 16; 102(3): 737-47).

In one embodiment, the monoclonal antibody coupled to a nucleic acid delivery composition, e.g., a polycationic:DNA complex, e.g., PEI:T-bet, is an anti-dendritic cell antibody. In one embodiment, the anti-dendritic cell antibody is an anti-CD11c antibody. Anti-CD11c antibodies are known in the art and are described in, for example, Liu, L-J, Watabe, S, Yang, J, et al: Topical application of HIV DNA vaccine with cytokine-expression plasmids induces strong antigen-specific immune responses. Vaccine in press, or can be obtained from, for example commercial sources, e.g., Pharmingen (HL3), Leinco Technologies, US Biological, etc.

In another embodiment, the anti-dendritic cell antibody is an anti-DC-SIGN (C-type lectin DC-specific intercellular adhesion molecule 3-grabbing nonintegrin; CD209) antibody. Suitable DC-SIGN monoclonal antibodies are known in the art and include for example, those described in WO05058244A2 (AZN-D1 and AZN-D2 and CSRD; also descrbed in Geijtenbeek, T. B. H., et al. 2000. Cell. 100:575-585; Geijtenbeek, T. B., et al. 2000. Cell. 100:587-597), AZN-L19 (described in, for example, Stuyt R J L, et al. Immunology. 2003; 110: 329-334), or available commercially from, for example, Acris Antibodies and/or R & D Systems (mAb 507 and 612).

In another embodiment, the anti-dendritic cell antibody is an anti-EMR4 antibody, 6F12 (also known as F4/80-like-receptor (FIRE)) (see, e.g., Caminschi I, et al. J Immunol 167 :3570-3576, 2001).

In one embodiment, the monoclonal antibody coupled to a nucleic acid delivery composition, e.g., a polycationic:DNA complex, e.g., PEI:T-bet, is an anti-monocyte antibody. In one embodiment, the anti-monocyte antibody is an anti-CD14 antibody. Anti-CD14 antibodies are known in the art and are described in, for example, Verbo, et al. (2003) J Infect Dis 187:1, or can be obtained from, for example commercial sources, e.g., AbD Serotec, Santa Cruz Biotechnology, etc.

In one embodiment, the monoclonal antibody coupled to a nucleic acid delivery composition, e.g., a polycationic:DNA complex, e.g., PEI:T-bet, is an anti-macrophage antibody. In one embodiment, the anti-macrophage antibody is an anti-CD16 antibody. Anti-CD16 antibodies are known in the art and can be obtained from, for example commercial sources, e.g., Abcam, LifeSpan Biosciences, etc. In another embodiment, the anti-macrophage antibody is an anti-CD11a antibody. Anti-CD11a antibodies are in the art and are described in, for example, U.S. Pat. No. 6,037,454 or can be obtained from, for example commercial sources, e.g., Abcam, etc.

In one embodiment, the monoclonal antibody coupled to a nucleic acid delivery composition, e.g., a polycationic:DNA complex, e.g., PEI:T-bet, is an anti-NK cell antibody. In one embodiment, the anti-NK cell antibody is an anti-CD56 antibody. Anti-CD56 antibodies are known in the art and can be obtained from, for example commercial sources, e.g., Zymed Laboratories, US Bio, etc.

In another embodiment, a targeting moiety is a single-chain variable region fragment (scFv) which specifically targets APCs and is described in, for US 20040146948.

The non-viral nucleic acid delivery compositions of the invention are generally prepared by complexing, e.g., mixing, a nucleic acid molecule with, for example, a polycationic compound, to create a complex. Use of such non-viral nucleic acid delivery compositions generally comprises in vitro or in vivo transfection of a cell with a nucleic acid delivery composition under conditions such that the complex passes from the medium into the cytoplasm of the cells, releases the nucleic acid from the complex into the cytosol of the cells, and transcription and expression of the nucleic acid in the transfected cells takes place. The complex may enter the cell by endocytocis and then escape from the vesicles to gain access to the cytoplasm of the cell. If the target cell is within a cell culture in vitro, the cell can be contacted with the complex by providing the cells with a growth medium containing the complex or by inserting a solution containing the complex into the growth media. If the target cell is within an organism in vivo, the contacting may occur by positioning the complex within the organism so that it has access to the target cell. For example, the complex may be administered by injecting a solution containing the complex into the circulatory system of the organism. A complex with a targeting moiety will allow the complex to be directed to a target cell with a target corresponding to the targeting moiety, e.g., a cell of the innate immune system. The complex may be administered to a subject by intramuscular, intraperitoneal, intraabdominal, subcutaneous, intravenous, and intraarterial delivery. Other methods of administration of the complex include parenteral, topical, transdermal, transmucosal, inhaled, and insertion into a body cavity such as by ocular, vaginal, buccal, transurethral, rectal, nasal, oral, pulmonary, and aural administration.

Other methods for both non-viral and viral methods for introducing nucleic acid into cells are known in the art and described below.

Direct Injection: Naked DNA can be introduced into cells in vivo by directly injecting the DNA into the cells (see e.g., Acsadi et al. (1991) *Nature* 332:815-818; Wolff et al. (1990) *Science* 247:1465-1468). For example, a delivery apparatus (e.g., a "gene gun") for injecting DNA into cells in vivo can be used. Such an apparatus is commercially available (e.g., from BioRad).

Receptor-Mediated DNA Uptake: Naked DNA can also be introduced into cells in vivo by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963-967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122-2126).

Retroviruses: Defective retroviruses are well characterized for use in gene transfer for gene therapy purposes (for a review see Miller, A. D. (1990) *Blood* 76:271). A recombinant retrovirus can be constructed having a nucleotide sequences of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150:4104-4115; U.S. Pat. Nos. 4,868,116; 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482-6486), hepatocytes (Herz and Gerard (1993) *Proc. Natl. Acad. Sci. USA* 90:2812-2816) and muscle cells (Quantin et al. (1992) *Proc. Natl. Acad. Sci. USA* 89:2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product.

b. Protein and Peptidic Agents

For stimulatory agents that comprise peptides or protein, the agents can be introduced into cells using methods known in the art for introducing peptides and proteins into cells in vivo or in vitro. Exemplary, non-limiting methods include, for example, micro-injection and electroporation, combining the protein with lipid vesicles, such as anionic or cationic lipid vesicles as described above, or combining the protein with fusiogenic lipids (Owais, et al. Eur. J. Biochem, 2000, Vol 267: 3946-3956; U.S. Pat. No. 5,631,237), or by creating a fusion protein with a protein transduction domain.

A protein or peptidic agent can also be introduced into a cell using a virus-like particles (VLPs) as a delivery vehicle. VLPs are structures resembling a virus particle but devoid of the viral genome. Accordingly, they are incapable of replication and devoid of pathogenicity. A VLP particle typically comprises at least one type of structural protein from a virus, such as a proteinaceous capsid (e.g. VLPs comprising a retrovirus, adenovirus or bacteriophage structural protein). In some cases the capsid will also be enveloped in a lipid bilayer originating from the cell from which the assembled VLP has been released (see, e.g., WO06059141A2).

In one embodiment, a protein or peptidic agent that selectively stimulates T-bet activity is introduced into a cell by non-covalent complexation with one or more of the peptides described in U.S. Pat. No. 6,841,535.

In one embodiment, an peptidic agent that selectively stimulates T-bet activity is introduced into a cell by operably linking a nucleic acid molecule encoding a T-bet polypeptide or biologically active fragment thereof with a PTD to form a PTD:T-bet fusion protein.

Protein-transduction domains (PTDs) mediate protein delivery into cells. PTDs or signal peptide sequences are naturally occurring polypeptides of 15 to 30 amino acids, which normally mediate protein secretion in the cells. They are composed of a positively charged amino terminus, a central hydrophobic core and a carboxyl-terminal cleavage site recognized by a signal peptidase. A purified fusion protein produced by an expression vector host cell system as described herein can be administered to the target cell, in vitro or in vivo. The protein transduction domain mediates the import of the fusion protein through the cell membrane of the target cell into the interior of the cell.

A number of membrane-translocating peptides can successfully mediate delivery of polypeptides, protein domains, and full-length protein, using solution-based protein transfection protocols. See generally, U.S. Pat. Nos. 7,166,692 and 7,101,844.

In one embodiment, a protein transduction domain (PTD) is a tat-derived peptide. (U.S. Pat. Nos. 5,804,604, 5,747,641, 5,674,980, 5,670,617, and 5,652,122).

In another embodiment, a PTD is penetratin. Penetratin can transport hydrophilic macromolecules across the cell membrane (Derossi et al., Trends Cell Biol., 8:84-87 (1998)). Penetratin is a 16 amino acid peptide which corresponds to amino acids 43-58 of the homeodomain of Antennapedia, a *Drosophila* transcription factor which is internalized by cells in culture.

In another embodiment a PTD is VP22. VP22 is a tegument protein from Herpes simplex virus type 1 (HSV-1) which has the ability to transport proteins and nucleic acids across a cell membrane (Elliot et al., Cell 88:223-233, 1997).

In yet another embodiment, a PTD suitable for use in the methods of the invention is membrane transduction sequence (MTS) also known as cytoplasmic penetration peptide (CPP) in FGF (Fibroblast Growth Factor) (Hawiger J. 1999; Hawiger J. 1997; Lin et. al., 1995; Liu et. al., 1996; Rojas et. al., 1998; and Wang et. al., 2002).

4. Treatment and/or Prevention of Ulcerative Colitis

An agent that selectively increases T-bet activity as described herein is useful in treating and/or preventing ulcerative colitis. The methods of the invention generally involve contacting a cell, e.g., cells of the innate immune system, e.g., dendritic cells, e.g., colonic dendritic cells and/or bone marrow dendritic cells, and/or monocytes, and/or macrophages, and/or NK cells, with an agent that selectively increases T-bet activity, i.e, a stimulatory agent. In order for T-bet activity to be increased in a cell, the cell is contacted with an agent in an amount sufficient to selectively increase the activity of T-bet. A sufficient amount of an agent that selectively increase T-bet activity is that amount which is sufficient to effect a desired result, e.g., preventing and/or treating ulcerative colitis in a subject. An amount sufficient to achieve a desired result, also includes, but is not limited to, for example, an amount that ameliorates disease, stabilizes a patient, prevents or delays the development of or progression of disease in a patient, decreases the type and/or number of symptoms associated with the disease, or decreases the frequency or severity of flare-ups of the disease. An effective amount can be determined based on one administration or repeated administration.

Methods of detection and measurement of the indicators above are known to those of skill in the art. Such methods include, but are not limited to, patient reported improvement/reduction in diarrhea, bloody diarrhea, abdominal pain, severe urgency to have a bowel movement, an increase in appetite, weight gain, etc. In addition measuring improvement in liver function, reduction of anemia, reduction of the level of C-reactive protein (CRP), reduction in the level of perinuclear antineutrophil antibody (PANCA) may also be used to determine an effective amount.

The methods of the invention may further comprise the administration of agent(s) or treatment regimes, e.g., surgery, antibiotics, anti-inflammatory agents, probiotics, prebiotics, etc., that are effective in treating ulcerative colitis. Preferred agent(s) and/or treatments are those which are art recognized and are routinely used to treat ulcerative colitis.

In one embodiment, the methods of the invention further comprise administering an antibiotic to a subject. Any antibiotic or combination of antibiotics used by one of skill in the art to treat ulcerative colitis are suitable for use with the methods of the invention. Non-limiting example include, vancomycin, metronidazole, neomycin, Ciprofloxacin, and ampicillin. In one embodiment, the antibiotic is Metronidazole. In another embodiment, the antibiotic is Ciprofloxacin.

In another embodiment, the methods of the invention further comprise administering a 5-aminosalicylic acid (5-ASA) compound to a subject. In one embodiment, the 5-aminosalicylic acid (5-ASA) compound is selected from the group consisting of Sulfasalazine, Olsalazine, Mesalamine.

In another embodiment, the methods of the invention further comprise administering a corticosteroid, e.g., prednisone, cyclosporine, tacrolimus, to a subject.

In another embodiment, the methods of the invention further comprise administering a probiotic, i.e., beneficial non-pathologic bacteria that are functionally defined by their ability to reduce inflammation when introduced into the inflamed intestine, to a subject. See, e.g., Sleator and Hill (2007) *Letts Applied Microbiol* 1-5, the contents of which is incorporated herein by reference. Probiotics suitable for use in the methods of the invention, include, but are not limited to *Bifidobacteria* sp, *Lactobacillus* sp., and *Bacteroides* sp. Probiotics may be delivered to a subject orally and/or rectally. Suitable vehicles for oral probiotic delivery include, but are not limited to, yoghurt and physiologic buffers.

In another embodiment, the methods of the invention further comprise administering a prebiotic, i.e., short-chain carbohydrates that alter the composition, or metabolism, of the gut microbiota in a beneficial manner, to a subject. See, e.g., McFarlane, et al. (2006) *Alimentary Pharmacol Therap* 24:701, the contents of which is incorporated herein by reference Prebiotics suitable for use in the methods of the invention, include, but are not limited to oligofructose, galacto-oligosaccharides and lactulose. Prebiotics may be delivered to a subject orally and/or rectally. Suitable vehicles for oral prebiotic delivery include, but are not limited to, yoghurt and physiologic buffers.

In another embodiment, the methods of the invention further comprise administering a humanized anti-integrin-alpha4beta7 antibody to a subject.

In one embodiment, the methods of the invention further comprise administering regulatory T cells to a subject. Regulatory T cells can be isolated from a population of cells obtained from the subject and expanded by standard methods. For example, peripheral blood mononuclear cells (PBMCs) can be obtained from the subject, e.g., by luekopheresis, and isolated by density gradient centrifugation, e.g., with Ficoll/Hypaque. Regulatory T cells can be enriched for example, by positive selection using antibodies to regulatory T cell surface markers, such as CD4, CD25, the α chain of the interleukin 2 receptor (IL-2R), and/or CD62L or other appropriate markers, such as the transcription factor Foxp3, for example, by incubating cells with a specific primary monoclonal antibody (mAb), followed by isolation of cells that bind the mAb using magnetic beads coated with a secondary antibody that binds the primary mAb. Regulatory T cells can also be isolated by automated magnetic cell sorter or by fluorescence activated cell sorting according to standard methods. Isolated regulatory T cells can be expanded in culture by incubating the cells in the presence of, for example, anti-CD3 and/or anti-CD28 monoclonal antibody coated beads or coated plates. Such in vitro expanded populations of regulatory T cells can be readministered to the subject. See, e.g., WO04112835A3, U.S. Pat. No. 6,746,670, US20070166307A, and U.S. Pat. No. 6,759,035.

5. Treatment and/or Prevention of Colon Cancer

An agent that selectively increases T-bet activity as described herein is useful in treating and/or preventing colon cancer. The methods of the invention generally involve contacting a cell, e.g., cells of the innate immune system, e.g., dendritic cells, e.g., colonic dendritic cells and/or bone marrow dendritic cells, /or monocytes, and/or macrophages, and/or NK cells, with an agent that selectively increases T-bet activity, i.e, a stimulatory agent. In order for T-bet activity to be increased in a cell, the cell is contacted with an agent in an amount sufficient to selectively increase the activity of T-bet. A sufficient amount of an agent that selectively increase T-bet activity is that amount which is sufficient to affect a desired result, e.g., preventing and/or treating colon cancer in a subject. An amount sufficient to achieve a desired result, also includes, but is not limited to, for example, an amount that ameliorates disease, stabilizes a patient, prevents or delays the development of or progression of disease in a patient, decreases the type and/or number of symptoms associated with the disease. An effective amount can be determined based on one administration or repeated administration.

Methods of detection and measurement of the indicators above are known to those of skill in the art. Such methods include, but are not limited to, determination of tumor burden, determination of tumor size, determination of tumor volume, determination of proliferation of secondary tumors, expression of genes in tumor tissue, presence of biomarkers, lymph node involvement, histologic grade, and nuclear grade.

The methods of the invention may further comprise the administration of agent(s) or treatment regimes, e.g., surgery, radiation therapy, chemotherapy, etc., that are effective in treating and/or preventing colon cancer. Preferred agent(s) and/or treatments are those which are art recognized and are routinely used to treat a colon cancer.

In one embodiment, the methods of the invention further comprise administering regulatory T cells to a subject as described above.

6. Prevention of Colonization of Colitogenic Bacteria

An agent that selectively increases T-bet activity as described herein is useful in preventing colonization of a subject's gastrointestinal tract with commensal bacteria that cause ulcerative colitis. The methods of the invention generally involve contacting a cell, e.g., cells of the innate immune system, e.g., dendritic cells, e.g., colonic dendritic cells and/or bone marrow dendritic cells, /or monocytes, and/or macrophages, and/or NK cells, with an agent that selectively increases T-bet activity, i.e, a stimulatory agent. In order for T-bet activity to be increased in a cell, the cell is contacted with an agent in an amount sufficient to selectively increase the activity of T-bet. A sufficient amount of an agent that selectively increase T-bet activity is that amount which is sufficient to affect a desired result, e.g., preventing colonization of a subject's gastrointestinal tract with commensal bacteria that cause ulcerative colitis and/or restore a desired balance to intestinal flora in a subject. An amount sufficient to achieve a desired result, also includes, but is not limited to, for example, an amount that decreases the amount of commensal anerobic bacteria in the colon of a subject, ameliorates ulcerative colitis and/or colon cancer (as described above), stabilizes a patient, prevents or delays the development of or progression of ulcerative colitis and/or colon cancer in a patient, decreases the type and/or number of symptoms associated with ulcerative colitis and/or colon cancer. An effective amount can be determined based on one administration or repeated administration.

Methods of detection and measurement of the indicators above are known to those of skill in the art. Such methods include, but are not limited to, an increase in tolerance to enteric commensal bacteria (Duchmann R, et al. (1995) Clin Exp Immunol 102: 448-455; Mow W S et al. (2004) Gastroenterology 126: 414-424), reduction in IL-1b, IL-6, TNF, IL-8, IL-8, IL-5, IL-13 levels and/or a decrease in the presence of commensal colonic bacteria.

The methods of the invention may further comprise the administration of agent(s) or treatment regimes, e.g., surgery, antibiotics, anti-inflammatory agents, probiotics, prebiotics, etc., that are effective in treating ulcerative colitis. Preferred agent(s) and/or treatments are those which are art recognized and are routinely used to treat ulcerative colitis.

In one embodiment, the methods of the invention further comprise administering an antibiotic to a subject. Any antibiotic or combination of antibiotics used by one of skill in the art to treat ulcerative colitis are suitable for use with the methods of the invention. Non-limiting example include, vancomycin, metronidazole, neomycin, Ciprofloxacin, and ampicillin. In one embodiment, the antibiotic is Metronidazole. In another embodiment, the antibiotic is Ciprofloxacin.

In another embodiment, the methods of the invention further comprise administering a corticosteroid, e.g., prednisone, cyclosporine, tacrolimus, to a subject.

In another embodiment, the methods of the invention further comprise administering a probiotic, i.e., beneficial non-pathologic bacteria that are functionally defined by their ability to reduce inflammation when introduced into the inflamed intestine, to a subject. See, e.g., Sleator and Hill (2007) *Letts Applied Microbiol* 1-5, the contents of which is incorporated herein by reference. Probiotics suitable for use in the methods of the invention, include, but are not limited to *Bifidobacteria* sp, *Lactobacillus* sp., and *Bacteroides* sp. Probiotics may be delivered to a subject orally and/or rectally. Suitable vehicles for oral probiotic delivery include, but are not limited to, yoghurt and physiologic buffers.

In another embodiment, the methods of the invention further comprise administering a prebiotic, i.e., short-chain carbohydrates that alter the composition, or metabolism, of the gut microbiota in a beneficial manner, to a subject. See, e.g., McFarlane, et al. (2006) *Alimentary Pharmacol Therap* 24:701, the contents of which is incorporated herein by reference Prebiotics suitable for use in the methods of the invention, include, but are not limited to oligofructose, galactooligosaccharides and lactulose. Prebiotics may be delivered to a subject orally and/or rectally. Suitable vehicles for oral prebiotic delivery include, but are not limited to, yoghurt and physiologic buffers.

In one embodiment, the methods of the invention further comprise administering regulatory T cells to a subject (as described above).

B. Methods of Prevention and Treatment of Ulcerative Colitis, Colorectal Cancer, and/or Prevention of Colonization of Commensal Bacteria that Cause Ulcerative Colitis in Subjects that Would Benefit from Increased T-bet Activity It has also been discovered that treatment of T-bet deficient animals with antibiotics abolishes both ulcerative colitis and colorectal carcinoma, and that feeding T-bet deficient animals probiotics abolishes ulcerative colitis.

Accordingly, in one embodiment, the instant invention provides methods for treating and/or preventing ulcerative colitis, colorectal cancer, as well as methods of preventing colonization of a subject's gastrointestinal tract with commensal bacteria that cause ulcerative colitis in a subject with a T-bet deficient milieu, a subject that would benefit from increased T-bet activity, e.g., a subject producing a T-bet protein having reduced activity or a subject producing a lower than normal or desirable level of T-bet protein, e.g., a subject with a less than desirable level, e.g., mRNA, protein, and/or activity, of T-bet, and/or T-bet, e.g., missense or nonsense, SNP(s). The methods generally involve administering a sufficient amount of an antibiotic or probiotic to the subject such that ulcerative colitis and/or colorectal cancer is treated and/or prevented and/or the colonization of a subject's gastrointestinal tract with commensal bacteria that cause ulcerative colitis is prevented. The methods may also involve the step of identifying a subject that would benefit from increased T-bet activity using the methods as described herein.

Non-limiting examples of suitable antibiotics and probiotics are described herein and may also be identified using screening assays that select for such compounds, as described in detail above.

1. Treatment and/or Prevention of Ulcerative Colitis

As described herein, an antibiotic and/or probiotic is useful in treating and/or preventing ulcerative colitis in a subject that would benefit from increased T-bet activity. The methods of the invention generally involve administering to the subject an antibiotic and/or a prebiotic in an amount sufficient to effect a desired result, e.g., preventing and/or treating ulcerative colitis in a subject. An amount sufficient to achieve a desired result, also includes, but is not limited to, for example, an amount that ameliorates disease, stabilizes a patient, prevents or delays the development of or progression of disease in a patient, decreases the type and/or number of symptoms associated with the disease, or decreases the frequency or severity of flare-ups of the disease. An effective amount can be determined based on one administration or repeated administration.

Methods of detection and measurement of the indicators above are known to those of skill in the art. Such methods include, but are not limited to, patient reported improvement/reduction in diarrhea, bloody diarrhea, abdominal pain, severe urgency to have a bowel movement, an increase in appetite, weight gain, etc. In addition measuring improvement in liver function, reduction of anemia, reduction of the level of C-reactive protein (CRP), reduction in the level of perinuclear antineutrophil antibody (PANCA) may also be used to determine an effective amount.

Any antibiotic or combination of antibiotics used by one of skill in the art to treat ulcerative colitis is suitable for use with the methods of the invention. Non-limiting example include, vancomycin, metronidazole, neomycin, Ciprofloxacin, and ampicillin. In one embodiment, the antibiotic is Metronidazole. In another embodiment, the antibiotic is Ciprofloxacin.

Any probiotic, i.e., beneficial nonpathologic bacteria that are functionally defined by their ability to reduce inflammation when introduced into the inflamed intestine, of a subject (see, e.g., Sleator and Hill (2007) *Letts Applied Microbiol* 1-5, the contents of which is incorporated herein by reference), or combination of probiotics may be used in the methods of the invention. Non-limiting exemplary Probiotics suitable for use in the methods of the invention, include, for example, *Bifidobacteria* sp, *Lactobacillus* sp., and *Bacteroides* sp. Probiotics may be delivered to a subject orally and/or rectally. Suitable vehicles for oral probiotic delivery include, but are not limited to, yoghurt and physiologic buffers.

The methods of the invention may further comprise the administration of agent(s) or treatment regimes, e.g., surgery, antibiotics, anti-inflammatory agents, probiotics, prebiotics, etc., that are effective in treating ulcerative colitis. Preferred agent(s) and/or treatments are those which are art recognized and are routinely used to treat ulcerative colitis.

In another embodiment, the methods of the invention further comprise administering a 5-aminosalicylic acid (5-ASA) compound to a subject. In one embodiment, the 5-aminosalicylic acid (5-ASA) compound is selected from the group consisting of Sulfasalazine, Olsalazine, Mesalamine.

In another embodiment, the methods of the invention further comprise administering a corticosteroid, e.g., prednisone, cyclosporine, tacrolimus, to a subject.

In another embodiment, the methods of the invention further comprise administering a humanized anti-integrin-alpha4beta7 antibody to a subject.

In one embodiment, the methods of the invention further comprise administering regulatory T cells to a subject. Regulatory T cells can be isolated from a population of cells obtained from the subject and expanded by standard methods. For example, peripheral blood mononuclear cells (PBMCs) can be obtained from the subject, e.g., by luekopheresis, and isolated by density gradient centrifugation, e.g., with Ficoll/Hypaque. Regulatory T cells can be enriched for example, by positive selection using antibodies to regulatory T cell surface markers, such as CD4, CD25, the $\alpha$ chain of the interleukin 2 receptor (IL-2R), and/or CD62L or other appropriate markers, such as the transcription factor Foxp3, for example, by incubating cells with a specific primary monoclonal antibody (mAb), followed by isolation of cells that bind the mAb using magnetic beads coated with a secondary antibody that binds the primary mAb. Regulatory T cells can also be isolated by automated magnetic cell sorter or by fluorescence activated cell sorting according to standard methods. Isolated regulatory T cells can be expanded in culture by incubating the cells in the presence of, for example, anti-CD3 and/or anti-CD28 monoclonal antibody coated beads or coated plates. Such in vitro expanded populations of regulatory T cells can be readministered to the subject. See, e.g., WO04112835A3, U.S. Pat. No. 6,746,670, US20070166307A, and U.S. Pat. No. 6,759,035.

2. Treatment and/or Prevention of Colon Cancer

As described herein, an antibiotic and/or probiotic is useful in treating and/or preventing colon cancer in a subject that would benefit from increased T-bet activity. The methods of the invention generally involve administering to the subject an antibiotic and/or a prebiotic in an amount sufficient to effect a desired result, e.g., preventing and/or treating colon cancer in a subject. An amount sufficient to achieve a desired result, also includes, but is not limited to, for example, an amount that ameliorates disease, stabilizes a patient, prevents or delays the development of or progression of disease in a patient, decreases the type and/or number of symptoms associated with the disease. An effective amount can be determined based on one administration or repeated administration.

Methods of detection and measurement of the indicators above are known to those of skill in the art. Such methods include, but are not limited to, determination of tumor burden, determination of tumor size, determination of tumor volume, determination of proliferation of secondary tumors, expression of genes in tumor tissue, presence of biomarkers, lymph node involvement, histologic grade, and nuclear grade.

Any antibiotic or combination of antibiotics used by one of skill in the art to treat ulcerative colitis is suitable for use with the methods of the invention. Non-limiting example include, vancomycin, metronidazole, neomycin, Ciprofloxacin, and ampicillin. In one embodiment, the antibiotic is Metronidazole. In another embodiment, the antibiotic is Ciprofloxacin.

Any probiotic, i.e., beneficial nonpathologic bacteria that are functionally defined by their ability to reduce inflammation when introduced into the inflamed intestine, of a subject (see, e.g., Sleator and Hill (2007) *Letts Applied Microbiol* 1-5, the contents of which is incorporated herein by reference), or combination of probiotics may be used in the methods of the invention. Non-limiting exemplary Probiotics suitable for use in the methods of the invention, include, for example, *Bifidobacteria* sp, *Lactobacillus* sp., and *Bacteroides* sp. Probiotics may be delivered to a subject orally and/or rectally. Suitable vehicles for oral probiotic delivery include, but are not limited to, yoghurt and physiologic buffers.

The methods of the invention may further comprise the administration of agent(s) or treatment regimes, e.g., surgery, radiation therapy, chemotherapy, etc., that are effective in treating and/or preventing colon cancer. Preferred agent(s) and/or treatments are those which are art recognized and are routinely used to treat a colon cancer.

In one embodiment, the methods of the invention further comprise administering regulatory T cells to a subject.

3. Prevention of Colonization of Colitogenic Bacteria

As described herein, an antibiotic and/or probiotic is useful in preventing colonization of a subject's gastrointestinal tract with commensal bacteria that cause ulcerative colitis in a subject that would benefit from increased T-bet activity. The methods of the invention generally involve administering to the subject an antibiotic and/or a prebiotic in an amount sufficient to effect a desired result, e.g., preventing colonization of a subject's gastrointestinal tract with commensal bacteria that cause ulcerative colitis and/or restore a desired balance to intestinal flora in a subject in a subject. An amount sufficient to achieve a desired result, also includes, but is not limited to, for example, an amount that decreases the amount of commensal anerobic bacteria in the colon of a subject, ameliorates ulcerative colitis and/or colon cancer (as described above), stabilizes a patient, prevents or delays the development of or progression of ulcerative colitis and/or colon cancer in a patient, decreases the type and/or number of symptoms associated with ulcerative colitis and/or colon cancer. An effective amount can be determined based on one administration or repeated administration.

Methods of detection and measurement of the indicators above are known to those of skill in the art. Such methods include, but are not limited to, an increase in tolerance to enteric commensal bacteria (Duchmann R, et al. (1995) Clin Exp Immunol 102: 448-455; Mow W S et al. (2004) Gastroenterology 126: 414-424), reduction in IL-1b, IL-6, TNF, IL-8, IL-8, IL-5, IL-13 levels and/or a decrease in the presence of commensal colonic bacteria.

Any antibiotic or combination of antibiotics used by one of skill in the art to treat ulcerative colitis is suitable for use with the methods of the invention. Non-limiting example include, vancomycin, metronidazole, neomycin, Ciprofloxacin, and ampicillin. In one embodiment, the antibiotic is Metronidazole. In another embodiment, the antibiotic is Ciprofloxacin.

Any probiotic, i.e., beneficial nonpathologic bacteria that are functionally defined by their ability to reduce inflammation when introduced into the inflamed intestine, of a subject (see, e.g., Sleator and Hill (2007) *Letts Applied Microbiol* 1-5, the contents of which is incorporated herein by reference), or combination of probiotics may be used in the methods of the invention. Non-limiting exemplary Probiotics suitable for use in the methods of the invention, include, for example, *Bifidobacteria* sp, *Lactobacillus* sp., and *Bacteroides* sp. Probiotics may be delivered to a subject orally and/or rectally. Suitable vehicles for oral probiotic delivery include, but are not limited to, yoghurt and physiologic buffers.

The methods of the invention may further comprise the administration of agent(s) or treatment regimes, e.g., surgery, antibiotics, anti-inflammatory agents, probiotics, prebiotics, etc., that are effective in treating ulcerative colitis. Preferred agent(s) and/or treatments are those which are art recognized and are routinely used to treat ulcerative colitis.

In another embodiment, the methods of the invention further comprise administering a corticosteroid, e.g., prednisone, cyclosporine, tacrolimus, to a subject.

In one embodiment, the methods of the invention further comprise administering regulatory T cells to a subject (as described above).

IV. Metabolic Profiling

Animals that have or are at risk for developing ulcerative colitis as described herein can be used as a source of biological samples (e.g., cell, tissue or body fluid samples) to generate a metabolic profile associated with ulcerative colitis or colorectal cancer or the propensity to develop ulcerative colitis or colorectal cancer.

Material suitable for use in such assays can be derived from a variety of sources. For example, nucleic acid molecules (e.g., mRNA or DNA, preferably genomic DNA) can be isolated from a cell from a living or deceased individual using standard methods. Cells can be obtained from biological samples, e.g., from tissue samples or from bodily fluid samples that contain cells, such as blood, urine, semen, or saliva. The term "biological sample" is intended to include tissues, cells and biological fluids containing cells which are isolated from an animal or subject, as well as tissues, cells and fluids present within an animal or subject.

Body samples may be obtained from an animal or subject by a variety of techniques known in the art including, for example, by the use of a biopsy or by scraping or swabbing an area or by using a needle to aspirate. Methods for collecting various body samples are well known in the art.

Tissue samples suitable for use in the methods of the invention may be fresh, frozen, or fixed according to methods known to one of skill in the art. In one embodiment, suitable tissue samples are sectioned and placed on a microscope slide for further analyses. In another embodiment, suitable solid samples, i.e., tissue samples, are solubilized and/or homogenized and subsequently analyzed as soluble extracts.

Methods of generating metabolic profiles are known in the art. Exemplary methods are described below:

A. Determining a Metabolic Profile

Metabolic profiles can be determined using a single technique for an intended use but may require the use of several different techniques for another intended use depending on such factors as the disease state involved, the types of small molecules present in a particular sample, the particular sample being assayed per se., etc.

The relevant information in a metabolic profile also may vary depending on the intended use of the compiled information. For example for some intended uses, the amounts of a particular molecule or a particular class of molecules may be relevant, but for other uses the distribution of types of molecules may be relevant. The ordinarily skilled artisan would be able to determine the appropriate metabolic profile for each method described herein by comparing metabolic profiles from diseased and/or test subjects with standard and/or healthy subjects. These comparisons can be made by individuals, e.g., visually, or can be made using software designed to make such comparisons, e.g., a software program may provide a secondary output which provides useful information to a user. For example, a software program can be used to confirm a profile or can be used to provide a readout when a comparison between profiles is not possible with a "naked eye". The selection of an appropriate software program, e.g., a pattern recognition software program, is within the ordinary skill of the art. It should be noted that the comparison of the profiles can be done both quantitatively and qualitatively.

The metabolic profiles can be obtained from an organism suffering from a disease state, genetic alteration, or any of the models discussed herein.

In one embodiment, HPLC columns equipped with colorometric array technology can be used to analyze biological samples, separate the compounds, and/or create metabolic profiles of the samples. Such HPLC columns have been used extensively in the past for serum, urine and tissue analysis and are suitable for metabolic small molecule analysis (Acworth et al., 300; Beal et al., J. Neurochem. 55, 1327-1339, 1990; Matson et al., Life Sci. 41, 905-908, 1987; Matson et al., Basic, Clinical and Therapeutic Aspects of Alzheimer's and Parkinson's Diseases, vol II, pp. 513-516, Plenum, N.Y. 1990; LeWitt et al., Neurology 42, 2111-2117, 1992; Milbury et al., J. Wildlife Manag., 1998; Ogawa et al., Neurology 42, 1702-1706, 1992; Beal et al., J. Neurol. Sci 108, 80-87, 1992, Matson et al., Clin. Chem. 30, 1477-1488, 1984; Milbury et al., Coulometric Electrode Array Detectors for HPLC, pp. 125-141, VSP International Science Publication; Acworth et al., Am. Lab 28, 33-38, 1996). HPLC columns equipped with coulometric arrays have been used for the simultaneous analysis of the majority of low-molecule weight, redox-active compounds in mitochondria. (Anal. Biochem. 263, 18-25, 1998).

For the detection and characterization of the metabolic small molecules in an effort to create comprehensive metabolic profiles, a multitude of detection methods can be used. These methods are described in more detail below.

1. Mass Spectroscopy (MS) Detectors:

The sample compound or molecule is ionized, it is passed through a mass analyzer, and the ion current is detected. There various methods for ionization. Examples of these methods of ionization include electron impact (EI) where an electric current or beam created under high electric potential is used to ionize the sample migrating off the column, chemical ionization utilizes ionized gas to remove electrons from the compounds eluting from the column; and fast atom bombardment where Xenon atoms are propelled at high speed in order to ionize the eluents from the column.

2. Pyrolysis Mass Spectrometry:

Pyrolysis is the thermal degradation of complex material in an inert atmosphere or vacuum. It causes molecules to cleave at their weakest points to produce smaller, volatile fragments called pyrolysate (Irwin 1982). Curie-point pyrolysis is a particularly reproducible and straightforward version of the technique, in which the sample, dried onto an appropriate metal is rapidly heated to the Curie-point of the metal. A mass spectrometer can then be used to separate the components of the pyrolysate on the basis of their mass-to-charge ratio to produce a pyrolysis mass spectrum (Meuzelaar et al 1982) which can then be used as a "chemical profile" or fingerprint of the complex material analyzed. The combined technique is known as pyrolysis mass spectrometry (PyMS).

3. Nuclear Magnetic Resonance (NMR) Detectors:

Certain nuclei with odd-numbered masses, including H and 13C, spin about an axis in a random fashion. When they are placed between poles of a strong magnet, the spins are aligned either parallel or anti-parallel to the magnetic field, with parallel orientation favored since it is slightly lower energy. The nuclei are then irradiated with electromagnetic radiation which is absorbed and places the parallel nuclei into a higher energy state where they become in resonance with radiation. Different spectra will be produced depending on the location of the H or 13C and on adjacent molecules or elements in the compound because all nuclei in molecules are surrounded by electron clouds which change the encompassing magnetic field and thereby alter the absorption frequency.

4. Refractive Index (RI):

In this method, detectors measure the ability of samples to bend or refract light. This property for each compound is called refractive index. For most RI detectors, light proceeds through a bi-modular flow to a photodetector. One channel of the flow-cell directs the mobile phase passing through the column while the other directs only the other directs only the mobile phase. Detection occurs when the light is bent due to samples eluting from the column, and is read as a disparity between the two channels. Laser based RI detectors have also become available.

5. Ultra-Violet (UV) Detectors:

In this method, detectors measure the ability of a sample to absorb light. This could be accomplished at a fixed wavelength usually 254 nm, or at variable wavelengths where one wavelength is measured at a time and a wide range is covered, alternatively Diode Array are capable of measuring a spectrum of wavelengths simultaneously. Sensitivity is in the $10^{-8}$ to $10^{-9}$ gm/ml range. Laser based absorbance or Fourier Transform methods have also been developed.

6. Fluorescent Detectors:

This method measure the ability of a compound to absorb then re-emit light at given wavelengths. Each compound has a characteristic fluorescence. Each compound has a characteristic fluorescence. The excitation source passes through the flow-cell to a photodetector while a monochromator measures the emission wavelengths. Sensitivity is $10^{-9}$ to $10^{-10}$ gm/ml. Laser based fluorescence detectors are also available.

7. Radiochemical Detection:

This method involves the use of radiolabeled material, for example, tritium ($^3$H) or carbon 14 ($^{14}$C). It operates by detection of fluorescence associated with beta-particle ionization, and it is most popular in metabolite research. The detector types include homogeneous method where addition of scintillation fluid to column effluent causes fluorescence, or heterogeneous detection where lithium silicate and fluorescence by caused by beta-particle emission interact with the detector cell. Sensitivity is $10^{-9}$ to $10^{-10}$ gm/ml.

8. Electrochemical Detection:

Detectors measure compounds that undergo oxidation or reduction reactions. Usually accomplished by measuring gains or loss of electrons from migration samples as they pass between electrodes at a given difference in electrical potential. Sensitivity of 10-12 to 10-13 gms/ml.

9. Light Scattering (LS) Detectors:

This method involves a source which emits a parallel beam of light. The beam of light strikes particles in solution, and some light is then reflected, absorbed, transmitted, or scattered. Two forms of LS detection may be used to measure transmission and scattering.

Nephelometry, defined as the measurement of light scattered by a particular solution. This method enables the detection of the portion of light scattered at a multitude of angles. The sensitivity depends on the absence of background light or scatter since the detection occurs at a black or null background. Turbidimetry, defined as the measure of the reduction of light transmitted due to particles in solution. It measures the light scatter as a decrease in the light that is transmitted through particulate solution. Therefore, it quantifies the residual light transmitted. Sensitivity of this method depends on the sensitivity of the machine employed, which can range from a simple spectrophotometer to a sophisticated discrete analyzer. Thus, the measurement of a decrease in transmitted light from a large signal of transmitted light is limited to the photometric accuracy and limitations of the instrument employed.

Near Infrared scattering detectors operate by scanning compounds in a spectrum from 700-1100 nm. Stretching and bending vibrations of particular chemical bonds in each molecule are detected at certain wavelengths. This is a fast growing method which offers several advantages; speed, simplicity of preparation of sample, multiple analyses from single spectrum and nonconsumption of the sample (McClure, 1994).

10. Fourier Transform Infrared Spectroscopy (FT-IR):

This method measures dominantly vibrations of functional groups and highly polar bonds. The generated fingerprints are made up of the vibrational features of all the sample components (Griffiths 1986). FT-IR spectrometers record the interaction of IR radiation with experimental samples, measuring the frequencies at which the sample absorbs the radiation and the intensities of the absorptions. Determining these frequencies allows identification of the samples chemical makeup, since chemical functional groups are known to absorb light at specific frequencies. Both quantitative and qualitative analysis are possible using the FT-IR detection method.

11. Dispersive Raman Spectroscopy:

Dispersive Raman Spectroscopy is a vibrational signature of a molecule or complex system. The origin of dispersive raman spectroscopy lies in the inelastic collisions between the molecules composing say the liquid and photons, which are the particles of light composing a light beam. The collision between the molecules and the photons leads to an exchange of energy with consequent change in energy and hence wavelength of the photon.

To create a metabolic profile biological samples are homogenized in standard ways known to those skilled in the art. Different fractionation procedures may be used to enrich the fractions for metabolic small molecules. The metabolic small molecules obtained will then be passed over several fractionation columns. The fractionation columns will employ a variety of detectors used in tandem or parallel to generate the metabolic profile for the biological sample.

For example, to generate a metabolic profile of water soluble molecules, the biological sample will be fractionated on HPLC columns with a water soluble array. The water soluble metabolic small molecules can then be detected using fluorescence or UV detectors to generate the metabolic profiles. Alternatively, electrochemical detectors can be used with diads to pick up redox active compounds and the absorbance of active compounds. For generating detecting non water soluble molecules, hydrophobic columns can also be used to generate metabolic profiles. In addition, gas chromatography combined with mass spectroscopy, liquid chromatography combined with mass spectroscopy, MALDI combined with mass spectroscopy, ion spray spectroscopy combined with mass spectroscopy, capillary electrophoresis, NMR and IR detection are among the many other combinations of separation and detection tools which can be used to generate metabolic profiles. The information generated by the metabolic profiles will be both qualitative and quantitative.

In another embodiment, a metabolic profile may be developed using a biological sample derived from a subject prior to the onset of ulcerative colitis, colorectal cancer, and/or colonization of a subject's gastrointestinal tract with commensal bacteria that cause ulcerative colitis. In another embodiment, a metabolic profile may be developed using a biological sample derived from a subject after the onset of ulcerative colitis, colorectal cancer, and/or colonization of a subject's gastrointestinal tract with commensal bacteria that cause ulcerative colitis.

Metabolic profiles from animals that have or are at risk of developing ulcerative colitis (e.g., a representative profile or a profile representing averages from a number of animals) are compared to those of normal animals (e.g. a representative profile or a mean profile) developed from normal animals. This comparison will reveal a profile or pattern of molecules associated with the disorder that is different from profiles obtained from normal animals. This pattern can then be used in methods of identifying dubjects that are at risk of developing ulcerative colitis and/or colorectal cancer.

V. Diagnostic and Prognostic Methods

The present invention also provides methods of determining whether or not a subject is at risk of developing ulcerative colitis or colorectal cancer. For example, the present invention provides methods of determining the predisposition of a subject to develop ulcerative colitis and colon cancer.

The present invention also provides methods of identifying a metabolic profile associated with the development and/or progression of ulcerative colitis and/or colorectal cancer. In such methods a biological sample derived from a subject, e.g., a subject that would benefit from increased T-bet activity or a genetically intact subject, is determined. This metabolic profile is compared to a standard profile derived from a control to thereby identify a subject at risk for development and/or progression of ulcerative colitis and/or colorectal cancer.

In one embodiment, a subject that would benefit from increased T-bet activity is a subject producing a T-bet protein having reduced activity or a subject producing a lower than normal or desirable level of T-bet protein, Such a subject may be one in which the amount of T-bet, e.g., the mRNA and/or protein level and/or activity of T-bet, is less than the level of T-bet as compared to a normal or control subject, and who is not at risk of or has not developed ulcerative colitis, colorectal cancer, and/or colonization of a subject's gastrointestinal tract with commensal bacteria that cause ulcerative colitis. In one embodiment, such a subject is identified by, e.g., genotyping, a sample from the subject for a polymorphism in the T-bet gene, e.g., a missense and/or nonsense SNP(s). In another embodiment, such a subject is identified by, e.g., phenotyping, a sample from a subject to determine the level of T-bet mRNA. In another embodiment, such a subject is identified by, e.g., phenotyping, a sample from a subject to determine the level of T-bet protein. In yet another embodiment, such a subject is identified by, e.g., phenotyping, a sample from a subject to determine the level of T-bet activity.

As used herein, the term "amount", with respect to T-bet present in a cell or sample refers to either (a) an absolute amount as measured in molecules, moles or weight per unit volume or cell or (b) a relative amount as designated, for example, by a numerical rating from 0 to 5.

The level or amount of T-bet in a cell or a sample derived from a subject is "altered" ("increased or decreased" or "higher or lower" than the normal level or amount of T-bet, if the amount of T-bet is greater or less, respectively, than the control amount by an amount that is greater than the standard error of the assay employed to assess the amount. The level or amount of T-bet in a cell or a sample derived from a subject can be considered "higher" or "lower" than the control amount if the difference in the control amount and the sample amount is at least about two, and preferably at least about three, four, or five times, higher or lower, respectively, than the standard error of control and sample measurements of T-bet.

The term "control level" or "control amount" of T-bet, refers to the level of T-bet in a cell or a sample derived from a subject not afflicted with or not at risk of developing ulcerative colitis, colorectal cancer, and/or colonization of a subject's gastrointestinal tract with commensal bacteria that cause ulcerative colitis. The "control level" may, for example, be determined by calculating the average level of T-bet present in cells or tissues that are known to express T-bet.

In general, it is preferable that the difference between the level of T-bet in a sample from a subject being treated for ulcerative colitis, colorectal cancer, and/or colonization of a subject's gastrointestinal tract with commensal bacteria that cause ulcerative colitis and the level of T-bet in control sample, is as great as possible. Although this difference can be as small as the limit of detection of the method for determining the level it is preferred that the difference be at least greater than the standard error of the assessment method, and preferably a difference of at least 2-, 3-, 4-, 5-, 6-, 7-, 8-, 9-, 10-, 15-, 20-, 25-, 100-, 500-, 1000-fold or greater than the standard error of the assessment method.

An alteration in the level of T-bet in control (e.g., non-ulcerative colitis, non-colorectal cancer) tissue can be assessed in a variety of ways. In one embodiment, the amount is assessed by assessing the level of T-bet in cells which appear to be, e.g., non-cancerous, non-colitogenic, and by comparing the foregoing normal level of T-bet with the amount of T-bet in the cells which are suspected of being, e.g., cancerous, colitogenic.

For example, when colonoscopy, laparoscopy or other medical procedure, reveals the presence of a tumor on one portion of an organ, the normal level of T-bet may be assessed using the non-affected portion of the organ, and this normal level may be compared with the level of T-bet in an affected portion (e.g., the tumor) of the organ.

Alternatively, and particularly as further information becomes available as a result of routine performance of the methods described herein, population-average values for "normal" level of T-bet may be used. In other embodiments, the "normal" level of T-bet may be determined by assessing the level of T-bet in a subject sample obtained from a non-ulcerative colitis, non-cancerous, non-commensal bacteria that cause ulcerative colitis colonized afflicted subject, from a subject sample obtained from a subject before the suspected onset of, e.g., cancer, in the subject, from archived subject samples, and the like.

A "higher level of expression and/or activity" of T-bet refers to an expression level and/or activity in a test sample that is greater than the standard error of the assay employed to assess expression and/or activity, and is preferably at least twice, and more preferably three, four, five or ten or more times the expression level and/or activity of T-bet in a control sample (e.g., a sample from a healthy subject not afflicted with or not at risk of developing ulcerative colitis, colorectal cancer, and/or colonization of a subject's gastrointestinal tract with commensal bacteria that cause ulcerative colitis) and preferably, the average expression level and/or activity of T-bet in several control samples.

A "lower level of expression and/or activity" of T-bet refers to an expression level and/or activity in a test sample that is greater than the standard error of the assay employed to assess expression and/or activity, but is preferably at least twice, and more preferably three, four, five or ten or more times less than the expression level of T-bet in a control sample (e.g., a sample that has been calibrated directly or indirectly against a panel of gastrointestinal or breast cancers with follow-up information which serve as a validation standard for prognostic ability of the She proteins) and preferably, the average expression level and/or activity of T-bet in several control samples.

As used herein, "control" refers to a level which is found in a normal subject or a group of subjects. As used herein, a "known standard" is a sample that contains a known level of a given molecule, e.g., T-bet. Such a known standard may be a positive or negative control. Reagents for generating a known standard include, without limitation, biological samples, e.g., cells, e.g., dendritic cells, from a subject who does not have or is not at risk of developing ulcerative colitis, colorectal cancer, and/or colonization of a subject's gastrointestinal tract with commensal bacteria that cause ulcerative colitis.

In one embodiment, the control or standard profile is an average of many samples obtained from more than one subject.

Such profiles may also be used for diagnostic, prognostic and for monitoring of clinical trial purposes.

The methods of the present invention can be practiced in conjunction with other methods used by the skilled practitioner to prognose and/or diagnose ulcerative colitis, colorectal cancer, and/or colonization of a subject's gastrointestinal tract with commensal bacteria that cause ulcerative colitis. For example, the methods of the invention may be performed in conjunction with a biochemical, morphological or cytological analysis of the sample obtained from the subject.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

This invention is further illustrated by the following examples, which should not be construed as limiting. The contents of all references, patents and published patent applications cited throughout this application are hereby incorporated by reference. Additionally, all nucleotide and amino acid sequences deposited in public databases referred to herein are also hereby incorporated by reference.

EXAMPLES

The Following Materials and Methods were Used in Examples 1-8
Generation of T-Bet−/−xRAG2−/− (TRUC) Mice, T-Bet/−x RAG2−/−xTNFR1/p55−/− Mice, and Cross-Fostering All animals were housed in microisolator cages in the barrier facility of the Harvard School of Public Health. All animal studies were carried out according to institutional and National Institutes of Health guidelines for animal use and care. All animals in the colony are specific pathogen free and are negative for *Helicobacter* hepaticus, bilis, and mwidarum.

The generation of mice with deletion of T-bet and RAG2 has been described (Lugo-Villarino et al. (2005) Proc Natl Acad Sci USA. 102(37):13248-13253).

TNFR1p55−/− mice were bred to TRUC knock-out mice. Triple heterozygote mice were generated and then bred to each other to generate triple homozygote knock-out mice. Genotyping has been described elsewhere: T-bet−/− (Szabo, S. J., et al. (2002). Science 295, 338-342), RAG2−/− (Horton, R. M., et al. (1995). Biotechniques 19, 690-691), and TNFR1p55−/− (Komatsu, M., et al. (2003). Blood 101, 3991-3999). For cross-fostering, on the day of birth the mother was removed from the cage where she had birthed her litter and placed in a freshly changed cage with the litter she would cross-foster. Pups were weaned between day 21-28.

For studies of the progeny of antibiotic treated animals, progeny were weaned at 21 days and examined six weeks after weaning. These animals had no exposure to antibiotics after weaning.

Histology

Colons were removed from euthanized mice and dissected free from the anus to distal to the cecum. Colonic contents were removed and colons were cleaned with phosphate buffer saline or Hanks' balanced salt solution prior to fixation in 4% PFA or 10% neutral buffered formalin (NBF) followed by routine paraffin embedding. After paraffin embedding, 0.5 micron sections were cut and stained with hematoxylin and eosin or as noted.

Sections were examined and the degree of colitis was blindly scored. Each of four histologic parameters were scored as absent (0), mild (1), moderate (2), or severe (3): mononuclear cell infiltraton, polymorphonuclear cell infiltration, epithelial hyperplasia, and epithelial injury, similar to previous studies (Neurath et al., 2002b). Colons from dextran sodium sulfate treated mice were scored using the following parameters scored on a scale of 0-4: percentage of colon involved by inflammation, percentage of crypt loss, presence of lymphoid follicles, edema, erosions, and density of inflammatory cells. The scores for the individual parameters were summed to give a total severity score.

Barrier Function Assay

Fluorescein-dextran, molecular weight 3000, was purchased from Invitrogen, Molecular Probes. Food was held for 12 hrs, a PBS enema was give 30 minutes prior to injection, and mice were sedated with ketamine and xylazine. Dextran (0.6 mg/gram mouse-weight) was delivered per rectum using a 3.5 Fr pediatric umbilical vein catheter. Mice were inverted for three minutes after injection to prevent retrograde flow. Blood samples were obtained via the tail vein prior to injection and at the indicated time points. Serum samples were prepared from the whole blood and mean fluorescence intensity was measured in a fluorimeter. Individual serum preinjection mean fluorescence intensity was used as the blank for each animal's sample. The mice were sacrificed at the conclusion of the experiment. Four-six animals were used per group and the experiment was repeated three times.

Preparation of Samples for Electron Microscopy

Colons were removed from wild type, T-bet−/−, RAG2−/−, and TRUC genotypes from one through 12 weeks of age. Colons were dissected as described above and the distal end was ligated prior to injection with fixative (2.5% glutaraldehyde, 2.5% formaldehyde and 0.02% picric acid in 0.1M sodium cacodylate buffer) and then ligated proximally. The whole colons were then immersed in the same fixative for at least 2 hours before further processing. Desired regions were dissected out, cut into 1 to 2 mm pieces, and after several rinses in distilled water osmicated in a mixture of 1% osmium tetroxide in 1.5% potassium ferrocyanide for 2 hours. After thorough rinses in water, the specimens were treated with 1% uranyl acetate in maleate buffer at pH 5.2 and rinsed again in water. All of these fixation steps were at room temperature. The subsequent dehydration steps were initiated in cold 50% and 95% ethanol and followed by dehydration in absolute ethanol at room temperature. After three changes in propylene oxide the specimens were embedded in Epon and polymerized at 60° C. Blocks were sectioned at 0.5 microns and stained with toluidine blue for light microscopy and appropriate thin sections were picked up on uncoated grids and stained with a mixture of saturated aqueous uranyl acetate and acetone followed by lead citrate staining. Thin sections were examined with a JEOL 1200 electron microscope.

Antibodies

Antibodies were obtained from BD Pharmingen unless otherwise noted: anti-B220/CD45R(RA3-6B2), anti-CD11c (HL3), anti-CD11b (M1/70), anti-MHC class II (AF6-120.1 and 39-10-8), anti-CD45 (30-F11), anti-Gr-1 (from eBiosciences), anti-F4/80(BM8 from eBiosciences), anti-CD8 (53-6.7), anti-CD49b (DX5) anti-CD4(RM4-5), anti-CD3 (DAKO cat #AO452), anti-S100 (Dako Inc.), anti-CD62L (MEL-14), and anti-CD25(PC61).

Immunohistochemistry

Immunostaining for T-bet was performed on paraformaldehyde-fixed paraffin-embedded tissue sections following microwave antigen retrieval in 1 uMEDTA, pH 8.0, with the previously described anti-T-bet monoclonal antibody (4B10; see, e.g., Szabo, S. J., et al. (2000). Cell 100, 655-669) using a standard indirect avidin-biotin horseradish peroxidase (HRP) method and diaminobenzidine (DAB) color development (Dorfinan, D. M., et al. (2003). Am J Clin Pathol 120, 866-873). T-bet staining was previously compared with that of mouse IgG isotype control antibody diluted to identical protein concentration for samples studied to confirm staining specificity (Dorfinan, D. M., et al. (2003). Am J Clin Pathol 120, 866-873). For double staining of human colonic biopsies with T-bet and S100(Dako Inc). T-bet staining was as above and in addition sections were also stained with goat anti-rabbit biotin, then by ABC-Alkaline-Phosphate (Vector Laboratories, Inc), followed by substrate, and then counterstained with 1% methyl green. For CD11c immunohistochemistry, antigen retrieval was performed with trypsin. Biotinylated anti-CD11c was employed followed by incubation with avidin-biotin-HRP with color development with DAB.

For immunofluorescence staining of colonic leukocytes, sections were stained with anti-CD3 and biotin anti-CD11c. CD3 staining was visualized using goat anti-rabbit-HRP, FITC-tyramide, followed by anti-FITC-Alexa 488 (Invitrogen, Molecular Probes). CD11c staining was visualized using streptavidin-HRP(NEN Life Science Products Inc., Boston, Mass., USA), biotin-tyramide(NEN Life Science Products Inc.), and streptavidin-Alexa 594 (Invitrogen, Molecular Probes) as the final fluorochrome. Sections were counterstained with DAPI (Sigma-Aldrich), viewed with an Olympus B40 microscope, and digitally photographed. Composites were assembled in Adobe Photoshop (Adobe Systems Inc., San Jose, Calif., USA).

TUNEL staining on the designated paraffin embedded tissues was performed using the fluorescein in situ cell death detection kit from Roche.

Anti-Cytokine Therapy

Anti-TNF-a (clone TN3-19.12), a hamster anti-mouse TNF-alpha neutralizing IgGl, and, control antibody, hamster anti-GST IgG were purchased from Leinco Technologies, Inc. TN3-19.12 or control were given intra-peritoneally at a dose of 15 microgram/gm mouse weight every seven days for four weeks. Animals were sacrificed one week following their last injection Colon Explant Culture Explant cultures were carried out following a modification of previously described procedures (Rakoff-Nahoum, S., et al. (2004). Cell 118, 229-241). 1 cm segments of the colon were washed in HBBS containing penicillin, streptomycin, and gentamicin. The segments were then cultured in 24 well flat bottom plates with RPMI media supplemented with penicillin, streptomycin, and gentamicin. The media was collected after 4 hrs and centrifuged to remove debris. After centrifugation the supernatant was aliquoted and stored at −80° C.

Measurement of Cytokines

Cytokines were measured in culture supernatants utilizing SearchLight high dynamic range (HDR) imaging and analysis. For TNF-a, the mouse BD OptEIA ELISA kit was used as per the manufacturer's instructions. Protein determinations were made of the supernatants to calculate the cytokine concentration of the supernatant in pg/mg.

Isolation of Colonic DCs for Flow Cytometry and Intracytoplasmic Cytokine Staining Mononuclear cells were isolated from the colon as has been previously described with modifications as noted (Camerini, V., et al. (1993). J Immunol 151, 1765-1776). In brief, colons were isolated, and the colonic contents were removed. The colons were opened vertically and washed with HBBS prior to being finely minced. Cell suspensions were generated using digestion with collagenase and dispase. Filtered single cell suspension were layered on to a Percoll gradient and the 30%/70% Percoll interface, enriched for mononuclear cells, was harvested.

Methods for flow cytometry and intra-cytoplasmic cytokine staining of colonic leukocytes are as described previously with modifications noted (Rigby, R. J., et al. (2005). Clin Exp Immunol 139, 245-256). In brief, cells were washed, suspended in PBS with 1% FBS and 2 mM EDTA, and incubated with Fc block (CD16/CD32) prior to staining. After cell surface labeling to identify the leukocyte sub-populations present, cells were fixed in 4% PFA, and then permeabilized with 0.05% saponin. Cells were stained with phycoerythrin-conjugated antibodies directed against TNF-alpha and the appropriate phycoerythrin-conjugated isotype controls in parallel. For flow cytometry experiments, samples were acquired using a Becton Dickinson LSR11 and data were analyzed using FACS Diva software. For colonic DCs, acquisition gates were constructed such that an equal number of CD11c+ class 11+ cells were collected from RAG2−/− and TRUC samples. Cell sorting was performed using a FACS Aria II.

Bone Marrow Dendritic Cell Culture

Bone marrow derived DCs were generated as previously described with the following modification: MACS bead depletion for MHC class II, CD8, CD4, and B220 was employed in lieu of hybridoma supernatant and complement mediated lysis and cells were cultured in the presence of GM-CSF (Inaba, K., et al. (1992). J Exp Med 176, 1693-1702).

Human Myeloid Dendritic Cells

CD14+ cells were isolated from pooled human buffy coats and cultured in GM-CSF and IL-4 as has been previously described (Sallusto, F., and Lanzavecchia, A. (1994). J Exp Med 179, 1109-1118).

Chromatin Immunoprecipitation and Real Time PCR Quantitation 20 million DCs, harvested on day 6 and then treated with mechanical disruption followed by LPS100 ng/ml for 24-30 hrs and IFNg 20 ng/mL, were used per immunoprecipitation reaction. 1/10 volume of fixative solution was added to the non-adherent mature DCs (11% Formaldehyde, 100 mM NaCl, 1 mM EDTA pH 8.0, 1 mM EGTA pH 8.0, 50 mM HEPES, pH 7.5). The cells were fixed for 30 minutes at room temperature for immunoprecipitation with a T-bet rabbit polyclonal antibody, commercially available from, for example, Abcam, Inc., MA. With the following exceptions, chromatin immunoprecipitations were performed as described in Ansel et al ((2006) Annu Rev Immunol. 24:607-56). Cells were sonicated on ice with a Kontes ultrasonicator set to 50% output for eight sonications (20 seconds on, 1 minute off). The Qiagen MinElute PCR purification kit was used to clean up the DNA samples. 1/20 volume of the ChIP sample was used per real time reaction. Real time PCR products were submitted to agarose gel electrophoresis using SyBR gold dye (Invitrogen, Molecular Probes) to verify amplification of products of the correct size. The sequences of the primers for quantitative real time PCR (qPCR) amplification were as follows: Primer Set B: forward primer TGGCGAGAGAATTAGATGTGGGTG and reverse primer TGCTCCTCATGTCTCTTTGCTCTG; Primer Set A: forward primer AGAAGGCTTGTGAGGTCCGTGAAT and reverse primer GTGCTTCTGAAAGCTGGGTGCATA. The Ensembl transcript ID # for the mouse TNF-α gene is ENSMUST00000025263. (3-actin genomic primers: forward primer: GGGATGTTTGCTCCAACCAA and reverse primer: GGCGCTTTTGACTCAGGATT. Primer sequences for the human TNF-α promoter are: forward primerCAGGCCTCAGGACTCAACACA reverse primer GCTGAGTCCTTGAGGGAGAGAA. qPCR reactions were carried out in an ABI Prism 7700 Sequencer Detector using SYBR green reagents as per standard protocols.

Broad Spectrum Antibiotic Treatment of TRUC Colitis

Mice were treated as described previously (Fagarasan, S., et al. (2002). Science 298, 1424-1427; Rakoff-Nahoum, S., et al. (2004). Cell 118, 229-241). Alterations are as noted: in brief, animals were provided ampicillin (1 g/L; Roche), vancomycin (1 gm/L; Henry Schein, Inc. (Hospira, Inc.)), neomycin sulfate (1 g/L; Sigma (Teva Pharmaceuticals)), and metronidazole (1 g/L; Sigma) dissolved in their autoclaved drinking water and their fluid intake was monitored. The duration of antibiotic treatment was six weeks.

Bacterial Culture

Bacteria culture methods were performed as described previously (Rakoff-Nahoum, S., et al. (2004). Cell 118, 229-241). In brief, fecal matter was obtained using sterile technique and weighed. Samples were placed in 15 ml tubes with thyoglycolate and vortexed. Contents were diluted and plated on universal and differential media for the growth of anaerobes and aerobes. After 48 hours for aerobes and 72 hrs for anaerobes at 37C, colonies were counted. Anaerobic cultures were grown in anaerobic chambers.

Adoptive Transfer Experiments

Peripheral lymph nodes were harvested and single cell suspension generated. Cells were depleted of CD8+, CD11c+, B220+, Ter-119+, DX5+, MHC class11+populations using MACS beads depletion. This enriched cell population was stained with anti-CD4 (clone RM4-5), anti-CD62L(clone MEL-14), and anti-CD25 (clone PC61) and subjected to fluorescence activated cell sorting. CD4+, CD62L hi, and CD25 positive and negative populations were collected. After collection cells were resuspended in PBS. 75,000 CD4+CD62L+CD25+ were injected per animal. $1\times10^6$ CD4+CD62L+CD25− cells were injected per animal as noted. For B cell adoptive transfer, splenic B cells were purified using MACS positive selection and $1\times10^6$ CD19+ were resuspended in PBS and injected per animals. After four weeks, animals were sacrificed and their colons were submitted to histologic analysis as described with the exception of mice who received the naive T cells or B cell adoptive transfers which were sacrificed at two weeks post-injection secondary to morbidity. Sham injected animals were injected with PBS.

Statistical Analysis

Statistical analysis was performed using the unpaired Student's t-test. Error bars represent standard deviations.

Example 1

Figure 1B:
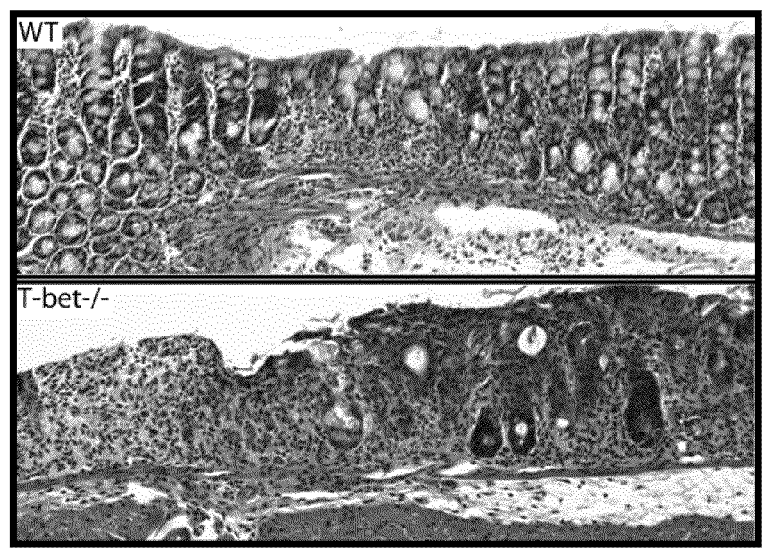

T-bet Expression Protects Against Colitis and T-bet−/−×RAG2−/− Mice Develop Spontaneous Colitis Dextran sodium sulfate (DSS) is a sulfated polysaccharide that induces colitis when administered orally because of direct toxicity for mucosal epithelium (Kitajima, S., et al. (1999). Exp Anim 48, 137-143). Mice lacking T-bet developed more severe colitis upon DSS administration than wild-type (WT) mice as evidenced by histology (FIGS. 1A and B). Specifically, colons from T-bet−/− mice displayed a more extensive and severe inflammatory infiltrate, containing both neutrophils and mononuclear cells, as well as more lymphoid aggregates. There was also more edema and mucosal damage in T-bet−/− colons, evidenced by the presence of more extensive ulceration and crypt loss (FIG. 1B). This observation was unexpected as short term treatment with DSS is considered a Type 1 model of colitis since type 1 cytokines, IFNg, IL-12, IL-1 and TNF-a, mediate colonic inflammation (Egger, B., et al. (2000). Digestion 62, 240-248). T-bet deficient T cells produce a so-called Type 2 cytokine profile characterized by overproduction of cytokines IL-4, IL-5, and IL-10 thought to be protective in the setting of most T cell-driven colitis models (Powrie, F., et al. (1993). Int Immunol 5, 1461-1471; Szabo, S. J., et al. (2002). Science 295, 338-342). Indeed, it had been earlier reported that T-bet deficiency is protective against the T cell adoptive transfer SCID model of colitis, which typically produces a Type 1 response (Neurath, M. F., et al. (2002b). J Exp Med 195, 1129-1143). Hence, it was reasoned that loss of T-bet in non-T cells, particularly non-adaptive immune system cells, might be responsible for the increased susceptibility to DSS-mediated colitis that was observed.

Figure 1C:
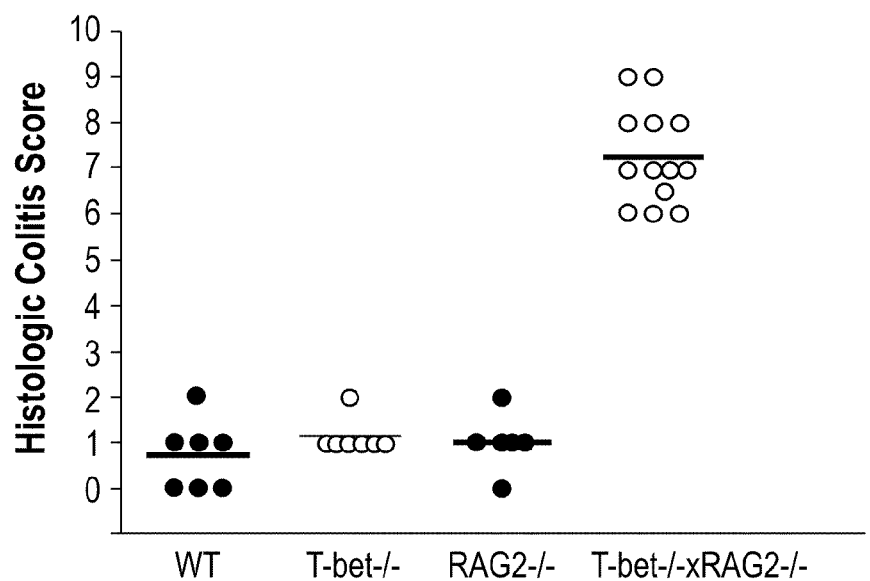
Figure 1D:
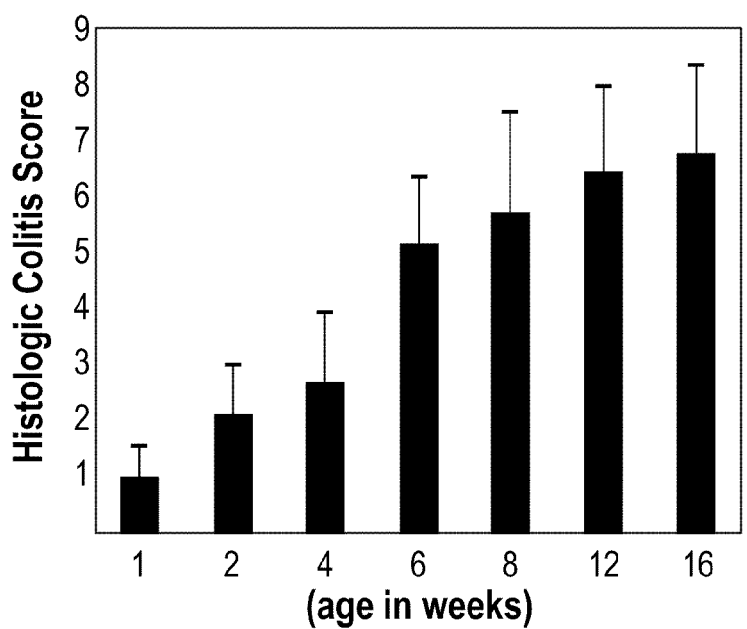

To more clearly delineate the role of T-bet in the innate immune system, T-bet−/− mice bred onto the RAG2−/− background, a strain which lacks T and B lymphocytes were examined. A histologic survey of the gastrointestinal tracts of the double deficient T-bet-/-xRAG2-/-, as compared to the single deficient RAG2-/-, T-bet-/-, and WT mouse strains in our colony revealed that the T-bet-/-xRAG2-/- mice spontaneously developed a highly penetrant and severe colitis (FIG. 1C). This colitis was apparent by four weeks of age and increased in severity over time (FIG. 1D). Of note, these animals are housed in a barrier facility that is documented to be free of known colitogenic pathogens such as *Helicobacter hepaticus*, bilis, and muridarum.

Example 2

Figure 2A:
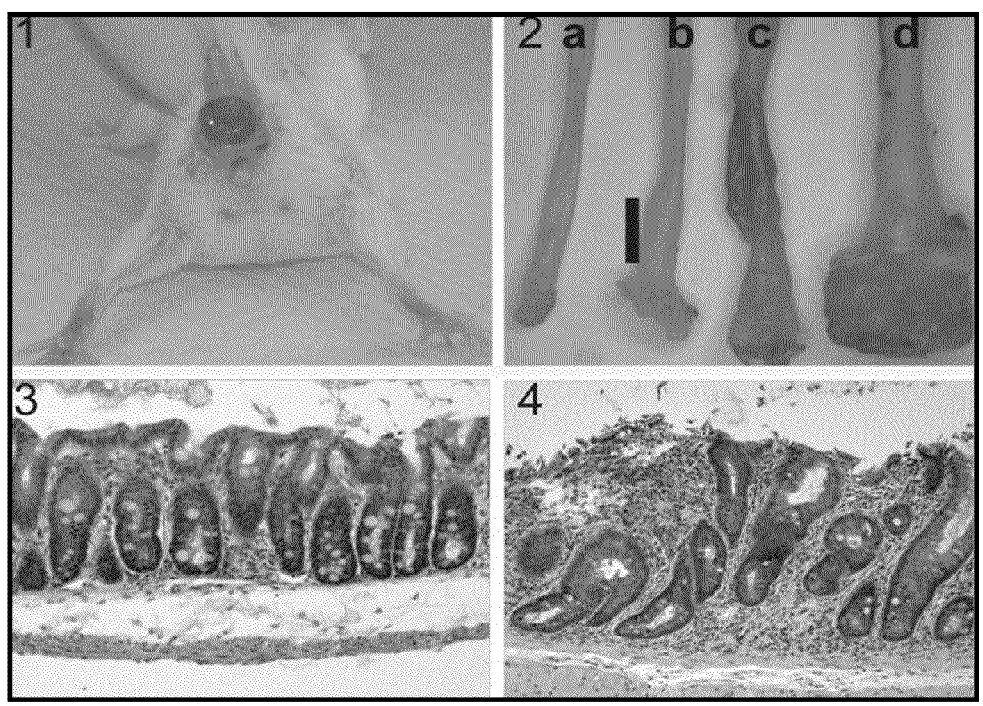
FIG. 2 shows that spontaneous colitis in TRUC mice phenocopies human ulcerative colitis and is characterized by a colonic epithelial barrier breach. (A) (1) TRUC mouse (eight weeks old) with anorectal prolapse. (2) Photograph of distal colons from RAG2−/− four weeks (a) and eight weeks (c) and from TRUC four weeks (b) and eight weeks (d) (anorectal junction at bottom). A solid vertical bar delineates the inflamed and thickened colonic wall appreciable at four weeks of age. Marked colonic wall thickening associated with prolapsed rectal mucosa is apparent in the eight week old TRUC mouse. (3) Normal colonic mucosa from a six-week old RAG2−/− mouse, 100×. (4) Representative disease from a six-week old TRUC mouse. Note mucosal thickening, surface ulceration, crypt distortion and hyperplasia, and a dense mixed inflammatory cell infiltrate in the lamina propria (compare to panel 3), 100×. (B)Increased permeability of the TRUC colonic epithelium precedes histologic colitis. Intrarectal FITC-dextran was administered to 3.5 week old T-bet−/−, RAG2−/−, and TRUC mice and their serum fluorescence was measured at the indicated time points. One representative experiment of three is shown with four-six mice per group, [p=0.0002, 60 min TRUC vs RAG2−/−]. (C) Colonic epithelial permeability increases with time. Intrarectal FITC-dextran was given to TRUC mice at four, five, and six weeks of age and their serum fluorescence measured at the indicated time points, [p=0.0036 60 min six vs five weeks]. One representative experiment of three is shown with five mice per group. The increased colonic epithelial permeability does not result from gross abnormalities in epithelial cell tight junctions. (D) The tight junctions from TRUC colons were surveyed by electron microscopy: representative images are shown from prior to two weeks (1), three weeks (2), and four weeks (3), 25,000×. (E) There are numerous colonic epithelial discontinuities present in the TRUC mice at 3.5 weeks of age. Representative electron microscopic images are shown, (1) 800× (2)1500× (3)1000× (4) 3000×. (F) There is increased apoptosis in the colonic epithelium of TRUC mice. Representative images of the colonic epithelium from WT, T-bet−/−, RAG2−/−, and TRUC mice at five weeks of age stained with DAPI (dark grey) and TUNEL (light grey), 200×. (G) Epithelial crypts and the number of TUNEL+ cells were counted across all the genotypes. Five slides were generated from each genotype group (two-three mice per genotype). A minimum of 500 crypts per genotype were scored. (H) There is increased apoptosis in the colonic epithelium of TRUC mice. TUNEL+ cells and the number of epithelial cells per crypt were counted across all four genotypes. Five slides were generated from each genotype group (two-three mice per genotype). Areas of the large bowel were randomly selected and epithelial cells, epithelial crypts, and TUNEL+ epithelial cells were counted. A minimum of 500 crypts per genotype were scored.
Figure 2B:
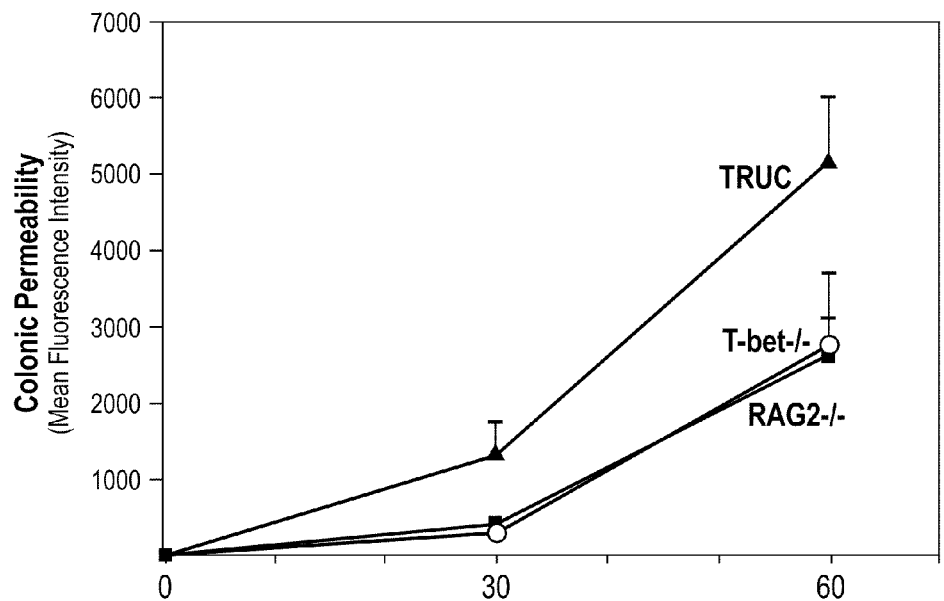
Figure 2C:
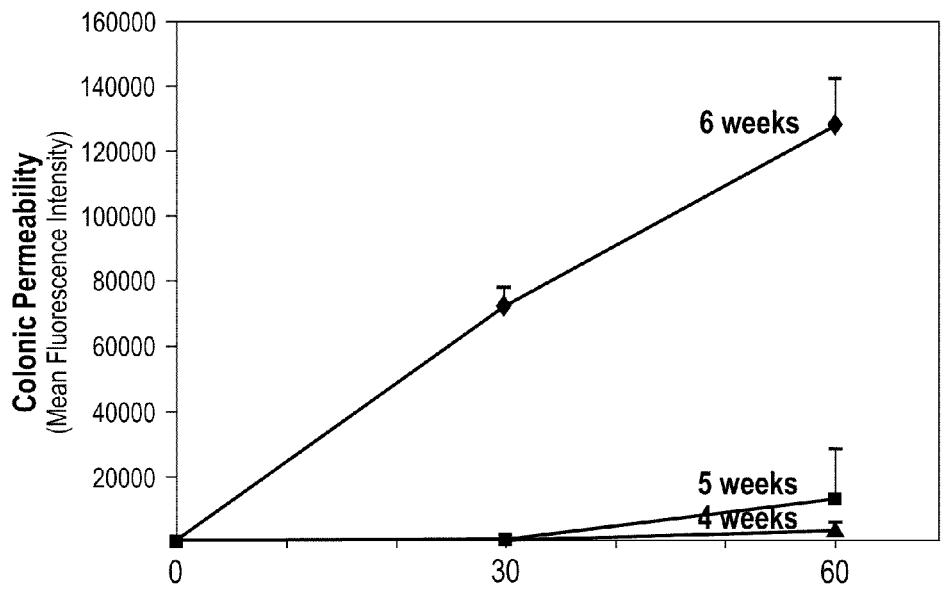
Figure 2D:
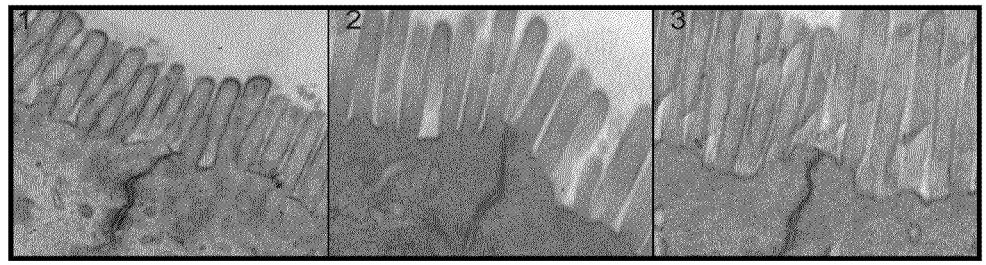
Figure 2E:
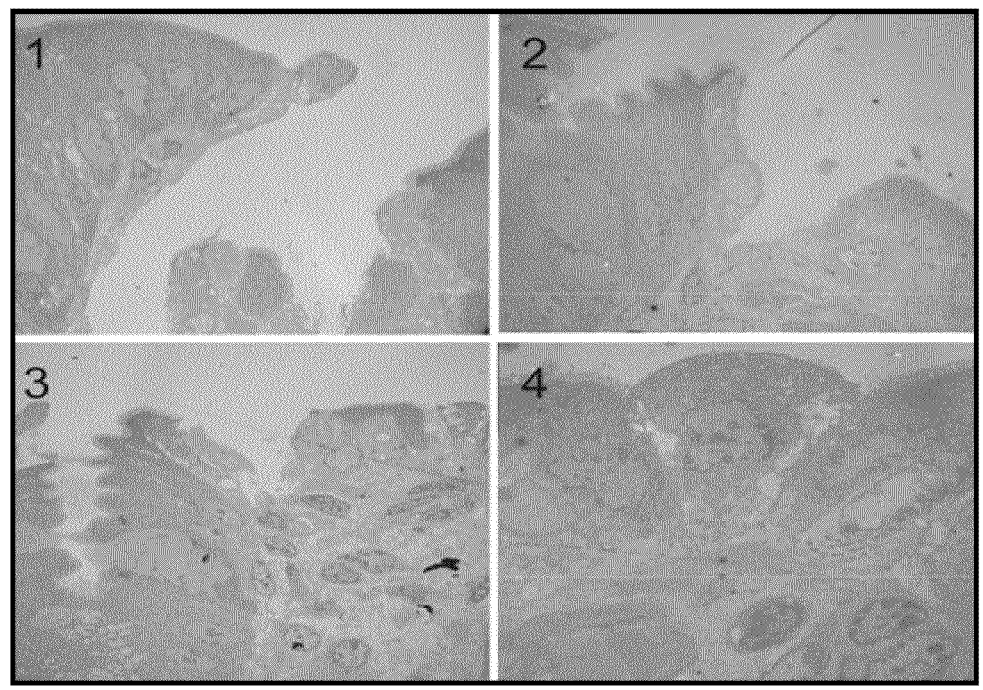

Spontaneous Colitis in TRUC Mice Phenocopies Human UC and is Characterized by an Early Colonic Epithelial Barrier Breach T-bet-/-xRAG2-/- mice develop a colitis that bears a striking resemblance to human UC (FIG. 2A). Inspection of T-bet-/-xRAG2-/- (herein referred to as TRUC [T-bet-/-x RAG-/- Ulcerative Colitis] mice is notable for the presence of anorectal prolapse (FIG. 2A 1), a consequence of rectal inflammation. Gross examination of TRUC colons demonstrated continuous inflammation of the rectum and left colon visible as early as four weeks of age (FIG. 2A 2b), as compared to an age matched RAG2-/-colon (FIG. 2A 2a). By eight weeks of age there was marked inflammation and colonic thickening in the TRUC mice (FIG. 2A 2d) but not in age matched RAG2-/- animals (FIG. 2A 2c). Microscopically, TRUC colitis phenocopies many aspects of human UC (FIG. 2A 4) with a mucosal mixed inflammatory infiltrate in the lamina propria containing both mononuclear and polymorphonuclear cells and neutrophil infiltration of the crypt and surface epithelium. Epithelial injury was present as evidenced by surface denudations/erosions and frank ulcerations associated with crypt distortion, crypt loss, and epithelial mucodepletion. The colonic epithelium in injured areas also showed marked regenerative changes, with crypt elongation, nuclear hyperchromasia, and increased mitotic activity. In addition, the stomach and small intestine appear grossly and microscopically normal, similar to UC but in contrast with Crohn's disease and most other spontaneous mouse models of colitis.

To gain insight into the early events in TRUC colitis, the affected mice were examined at time points starting from one week postnatally. Microscopically, there was no evidence of colitis until four weeks of age in the TRUC mice (FIG. 1D). To determine if there were discernable abnormalities in the colonic permeability that preceded the overt histologic evidence of colitis, the integrity of the colonic epithelial barrier in 3.5 week-old mice (the earliest age at which mice were able to survive the procedure) was tested, by instilling intra-rectal fluorescently-labeled dextran (MW 3000) and examining the rate at which the dye crossed into the serum over time (Karhausen, J., et al. (2004). J Clin Invest 114, 1098-1106). It was found that TRUC mice had significantly increased permeability compared to RAG2-/- and T-bet-/- mice (FIG. 2B). The TRUC mice had a two-fold higher serum fluorescence at 3.5 weeks ($p=0.0002$ TRUC vs RAG2-/-), and colonic permeability continued to increase with age, with a 3-fold increase between four and five weeks and an 8.6 fold increase between five and six weeks ($p=0.00036$) (FIG. 2C). Thus, a decrease in colonic epithelial integrity precedes histologically detectable colitis and worsens as the colitis progresses.

Several previous studies suggest a role for abnormal tight junctions in IBD pathogenesis it was determined whether the increased colonic permeability observed here was due to a defect in tight junctions (Bruewer, M., et al. (2006). Ann NY Acad Sci 1072, 242-252; Clayburgh, D. R., et al. (2004). Lab Invest 84, 282-291; Prasad, S., et al. (2005). Lab Invest 55, 1139-1162; Zeissig, S., et al. (2007). Gut 56, 61-72). Colonic mucosas from animals of all four genotypes (T-bet-/-, RAG2-/-, WT, and TRUC) at ages ranging from less than two weeks through twelve weeks were examined by electron microscopy. The epithelial junctions surveyed appeared ultrastructurally intact for all genotypes. Representative images are shown for TRUC mice (FIG. 2D) at two weeks of age (Panel 1), three weeks (Panel 2), and four weeks (Panel 3).

Figure 2F:
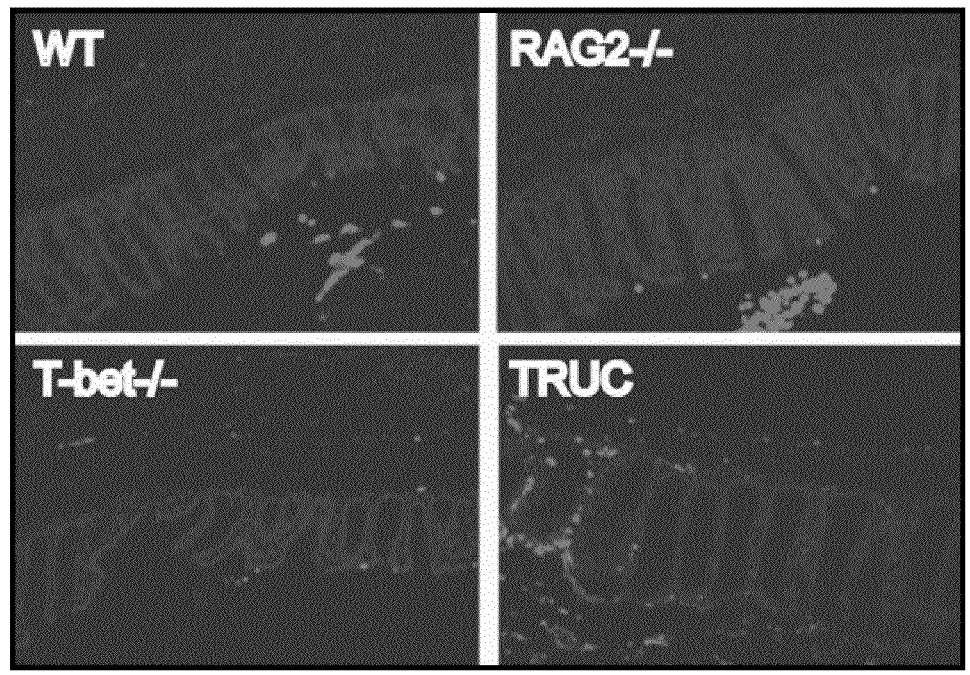
Figure 2G:
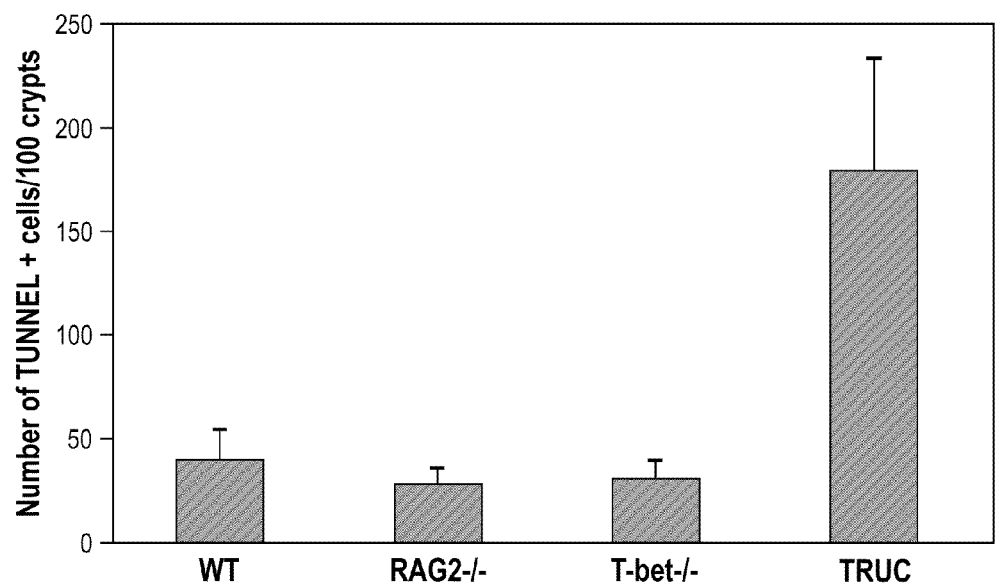

Numerous, large epithelial discontinuities were observable on electron micrographs by 3.5 weeks of age (FIG. 2E 1-4), which played a major role in the increased permeability. In addition, the degree of cell death was well above the intrinsic normal rate of epithelial turnover. Epithelial apoptosis was quantified by TUNEL staining colons of five week old mice—an age at which TRUC mice have developed a high degree of colonic permeability (FIG. 2C). While TUNEL+ cells were noted at the top of the crypts in all genotypes, TUNEL+ cells were distributed throughout the crypt in the TRUC mice and in many cases the entire crypt consisted of TUNEL+ cells (FIG. 2F). Quantitation of the number of TUNEL+ cells/100 crypts is shown for all four genotypes with the TRUC mice having 4-5 fold more TUNEL+ cells/ 100 crypt than all the other genotypes (FIG. 2G). This trend is accentuated if TUNEL+ cells/epithelial cells/crypt.

Example 3

TNF-alpha Drives Tissue Injury in TRUC Colitis and TNF-alphaover-production Maps to Colonic Dendritic Cells (DCS)

Figure 3A:
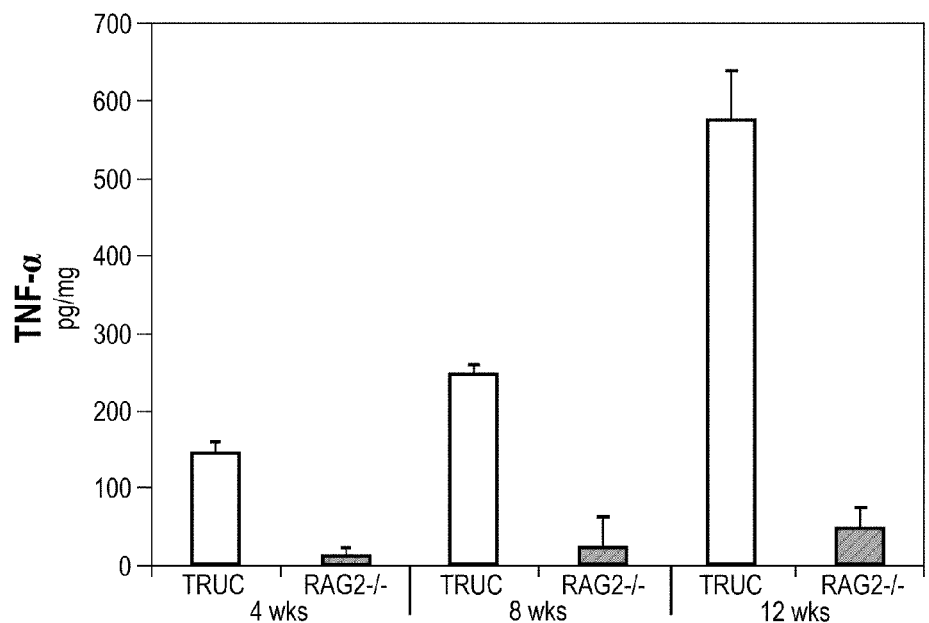
FIG. 3 shows that TNF-α drives tissue injury in TRUC colitis and TNF-α overproduction maps to colonic DCs. (A) TNF-alpha is increased in colon explant cultures from TRUC mice. ELISAs for TNF-α were performed on colon explant cultures from TRUC and RAG2−/− mice at four, eight, and twelve weeks of age. TRUC mice (open blocks) have consistently elevated levels of TNF-α as compared to RAG2−/− mice (shaded blocks). One representative experiment of three is shown with samples pooled from four mice per group. (B) The colonic cytokine milieu of non-TNF-α cytokines in TRUC mice is not markedly different from RAG2−/− mice. Colon explant cultures were performed on TRUC and RAG2−/− colons at four weeks of age. Supernatants were pooled from four animals per group and IL-23, IL-13, IL-12p40, IL-10, IL-6, IL-1a, IL-1b, and IFNg levels were measured. The data represent the mean of three independent experiments, error bars denote standard deviation. (C) Anti-TNF-α neutralizing antibody cures TRUC colitis. TRUC mice were treated with anti-mouse TNF-α antibody (clone TN3-19.12) or an isotype control for four weeks. Anti-TNF-α antibody treated TRUC mice had no evidence of colitis, p=0.0023. One representative experiment of three is shown with four mice per group. (D) Treatment with anti-TNF-α neutralizing antibody specifically decreased the number of apoptotic epithelial cells, p=0.0016. (E) TNF-α mediated epithelial apoptosis is a direct effect of TNF-α signaling through TNFR1/p55. TRUC×TNFR1/p55−/− mice sacrificed at 8 weeks show no histologic evidence of colitis. Age matched TRUC mice are shown for comparison, p<0.0001. Cell suspensions were generated from colonic tissue, stained with antibodies directed against cell surface markers, and permeabilized to allow for detection of intracytoplasmic TNF-α by flow cytometry. (F) CD45 (common leukocyte antigen) staining demonstrated that TNF-α was predominantly produced by immunocytes. Cells from RAG2−/− mice were used as staining controls throughout. Antibodies against Gr-1, F4/80, and CD11c paired with class II were used to identify the immunocyte population with the highest TNF-alpha production. (G) The highest levels of TNF-α staining mapped to the CD11c, MHC class II positive population. (H) Colonic DC production of TNF-α changes during the disease course of colitis and is elevated as early as two weeks of age. The mean and standard deviation of three independent experiments are plotted. Vertical bars denote the right-sided tail of the isotype control staining. Data are representative of three independent experiments and samples were pooled from 10-20 mice per group.
Figure 3B:
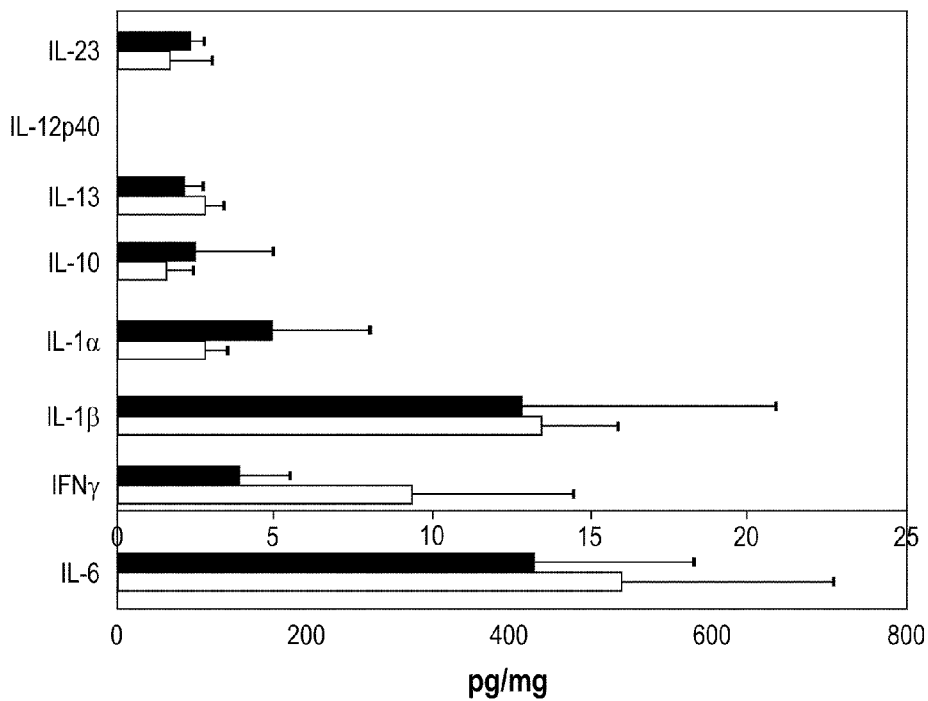
Figure 3C:
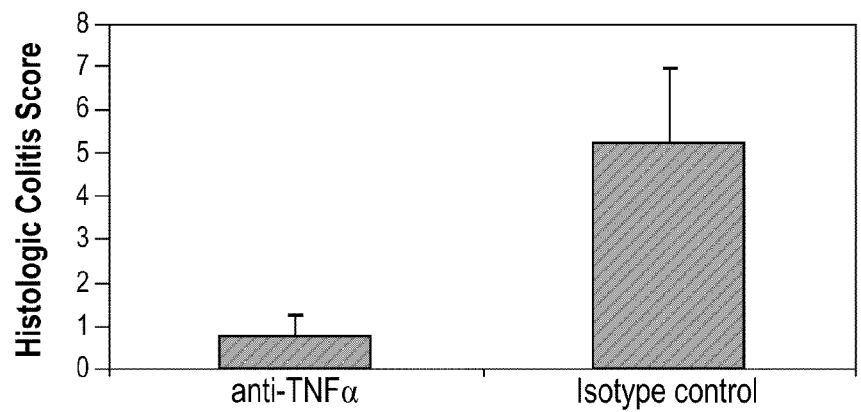
Figure 3D:
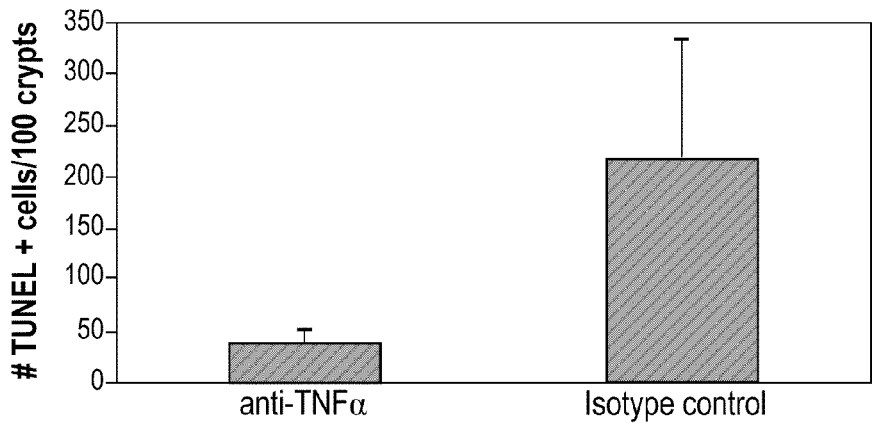

The factors responsible for the high levels of colonic epithelial cell death in TRUC mice were determined, since this appeared to be one of the primary initial events in the development of colitis. Since T-bet is an important positive and negative regulator of several cytokines, the colonic cytokine milieu of TRUC was analyzed using RAG2-/- mice as a control in colon explant cultures. One cytokine, TNF-a, was significantly elevated in the TRUC explant cultures even at four weeks of age and steadily increased over time (FIG. 3A). There were no marked differences in the levels of IFNg, IL-1a, IL-1b, IL-6, IL-10, IL-12, IL-13, or IL-23 at four weeks of age (FIG. 3B), all of which are cytokines previously implicated in playing a role in mediating inflammation in IBD (Hue, S., et al. (2006). J. Exp Med 203, 2473-2483; Strober, W., et al. (2002). Annu Rev Immunol 20, 495-549). TNF-alpha is a well-known key effector cytokine in IBD that is postulated to lead to an increased inflammatory tone of the intestinal epithelium (O'Shea, J. J., et al. (2002). Nat Rev Immunol 2, 37-45). TNF-alpha neutralizing antibody therapy is widely used in the treatment of IBD and is an effective treatment for steroid refractory UC (Rutgeerts, P., et al. (2005). N Engl J Med 353, 2462-2476). To test whether development of colitis was dependent on TNF-a, TRUC mice were treated with the anti-TNF-alpha antibody (TN3-19.12) or isotype (IgG) control. Treatment began at four weeks of age and mice received 15 mg/kg body weight of antibody weekly for four weeks. Remarkably, anti-TNF-alpha antibody therapy almost completely suppressed TRUC colitis as evidenced by colon weight and the histologic analysis of colons (FIG. 3C). In fact, the microscopic appearance of colons from TRUC mice treated with anti-TNF-alpha was indistinguishable from the unaffected RAG2-/- control mice. Of particular interest was the effect of TNF-alpha antibody treatment on the survival of colonic epithemim (Suenaert, P., et al. (2002). Am J Gastroenterol 97, 2000-2004; Zeissig, S., et al. (2004). Gut 53, 1295-1302). Specifically, treatment with anti-TNF-alpha decreased the number of apoptotic epithelial cells to normal levels when colons from mice, treated from four-eight weeks of age, were examined (FIG. 3D). The effectiveness of treatment with the anti-TNF-alpha antibody mirrors what has been observed in patients with CD and in a subset of patients with UC, and reveals the similarity between this mouse model and human UC.

Figure 3E:
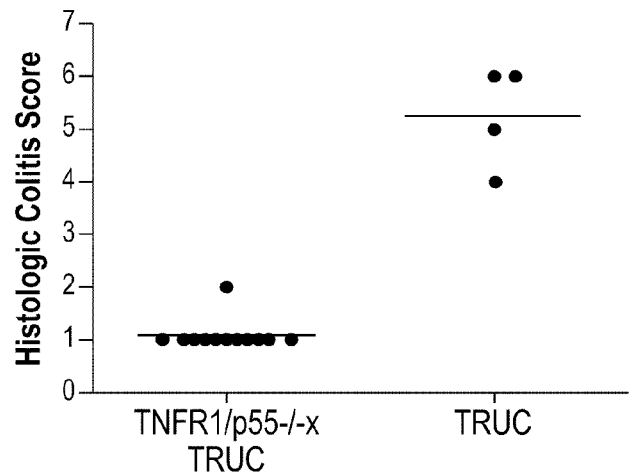

The mechanisms by which TNF-alpha contributes to the etiology of colitis and the means by which anti-TNF-alpha antibody treatment mediates its therapeutic effect remain unclear. TNF-alpha can modulate either pro-survival or pro-death signaling pathways in cells. To discern whether epithelial cell death is a direct or indirect effect of TNF-a, TRUC mice that were also deficient in TNF-alpha receptor were generated by crossing them onto TNFR1/p55−/− mice. At eight weeks of age these triple-deficient mice showed no evidence of colitis, suggesting that TNF-alpha signaling through TNFR1/p55 is a central event in disease pathophysiology (FIG. 3E). These experiments established the centrality of TNF-alpha in this model, and led to the question of what cell type (or types) was responsible for TNF-alpha production in the colon.

Figure 3F:
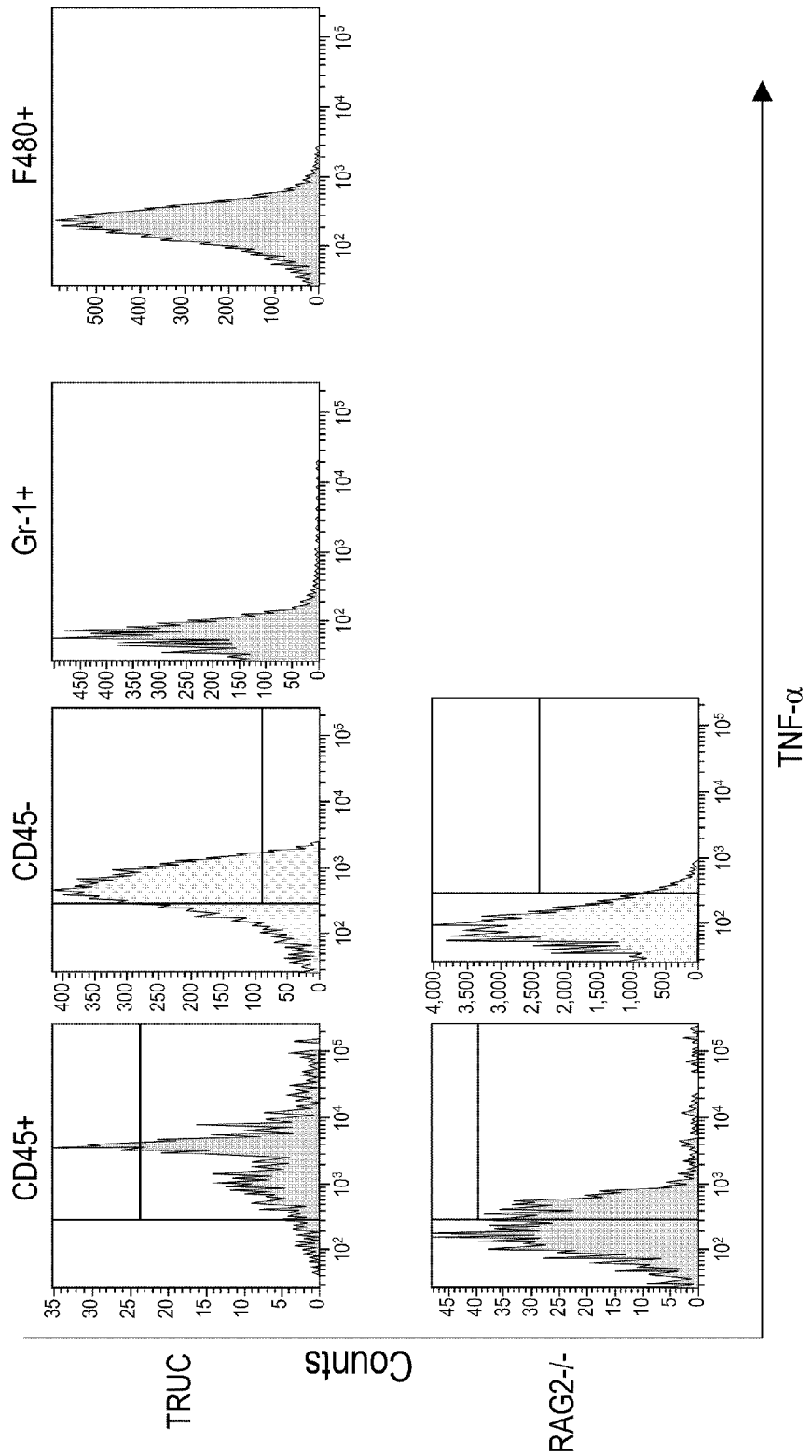
Figure 3G:
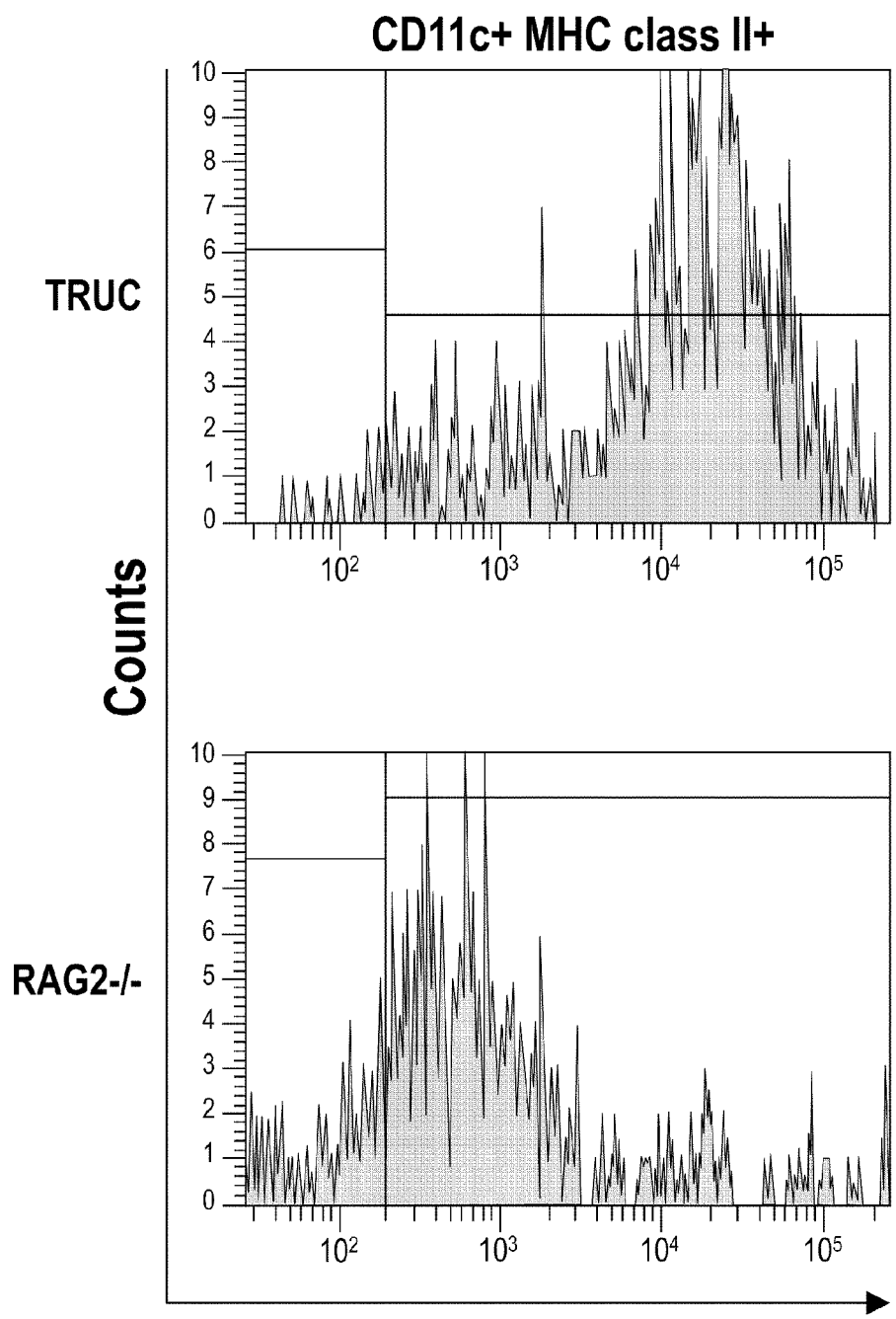
Figure 3H:
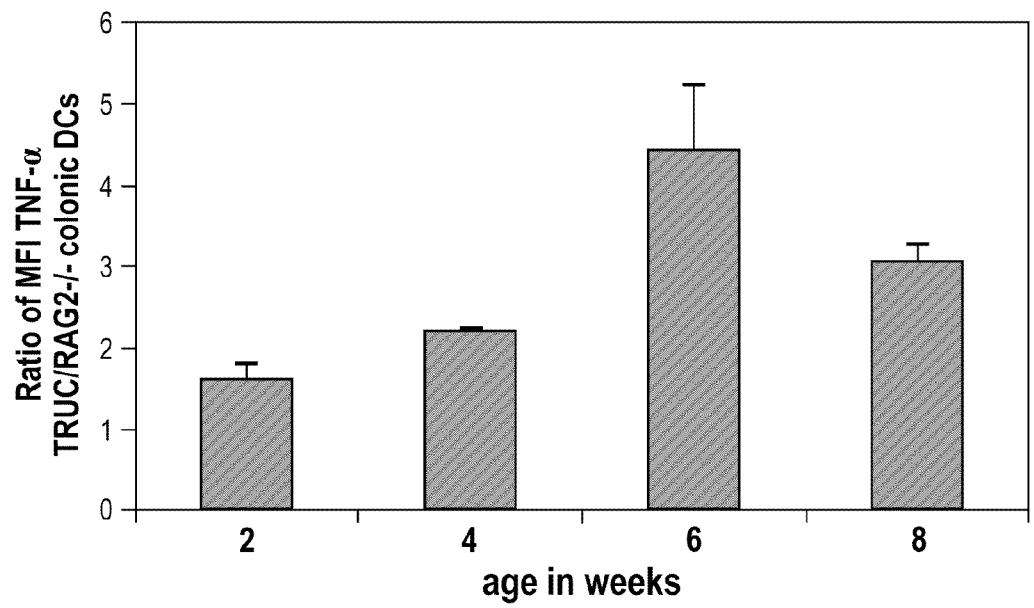

To investigate this issue further, single-cell suspensions from the colons of TRUC and RAG2−/− (control) mice were generated and intracellular cytokine analysis by flow cytometry was performed. Leukocyte (CD45+) populations had significantly higher staining for TNF-alpha than epithelial and other non-leukocyte cells (FIG. 3F). Among the leukocyte subsets, there was no observable staining for NK cells by flow cytometry or immunohistochemistry in TRUC colons. TNF-alpha was stained for in other innate immune cells in the colon including macrophages (F4/80), granulocytes, neutrophils (Gr-1) (FIG. 3F), and DCs (CD11c and MHC class II) (FIG. 3G). TNF-alpha production by macrophages, granulocytes, or neutrophils could not account for the levels of TNF-alpha observed (FIG. 3F). In contrast, there was significant accumulation of TNF-alpha in TRUC colonic DCs (FIG. 3G). Hence, colonic DCs are the principal cell type responsible for TNF-alpha production. The time course of TNF-alpha production was therefore examined by TNF-alpha staining of DCs from the TRUC and RAG2−/− colons from mice aged two through eight weeks (FIG. 3H). Significantly, TNF-alpha staining was detected and was increased by as early as two weeks of age, prior to any observed epithelial discontinuities by microscopy. These data show that in TRUC mice, overproduction of TNF-alpha by colonic DCs precedes the development of epithelial barrier abnormalities and histologic colitis.

Example 4

T-bet Regulates Production of TNF-alpha in DCs

To understand how the absence of T-bet leads to TNF-alpha overproduction, it was determined if T-bet was, in fact, expressed in colonic DCs as it is in DCs in the peripheral lymphoid system. Mucosal surfaces like the intestine are populated by specialized DCs (Iwasaki, A. (2007). Annu Rev Immunol 25, 381-418; Niess, J. H., and Reinecker, H. C. (2005). Curr Opin Gastroenterol 21, 687-691). Colonic DCs principally function to regulate mucosal immunity and tolerance (Kelsall, B. L., and Leon, F. (2005). Immunol Rev 206, 132-148; Macpherson, A. J., et al. (2005). Immunology 115, 153-162). However, upon recognition of pathogenic bacteria invading the epithelial barrier, these DCs must induce protective immunity (Niess, J. H., and Reinecker, H. C. (2006). Curr Opin Gastroenterol 22, 354-360).

Figure 4A:
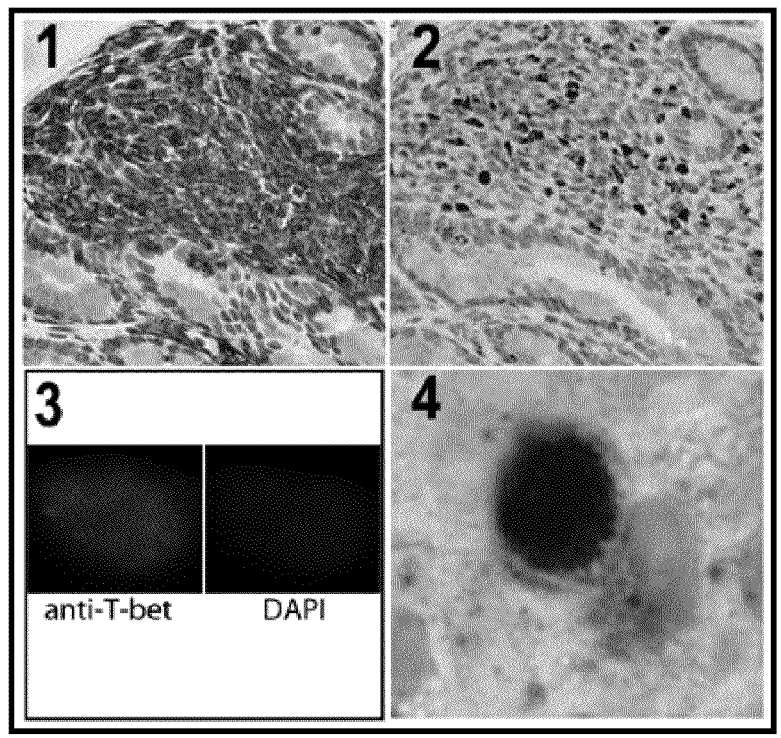
FIG. 4 shows that T-bet regulates production of TNF-α in DCs. (A) T-bet is expressed in colonic DCs. (1) CD11c staining of RAG2−/− colonic mucosa, 200×. (2) A serial section of (1) stained with the anti-T-bet antibody, 4B10, 200×. (3) Representative image of a sorted colonic, mouse DC stained with anti-T-bet antibody (light grey) and DAPI (dark grey), 1000×. (4) Representative human colonic biopsy with a DC shown stained with the DC marker S100 (light grey), anti-T-bet (dark grey), and counter-stained with methyl green, 1000×. (B) Loss of T-bet expression in bone marrow derived DCs results in increased production of TNF-α. (C) Quantitative, real time PCR of chromatin immunoprecipitation samples performed on mouse bone marrow DCs revealed that T-bet bound two regions of the TNF-α promoter, amplified by primer sets A and B, approximately 500 and 1200 base pairs upstream of the transcriptional start site. Data represent the mean of three independent experiments. A schema of the promoter showing putative T-box consensus sites and the location of primers used is shown. (D) Quantitative, real time PCR of chromatin immunoprecipitation samples performed on human myeloid derived DCs demonstrated that T-bet bound the TNF-α promoter approximately 500 base pairs upstream of the transcriptional start site, one representative experiment of three performed is shown.
Figure 4B:
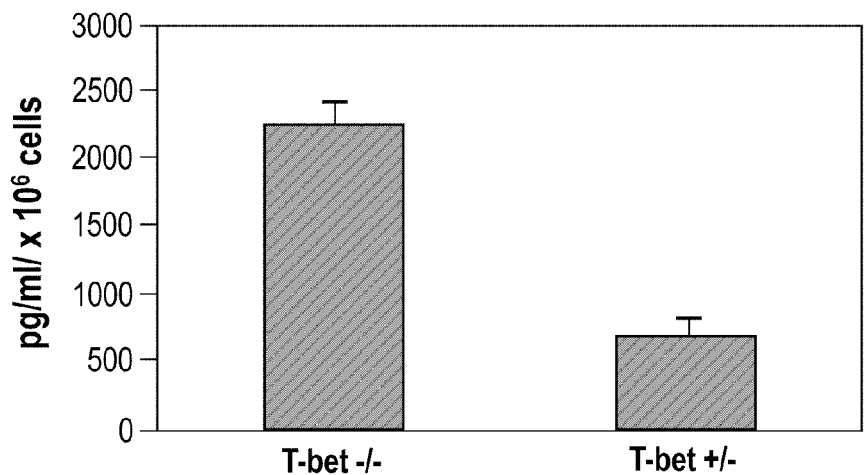

RAG2−/− colons were stained with CD11c to identify DCs. Adjacent serial sections were used to stain for T-bet as the staining protocols are not compatible for simultaneous staining (FIG. 4A 1 and 2). Although the required serial sectioning prevents precise co-localization, there are numerous T-bet+ cells in areas of dense CD11c staining. To confirm this finding, colonic DCs from RAG2−/− mice were isolated with antibodies directed against MHC class II and CD11c using fluorescence-activated cell sorting. The sorted DCs were stained with antibody directed against T-bet and DAPI. T-bet staining (light grey) is evident and, as expected from previous analysis in T cells, there is co-localization with the DAPI (dark grey) stain in the nucleus (FIG. 4A 3).

Figure 4C:
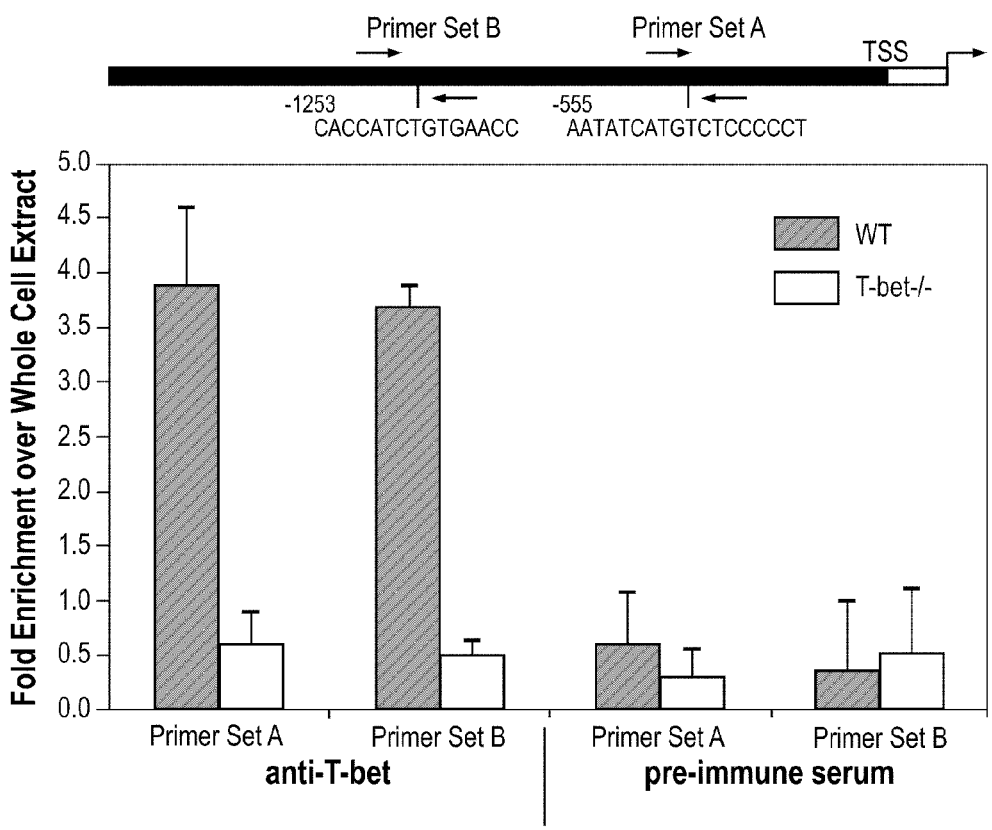
Figure 4D:
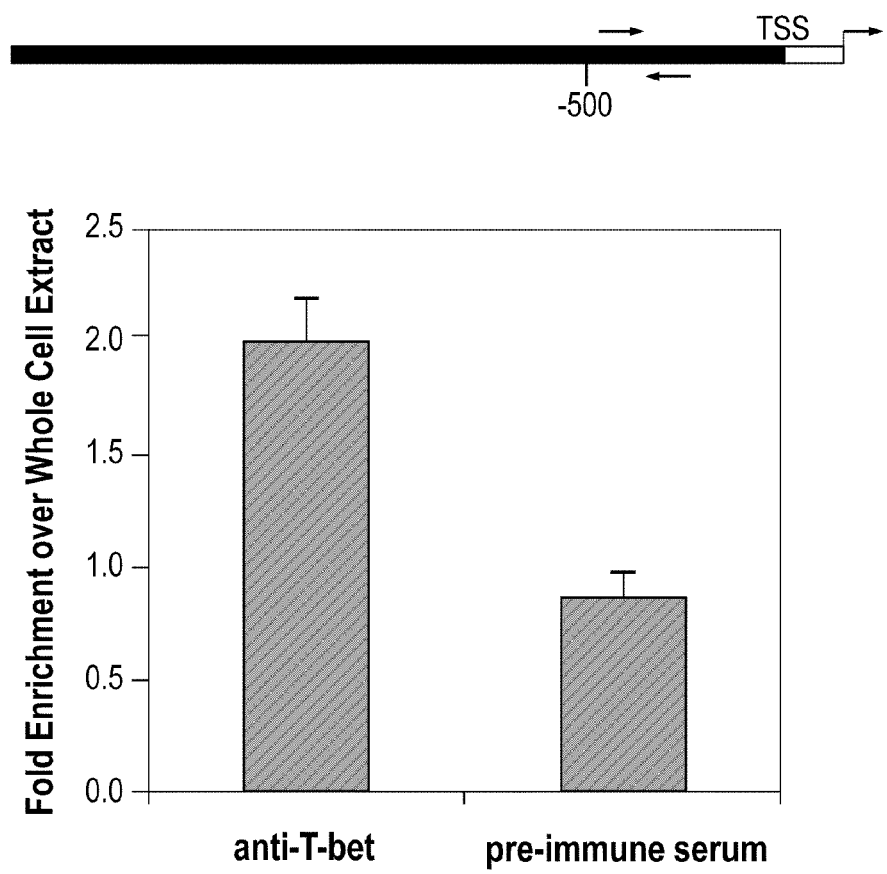
Figure 5A:
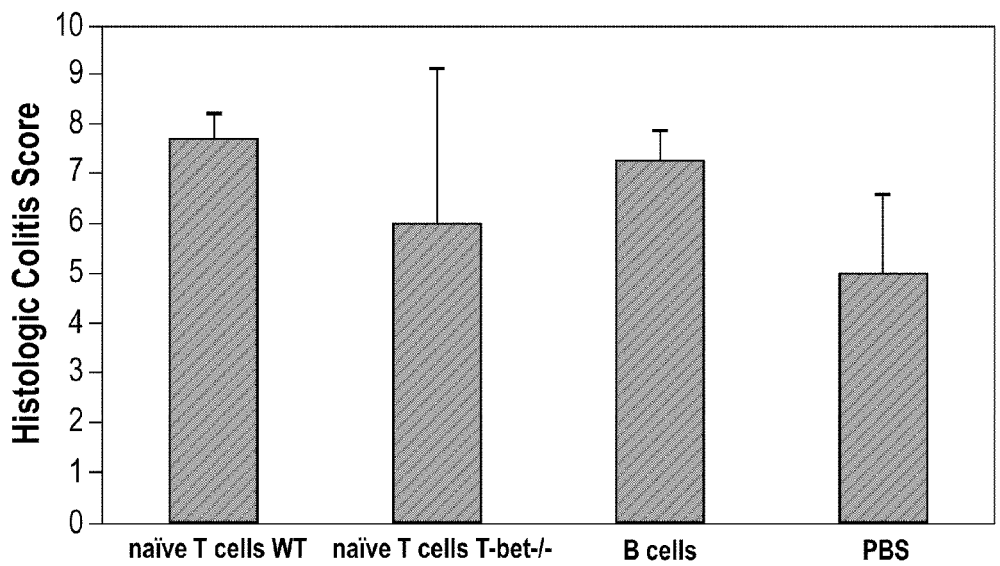
FIG. 5 shows that CD4+CD25+ T-regulatory cells control TRUC (A). Four week old TRUC mice were injected with PBS, 1×10⁶ B cells, or 1×10⁶ naive T cells, WT or T-bet−/−, colitis scores are shown at two weeks post-injection. Representative data are shown from one of three experiments performed with 4 mice per group. (B). Four week old TRUC mice were injected with 75,000 T-regulatory cells (CD4+ CD25+CD62L4), WT or T-bet−/−, or PBS. Mice were sacrificed at eight weeks of age (four weeks post-injection). One representative experiment of three is shown, with six-eight mice per group. (C) A representative photomicrograph of a colon from a TRUC mouse treated with a T-regulatory cell infusion. T-regs (light grey), visualized with an antibody directed against CD3, and DCs (medium grey), visualized with an anti-CD11c antibody, are in contact within the colonic lamina propria, 400×.

To verify the relevance of T-bet for the human enteric mucosal innate immune system, T-bet expression in human colonic biopsies was examined. Formalin-fixed, paraffin-embedded biopsy specimens were stained with antibodies directed against the DC marker S100 (light grey) and T-bet (dark grey). A representative image of a DC with T-bet staining is shown (FIG. 5A 4). Demonstration of T-bet expression in the mucosal innate immune system in human colonic DCs is a novel observation as T-bet expression had only previously been demonstrated in human colonic T cells (Neurath, M. F., et al. (2002b). J Exp Med 195, 1129-1143). There was no T-bet expression in colonic epithelial cells (FIG. 4A 2) by immunohistochemistry nor has T-bet been detectable in colonic epithelial cell lysates. Thus, T-bet is indeed expressed in both mouse and human colonic DCs.

T-bet's role in DC TNF-alpha production was also determined. As yields of colonic DCs from wild type mice are insufficient for biochemical examination more tractable DC culture systems were turned to or further experiments. Mouse bone marrow DC (BMDC) cultures fiirnish adequate numbers of cells. However, as the TNF-alpha production phenotype was observed in colonic DCs, it was required to ensure that T-bet−/− BMDCs overproduce TNF-alpha in a similar fashion. DCs were generated from T-bet−/− and WT mice and treated with LPS to induce maturation. T-bet−/− BMDCs consistently produced more TNF-alpha than WT BMDCs (FIG. 4 B). The observations that loss of T-bet expression in colonic and BMDCs results in increased TNF-alpha production suggested that T-bet may directly regulate TNF-alpha in DCs.

Chromatin immunoprecipitation (ChIP) assays were performed to determine if T-bet bound the TNF-alpha promoter. Two putative T-box consensus sites at approximately −1200 and −500 relative to the transcription start site (TSS) in the mouse TNF-alpha promoter were identified and tested their ability to interact with T-bet. T-bet bound the TNF-alpha promoter at approximately −1200 and −500 as demonstrated by ChIP and quantitative real timer PCR (qPCR) (FIG. 4C). In these experiments, both T-bet−/− BMDCs and pre-immune sera were used as confirmatory controls. T-bet did not bind the TNF-alpha promoter at regions examined upstream of −1200. To confirm that similar regulation by T-bet occurs in human DCs, ChIP assays in human myeloid DCs were performed. There is little sequence homology between the 5' untranslated region of the mouse and human TNF-alpha promoters and in addition T-box consensus sites can be rather degenerate. Similar to the findings with mouse BMDCs, T-bet bound the human TNF-alpha promoter as demonstrated by ChIP and qPCR (FIG. 4D) at approximately −400 relative to the TSS but did not bind more upstream as was the case with the mouse promoter. Therefore, TNF-alpha is a key effector cytokine in TRUC mice as it is in human UC, that TRUC colonic DCs overproduce TNF-alpha prior to a perceptible epithelial barrier breach, and that T-bet directly binds the TNF-alpha promoter. These data establish a link between T-bet and TNF-alpha but do not address why TRUC mice developed spontaneous colitis and T-bet-deficient mice on an immunologically intact background did not. LPS matured T-bet-/- BMDCs do produce more TNF-alpha than wild type BMDCs suggesting that a lymphocyte population not present in the RAG2-/- mice was responsible for controlling this TLR driven TNF-alpha overproduction.

CD4+CD25+ T-regulatory cells control TRUC colitis T-bet-/- immunosufficient mice failed to develop spontaneous colitis although they did display increased susceptibility to DSS and have been shown to have increased susceptibility to oxazolone-induced colitis, a Th2 drive model of colitis (Boirivant, M., et al. (1998). J Exp Med 188, 1929-1939; Neurath, M. F., et al. (2002b). J Exp Med 195, 1129-1143). T-bet-/- and WT mice possess an adaptive immune system as do the majority of patients with IBD. To test the hypothesis that a component of the adaptive immune system might act as a repressor of colitis in immunosufficient hosts, adoptive transfer experiments were performed in TRUC hosts. Transfer of naive CD4 T cells or B cells did not protect against disease. Adoptive transfer of naive CD4+ T cells, into TRUC hosts did not prevent TRUC mice from developing colitis as evidenced by the histologic colitis scores (FIG. 5A), as might be expected based on the extensive studies of the T cell mediated SCID colitis model (Leach, M. W., et al. (1996). Am J Pathol 148, 1503-1515; Powrie, F., et al. (1993). Int Immunol 5, 1461-1471). The transfer of T-bet-/- naive T cells into TRUC mice also did not prevent TRUC mice from developing colitis. Adoptive transfer of B cells into TRUC mice was not protective either (FIG. 5A) in contrast to what has been observed with adoptive transfer of B cells into the NFATc2-/-xRAG2-/- model of colitis where such transfer ameliorated disease (Gerth, A. J., et al. (2004). Gastroenterology 126, 1115-1121) but was consistent with the finding that B cells do not play a protective or destructive role in other models of colitis (Ma, A., et al. (1995). J Exp Med 182, 1567-1572). Hence, the protection observed could not be attributed to conventional T helper or B lymphocytes.

Figure 5B:
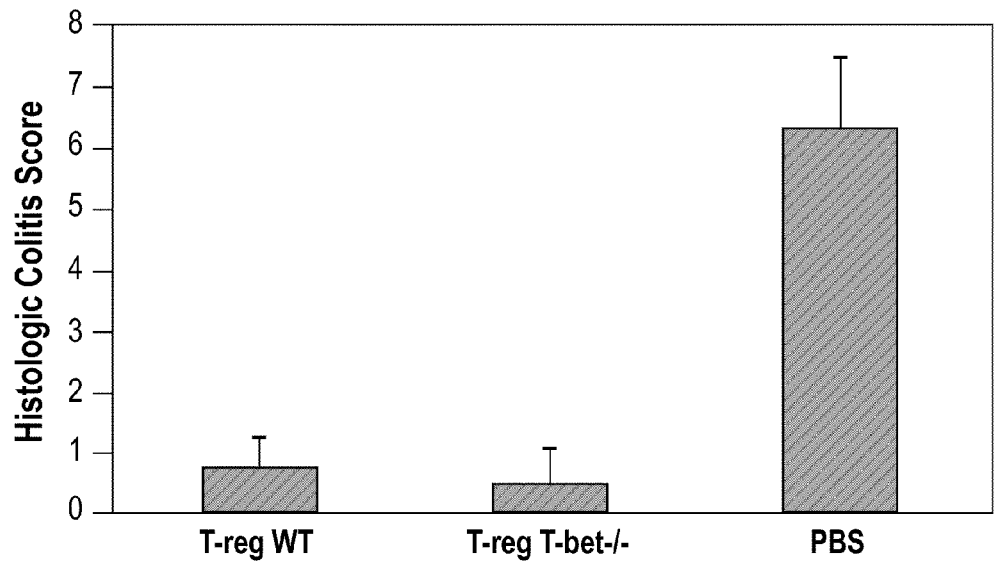

The CD4 T-regulatory cell type is a potent repressor of effector T cell function. Thus it was possible that the presence of T-regulatory cells (T-regs) in the T-bet-/- host might have prevented the development of colitis. It was determined whether transfer of T-regs might ameliorate TRUC colitis as adoptive transfer of T-regs reverses intestinal inflammation in H. hepaticus infected RAG2-/- mice, an innate immune system dependent model of colitis (Maloy, K. J., et al. (2005). Immunol Lett 97, 189-192; Maloy, K. J., et al. (2003). J Exp Med 197, 111-119). Adoptive transfer of either WT or T-bet-/- T-regs indeed controlled the colitis as evidenced by histology (FIG. 5B). Colons from animals infused with T-regs were free of any signs of active injury or abnormal accumulation of either mononuclear or polymorphonuclear immune cells. When TRUC colons were imaged to document that the transferred cells had trafficked to the colon, the location of T-regs by immunofluorescently staining for CD3 in TRUC colons which contain no endogenous CD3+ cells were visualized. Interestingly, the CD3+ cells were visible in close contact with DCs as demonstrated by co-staining with CD11c (FIG. 5C) suggesting that cross-talk between T-regs and DCs may help suppress the T-bet deficient DC pro-inflammatory phenotype.

Example 5

The TRUC Colonic Environment is a Niche that Supports a Colitogenic Microbial Community Whose Suppression Prevents Colitis Across Generations The colonic luminal contents are abundant in microbiota (Hooper, L. V., and Gordon, J. I. (2001). Science 292, 1115-1118) and intestinal DCs constantly sample these microbes (Chieppa, M., et al. (2006). J Exp Med 203, 2841-2852; Milling Milling, S. W., et al (2005). Trends Immunol 26, 349-352; Niess, J. H., et al. (2005). Science 307, 254-258; Rescigno, M., et al. (2001). Nat Immunol 2, 361-367). The vast majority of animal models of colitis are microbe-dependent and patients with IBD often have favorable if not durable responses to antibiotic therapy (Sands, B. E. (2007). J Gastroenterol, 16-25; Strober, W., et al. (2002). Annu Rev Immunol 20, 495-549). As such it was determined if TRUC colitis was driven by the gut microbiota. Mice were treated with a cocktail of broad spectrum antibiotics: vancomycin (V), metronidazole (M), neomycin, and ampicillin—a combination which has been previously shown to deplete enteric microbial communities (Fagarasan, S., et al. (2002). Science 298, 1424-1427; Rakoff-Nahoum, S., et al. (2004). Cell 118, 229-241). Treatment with the VMNA combination cured the mice of their colitis, and selective treatment with metronidazole alone cured the colitis as well, as demonstrated by the histologic scores (FIG. 6 A). By conventional culturing of fecal pellets from VMNA antibiotic-treated and control mice, it was discovered that while aerobic colony counts remained relatively unchanged with treatment $10^{10.11}$ vs $10^{10.16}$, anaerobic colony counts were dramatically decreased $10^{9.74}$ VS$<10^{4.01}$ ($\log_{10}$CFU/gram dry weight of stool). Antibiotic treatment over a several month period induced not only a 100,000-fold decrease in the culturable fecal anaerobes but also remission in all treated TRUC mice. These two observations drew attention to the potential pathogenicity of the anaerobic commensals in TRUC.

Figure 6A:
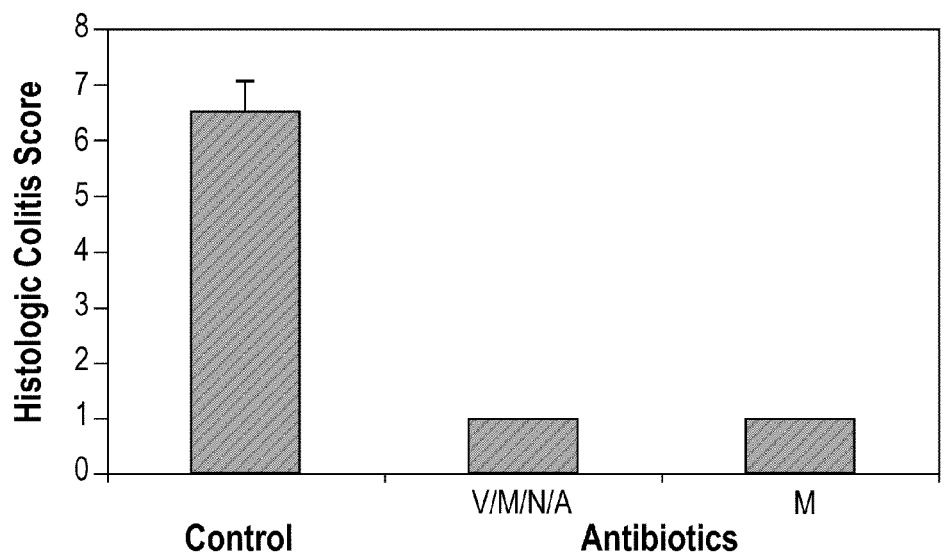
FIG. 6 shows that the TRUC niche generates a colitogenic microbial community which is transmissible to T-bet sufficient mice. (A) The colitis of TRUC mice is microbe dependent. Treatment of TRUC mice with broad spectrum antibiotics improves their colitis. Six week old TRUC mice were treated with vancomycin (V), metronidazole (M), neomycin (N), and ampicillin (A) or metronidazole (M) alone for six weeks. One representative experiment of three with four mice per group is shown. (B) Adult progeny of antibiotic-treated mice show no evidence of colitis. Mice from three separate litters are shown for antibiotic treated breeders and one litter is shown from untreated breeders, p<0.0001. TRUC colitis is transmissible to RAG2−/− mice (C) and WT mice (D). RAG2−/− or WT mice cross-fostered by a TRUC female develop colitis. Colitis histologic scores are shown for individual mice from three independent experiments (TRUC and RAG2−/−) and two independent experiments (TRUC and WT). RAG2−/− mice reared by a RAG2−/−female and WT mice reared by a WT female are shown for comparison.
Figure 6B:
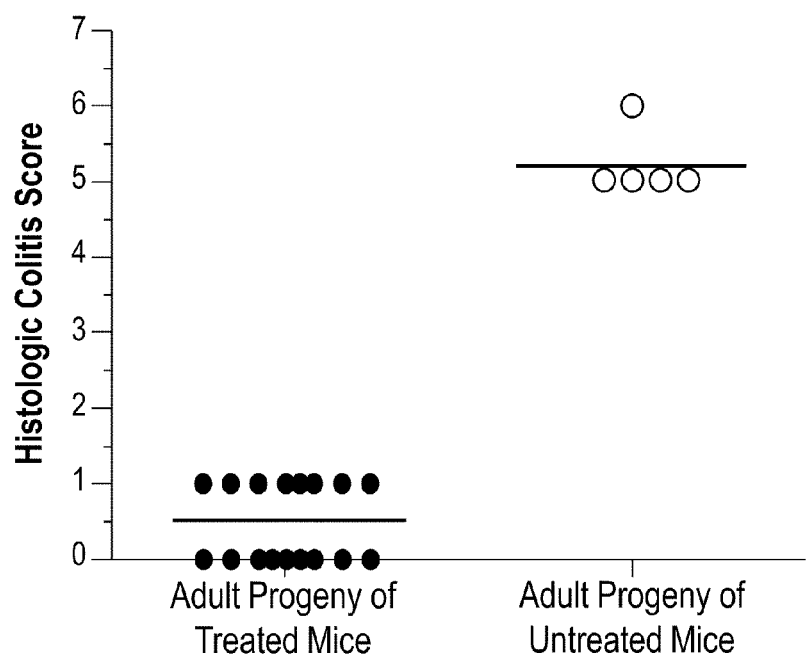
Figure 6C:
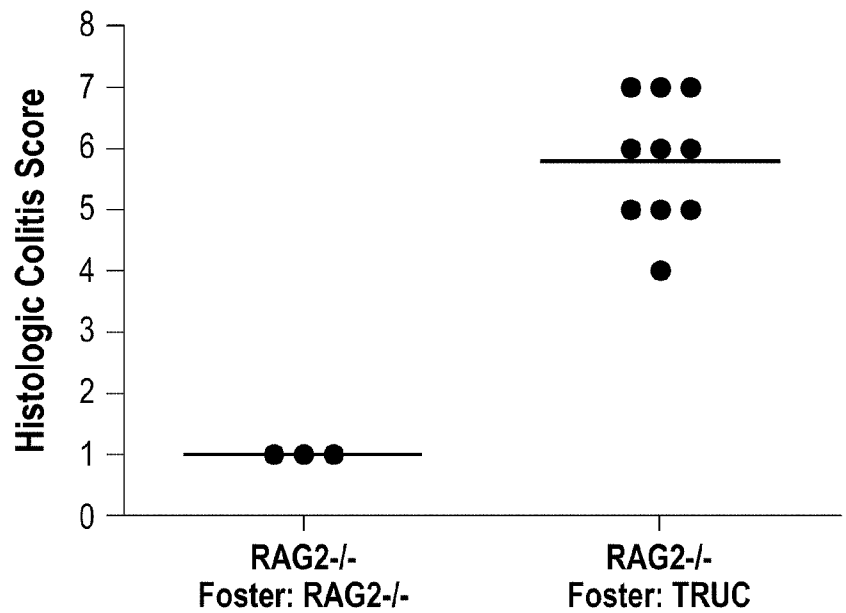
Figure 6D:
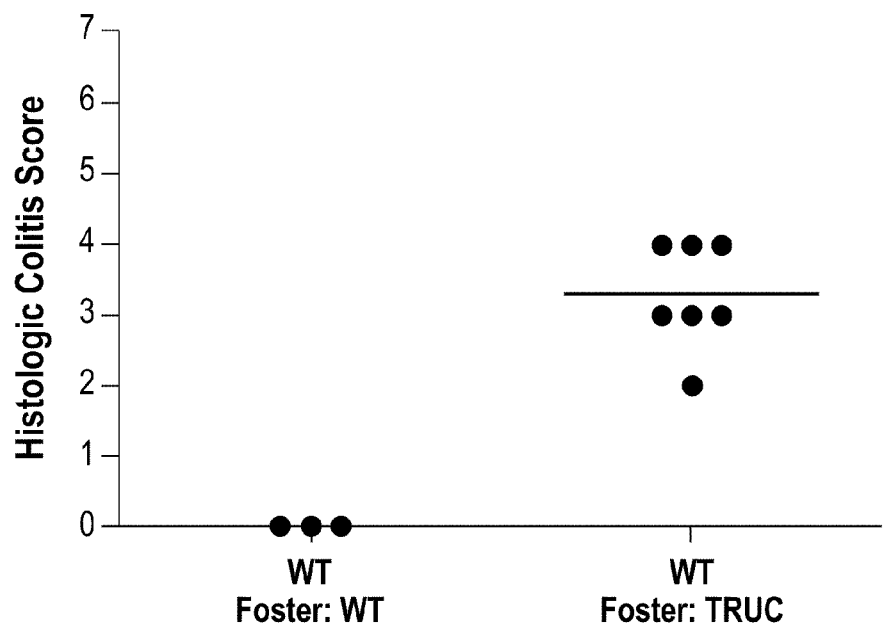
Figure 7A:
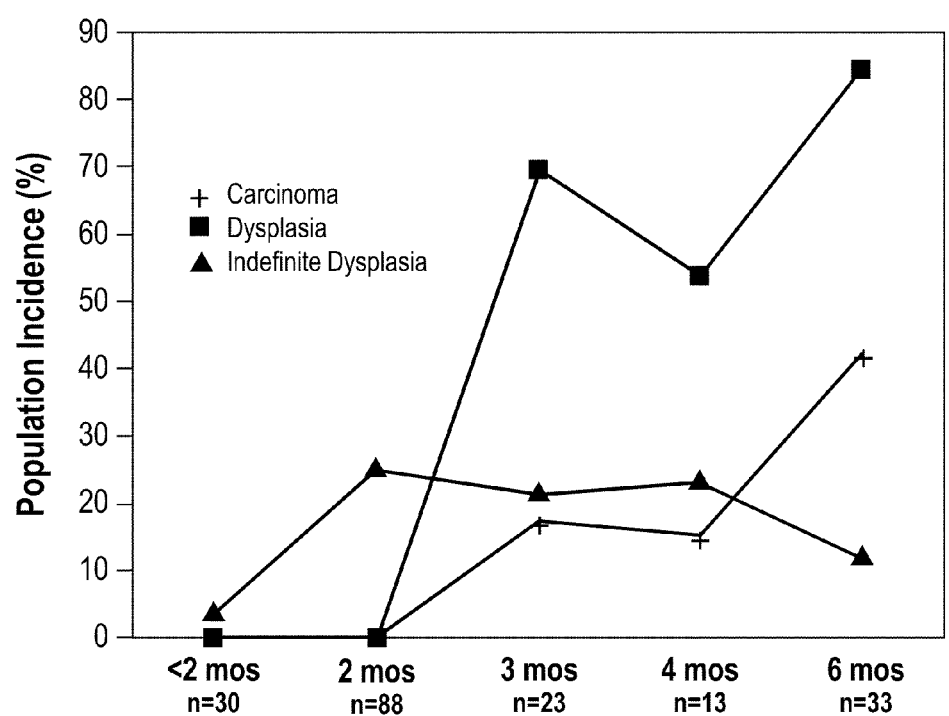
FIG. 7 shows that TRUC ulcerative colitis progresses to the development of dysplatic and neoplastic lesions and ultimately adenocarcinoma of the colon (A). COX-2 expression (B), altered TP53 (C), and β-catenin expression all increase in TRUC mice.
Figure 7B:
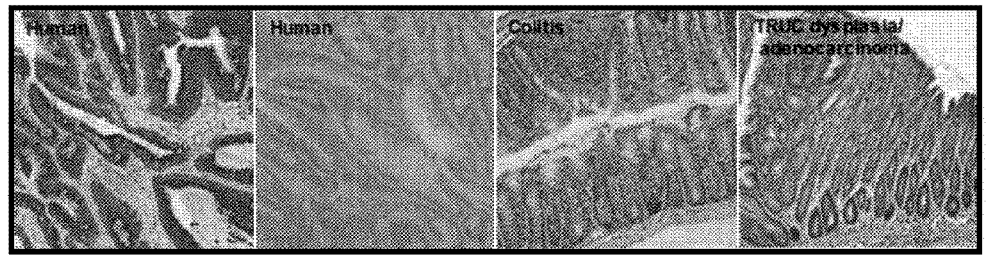
Figure 7C:
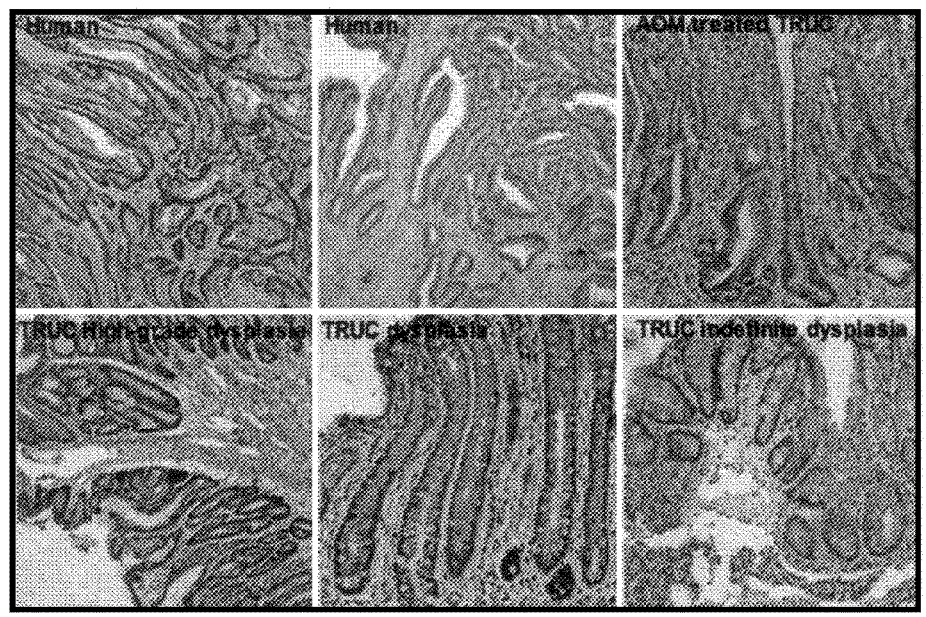

These results demonstrating the microbial dependence of TRUC colitis called us to question the origin of the pathogenic TRUC microbial community. Specifically, did pathogenic anaerobic commensals expand anew at each generation in response to the developing TRUC colonic niche, or were colitogenic microbes propagated trans-generationally from founder TRUC mice? Genetic susceptibilities are clearly heritable and microbial communities are also "heritable", as they are passed from parent to offspring (Ley, R. E., et al. (2005). Proc Natl Acad Sci USA 102, 11070-11075). The observations herein about the microbial dependence of TRUC colitis raised the issue of whether the TRUC colitogenic microbial community was vertically transmissible. TRUC colitis is highly penetrant and mice develop colitis at a young age. When TRUC mice were bred, their progeny had colitis, raising the issue as to whether the progeny of antibiotic-treated TRUC mice would develop colitis. To find out whether this phenomenon contributed to TRUC colitis, antibiotic-treated mice were bred and their progeny examined, who had no exposure to antibiotics after weaning, after they matured to adulthood. Notably, the progeny had no evidence of colitis. Colitis scores are shown for the adult progeny of antibiotic-treated and untreated breeders (FIG. 6B). Thus, in TRUC mice, such treatment cures them of disease and prevents their progeny from developing colitis into adulthood.

Example 6

TRUC Colitis is Communicable to T-bet Sufficient Mice

Cross-fostering experiments were performed to determine if TRUC intestines possessed a microbial community that was colitogenic in T-bet sufficient/WT mice. Specifically, a mother different from the birth mother was provided at the day of birth to RAG2-/- and wild type mice and assessed the development of colitis in these cross-fostered progeny. Adult RAG2-/- and wild type mice cross-fostered by TRUC mothers Developed colitis that was histologically similar to TRUC (FIGS. 6 C and D). Histological scores of the colons from conventionally reared RAG2-/- and WT mice are shown for comparison. The colitis of cross-fostered RAG2-/- pups was more severe than that of cross-fostered wild type pups. Hence, genetically "resistant" strains can acquire colitis from association with the pathogenic microbiota of affected mice. These results in aggregate suggest that not only is TRUC colitis communicable but also that the T-bet deficient mucosal innate immune system creates a niche for a colitogenic microbial community.

Example 7

TRUC Mice Develop Colon Cancer

Colorectal cancer (CRC) is the second leading cause of cancer-related death worldwide. Patients with inflammatory bowel disease are among the highest risk groups for the development of CRC. A robust, spontaneous mouse model of ulcerative colitis (UC) and colorectal cancer has been generated. These mice are deficient in both the T-bet and RAG2 genes and are herein referred to as TRUC (T-bet-/- RAG2-/- ulcerative colitis). In patients with UC, their risk of developing CRC increases with time—two percent after ten years, eight percent after twenty years, and eighteen percent after thirty years. TRUC mice develop dysplastic and neoplastic lesions over a comparable mouse time line. Dysplasia is detectable in 10% of eight week old TRUC and steadily and markedly increases as the mice age, with 85% of 6 month old TRUC exhibiting dysplasia. TRUC display pre-dominantly flat dysplastic lesion buts also occasional adenomas. Adenocarcinoma is present in TRUC as young as three months of age (17%) and the incidence of these intramucosal and submucosal neoplasias increases as the mice age with 42% of six month old TRUC exhibiting adenocarcinomas.

The progression of genetic changes that underpin colitis associated CRC (caCRC) differs from those that drive the so called sporadic CRC and TRUC mice recapitulate caCRC pathways.

Chromosomal instability driven by colitic inflammation is an early event in driving dysplastic changes in human caCRC. Fow cytometry based aneuploidy analysis has been performed and demonstrates that this phenomenon occurs in TRUC mice.

Cyclooxygenase II (COX-2) expression in the colonic microenvironment is a key inflammatory mediator that contributes to chromosomal instability and strong COX-2 expression in immune cells in TRUC colitis, dysplasia, and carcinoma and in dysplastic and neoplastic epithelial cells from TRUC mice has been documented.

p53 mutations occur in the regenerative to dysplastic transition in human caCRC. Using immunohistochemistry, it has been shown that p53 expression, both wild type and mutant, is upregulated in TRUC mice. In contrast with caCRC, P53 mutations are a late not early event in sporadic CRCs occurring in the transition between late adenoma to carcinoma.

In caCRC, APC mutations are a late event characterizing the transition between high grade dysplasia to carcinoma. β-catenin immunohistochemical stainining demonstrates this finding in TRUC as well. Thus TRUC replicates the key molecular mechanisms of human caCRC.

Example 8

Feeding Priobiotics to TRUC Mice Abolishes Ulcerative Colitis

Mice were treated with 30-50 microliters of prebiotic+probiotic–sample or prebiotic+probiotic+sample directly administered into the oral cavity per mouse, with the addition of 1000 microliters prebiotic+probiotic–or prebiotic+probiotic+sample available ad lib to the mice per cage receiving the 50 microliter dose.

Figure 8:
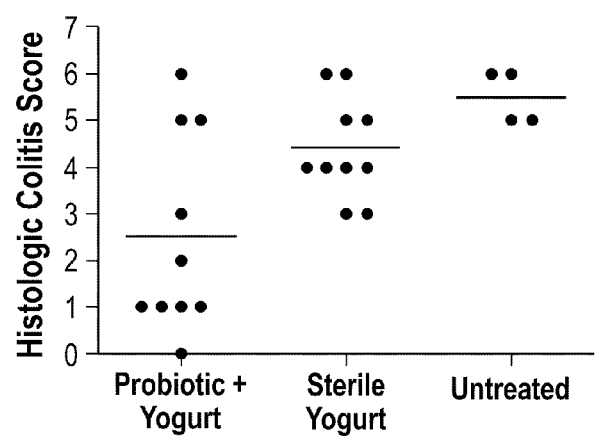
FIG. 8 shows that feeding probiotics to TRUC mice prevents ulcerative colitis.

As shown in FIG. 8, feeding probiotics to TRUC mice prevents ulcerative colitis.

The Following Materials and Methods were used in Examples 9-1

Husbandry of Conventionally-raised Mice

T-bet-/-×Rag2$^{-/-}$ and Rag2$^{-/-}$ mice and their genotyping have been described previously (Lugo-Villarino et al., 2005). Mice were housed in micro-isolator cages in a barrier facility located in the Harvard School of Public Health, under a 12 h light cycle. Animals were fed Pico 20 Lab Diet 5058 (Purina) ad libitum. Animal studies and experiments were approved and carried out according to Harvard University's Standing Committee on Animals and NIH guidelines for animal use and care. Mice in the colony were specified pathogen-free, and negative for *Helicobacter hepaticus, H. bilis*, and *H. muridarum* but have 16S rRNA and qPCR evidence of *Helicobacter ganmani* in their cecal contents and feces.

16S rRNA-based Analyses of Fecal Microbial Communities

Community DNA preparation—Fecal samples were flash frozen immediately after collection and stored at −80° C. before processing. DNA was extracted by bead-beating followed by phenol-chloroform extraction as described previously (Turnbaugh et al., 2009).

Sequencing and analysis of 16S rRNA gene amp/icons—The V2 region (primers 8F-338R) of bacterial 16S rRNA genes was targeted for amplification and multiplex pyrosequencing with error-correcting barcodes (Hamady et al., 2008). A total of 75,145 high-quality reads were generated from 32 samples (2,348±343 reads per sample). V2 16S rRNA gene sequencing data were pre-processed to remove sequences with low quality scores, sequences with ambiguous characters, and sequences outside the length bounds (200-300 nucleotides). All subsequent data processing and analyses were done using QIIME software. In summary, 16S rRNA reads were binned according to their sample-specific, error-correcting barcode incorporated into the reverse primer. Similar sequences were binned into operational taxonomic units (OTUs) using cd-hit with minimum pairwise identity of 97% (Li et al., 2001). A total of 3,229 species-level OTUs were identified in the 32 fecal communities. A phylogenetic tree was built from one representative sequence from each OTU by using FastTree's approximately-maximum-likelihood implementation, and the tree used for unweighted UniFrac analysis (Price et al., 2009). A matrix of UniFrac distance measurements for all pairwise comparisons of communities was constructed and used to generate Principal Coordinates Analysis (PCoA) plots. Taxonomy was assigned using the RDP database (Cole et al., 2009). The Mann-Whitney test was used to calculate which of the 3,229 OTUs were significantly different in their proportional representation in the fecal communities of mice belonging to the two genotypes. Raw p-values were adjusted for multiple comparisons using Bonferroni and False Discovery Rate (FDR) methods.
Culture-based Studies of Fecal Microbial Community Structure Stool Collection—A minimum of three fecal pellets were collected directly upon expulsion from each individual mouse, in a laminar flow hood. Each mouse (3 per genotype; TRUC and Rag2$^{-/-}$, all female) was sampled every two weeks, at the same time of day from two weeks of age through ten weeks of age. Mothers were sampled once when their pups were two weeks old.

Culture—Fecal pellets were collected into tubes containing PBS supplemented with 0.05% cysteine HCl. Serial 10-fold dilutions were made and plated on non-selective media (tryptic soy agar with 5% sheep blood, and Brucella blood agar (Remel)), selective media (MacConkey, Bile Esculin, and Bacteroides Bile Esculin agar (Remel)), and differential media (Rogosa (Difco), Brucella agar with laked blood, kanamycin, and vancomycin (Remel)) and Columbia medium containing colistin, naldixic acid, and aztreonam (Remel)) for recovery of aerobic and anaerobic bacteria. Anaerobes were incubated at 37° C. in a Coy Anaerobic chamber for a minimum of 5 d. Aerobes were incubated for 24-48 h at 37° C.

Colonies were described, enumerated, and sub-cultured. All bacterial concentrations are expressed as colony forming units (cfu) per gram fecal dry weight. Gram-stain analysis was performed and identification methods included: long chain fatty acid analysis using the Sherlock GC-FAME platform from MIDI (Newark, Del.), API kits from bioMerieux (Marcy l'Etoile, France), and/or Vitek2 from bioMerieux. Gas chromatography-based short chain fatty acid analysis was also employed to confirm the identification of several Gram-positive anaerobes. A.B.0 reviewed all final identifications. The identities of Klebsiella pneumoniae and Proteus mirabilis were cross-validated using several of these methods. In vitro antibiotic sensitivities were performed as per Clinical Laboratory and Standards Institute guidelines, on the Vitek 2 system using the AST-GN 13 card (bioMerieux).
Fecal Collection and Culture of Gram-negative Aerobes Individual mice were placed in autoclaved plastic cages. Fecal pellets were transferred immediately upon expulsion into capped microfuge tubes. 4-6 pellets were collected per mouse per time point. All Rag2$^{-/-}$ mice in FIG. 2F were sampled twice over a 3d period for each weekly time point. Pellets were resuspended in sterile PBS and 10-fold serial dilutions were generated, plated on MacConkey's medium, and incubated in ambient air at 37° C. overnight. Biochemical assays with the API-20E panel (bioMerieux) confirmed that colony morphology correlated with Klebsiella pneumoniae, Proteus mirabilis, or E. coli: therefore, these organisms were subsequently identified based on their colony morphotypes.

Figure 9:
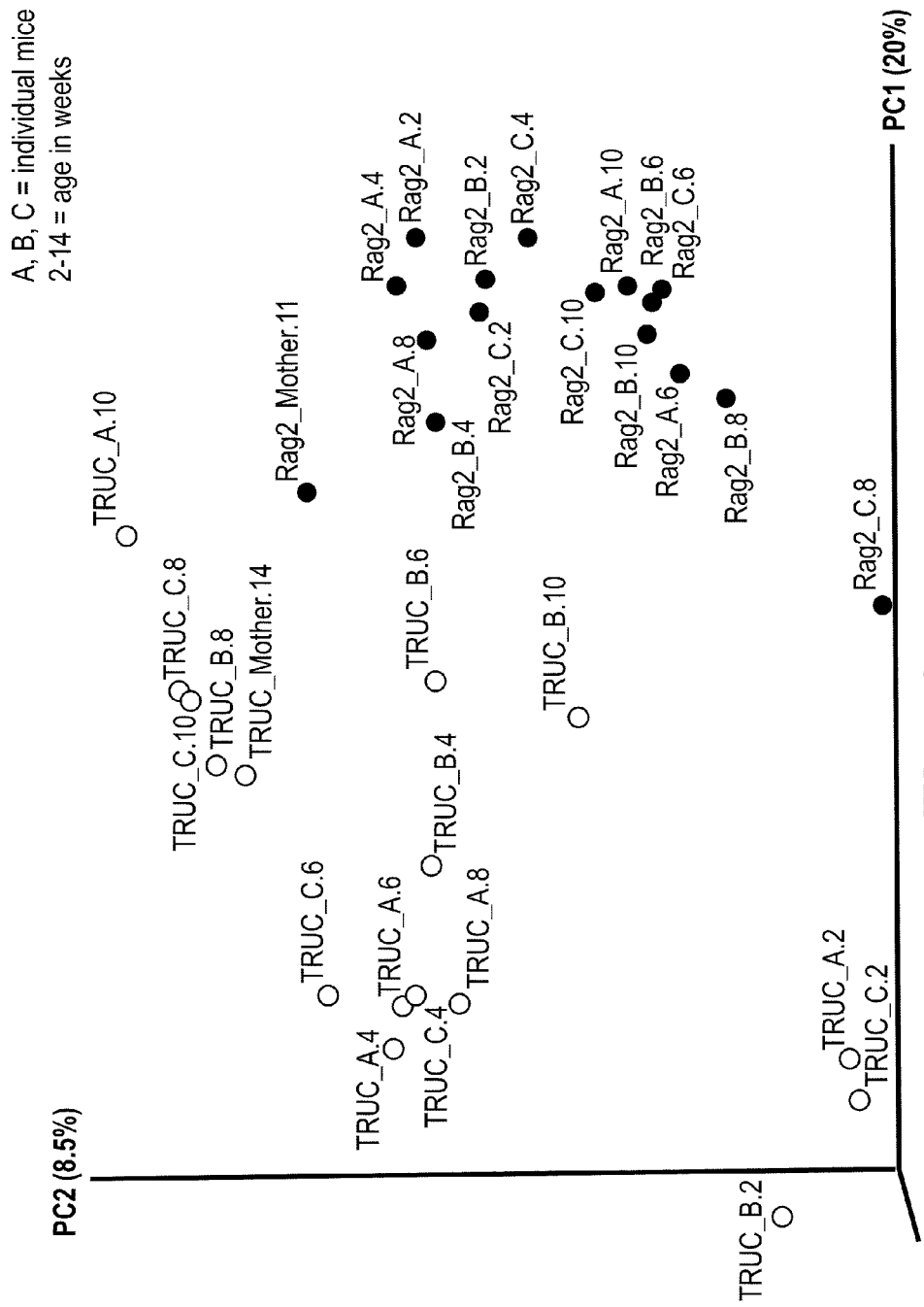
FIG. 9. 16S rRNA-based time series analysis of T-bet$^{-/-}$× Rag2$^{--/-}$ (TRUC) vs Rag2$^{-/-}$ fecal microbiota. Host genotype influences microbial community structure. Principal coordinates analysis of unweighted UniFrac distances from 2-10 week TRUC (n=3) and Rag2$^{--/-}$ (n=3) mice and their mothers. Abbreviations: A, B, C, individual pups by genotype, followed over time (A.2, A.4, A.6, A.8, and A.10 refers to animal A sampled at 2, 4, 6, and 10 weeks of age).

The lower limit of detection for these studies was $10^{4.4}$ cfu/gram fecal dry weight. A minimum of 30 colonies or a maximum of 300 colonies was counted at a given dilution and the serial dilution had to appropriately reflect the colony counts for the quantitative counts to pass our quality control standards.
Histology Colons were harvested upon sacrifice and colonic contents were removed prior to fixation in 4% paraformaldehyde. Following paraffin embedding, sections (0.5 ttm thick) were cut and stained with hematoxylin and eosin. Histopathology was evaluated in a blinded fashion (with respect to genotype and experimental protocol) using four parameters: mononuclear cell infiltration, polymorphonuclear cell infiltration, epithelial hyperplasia, and epithelial injury that were scored as absent (0), mild (1), moderate (2), or severe (3) as described previously(Neurath et al., 2002).
Antibiotic Treatment of TRUC Colitis Mice were treated with the following antibiotics dissolved in their autoclaved drinking water as indicated: ampicillin (1 g/L; Roche), vancomycin (500 mg/L; Sigma), neomycin sulfate (1 g/L; Sigma), metronidazole (1 g/L; Sigma, solubilized with 15 ml of 0.1N acetic acid/L), and gentamicin (2 g/L; Cell Gro); and fluid intake monitored.
Cross-Fostering On the day of birth, the mother was removed from the birthing cage and placed in a clean cage. A litter of pups with the designated genotype was then transferred into the cage. Pups were weaned on postnatal day 21 (Garrett et al., 2007).
Dextran Sulfate Sodium Treatment Dextran sulfate sodium (M.W. 40-50,000; USB Cat# 14489) was dissolved in drinking water at a final concentration of 4% (w/v) and provided for 7d.
Gnotobiotic Experiments Conventionally-raised, specified pathogen free T-bet$^{-/-}$× Rag2$^{-/-}$ mice were re-derived as germ-free in the gnotobiotic facility at Washington University. At 6 weeks of age, germ-free mice were transported in a germ-free state using a specialized shipping apparatus (Taconic Laboratories), to the Harvard Digestive Disease Center (HDDC) gnotobiotic mouse facility. After transfer to flexible film gnotobiotic isolators, mice were monitored for one week and their germ-free status confirmed by culture and qPCR of fecal bacterial cDNA (16S generic primer set (FOR: 5' TCCTACGGGAG-GCAGCAGT and REV: 5' GGACTACCAGGG-TATCTAATCCTGTT) (Nadkarni et al., 2002). One cohort of five mice was maintained germ-free. Another cohort of five mice (3 female and 2 male) was co-colonized by introducing $4.8 \times 10^8$ cfu of Klebsiella pneumoniae and $9.2 \times 10^8$ cfu of Proteus mirabilis into their oral cavity and by simultaneously spreading an equivalent amount of organisms on their fur and anus. Fecal samples were collected to define levels of colonization of these organisms 48 h after inoculation, and weekly thereafter for 8 weeks.
Invasion Experiments $2 \times 10^7$ cfu of Klebsiella pneumoniae, Proteus mirabilis, E. coli, or both Klebsiella pneumoniae and Proteus mirabilis (all isolated from the TRUC mother in FIG. 9) were gently instilled into the oral cavity of each mouse using a sterile pipette tip, and 1×107 cfu was placed into a new container of their drinking water every other day.
Anti-TNF-α Treatment anti-TNF-α (clone TN3-19.12), a hamster anti-mouse TNF-α neutralizing IgGl antibody and control Ab (hamster anti-GST IgGl) were purchased from Leinco Technologies. Mice were injected with these reagents (15 mg/kg) on a weekly basis for four weeks (Garrett et al., 2007).
Adoptive Transfer of T-regulatory Cells Peripheral lymph nodes were harvested and cell suspensions were generated as previously described. Fluorescence activated cell sorted C114$^+$CD62L$^{hi}$CD25$^+$ cells were collected and resuspended in PBS. 75,000 cells were injected per mouse. An equivalent amount of PBS was injected in the control group. 10 mice were injected with T-regulatory cells and nine mice with PBS. All mice were 4 weeks of age at the time of injection (Garrett et al., 2007). This experiment was stopped when the mice were 12 weeks old (as opposed to 14 weeks of age in the TNF-a blockade experiment), because two mice in the control group became quite moribund from their colitis, and euthanasia was indicated as per our animal protocol.

TNF-α Bacterial Co-culture

TNF-a (final concentration 100u,g/mL culture medium), or PBS alone, was added to cultures of the designated microbes and bacterial concentrations (efu/ml) were followed during a 6 h incubation (37° C. with agitation in ambient air) at 2 h intervals. Bacteria were cultured in Luria Broth and plated on MacConkey's medium.

Cytokine Assays in Milk

Lactating mice were injected with 2 U oxytocin (Sigma-Aldrich) i.p. and milk was collected using a suction-powered milking apparatus (Wilson and Butcher, 2004). Milk was then centrifuged (14,000×g for 5 min) at room temperature, fat was discarded, and the remaining material was stored at −20° C. until use (Wilson and Butcher, 2004). Cytokines were measured in defatted fractions using SearchLight high dynamic range imaging and analysis service unless otherwise indicated. For TNF-a, the mouse OptEIA ELISA kit (BD Biosciences) was used according to the manufacturer's instructions. Low levels of TNF-α (10 pg/ml) were detected in TRUC but not in Rag2 milk (FIG. S5); these low levels in TRUC animals are likely attributable TNF-a sequestration by TNF-R, as milk is known to contain high levels of TNF-R1 and TNF-R2 (Buescher and Malinowska, 1996).

Statistical Analysis. The Prism graphing and analysis program was used for calculation of statistical measures including mean values, standard deviations, p-values (Mann-Whitney test), and two-way ANOVA.

Example 9

16S rRNA-Based Time Series Analysis of T-bet$^{-/-}$× Rag-/- (TRUC) vs Rag2$^{-/-}$ Fecal Microbiota This example ustilized offspring of a conventionally-raised, specified pathogen-free T-bet-/-xRag2$^{-/-}$ mother and a Rag2$^{-/-}$ mother. Fecal samples were collected from mothers at a single time point, and their female pups (n=3/genotype) at multiple time points, beginning at two weeks of age and continuing at two week intervals until the animals were 10 weeks-old. A culture-independent survey of their fecal microbiota was carried out by multiplex pyrosequencing of amplicons generated from the V2 region of bacterial 16S rRNA genes (n=32 samples; 2,348±343 reads per sample). UniFrac is a metric that measures the degree of similarity of communities based on the degree to which they share branch length on a phylogenetic tree constructed from all 16S rRNA sequences generated from a survey. Principal coordinates analysis (PCoA) plots based on unweighted UniFrac measurements disclosed a correlation between host genotype and community phylogeny at all ages surveyed (FIG. 9A). A total of 69 species-level phylogenetic types, belonging to 4 major bacterial phyla, exhibited significant differences, at various ages, in the fecal communities of mice belonging to the two genotypes. Compared to Rag2$^{-/-}$ controls, TRUC mice had a significantly higher proportional representation of species-level operational taxonomic units (OTUs) belonging to the order Bacteroidales (phylum Bacteroidetes; p=0.00643, Mann-Whitney test with Bonferroni-correction), and significantly lower proportional representation of OTUs belonging to the orders Clostridiales (phylum Firmicutes; p=0.0201, Mann-Whitney test with Bonferroni-correction) and Deltaproteobacteria (phylum Proteobacteria; p=0.0299, Mann-Whitney test with Bonferroni-correction).

Example 10

Klebsiella pneumoniae and Proteus mirabilis Correlate with the Presence of Colitis in TRUC Mice This example identifies taxa that could be cultured and used to test Koch's postulates about their role in disease initiation and progression, we followed these culture-independent assays with a time-series, culture-based survey. A total of 57 bacterial species were recovered and identified from fecal pellets obtained from 3 TRUC and 3 Rag2$^{-/-}$ mice surveyed at 2, 4, 6, 8, and 10 weeks of age, and their mothers.

Figures 10A, 10B:
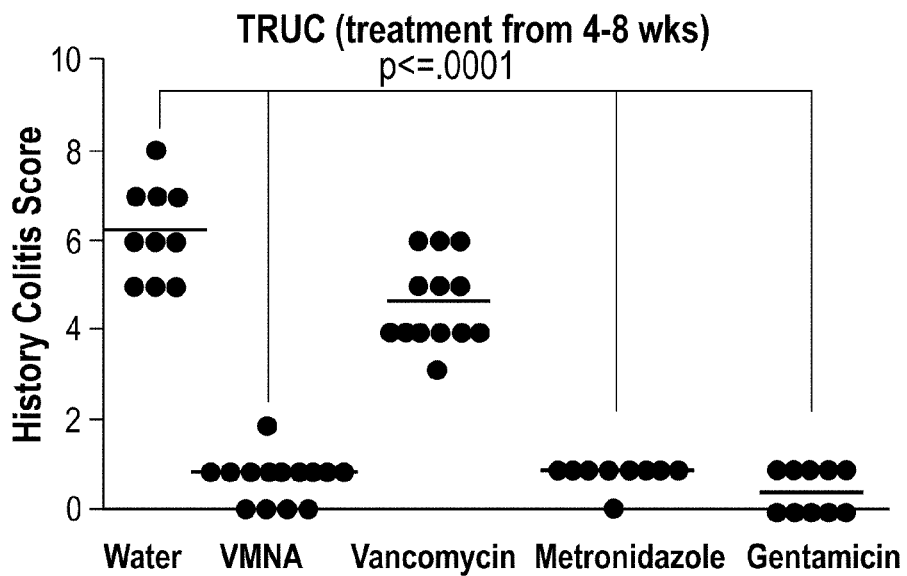
FIG. 10. The presence of *Klebsiella pneumoniae* and *Proteus mirabilis* correlates with the presence of colitis in TRUC mice. (A) Histologic colitis scores demonstrate the in vivo antibiotic sensitivities of TRUC colitis. Each dot represents an individual mouse treated for four weeks with the indicated antibiotics dissolved in drinking water. 'MINA refers to treatment with a combination of vancomycin, metronidazole, neomycin, and ampicillin. Horizontal bars represent the mean. p-value<0.0001 defined by Mann-Whitney test. (B) Summary of in vitro antibiotic sensitivities for several species selectively detected in TRUC fecal microbiota. (C) Culture-based survey of Gram-negative aerobes present in fecal samples from TRUC (shaded circles) and Rag2−/− (open circles) at 2-20 weeks of age. Fecal samples were collected and cultured twice at each time point from Rag2−/− mice. (D) In vivo sensitivity of *Klebsiella pneumoniae* (squares) and *Proteus mirabilis* (circles), as defined by culture-base surveys of TRUC fecal samples collected 1 d before (shaded symbol) and 1 d after (open symbol) treatment with antibiotic. Each dot represents data from a fecal sample obtained from one mouse. Horizontal bars represent the mean value.
Figure 10C:
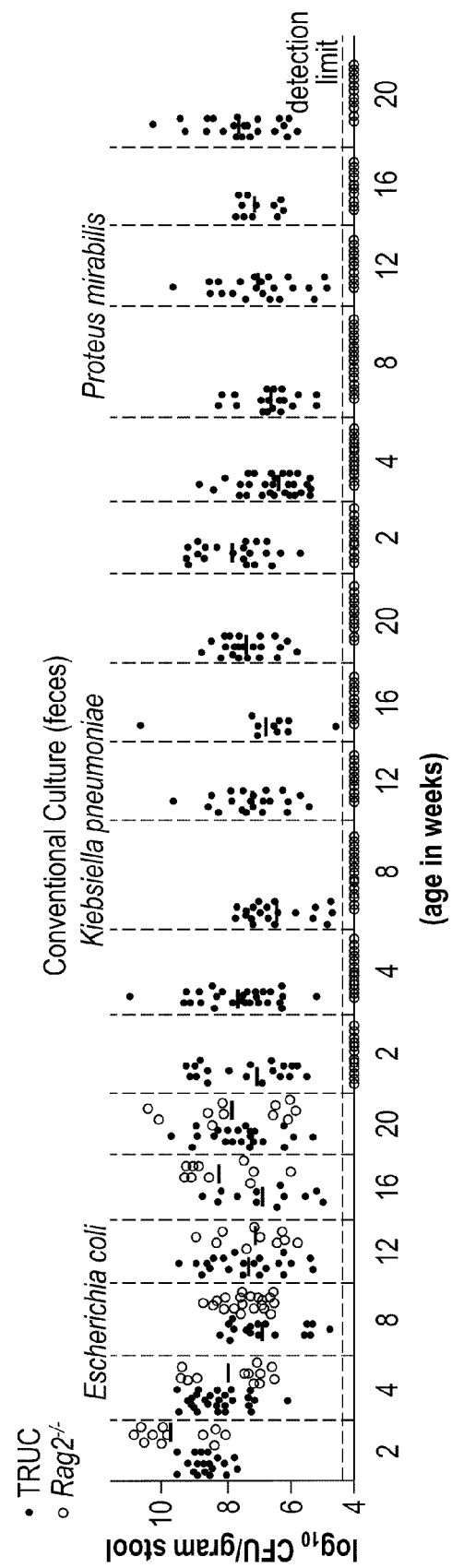

Gentamicin is able to ameliorate and cure TRUC while vancomycin treatment does not. When we assayed the subset of 7 bacterial species selectively recovered from TRUC but not Rag2$^{-/-}$ fecal samples for the corresponding in vitro antibiotic sensitivities (FIG. 10A), we identified two members of the Enterobacteriaceae, Klebsiella pneumoniae and Proteus mirabilis. Before beginning direct tests of their role in disease pathogenesis, we carried out a culture-based survey of a larger number of TRUC and Rag2-/- mice (n=10-30 animals surveyed/genotype/time point; each fecal sample assayed twice at each time point for Rag2$^{-/-}$ animals). Klebsiella pneumoniae and Proteus mirabilis were below our limits of detection (4.4 log$_{10}$CFU/g fecal material), in all Rag2$^{-/-}$ mice at all time points surveyed, while both species were detected in all TRUC mice tested, at every time point examined (FIG. 10C).

Figure 10D:
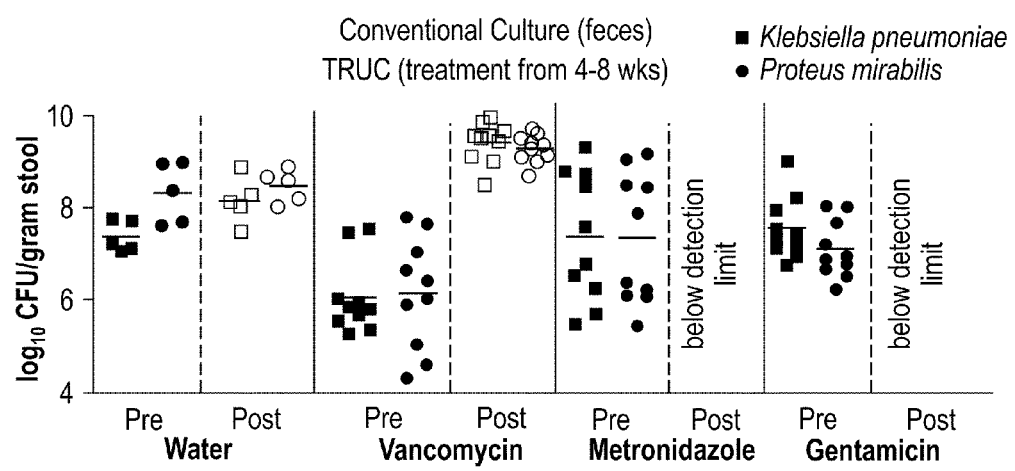

We subsequently treated 4-week old TRUC mice with antibiotics using a protocol shown previously to ameliorate colitis, and cultured feces obtained 1d before and 1d after antibiotic administration. After treatment with gentamicin or metronidazole, fecal levels of K. pneumoniae and P. mirabilis were below our limit of detection (FIG. 10D). In contrast, treatment with vancomycin neither abolished colitis nor reduced levels of K. pneumoniae and P. mirabilis (FIG. 10B, D).

Example 11

Figure 11A:
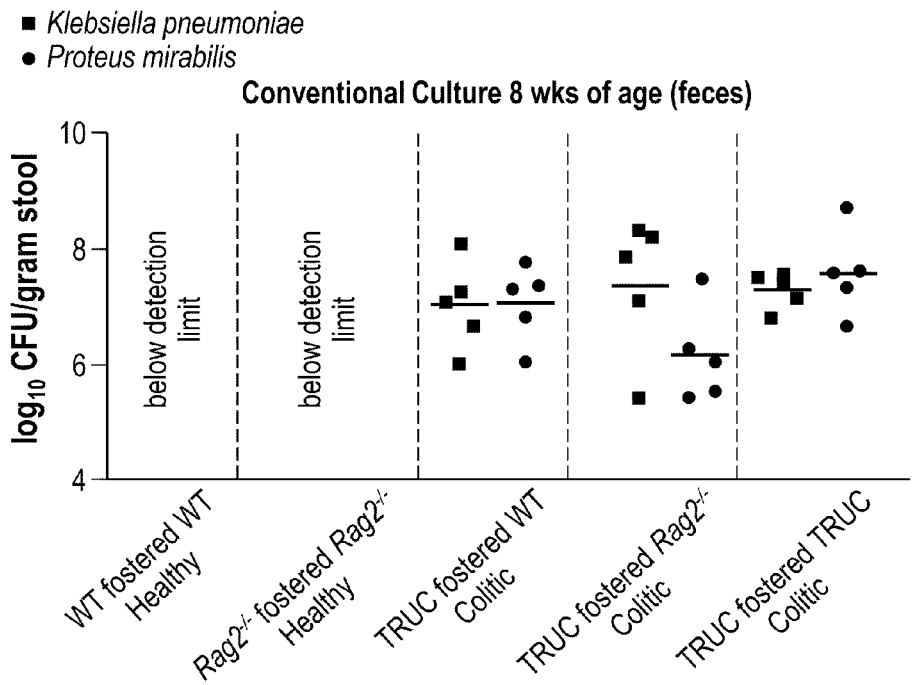
FIG. 11. *Klebsiella pneumoniae* and *Proteus mirabilis* elicit colitis but require a maternally-transmitted endogenous microbial community for maximal intestinal inflammation. (A) *Klebsiella pneumoniae* (squares) and *Proteus mirabilis* (circles) are detected in the fecal microbiota of TRUC cross-fostered Rag2$^{-/-}$ and WT mice at 8 weeks of age. TRUC-fostered TRUC, Rag2$^{-/-}$-fostered Rag$^{-/-}$, and WT-fostered WT are shown as controls. Limits of detection; 10" cfu/g dry weight of feces. Each filled square or circle represents a fecal sample from a different animal. (B) Histologic colitis scores of germ-free TRUC and germ-free TRUC mice co-colonized with *Klebsiella pneumoniae* and *Proteus mirabilis* from the TRUC mother in FIG. 1. (C) *Klebsiella pneumoniae* and *Proteus mirabilis* fecal cfu in Rag2$^{-/-}$ and WT mice treated every other day from 2-10 weeks of age with 10⁷ cfu of E. cob *Proteus mirabilis, Klebsiella pneumoniae*, or a combination of both added to their drinking water (all strains isolated from the TRUC mother in FIG. 1). (D) Histologic scores for colitis in the mice shown in panel C as assayed at sacrifice at 10 weeks of age. Each filled circle represents a separate animal in the treatment group. p-values shown were calculated using the Mann-Whitney test FIG. 12. *Klebsiella pneumoniae* and *Proteus mirabilis* colonization patterns change in response to immunotherapies. (A) Successful immunotherapy by TNF-a blockade alters levels of culturable Enterobacteriaceae in the feces. TRUC mice were treated with curative anti-TNE-(15 mg/kg every week) (open circles) or isotype control (shaded circles) for four weeks, after which time therapy was stopped. Enterobacteriaceae levels were defined by culture of fecal samples obtained 1 day before, during, and after treatment (up to 14 weeks of age). Circles represent the mean value of anti-TNF-a mice (n=10) and isotype controls (n=10). Error bars represent the standard deviation. (B) Successful immunotherapy by T-reg infusion does not produce statistically significant differences in the levels of culturable Enterobacteriaceal species compared to vehicle-treated controls. TRUC mice were injected once with 75,000 CD4$^+$CD62$^{hi}$CD25$^+$T-regulatory cells (n=10) or PBS (n=9).
Figure 11B:
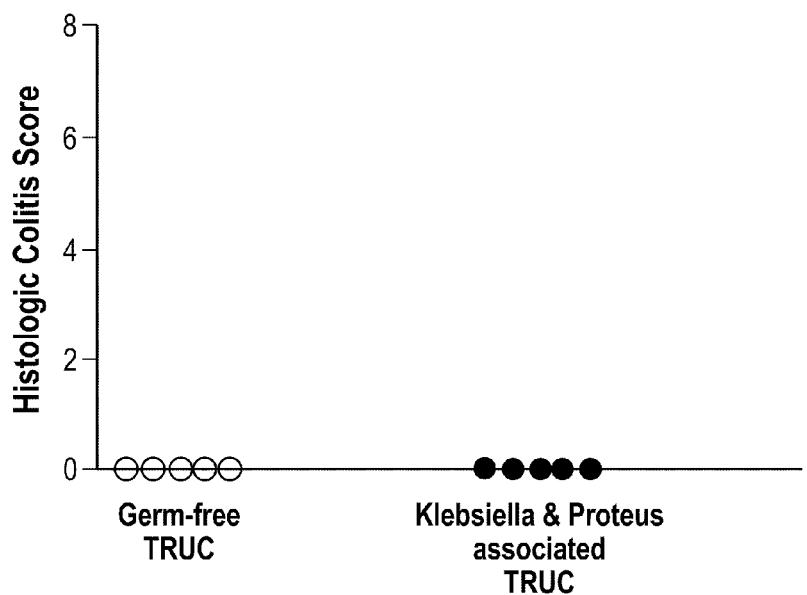

Klebsiella pneumoniae and Proteus mirabilis Elicit Colitis but Require a Maternally-transmitted Endogenous Microbial Community for Maximal Intestinal Inflammation To further evaluate the relevance of K. pneumoniae and P. mirabilis, we took advantage of a transmissible model of TRUC (Garrett et al., 2007). Following postnatal exposure to a TRUC dam, wild-type (WT) and Rag2$^{-/-}$ mice develop histopathologic features of colitis (penetrance of phenotype: 94% at 8 weeks of age) (Garrett et al., 2007). Therefore we cultured fecal samples obtained from WT and Rag2$^{-/-}$ mice that developed colitis as a result of TRUC cross-fostering (FIG. 11A). K. pneumoniae and P. mirabilis were detected in all fecal samples obtained from 8 week old TRUC-fostered Rag2-/- and WT pups, and at levels comparable to age-matched TRUC-fostered TRUC mice. In contrast, neither of these organisms was detected in any control Rag2$^{-/-}$ fostered Rag$^{-/-}$ or WT-fostered WT animals (n=2 foster mothers/genotype; 2-3 pups per litter surveyed; FIG. 11A).

To investigate the effects of inflammation on intestinal colonization by K. pneumoniae and P. mirabilis, we treated 8 week-old WT and Rag2$^{-/-}$ mice with dextran sulfate sodium, a mucosal disruptant and irritant, to induce colitis (n=8 mice/ genotype). We did not detect culturable *K. pneumoniae* or *P. mirabilis* in the fecal microbiota of any of these mice during our period of surveillance (n=8 mice/genotype; samples collected before and 1d after the completion of a one week treatment course) arguing against an inflammatory response per se causing expansion of cultivatable *K. pneumoniae* and *P. mirabilis* in TRUC mice.

Figure 11C:
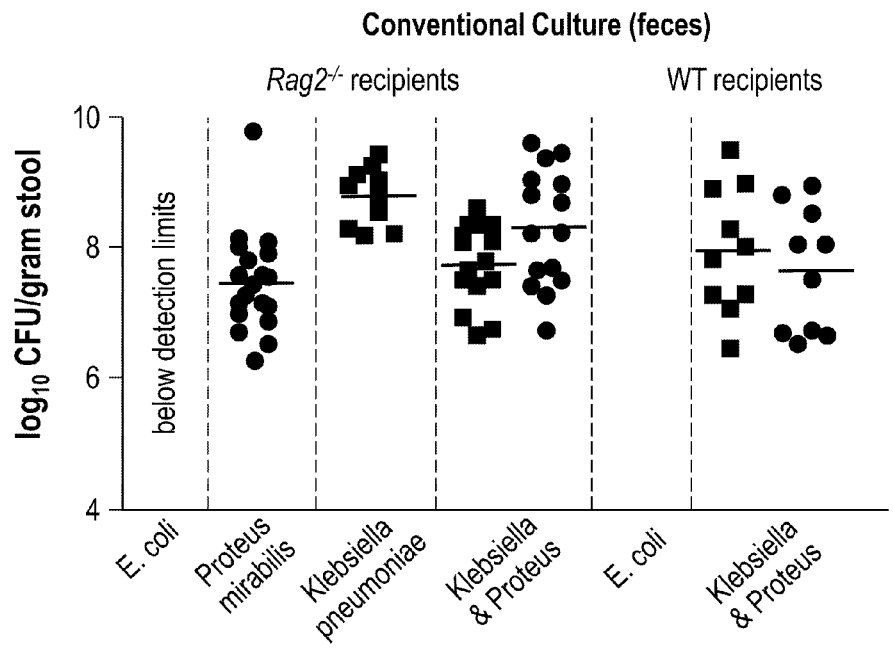
Figure 11D:
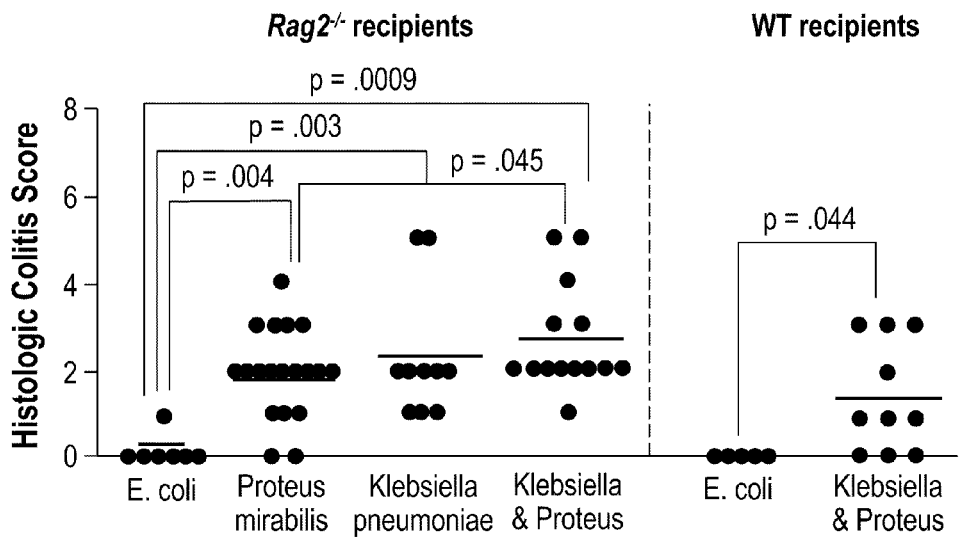
Figure 14:
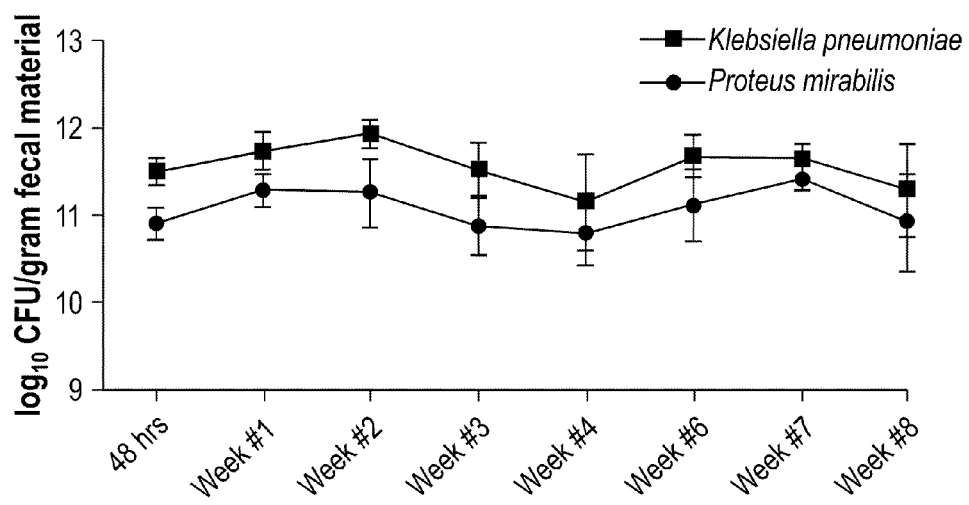
FIG. 14. Fecal bacterial counts for co-colonized gnotobiotic TRUC mice. Mean values±1 S.D. are shown for *Klebsiella pneumoniae* (squares) and *Proteus mirabilis* (circles) (n=5 mice).

To directly test the colitogenic potential of *K. pneumoniae* and *P. mirabilis*, we re-derived conventionally-raised TRUC mice as germ-free and co-colonized the animals with these two Enterobacteriaceae at 8 weeks of age for 8 weeks (n=5 mice). Both organisms established themselves in these guts of all recipients (mean value $10^{11.29 \pm 10.46}$ cfu/microbial species/g dry weight of feces; assayed 48 h and weekly after the initial gavage (FIG. 14). Colonic inflammation did not develop in these co-colonized gnotobiotic TRUC mice, raising the question of whether interactions between *K. pneumoniae* and *P. mirabilis* and other members of a gut microbial community are required to ignite the immuno-inflammatory cascade that leads to colitis. To evaluate this possibility, we colonized 2 week-old specified pathogen-free WT and Rag2$^{-/-}$ mice with *Klebsiella pneumoniae, P. mirabilis,* or a combination of *K. pneumoniae* and *P. mirabilis* (both strains recovered from feces obtained from a female TRUC mother); note that organisms were administered by direct oral instillation of $10^{7.301}$ cfu, and by addition of $10^7$ cfu to the drinking water every other day for 8 weeks; n=5-18 mice/treatment group). Control groups of mice received a TRUC-derived *E. coli* strain. Both *K. pneumoniae* and *P. mirabilis* established themselves in the gut microbiota of both RAG2-/-- and WT (as defined by cfu assays of feces obtained 2d after the completion of an 8-week course of treatment; FIG. 11C). Feces from WT and Rag2 hosts contain *E. coli* but we have not distinguished these indigenous strains from the exogenously administered TRUC-associated *E. coli* strain. While no colonic inflammation was observed with *E. coli* inoculation (FIG. 11D), treatment with *P. mirabilis, K. pneumoniae,* or a combination of the two organisms, induced inflammation in both WT and Rag2-/- mice with the severity of the colitis being significantly greater in Rag2$^{-/-}$ mice exposed to both species, compared to *P. mirabilis* alone (FIG. 11D). Taken together, these results support the notion that interactions between these two Enterobacteriaceae and members of the microbiota are able to elicit colitis, even in mice that are not genetically predisposed to developing immunopathologic responses.

The penetrance and severity of colitis observed in the Enterobacteriaceae colonization experiments was decreased compared to what we had previously observed in the spontaneous TRUC model and in neonatal cross-fostering experiments (TRUC-Rag2-/- and TRUC-WT cross where the mean colitis score for Rag2-/- recipients was 5.8+1.09 and for WT recipients 3.28+0.76) (Garrett et al., 2007). Instead, it resembled what we had observed in experiments where adult TRUC mice were co-housed with adult Rag2-/- or WT mice (Garrett et al., 2007), speaking to a possible role of maternal programming in structuring TRUC microbial communities in the neonate. Consistent with this, we found that TRUC milk has a pro-inflammatory cytokine profile and that the microbiota of 2 week old TRUC mice clusters in a distinct group as judged by PCoA plots of UniFrac measurements of 16S rRNA-defined communities (FIG. 9A).

Example 12

Figure 12A:
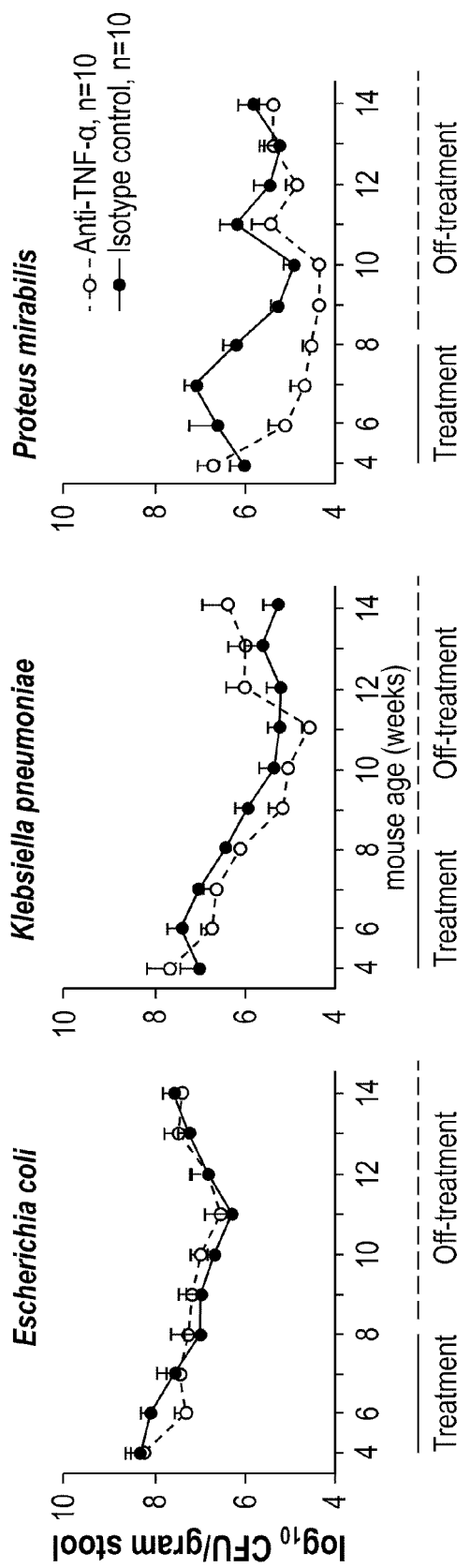
Figure 16:
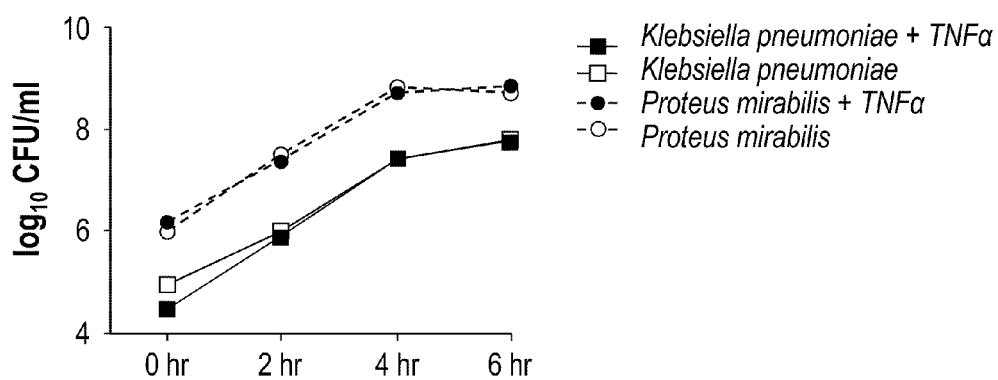
FIG. 16. TNF-a does not affect the growth kinetics of *Klebsiella pneumoniae* or *Proteus mirabilis* cultured in vitro. Bacteria were cultured for 6 hrs in the presence or absence of TNF-a 100 ug/ml and colony counts performed at 2 h time points. Results are representative of two independent experiments.
Figure 17:
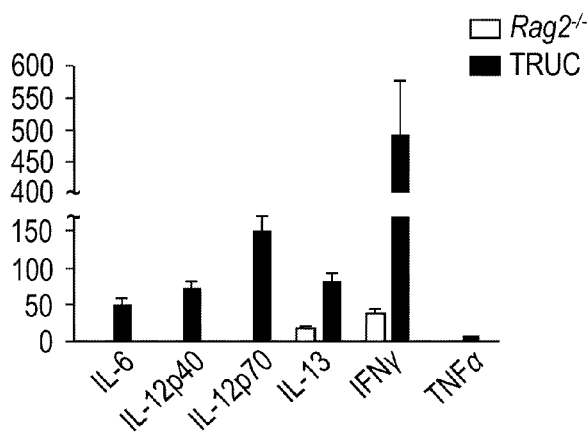
FIG. 17. Increased pro-inflammatory cytokines in TRUC vs Rag2$^{+-}$ milk. ELISA-based cytokine determinations from milk samples pooled from six lactating TRUC or Rag2-1- females. Bars represent the mean value of triplicates determinations/sample. Error bars are 1 S.D.

*Klebsiella pneumoniae* and *Proteus mirabilis* Colonization Pattern Change in Response to Immunotherapy We next asked whether *K. pneumoniae* and *P. mirabilis* colonization patterns might change in response to two immunotherapeutic interventions previously shown to cure TRUC colitis; i.e., TNF-a neutralization and T-regulatory cell (T-reg) transfer, (Garrett et al., 2007). We used quantitative culture-based methods to assay *K. pneumoniae* and *P. mirabilis* levels in feces prior to treatment of 4 week-old TRUC mice with anti-TNF-a, during weekly treatment for 4 weeks, and for six weeks after the last dose (FIG. 12A) (n=10 mice treated with antiTNF-a and n=10 treated with an isotype control). The differences in fecal *K. pneumoniae* levels between the TNF-a neutralization and isotype control groups were significantly different after animals had been treated for 7 weeks (i.e. were 11 weeks-old; p=0.0172; Mann-Whitney test) and for *Proteus mirabilis* after a shorter period of treatment (p=0.008, p=0.0012, p=0.0004, and p=0.0403 at 7, 8, 9 and 10 weeks of age). Two way ANOVA revealed that anti-TNF-a neutralization accounted for 10.72% of the total variance observed in fecal *P. mirabilis* levels (after adjusting for matching: F=22.83. DFn=1 DFd=18, p=0.0002). Control experiments showed that TNF-a did not affect the growth kinetics of either *K. pneumoniae* or *P. mirabilis* under in vitro mono-culture conditions (FIG. 16).

Figure 12B:
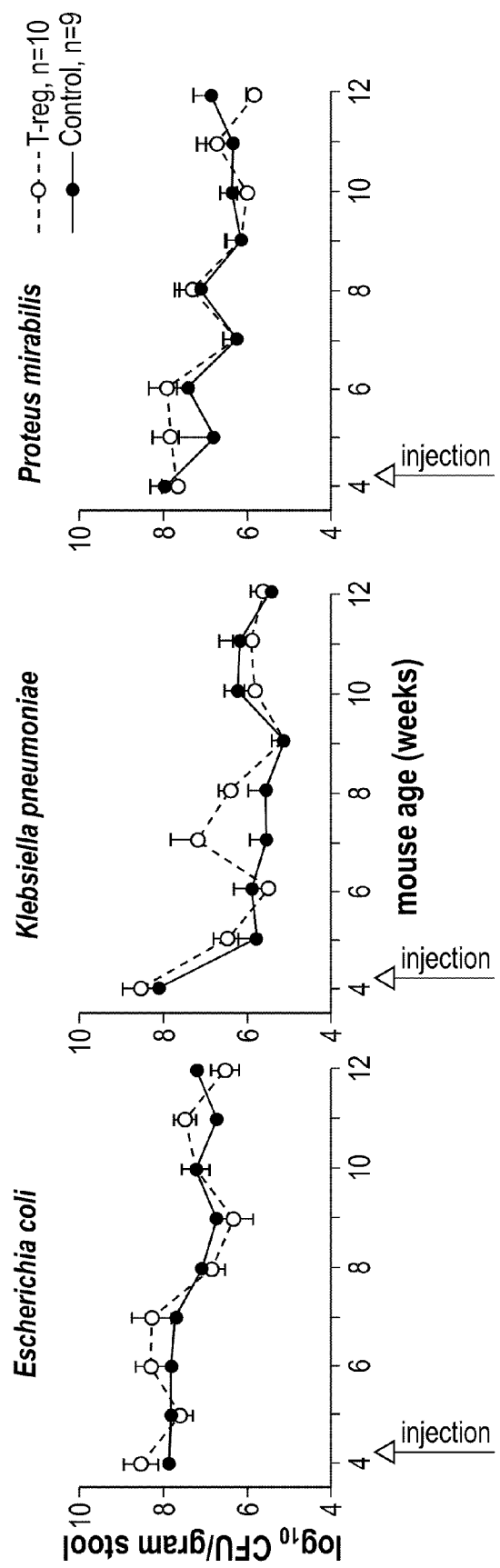
Figure 13:
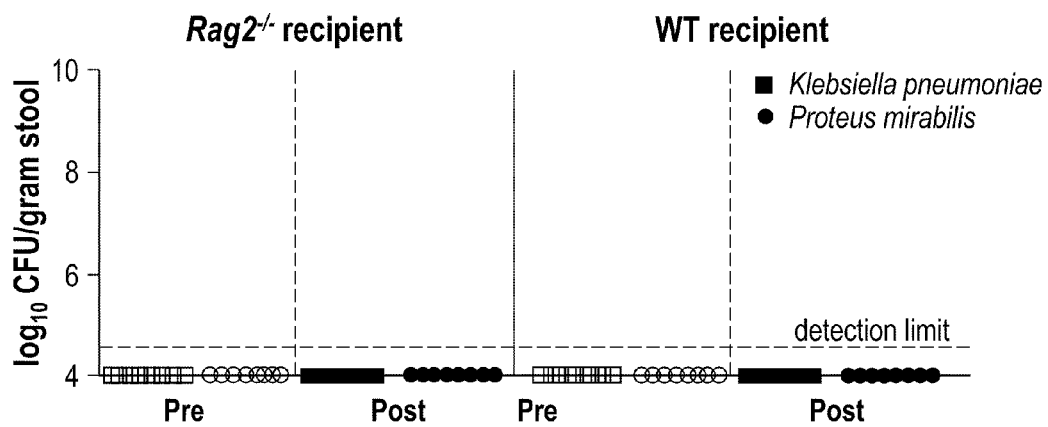
FIG. 13. Dextran sulfate sodium does not alter fecal levels of culturable *Klebsiella pneumoniae* and *Proteus mirabilis* in Rag.1$^{1m}$ and WT mice. Fecal bacterial counts for mice before and after treatment with 4% dextran sulfate sodium are shown (n=8/genotype). Levels of *Klebsiella pneumoniae* (squares) and *Proteus mirabilis* (circles) were below the lower limit of detection in all animals. Colony counts are expressed as $log_{10}$-cfu/gram fecal material.
Figure 15:
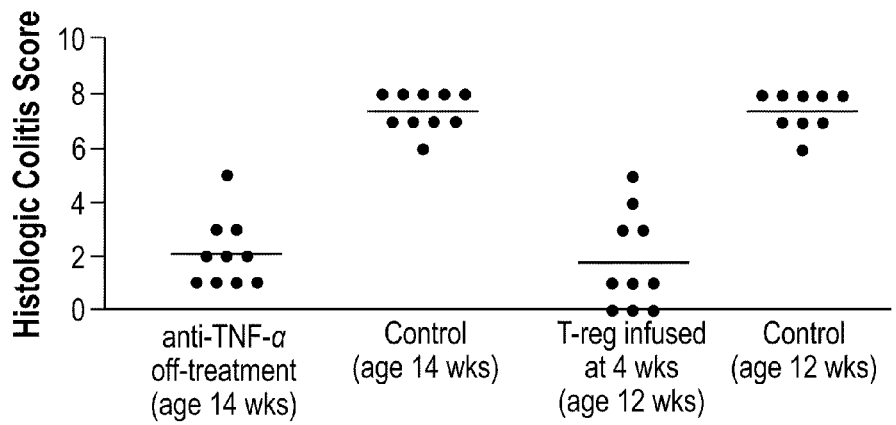
FIG. 15. Histologic colitis scores for anti-TNF-a and T-regulatory cell infused TRUC mice off-therapy. Histologic colitis scores are shown for individual mice, the horizontal bar represents the mean.

A similar analysis was performed in TRUC mice that had received 75,000 purified wild type T-reg cells at 4 weeks of age (histologic colitis scores at 12 weeks of age are shown in FIG. 15). Surprisingly, while T-reg infusion ameloriated this colitis (Garrett et al., 2007), it did not affect fecal levels of either of these two Enterobacteriaceae species (FIG. 12B). These results further demonstrate that *K. pneumoniae* and *P. mirabilis* levels are not simply associated with inflammation per se, as both these modalities reduced host inflammation but did not uniformly alter Enterobacteriaceal representation. Our results illustrate that certain host-directed treatments may exert their effects not only by altering host inflammatory pathways but also by directly impacting the microbiota itself.

Gut microbiota transmission experiments demonstrated that two Enterobacteriaceae, *Klebsiella pneumoniae* and *Proteus mirabilis*, together with other members of the microbiota can elicit colitis even in wild-type animals.

Equivalents

Those skilled in the art will recognize, or be able to ascertain using no more than routine experimentation, many equivalents to the specific embodiments of the invention described herein. Such equivalents are intended to be encompassed by the following claims.

SEQUENCE LISTING

<160> NUMBER OF SEQ ID NOS: 4

<210> SEQ ID NO 1
<211> LENGTH: 1608
<212> TYPE: DNA
<213> ORGANISM: Homo sapiens

```
<220> FEATURE:
<221> NAME/KEY: CDS
<222> LOCATION: (1)..(1605)

<400> SEQUENCE: 1 atg ggc atc gtg gag ccg ggt tgc gga gac atg ctg acg ggc acc gag      48
Met Gly Ile Val Glu Pro Gly Cys Gly Asp Met Leu Thr Gly Thr Glu
 1               5                  10                  15 ccg atg ccg ggg agc gac gag ggc cgg gcg cct ggc gcc gac ccg cag      96
Pro Met Pro Gly Ser Asp Glu Gly Arg Ala Pro Gly Ala Asp Pro Gln
             20                  25                  30 cac cgc tac ttc tac ccg gag ccg ggc gcg cag gac gcg gac gag cgt     144
His Arg Tyr Phe Tyr Pro Glu Pro Gly Ala Gln Asp Ala Asp Glu Arg
         35                  40                  45 cgc ggg ggc ggc agc ctg ggg tct ccc tac ccg ggg ggc gcc ttg gtg     192
Arg Gly Gly Gly Ser Leu Gly Ser Pro Tyr Pro Gly Gly Ala Leu Val
     50                  55                  60 ccc gcc ccg ccg agc cgc ttc ctt gga gcc tac gcc tac ccg ccg cga     240
Pro Ala Pro Pro Ser Arg Phe Leu Gly Ala Tyr Ala Tyr Pro Pro Arg
 65                  70                  75                  80 ccc cag gcg gcc ggc ttc ccc ggc gcg ggc gag tcc ttc ccg ccg ccc     288
Pro Gln Ala Ala Gly Phe Pro Gly Ala Gly Glu Ser Phe Pro Pro Pro
                 85                  90                  95 gcg gac gcc gag ggc tac cag ccg ggc gag ggc tac gcc gcc ccg gac     336
Ala Asp Ala Glu Gly Tyr Gln Pro Gly Glu Gly Tyr Ala Ala Pro Asp
            100                 105                 110 ccg cgc gcc ggg ctc tac ccg ggg ccg cgt gag gac tac gcg cta ccc     384
Pro Arg Ala Gly Leu Tyr Pro Gly Pro Arg Glu Asp Tyr Ala Leu Pro
        115                 120                 125 gcg gga ctg gag gtg tcg ggg aaa ctg agg gtc gcg ctc aac aac cac     432
Ala Gly Leu Glu Val Ser Gly Lys Leu Arg Val Ala Leu Asn Asn His
    130                 135                 140 ctg ttg tgg tcc aag ttt aat cag cac cag aca gag atg atc atc acc     480
Leu Leu Trp Ser Lys Phe Asn Gln His Gln Thr Glu Met Ile Ile Thr
145                 150                 155                 160 aag cag gga cgg cgg atg ttc cca ttc ctg tca ttt act gtg gcc ggg     528
Lys Gln Gly Arg Arg Met Phe Pro Phe Leu Ser Phe Thr Val Ala Gly
                165                 170                 175 ctg gag ccc acc agc cac tac agg atg ttt gtg gac gtg gtc ttg gtg     576
Leu Glu Pro Thr Ser His Tyr Arg Met Phe Val Asp Val Val Leu Val
            180                 185                 190 gac cag cac cac tgg cgg tac cag agc ggc aag tgg gtg cag tgt gga     624
Asp Gln His His Trp Arg Tyr Gln Ser Gly Lys Trp Val Gln Cys Gly
        195                 200                 205 aag gcc gag ggc agc atg cca gga aac cgc ctg tac gtc cac ccg gac     672
Lys Ala Glu Gly Ser Met Pro Gly Asn Arg Leu Tyr Val His Pro Asp
    210                 215                 220 tcc ccc aac aca gga gcg cac tgg atg cgc cag gaa gtt tca ttt ggg     720
Ser Pro Asn Thr Gly Ala His Trp Met Arg Gln Glu Val Ser Phe Gly
225                 230                 235                 240 aaa cta aag ctc aca aac aac aag ggg gcg tcc aac aat gtg acc cag     768
Lys Leu Lys Leu Thr Asn Asn Lys Gly Ala Ser Asn Asn Val Thr Gln
                245                 250                 255 atg att gtg ctc cag tcc ctc cat aag tac cag ccc cgg ctg cat atc     816
Met Ile Val Leu Gln Ser Leu His Lys Tyr Gln Pro Arg Leu His Ile
            260                 265                 270 gtt gag gtg aac gac gga gag cca gag gca gcc tgc aac gct tcc aac     864
Val Glu Val Asn Asp Gly Glu Pro Glu Ala Ala Cys Asn Ala Ser Asn
        275                 280                 285 acg cat atc ttt act ttc caa gaa acc cag ttc att gcc gtg act gcc     912
Thr His Ile Phe Thr Phe Gln Glu Thr Gln Phe Ile Ala Val Thr Ala
```

```
                       290                 295                 300
tac cag aat gcc gag att act cag ctg aaa att gat aat aac ccc ttt      960
Tyr Gln Asn Ala Glu Ile Thr Gln Leu Lys Ile Asp Asn Asn Pro Phe
305                 310                 315                 320 gcc aaa gga ttc cgg gag aac ttt gag tcc atg tac aca tct gtt gac     1008
Ala Lys Gly Phe Arg Glu Asn Phe Glu Ser Met Tyr Thr Ser Val Asp
                325                 330                 335 acc agc atc ccc tcc ccg cct gga ccc aac tgt caa ttc ctt ggg gga     1056
Thr Ser Ile Pro Ser Pro Pro Gly Pro Asn Cys Gln Phe Leu Gly Gly
            340                 345                 350 gat cac tac tct cct ctc cta ccc aac cag tat cct gtt ccc agc cgc     1104
Asp His Tyr Ser Pro Leu Leu Pro Asn Gln Tyr Pro Val Pro Ser Arg
        355                 360                 365 ttc tac ccc gac ctt cct ggc cag gcg aag gat gtg gtt ccc cag gct     1152
Phe Tyr Pro Asp Leu Pro Gly Gln Ala Lys Asp Val Val Pro Gln Ala
    370                 375                 380 tac tgg ctg ggg gcc ccc cgg gac cac agc tat gag gct gag ttt cga     1200
Tyr Trp Leu Gly Ala Pro Arg Asp His Ser Tyr Glu Ala Glu Phe Arg
385                 390                 395                 400 gca gtc agc atg aag cct gca ttc ttg ccc tct gcc cct ggg ccc acc     1248
Ala Val Ser Met Lys Pro Ala Phe Leu Pro Ser Ala Pro Gly Pro Thr
                405                 410                 415 atg tcc tac tac cga ggc cag gag gtc ctg gca cct gga gct ggc tgg     1296
Met Ser Tyr Tyr Arg Gly Gln Glu Val Leu Ala Pro Gly Ala Gly Trp
            420                 425                 430 cct gtg gca ccc cag tac cct ccc aag atg ggc ccg gcc agc tgg ttc     1344
Pro Val Ala Pro Gln Tyr Pro Pro Lys Met Gly Pro Ala Ser Trp Phe
        435                 440                 445 cgc cct atg cgg act ctg ccc atg gaa ccc ggc cct gga ggc tca gag     1392
Arg Pro Met Arg Thr Leu Pro Met Glu Pro Gly Pro Gly Gly Ser Glu
    450                 455                 460 gga cgg gga cca gag gac cag ggt ccc ccc ttg gtg tgg act gag att     1440
Gly Arg Gly Pro Glu Asp Gln Gly Pro Pro Leu Val Trp Thr Glu Ile
465                 470                 475                 480 gcc ccc atc cgg ccg gaa tcc agt gat tca gga ctg ggc gaa gga gac     1488
Ala Pro Ile Arg Pro Glu Ser Ser Asp Ser Gly Leu Gly Glu Gly Asp
                485                 490                 495 tct aag agg agg cgc gtg tcc ccc tat cct tcc agt ggt gac agc tcc     1536
Ser Lys Arg Arg Arg Val Ser Pro Tyr Pro Ser Ser Gly Asp Ser Ser
            500                 505                 510 tcc cct gct ggg gcc cct tct cct ttt gat aag gaa gct gaa gga cag     1584
Ser Pro Ala Gly Ala Pro Ser Pro Phe Asp Lys Glu Ala Glu Gly Gln
        515                 520                 525 ttt tat aac tat ttt ccc aac tga                                     1608
Phe Tyr Asn Tyr Phe Pro Asn
    530                 535

<210> SEQ ID NO 2
<211> LENGTH: 535
<212> TYPE: PRT
<213> ORGANISM: Homo sapiens

<400> SEQUENCE: 2

Met Gly Ile Val Glu Pro Gly Cys Gly Asp Met Leu Thr Gly Thr Glu
1               5                   10                  15

Pro Met Pro Gly Ser Asp Glu Gly Arg Ala Pro Gly Ala Asp Pro Gln
            20                  25                  30

His Arg Tyr Phe Tyr Pro Glu Pro Gly Ala Gln Asp Ala Asp Glu Arg
        35                  40                  45

Arg Gly Gly Gly Ser Leu Gly Ser Pro Tyr Pro Gly Gly Ala Leu Val
```

```
            50                  55                  60
Pro Ala Pro Pro Ser Arg Phe Leu Gly Ala Tyr Ala Tyr Pro Pro Arg
 65                  70                  75                  80

Pro Gln Ala Ala Gly Phe Pro Ala Gly Glu Ser Phe Pro Pro Pro
                 85                  90                  95

Ala Asp Ala Glu Gly Tyr Gln Pro Gly Glu Gly Tyr Ala Ala Pro Asp
                100                 105                 110

Pro Arg Ala Gly Leu Tyr Pro Gly Arg Glu Asp Tyr Ala Leu Pro
                115                 120                 125

Ala Gly Leu Glu Val Ser Gly Lys Leu Arg Val Ala Leu Asn Asn His
130                 135                 140

Leu Leu Trp Ser Lys Phe Asn Gln His Gln Thr Glu Met Ile Ile Thr
145                 150                 155                 160

Lys Gln Gly Arg Arg Met Phe Pro Phe Leu Ser Phe Thr Val Ala Gly
                165                 170                 175

Leu Glu Pro Thr Ser His Tyr Arg Met Phe Val Asp Val Val Leu Val
                180                 185                 190

Asp Gln His His Trp Arg Tyr Gln Ser Gly Lys Trp Val Gln Cys Gly
                195                 200                 205

Lys Ala Glu Gly Ser Met Pro Gly Asn Arg Leu Tyr Val His Pro Asp
210                 215                 220

Ser Pro Asn Thr Gly Ala His Trp Met Arg Gln Glu Val Ser Phe Gly
225                 230                 235                 240

Lys Leu Lys Leu Thr Asn Asn Lys Gly Ala Ser Asn Asn Val Thr Gln
                245                 250                 255

Met Ile Val Leu Gln Ser Leu His Lys Tyr Gln Pro Arg Leu His Ile
                260                 265                 270

Val Glu Val Asn Asp Gly Glu Pro Glu Ala Ala Cys Asn Ala Ser Asn
                275                 280                 285

Thr His Ile Phe Thr Phe Gln Glu Thr Gln Phe Ile Ala Val Thr Ala
                290                 295                 300

Tyr Gln Asn Ala Glu Ile Thr Gln Leu Lys Ile Asp Asn Asn Pro Phe
305                 310                 315                 320

Ala Lys Gly Phe Arg Glu Asn Phe Glu Ser Met Tyr Thr Ser Val Asp
                325                 330                 335

Thr Ser Ile Pro Ser Pro Gly Pro Asn Cys Gln Phe Leu Gly Gly
                340                 345                 350

Asp His Tyr Ser Pro Leu Leu Pro Asn Gln Tyr Pro Val Pro Ser Arg
                355                 360                 365

Phe Tyr Pro Asp Leu Pro Gly Gln Ala Lys Asp Val Val Pro Gln Ala
370                 375                 380

Tyr Trp Leu Gly Ala Pro Arg Asp His Ser Tyr Glu Ala Glu Phe Arg
385                 390                 395                 400

Ala Val Ser Met Lys Pro Ala Phe Leu Pro Ser Ala Pro Gly Pro Thr
                405                 410                 415

Met Ser Tyr Tyr Arg Gly Gln Glu Val Leu Ala Pro Gly Ala Gly Trp
                420                 425                 430

Pro Val Ala Pro Gln Tyr Pro Pro Lys Met Gly Pro Ala Ser Trp Phe
                435                 440                 445

Arg Pro Met Arg Thr Leu Pro Met Glu Pro Gly Pro Gly Gly Ser Glu
                450                 455                 460

Gly Arg Gly Pro Glu Asp Gln Gly Pro Pro Leu Val Trp Thr Glu Ile
465                 470                 475                 480
```

```
Ala Pro Ile Arg Pro Glu Ser Ser Asp Ser Gly Leu Gly Glu Gly Asp
            485                 490                 495

Ser Lys Arg Arg Arg Val Ser Pro Tyr Pro Ser Ser Gly Asp Ser Ser
        500                 505                 510

Ser Pro Ala Gly Ala Pro Ser Pro Phe Asp Lys Glu Ala Glu Gly Gln
        515                 520                 525

Phe Tyr Asn Tyr Phe Pro Asn
        530                 535

<210> SEQ ID NO 3
<211> LENGTH: 1593
<212> TYPE: DNA
<213> ORGANISM: Mus musculus
<220> FEATURE:
<221> NAME/KEY: CDS
<222> LOCATION: (1)..(1590)

<400> SEQUENCE: 3 atg ggc atc gtg gag ccg ggc tgc gga gac atg ctg acc ggc acc gag      48
Met Gly Ile Val Glu Pro Gly Cys Gly Asp Met Leu Thr Gly Thr Glu
 1               5                  10                  15 ccg atg ccg agt gac gag ggc cgg ggg ccc gga gcg gac caa cag cat      96
Pro Met Pro Ser Asp Glu Gly Arg Gly Pro Gly Ala Asp Gln Gln His
             20                  25                  30 cgt ttc ttc tat ccc gag ccg ggc gca cag gac ccg acc gat cgc cgc     144
Arg Phe Phe Tyr Pro Glu Pro Gly Ala Gln Asp Pro Thr Asp Arg Arg
         35                  40                  45 gca ggt agc agc ctg ggg acg ccc tac tct ggg ggc gcc ctg gtg cct     192
Ala Gly Ser Ser Leu Gly Thr Pro Tyr Ser Gly Gly Ala Leu Val Pro
     50                  55                  60 gcc gcg ccg ggt cgc ttc ctt gga tcc ttc gcc tac ccg ccc cgg gct     240
Ala Ala Pro Gly Arg Phe Leu Gly Ser Phe Ala Tyr Pro Pro Arg Ala
 65                  70                  75                  80 cag gtg gct ggc ttt ccc ggg cct ggc gag ttc ttc ccg ccg ccc gcg     288
Gln Val Ala Gly Phe Pro Gly Pro Gly Glu Phe Phe Pro Pro Pro Ala
                 85                  90                  95 ggt gcg gag ggc tac ccg ccc gtg gat ggc tac cct gcc cct gac ccg     336
Gly Ala Glu Gly Tyr Pro Pro Val Asp Gly Tyr Pro Ala Pro Asp Pro
            100                 105                 110 cgc gcg ggg ctc tac cca ggg ccg cgc gag gac tac gca ttg ccc gcg     384
Arg Ala Gly Leu Tyr Pro Gly Pro Arg Glu Asp Tyr Ala Leu Pro Ala
        115                 120                 125 ggg ttg gag gtg tct ggg aag ctg aga gtc gcg ctc agc aac cac ctg     432
Gly Leu Glu Val Ser Gly Lys Leu Arg Val Ala Leu Ser Asn His Leu
    130                 135                 140 ttg tgg tcc aag ttc aac cag cac cag aca gag atg atc atc act aag     480
Leu Trp Ser Lys Phe Asn Gln His Gln Thr Glu Met Ile Ile Thr Lys
145                 150                 155                 160 caa gga cgg cga atg ttc cca ttc ctg tcc ttc acc gtg gcc ggg ctg     528
Gln Gly Arg Arg Met Phe Pro Phe Leu Ser Phe Thr Val Ala Gly Leu
                165                 170                 175 gag ccc aca agc cat tac agg atg ttt gtg gat gtg gtc ttg gtg gac     576
Glu Pro Thr Ser His Tyr Arg Met Phe Val Asp Val Val Leu Val Asp
            180                 185                 190 cag cac cac tgg cgg tac cag agc ggc aag tgg gtg cag tgt gga aag     624
Gln His His Trp Arg Tyr Gln Ser Gly Lys Trp Val Gln Cys Gly Lys
        195                 200                 205 gca gaa ggc agc atg cca ggg aac cgc tta tat gtc cac cca gac tcc     672
Ala Glu Gly Ser Met Pro Gly Asn Arg Leu Tyr Val His Pro Asp Ser
    210                 215                 220 ccc aac acc gga gcc cac tgg atg cgc cag gaa gtt tca ttt ggg aag     720
```

```
                        -continued

Pro Asn Thr Gly Ala His Trp Met Arg Gln Glu Val Ser Phe Gly Lys
225                 230                 235                 240 cta aag ctc acc aac aac aag ggg gct tcc aac aat gtg acc cag atg      768
Leu Lys Leu Thr Asn Asn Lys Gly Ala Ser Asn Asn Val Thr Gln Met
                    245                 250                 255 atc gtc ctg cag tct ctc cac aag tac cag ccc cgg ctg cac atc gtg      816
Ile Val Leu Gln Ser Leu His Lys Tyr Gln Pro Arg Leu His Ile Val
                260                 265                 270 gag gtg aat gat gga gag cca gag gct gcc tgc agt gct tct aac aca      864
Glu Val Asn Asp Gly Glu Pro Glu Ala Ala Cys Ser Ala Ser Asn Thr
            275                 280                 285 cac gtc ttt act ttc caa gag acc cag ttc att gca gtg act gcc tac      912
His Val Phe Thr Phe Gln Glu Thr Gln Phe Ile Ala Val Thr Ala Tyr
        290                 295                 300 cag aac gca gag atc act cag ctg aaa atc gac aac aac ccc ttt gcc      960
Gln Asn Ala Glu Ile Thr Gln Leu Lys Ile Asp Asn Asn Pro Phe Ala
305                 310                 315                 320 aaa gga ttc cgg gag aac ttt gag tcc atg tac gca tct gtt gat acg     1008
Lys Gly Phe Arg Glu Asn Phe Glu Ser Met Tyr Ala Ser Val Asp Thr
                    325                 330                 335 agt gtc ccc tcg cca cct gga ccc aac tgt caa ctg ctt ggg gga gac     1056
Ser Val Pro Ser Pro Pro Gly Pro Asn Cys Gln Leu Leu Gly Gly Asp
                340                 345                 350 ccc ttc tca cct ctt cta tcc aac cag tat cct gtt ccc agc cgt ttc     1104
Pro Phe Ser Pro Leu Leu Ser Asn Gln Tyr Pro Val Pro Ser Arg Phe
            355                 360                 365 tac ccc gac ctt cca ggc cag ccc aag gat atg atc tca cag cct tac     1152
Tyr Pro Asp Leu Pro Gly Gln Pro Lys Asp Met Ile Ser Gln Pro Tyr
        370                 375                 380 tgg ctg ggg aca cct cgg gaa cac agt tat gaa gcg gag ttc cga gct     1200
Trp Leu Gly Thr Pro Arg Glu His Ser Tyr Glu Ala Glu Phe Arg Ala
385                 390                 395                 400 gtg agc atg aag ccc aca ctc cta ccc tct gcc ccg ggg ccc act gtg     1248
Val Ser Met Lys Pro Thr Leu Leu Pro Ser Ala Pro Gly Pro Thr Val
                    405                 410                 415 ccc tac tac cgg ggc caa gac gtc ctg gcg cct gga gct ggt tgg ccc     1296
Pro Tyr Tyr Arg Gly Gln Asp Val Leu Ala Pro Gly Ala Gly Trp Pro
                420                 425                 430 gtg gcc cct caa tac ccg ccc aag atg agc cca gct ggc tgg ttc cgg     1344
Val Ala Pro Gln Tyr Pro Pro Lys Met Ser Pro Ala Gly Trp Phe Arg
            435                 440                 445 ccc atg cga act ctg ccc atg gac ccg ggc ctg gga tcc tca gag gaa     1392
Pro Met Arg Thr Leu Pro Met Asp Pro Gly Leu Gly Ser Ser Glu Glu
        450                 455                 460 cag ggc tcc tcc ccc tcg ctg tgg cct gag gtc acc tcc ctc cag ccg     1440
Gln Gly Ser Ser Pro Ser Leu Trp Pro Glu Val Thr Ser Leu Gln Pro
465                 470                 475                 480 gag ccc agc gac tca gga cta ggc gaa gga gac act aag agg agg agg     1488
Glu Pro Ser Asp Ser Gly Leu Gly Glu Gly Asp Thr Lys Arg Arg Arg
                    485                 490                 495 ata tcc ccc tat cct tcc agt ggc gac agc tcc tct ccc gct ggg gcc     1536
Ile Ser Pro Tyr Pro Ser Ser Gly Asp Ser Ser Ser Pro Ala Gly Ala
                500                 505                 510 cct tct cct ttt gat aag gaa acc gaa ggc cag ttt tat aat tat ttt     1584
Pro Ser Pro Phe Asp Lys Glu Thr Glu Gly Gln Phe Tyr Asn Tyr Phe
            515                 520                 525 ccc aac tga                                                          1593
Pro Asn
    530
```

<210> SEQ ID NO 4
<211> LENGTH: 530
<212> TYPE: PRT
<213> ORGANISM: Mus musculus

<400> SEQUENCE: 4

```
Met Gly Ile Val Glu Pro Gly Cys Gly Asp Met Leu Thr Gly Thr Glu
  1               5                  10                  15

Pro Met Pro Ser Asp Glu Gly Arg Gly Pro Ala Asp Gln Gln His
             20                  25                  30

Arg Phe Phe Tyr Pro Glu Pro Gly Ala Gln Asp Pro Thr Asp Arg Arg
             35                  40                  45

Ala Gly Ser Ser Leu Gly Thr Pro Tyr Ser Gly Gly Ala Leu Val Pro
 50                  55                  60

Ala Ala Pro Gly Arg Phe Leu Gly Ser Phe Ala Tyr Pro Pro Arg Ala
 65                  70                  75                  80

Gln Val Ala Gly Phe Pro Gly Pro Gly Glu Phe Phe Pro Pro Ala
             85                  90                  95

Gly Ala Glu Gly Tyr Pro Pro Val Asp Gly Tyr Pro Ala Pro Asp Pro
            100                 105                 110

Arg Ala Gly Leu Tyr Pro Gly Pro Arg Glu Asp Tyr Ala Leu Pro Ala
            115                 120                 125

Gly Leu Glu Val Ser Gly Lys Leu Arg Val Ala Leu Ser Asn His Leu
130                 135                 140

Leu Trp Ser Lys Phe Asn Gln His Gln Thr Glu Met Ile Ile Thr Lys
145                 150                 155                 160

Gln Gly Arg Arg Met Phe Pro Phe Leu Ser Phe Thr Val Ala Gly Leu
            165                 170                 175

Glu Pro Thr Ser His Tyr Arg Met Phe Val Asp Val Val Leu Val Asp
            180                 185                 190

Gln His His Trp Arg Tyr Gln Ser Gly Lys Trp Val Gln Cys Gly Lys
            195                 200                 205

Ala Glu Gly Ser Met Pro Gly Asn Arg Leu Tyr Val His Pro Asp Ser
210                 215                 220

Pro Asn Thr Gly Ala His Trp Met Arg Gln Glu Val Ser Phe Gly Lys
225                 230                 235                 240

Leu Lys Leu Thr Asn Asn Lys Gly Ala Ser Asn Asn Val Thr Gln Met
            245                 250                 255

Ile Val Leu Gln Ser Leu His Lys Tyr Gln Pro Arg Leu His Ile Val
            260                 265                 270

Glu Val Asn Asp Gly Glu Pro Glu Ala Ala Cys Ser Ala Ser Asn Thr
            275                 280                 285

His Val Phe Thr Phe Gln Glu Thr Gln Phe Ile Ala Val Thr Ala Tyr
            290                 295                 300

Gln Asn Ala Glu Ile Thr Gln Leu Lys Ile Asp Asn Asn Pro Phe Ala
305                 310                 315                 320

Lys Gly Phe Arg Glu Asn Phe Glu Ser Met Tyr Ala Ser Val Asp Thr
            325                 330                 335

Ser Val Pro Ser Pro Gly Pro Asn Cys Gln Leu Leu Gly Gly Asp
            340                 345                 350

Pro Phe Ser Pro Leu Leu Ser Asn Gln Tyr Pro Val Pro Ser Arg Phe
            355                 360                 365

Tyr Pro Asp Leu Pro Gly Gln Pro Lys Asp Met Ile Ser Gln Pro Tyr
            370                 375                 380

Trp Leu Gly Thr Pro Arg Glu His Ser Tyr Glu Ala Glu Phe Arg Ala
```

-continued

| | | | | | | | | | | | | | | | |
|---|---|---|---|---|---|---|---|---|---|---|---|---|---|---|---|
| 385 | | | | | 390 | | | | | 395 | | | | | 400 |
| Val | Ser | Met | Lys | Pro<br>405 | Thr | Leu | Leu | Pro | Ser<br>410 | Ala | Pro | Gly | Pro | Thr<br>415 | Val |
| Pro | Tyr | Tyr | Arg<br>420 | Gly | Gln | Asp | Val | Leu<br>425 | Ala | Pro | Gly | Ala | Gly<br>430 | Trp | Pro |
| Val | Ala | Pro<br>435 | Gln | Tyr | Pro | Pro | Lys<br>440 | Met | Ser | Pro | Ala | Gly<br>445 | Trp | Phe | Arg |
| Pro | Met | Arg<br>450 | Thr | Leu | Pro | Met<br>455 | Asp | Pro | Gly | Leu | Gly<br>460 | Ser | Ser | Glu | Glu |
| Gln<br>465 | Gly | Ser | Ser | Pro | Ser<br>470 | Leu | Trp | Pro | Glu | Val<br>475 | Thr | Ser | Leu | Gln | Pro<br>480 |
| Glu | Pro | Ser | Asp | Ser<br>485 | Gly | Leu | Gly | Glu | Gly<br>490 | Asp | Thr | Lys | Arg | Arg<br>495 | Arg |
| Ile | Ser | Pro | Tyr<br>500 | Pro | Ser | Ser | Gly | Asp<br>505 | Ser | Ser | Ser | Pro | Ala<br>510 | Gly | Ala |
| Pro | Ser | Pro<br>515 | Phe | Asp | Lys | Glu | Thr<br>520 | Glu | Gly | Gln | Phe | Tyr<br>525 | Asn | Tyr | Phe |
| Pro | Asn<br>530 | | | | | | | | | | | | | | |

What is claimed is:

1. A method for evaluating the ability of a test compound to modulate spontaneous ulcerative colitis, comprising:
    administering the test compound to a transgenic postnatal mouse whose genome comprises homozygous null mutations in each of the endogenous T-bet and Rag2 genes, wherein said homozygous null mutations have been introduced into said mouse genome by homologous recombination, said mouse having a phenotype, relative to a wild-type phenotype, of spontaneous ulcerative colitis comprising increased permeability of the colonic epithelium, increased apoptosis in the colonic epithelium and colonic wall thickening associated with prolapsed rectal mucosa; and
    determining the ability of the test compound to modulate permeability of the colonic epithelium, apoptosis in the colonic epithelium or colonic wall thickening associated with prolapsed rectal mucosa;
    to thereby evaluate the ability of the test compound to modulate spontaneous ulcerative colitis.

2. The method of claim 1, wherein the ability of the test compound to reduce TNFα production by colonic dendritic cells is measured.

3. The method of claim 1, wherein the effect of the test compound on the permeability of the intestines is measured.

4. The method of claim 1, wherein the effect of the test compound on apoptosis of colonic epithelium is determined.

5. The method of claim 1, wherein the effect of the test compound on dysplastic changes in colon cells is measured.

6. The method of claim 1, wherein the effect of the test compound on expression of cyclooxygenase-2 (COX-2) expression is measured.

7. The method of claim 1, wherein the effect of the test compound on β-catenin expression is measured.

8. The method of claim 1, wherein the effect of the test compound on the presence of TP53 mutations is measured.

9. The method of claim 1, wherein the effect of the test compound on the presence of *Klebsiella pneumonia* or *Proteus mirabilis* is measured.

* * * * *